United States Patent [19]
Huganir et al.

[11] Patent Number: 6,001,575
[45] Date of Patent: Dec. 14, 1999

[54] THERAPEUTIC USES OF GRIP AND GRIP-RELATED MOLECULES

[75] Inventors: Richard L. Huganir; Hualing Dong, both of Baltimore, Md.

[73] Assignee: Johns Hopkins University, Baltimore, Md.

[21] Appl. No.: 09/045,632

[22] Filed: Mar. 19, 1998

Related U.S. Application Data

[60] Provisional application No. 60/041,016, Mar. 19, 1997.

[51] Int. Cl.$^6$ .............................. C12Q 1/68; C12P 21/06; C07H 17/00; C07K 14/00
[52] U.S. Cl. ............................. 435/6; 435/69.1; 435/325; 435/253.2; 435/320.1; 536/23.1; 530/300; 530/350
[58] Field of Search ........................ 536/23.1; 435/69.1, 435/325, 25.3, 320.1, 6; 530/350, 300

[56] References Cited

PUBLICATIONS

Dong et al., *Nature,* 386:279 (1997).
S. Nakanishi, *Science,* 258:597 (1992).
J.E. Brenman, et al., *Cell,* 84: 757 (1996).
S.N. Gomperts, *Cell,* 84: 659 (1996).
F. Striggow and B.E. Ehrlich, *Curr. Opin. in Cell Biol.,* 8: 490 (1996).
N. Brose, et al., *J. Biol. Chem.,* 268: 22663 (1993).
U. Kistner, et al., *J. Biol. Chem.,* 268: 4580 (1993).
L. Lau and R.L. Huganir, *J. Biol. Chem.,* 270: 20036 (1995).
L. Lau, et al., *J. Biol. Chem.,* 271: 21622 (1996).
B.M. Muller et al., *J. Neurosci,* 15: 2354 (1995).
M. Niethammer, *J. Neurosci,* 16: 2157 (1996).
R.S. Petralia, *J. Neurosci,* 14: 667 (1994b).
G.M. Durand, et al., *Nature,* 381(6577): 71 (1996).
E. Kim, et al., *Nature,* 378: 85 (1995).
D. Liao, *Nature,* 375 (6530): 400 (1995).
S. Fields and O. Song, *Nature,* 340: 245 (1989).
J.A. Bennett and R. Dingledine, *Neuron,* 14: 373 (1995).
K. Cho, et al., *Neuron,* 9: 929 (1992).
J.T.R. Isaac, et al., *Neuron,* 15(2): 427 (1995).
B.M. Muller, et al., *Neuron,* 17: 255 (1996).
K.W. Roche, et al., *Neuron,* 16: 1179 (1996).
E. Kim, et al., *Neuron,* 17: 103 (1996).
P. Chevray and D. Nathans, *Proc. Natl. Acad. Sci. USA,* 89: 5789 (1992).
M.W. Wood, et al., *Proc. Natl. Acad. Sci. USA,* 92: 4882 (1995).
A.M. Craig, et al., *Proc. Natl. Acad. Sci. USA,* 91: 12373 (1994).
M.D. Ehlers, et al., *Science,* 269: 1734 (1995).
H. Kornau, et al., *Science,* 269: 1737 (1995).
M.B. Kennedy, *Trends in Biochem. Sci.,* 20: 350 (1995).
P.H. Seeberg, *Trends in Neurosci.,* 16: 359 (1993).

*Primary Examiner*—Karen Cochrane Carlson
*Attorney, Agent, or Firm*—Peter F. Corless; Robert L. Buchanan; Dike, Bronstein, Roberts & Cushman, LLP

[57] ABSTRACT

This invention features GRIP and GRIP-related molecules relating to a gluatamate receiptor. In one aspect, the invention provides methods for detecting expression, drug screening, and treatment of disorders involving GRIP or GRIP 2 such a neuronal and fertility disorders.

34 Claims, 76 Drawing Sheets

FIG. 3

| | | |
|---|---|---|
| 1 | MIAVSFKCRCQIILRRLITKDESPYTKSASQTKPPDGALAVRRQSIPEEFKG | 50 |
| 51 | STVVELMKKEGTTLGCTVSGGIDKDGKPRVSNLRQGGIAARSDQLDVGDY | 100 |
| 101 | IKAVNGINLAKFRHDEIISLLKNVGERVVLEVEYELPPVSIQGSSVMFRT | 150 |
| 151 | VEVTLHKEGNTFGFVIRGGAHDDRNKSRPVVITCBRPGGPDDREGTIKPG | 200 |
| 201 | DRLLSVDGIRLLGTTHAEAMSILKQCGQEATLLIEYDVSAMDSVATASGP | 250 |
| 251 | LLVEVAKTPGASLGVALTTSVCCNKQVIVIDKIKSASIADRCGALHVGDH | 300 |
| 301 | ILSIDGTSMEYCTLAEATQFLGNTTDQVKLEILPHHQTRLALKGPDHVKI | 350 |
| 351 | QRSDRQLPWDPWASSQCSVHTNHHHNPHHPDHCRVPALGFPKALTPNSPP | 400 |
| 401 | AMVSSSSPTSMSAYSLSSLNMGTLPRSLYSTSPRGTMMRRRLKKKDFKSS | 450 |
| 451 | LSLASSTVGLAGQVVHTETTEVVLTADPVTGFGIQLQGSVFATETLSSPP | 500 |
| 501 | LISYIEADSPAERCGVLQIGDRVMAINGIPTEDSTFEEANQLLRDSSITS | 550 |
| 551 | KVTLEIEFDVAESVIPSSGTFHVKLPKKHSVELGITISSPSSRKPGDPLV | 600 |
| 601 | ISDIKKGSVAHRTGTLELGDKLLAIDNIRLDSCSMEDAVQILQQCEDLVK | 650 |
| 651 | LKIRKDEDNSDEQESSGAIIYTVELKRYGGPLGITISGTEEPFDPIIISS | 700 |
| 701 | LTKGGLAERTGAIHIGDRILAINSSSLKGKPLSEDIHLLQMAGETVTLKI | 750 |
| 751 | KKQTDAQPASSPKKLPIPSHSSDLGDGEEDPSPIQRPGKLSDVYPSTVPS | 800 |
| 801 | VDSAVDSWDGSGIDARYGSQGTTFQTSGYNFNTYDWRSPKKRASLSPVPK | 850 |
| 851 | PRSQTYPDVGLSNEDWDRSTASGFAGASDSADAEQEENFWSQALEDLETC | 900 |
| 901 | GQSGILRELEATIMSGSTMSLNHEAPTARSQLGRQASFQERSNSRPHYSQ | 950 |
| 951 | TTRSNTLPSDBGRKSVTLRKMKQEIKEIMSPTPVELHKVTLYKDSGMEDF | 1000 |
| 1001 | GFSVADGLLEKGVYKNIRPAGPGDLGGLKPYDRLLQVNHVRTRDFDCCL | 1050 |
| 1051 | VVPLIAESGNKLDLVISRNPLASQKSIEQPALPSDWSEQNSAFFQQPSHG | 1100 |
| 1101 | GNLETREPTNTL | 1112 |

```
              1           10          20          30
DLG-D1      DIQLERGN  SG    LGFSIAGGTDNPHIGTDTS
DLG-D2      EIDLVKGG  KK    LGFSIAGGIGNQHIPGDNG
DLG-D3      TITIQKGP  QG    LGFNIVGGEDGQ        G
PSD95-D1    EITLERGN  SG    LGFSIAGGTDNPHIGDDPS
PSD95-D2    EIKLIKGP  KG    LGFSIAGGVGNQHIPGDNS
PSD95-D3    RIVIHRGS  TG    LGFNIVGG        EDGEG
SAP97-D1    EITLERGN  SG    LGFSIAGGTDNPHIGDDSS
SAP97-D2    EIKLIKGP  KG    LGFSIAGGVGNQHIPGDNS
SAP97-D3    KVVLHRGS  TG    LGFNIVGG        EDDEG
GRIP-D1     TVVELIKK  EGTT  LGLTVSGGIDKDGKPR
GRIP-D2     EVTLHK    EGNT  FGFVIRGGAHDDRNKSRP
GRIP-D3     LVEVAKTP  GAS   LGVALTTSVCCNKQV
GRIP-D4     EVVLTADPVTG     FGIQLQGSVFATETLSSPP
GRIP-D5     HVKLPKKHSVE     LGITISSPSSRK    PGD P
GRIP-D6     TVELKKY   GG    PLGITISGTEE     PFD P
GRIP-D7     KVTLYKDS        GMEDFGFSVADGLLEKGVYVKN
```

FIG. 4A

```
              40          50          60
DLG-D1      IYITKLISGGAAAADGRLSINDIIVSVNDVS
DLG-D2      IYVTKLTDGGRAQVDGRLSIGDKLIAVRTNGSE
DLG-D3      IYVSFILAGGPADLGSELKRGDQLLSVNNVN
PSD95-D1    IFDTKIIPGGAAQDGRLRVNDSILFVNEVD
PSD95-D2    IYVTKIIEGGAAHKDGRLQIGDKILAVNSVG
PSD95-D3    IFISFILAGGPADLSGELRKGDQILSVNGVD
SAP97-D1    IFITKIITGGAAQDGRLRVNDCILRVNEAD
SAP97-D2    IYVTKIIEGGAAHKDGRLQIGDKLLAVNSVC
SAP97-D3    IFISFILAGGPADLSGELRKGDRIISVNSVD
GRIP-D1         VSNLRQGGIAARSDQLDVGDYIKAVNGIN
GRIP-D2     VVITCVRPGGPDDREGTIKPGDRLLSVDGIR
GRIP-D3     IVIDKIKSASIADRCGALHVGDHILSIDGTS
GRIP-D4      IISYIEADSPAERCGVLQIGDRVMAINGIP
GRIP-D5     LVISDIKKGSVAHRTGTLELGDKLLAIDNIR
GRIP-D6     IIISSITKGGLAERTGAIHIGDRILAINSSS
GRIP-D7     IRPAG?GDLGGL  KP        YDRLLQVNH
```

FIG. 4B

```
                    70              80              90
DLG-D1      VVDVPHASAVDALKKA    GNVVKLHVKRK
DLG-D2      KNLENVTHELAVATLKSI  TDKVTLIIGKT
DLG-D3      LTHATHEEAAQALKTS    GGVVTLLAQYRP
PSD95-D1    VREVTHSAAVEALKEA    GSIVRLYVMRR
PSD95-D2    LEDVMHEDAVAALKNT    YDVVYLKVAKP
PSD95-D3    LRNASHEQAAIALKNA    GQTVTIIAQYK
SAP97-D1    VRDVTHSKAVEALKEA    GSIVRLYVKRR
SAP97-D2    LEEVTHEEAVTALKNT    SDFVYLKAAKP
SAP97-D3    LRAASHEQAAAALKNA    GQAVTIVAQYR
GRIP-D1     LAKFRHDEIISLLKNV    GERVVLEVEYE
GRIP-D2     LLGTTHAEAMSILKQC    GDEATLLIEYD
GRIP-D3     MEYCTLAEATQFLGNT    TDQVKLEILPHHQTR
GRIP-D4     TEDSTFEEANQLLRDS    SITSKVTLEIEF
GRIP-D5     LDSCSMEDAYQILQQC    EDLVKLKIRKD
GRIP-D6     LKGKPLSEDIHLLQMA    GETVTLKIKKQ
GRIP-D7     VRTRDFDCCLVVDLIAESGNKLDLVISRN
```

FIG. 4C

| CONSTRUCTS | LAST 15 AMINO ACIDS | HIS 3 | β-GAL |
|---|---|---|---|
| GLUR2C | YKEGYNVYGIESVKI* | + | + |
| GLUR2C(1878E) | YKEGYNVYGRESVKI* | + | + |
| GLUR2C(E379R) | YKEGYNVYGIRSVKI* | + | + |
| GLUR2C(Δ7) | YKEGYNVY* | - | - |
| GLUR1C | CMSHSSGMPLGATGL* | - | - |
| NR2A-C | NRRVYKXMPSIESOV* | - | - |
| NR2B-C | NGHVYEKLSSIESOV* | - | - |

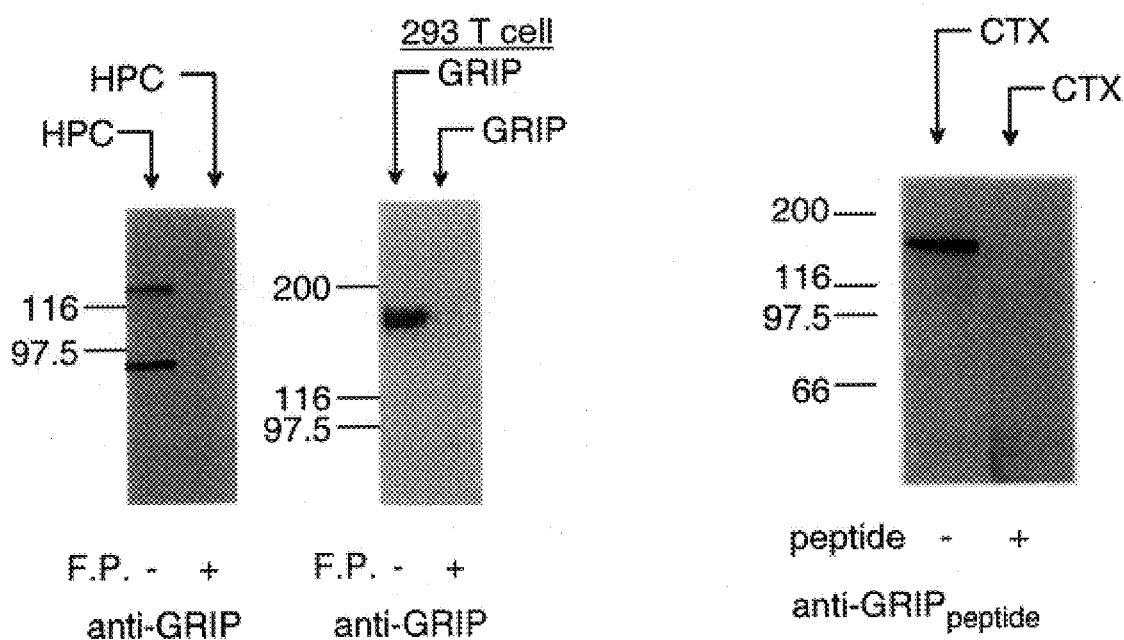
FIG. 8A
FIG. 8B
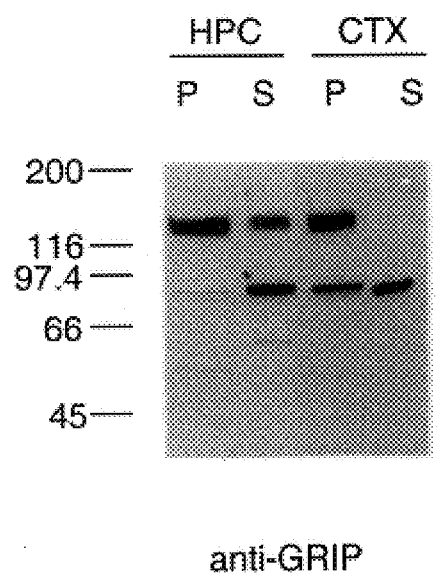
FIG. 8C

```
SEQ ID NO:1:
AGCTCCACCA GATGACATGT AGCGCGCGGG ACCTCTGCAT CAGCCAAGAG GAATTAAGCT    60
TTGTCACTCC CCACTGGGAC TACCTTCCTC CTGGTATGTG CGCAAGGAAT TCATATACTG   120
CTGCTCGCCG CCGCAGGCAC CAGAGCAGAG CCCTGTGTGC ACTTTGGCAG AGATCAGGGA   180
GCAAGAATGA TAGCTGTCTC TTTTAAATGC CGCTGTCAGA TTCTAAGGCG ACTTACCAAA   240
GATGAGAGTC CCTACACTAA ATCTGCCAGC CAGACAAAGC CGCCCGATGG AGCATTGGCT   300
GTGAGGAGAC AGAGCATCCC AGAGGAATTC AAGGGCTCCA CCGTGGTGGA GCTGATGAAG   360
AAGGAGGAA CCACTCTTGG CCTGACGGTA TCAGGAGGAA TCGATAAAGA TGGAAAGCCA   420
AGAGTGTCCA ACCTGCGGCA GGGAGGGATT GCTGCCAGCT GTGACCAGCT GGATGTGGGC   480
GACTACATCA AAGCGGTGAA TGGGATCAAC CTGGCCAGAA TCCGCCATGA TGAGATCATC   540
AGCCTGCTGA AAAATGTTGG GGAAAGAGTG GTCCTGGAGG TCGAGTATGA GCTTCCACCG   600
GTCTCTATCC AAGGATCGAG TGTTATGTTC CGAACAGTGG AGGTCACCTT GCACAAAGAA   660
GGCAACACCT TTGGTTTTGT CATCCGAGGG GGAGCGCATG ATGACAGAAA TAAGTCCCGT   720
CCAGTGTGTGA TAACCTGTGT TCGTCCTGGA GGGCCTGCTG ACAGAGAGG CACCATCAAA   780
CCTGGAGACA GGTTGCTCAG TGTGGATGGA ATTCGGCTTC TGGGAACCAC CCATGCTGAG   840
GCCATGAGCA TCCTTAAACA GTGCGGACAA GAAGCAACGC CCTGATAGA ATATGATGTC   900
AGCCTGATGG ATTCTGTAGC AACAGCATCC GGGCCACTAC TAGTTGAAGT TGCCAAAACT   960
CCCGGTGCAA GCCTTGGGGT TGCACTAACT ACCTCCGTGT GCTGTAACAA ACAAGTCATC  1020
GTCATAGACA AAATCAAATC TGCAAGCATT GCGGGGCGCT ACATGTGGGA ACATGTGGGA  1080
GACCACATCC TCTCCATCGA CGGCACGAGC CGGAAGCGC AGAAGCAACC  1140
CAGTTCCTGG CCAACACCAC TGACCAGGTC AAGCTGGAGA TTCTCCCACA CCATCAGACC  1200
CGCCTGGCCC TGAAGGGACC TGACCATGTG AAAAATTCAGA GGAGGACAG ACAGCTTCCC  1260
TGGGATCCCT GGGCCAGCAG CCAGTGCAGC GTTCATACCA ACCATCACCA TAACCCGCAC  1320
CACCCAGACC ATTGCCGAGT ACCAGCCCTG GGTTTTCCGA AAGCGCTTAC TCCAAACAGC  1380
CCTCCGGCTA TGGTGTCCTC GTCCTCTCCT ACCTCACTGA GTGCGTACAG CCTGAGTTCC  1440
CTGAACATGG GGACTTTACC TCGAAGCCTC TACTCTACTA GTCCACGAGG AACCATGATG  1500
AGGAGGAGAC TGAAAAAGAA GGACTTCAAA AGCTCACTGT CTTTAGCTTC TAGCACTGTG  1560
```

FIG. 11A

```
GGATTGGCTG GACAGGTTGT TCACACTGAA ACCACAGAGG TTGTGCTGAC GGCTGATCCT 1620
GTCACTGGCT TTGGAATCCA ACTGCAGGGC AGCGTGTTTG CCACAGAGAC TCTCTCCTCC 1680
CCACCTCTGA TTTCCTATAT TGAAGCTGAC AGCCCAGCAG AGAGATGTGG TGTGCTGCAG 1740
ATTGGAGACA GAGTCATGGC CATTAATGGA ATCCCAACAG AAGACAGCAC CTTTGAGGAA 1800
GCCAATCAGC TCCTTCGAGA CTCTTCCATC ACGAGCAAAG TCACACTGGA AATCGAGTTT 1860
GATGTTGCAG AATCTGTCAT CCCAAGTAGT GGAACATTTC ATGTAAAACT GCCTAAGAAG 1920
CACAGCGTGG AGCTTGGAAT AACCATCAGT TCGCCATCCA GTAGAAAACC AGGGGACCCT 1980
CTCGTCATTT CAGATATCAA GAAAGGCAGT GTGGCACACA GAACTGGAAC TCTGGAACTT 2040
GGAGATAAAT TGCTCGCCAT AGATAACATC CGGTTGGACA GCTGTTCCAT GGAAGATGCA 2100
GTCCAGATCC TCCAGCAGTG GTGAAGCTCA GTGAAGCTCA AAATCCGCAA AGATGAAGAT 2160
AACTCAGATG AGCAAGAGAG TTCCGGGGCG ATTATTTACA CGGTGGAGCT GAAGCGCTAT 2220
GGGGGCCCCC TTGGCATCAC CATTTCTGGA ACGGAAGAGC CCTTTGATCC TATTATCATC 2280
TCGAGCCTCA CTAAAGGGGG ATTAGCTGAA AGGACTGGAG CGATCCACAT CGGAGATCGA 2340
ATCCTAGCCA TCAATAGCAG TAGCTTGAAG GGGAAGCCTC TGAGTGAAGC CATCCACTTG 2400
CTACAGATGG CGGGAGAGAC TGTCACCCTG AAAATTAAGA AGCAGACAGA TGCTCAACCT 2460
GCCTCAAGTC CCAAGAAGCT GCCCATCCCC AGCCACTCAA GTGACCTAGG AGATGGTGAG 2520
GAGGACCCCT CCCAATACA AAGGCCCTGGC AAGCTCTCTG ACGTGTACCC CTCCACAGTA 2580
CCCAGCGTGG ACACGTGCTGT GGACTCCTGG GACGGATCTG GAATAGATGC CAGGTATGGG 2640
AGTCAAGGCA CGACTTTTCA GACTTCAGGG TACAATTTCA ACACCTATGA CTGGAGGAGT 2700
CCGAAGAAAA GAGCCAGCCT GTCCCCGGTC CCCAAGCCTC GAAGCCAGAC ATACCCAGAT 2760
GTGGGCTTGA GTAATGAAGA CTGGGACCGG TCCACAGCCA GTGGCTTCGC CGGGGCTTCT 2820
GACAGTGCAG ACGCTGAACA AGAGGAAAAC TTCTGGGTCTC AAGCATTGGA GGACCTGGAG 2880
ACCTGCGGCC AGTCGGGAAT CCTGAGAGAG CTCGAGGCAA CAATCATGTC GGGGAGCACT 2940
ATGAGTTTGA ATCATGAGGC TCCAACGGCT CGCAGTCAGC TGGGGCGACA GGCCAGCTTC 3000
CAGGAACGGA GCAATTCGAG GCCACACTAT AGCCAAAACGA CTCGCAGCAA CACTCTGCCC 3060
TCGGATGTGG GCAGAAAGTC TGTGACCCCTG CGGAAAAATGA AGCAAGAAAT CAAGGAGATT 3120
ATGTCCCCAA CTCCCGTGGA GCTTCACAAG GTGACCTTAT ACAAAGACTC TGGCATGGAG 3180
```

```
GACTTTGGGT TCAGTGTGGC AGATGGCCTG CTGGAGAAAG GGGTGTATGT CAAAAATATC 3240
CGCCCAGCTG GGCCAGGTGA TCTTGGAGGC TTGAAGCCTT ATGACAGGCT CTTACAGGTT 3300
AACCACGTCC GAACGAGAGA CTTCGACTGC TGCCTGGTGG CCTCCCTCAT AGCCGAATCC 3360
GGTAACAAGC TGGACCTGGT TATTAGCAGA AACCCGCTGG CCTCCCAGAA GTCGATAGAA 3420
CAGCCGGCTC TGCCCAGTGA CTGGAGCGAA CAGAACAGCG CTTTCTTCCA GCAGCCCAGC 3480
CACGGTGTA ACCTAGAGAC ACGAGAACCC ACTAACACAT TATAGCATTA CTTTTATAAA 3540
GCAGGACGAA AGACGATATC TACATGGTGC TAAAACAAAA CAGAACAGAA CAGAACAGAA 3600
CAGAACAGAA CAGAACAGAA CAGAACAGAA CAGAACAGAA CAACCCTTTA AGATTTCTTG TGACAGCTTG 3660
AAGCACAGAG AATCACCGTG GCATTAATTG CAAAGCACAG GGGTCTTTTA AATCTCCCTC 3720
ATAGCTCATG TTCTCATCCC TTCCCAACTA GAAGAGGTTT CTTTTAGGAT GACCACTCTG 3780
TTAACTGGCG GGTCCTCCTC TGCCGGGGGT GGGGAGGCCC CTTCGGTAGA CAATAAAGAG 3840
GAAGGCAGCC CACCCCTTCC CCCACCCCAA TCAAGATCAG AGGAAAACTTT TTACAATTCA 3900
CCTTACTGTC ACTTTTAACA GAGAGAAACA TCCCTTTGAA AATATTCTCT ATGGTAATTT 3960
CCTGAATGGA GTAAGTTTCT TACTATAACG TCATTAGTGT AAGAACACGA TCAATATGGA 4020
TTTACACATA GCTGGCCCTG CTAGGGGAGC TAGGATGGGT TTCTTAAAAT GCCTGCCGCG 4080
GTGGGAGGGG CACAGGTATA ACATTAGGTT TTCTTAAAAT ATTTCAGCAA CAGTGCACGT 4140
TGGAGACCAT AATAGGTGGT GGTAAATGTT TCGCCCAAAT ATAGGAATGA TTTTAACTAA 4200
GATGTATGCT ATTCCCTATG CAAACAGGA TCAAACAGGA TATGTCTTGT GACCTGTTTT 4260
TTTTTTTCCT TAAGGACACA TTCTTTTTTT TTTTTTTAAT AGCTGAAAAA AATCTCTGGT 4320
AATGAATTAG AGTGTGTGGT AACACTGAGC AACACTGAGT TGACCCTATT TTTAAAATCC 4380
AAGACTAAGA ATTTAAGGAG TGAAGAGTCT AATGAAATGA GATTCACTTT CTGGGTAGGC 4440
AAACAGAACT CATGCAGCTC AGAAGTCTGC AGACTGCTAC ACCGAGGGGT GCACAGCACA 4500
ATGACTTAAG GACGACGACG ATTTGGT                                     4527
```

FIG. 11C

SEQ ID NO:2:

| | | | | | | | | | | | | | |
|---|---|---|---|---|---|---|---|---|---|---|---|---|---|
| Met | Ile | Ala | Val | Ser | Phe | Lys | Cys | Arg | Cys | Gln | Ile | Leu | Arg | Arg | Leu |
| 1 | | | | 5 | | | | | 10 | | | | | 15 | |
| Thr | Lys | Asp | Glu | Ser | Pro | Tyr | Thr | Lys | Leu | Ala | Ser | Gln | Thr | Lys | Pro |
| | | | 20 | | | | | 25 | | | | | 30 | | |
| Pro | Asp | Gly | Ala | Leu | Ala | Val | Arg | Arg | Gln | Ser | Ile | Pro | Glu | Glu | Phe |
| | | 35 | | | | | 40 | | | | | 45 | | | |
| Lys | Gly | Ser | Thr | Val | Val | Glu | Leu | Met | Lys | Lys | Glu | Lys | Gly | Thr | Leu |
| | 50 | | | | | 55 | | | | | 60 | | | | |
| Gly | Leu | Thr | Val | Ser | Gly | Gly | Ile | Asp | Lys | Asp | Gly | Lys | Pro | Arg | Val |
| 65 | | | | | 70 | | | | | 75 | | | | | 80 |
| Ser | Asn | Leu | Arg | Gln | Gly | Gly | Ile | Ala | Ala | Ala | Arg | Ser | Asp | Gln | Leu | Asp |
| | | | | 85 | | | | | 90 | | | | | 95 | |
| Val | Gly | Asp | Tyr | Ile | Lys | Ala | Val | Asn | Gly | Ile | Asn | Leu | Ala | Lys | Phe |
| | | | 100 | | | | | 105 | | | | | 110 | | |
| Arg | His | Asp | Glu | Ile | Ile | Ser | Leu | Leu | Lys | Asn | Val | Gly | Glu | Arg | Val |
| | | 115 | | | | | 120 | | | | | 125 | | | |
| Val | Leu | Glu | Val | Glu | Tyr | Glu | Leu | Pro | Pro | Val | Ser | Ile | Gln | Gly | Ser |
| | 130 | | | | | 135 | | | | | 140 | | | | |
| Ser | Val | Met | Phe | Arg | Thr | Val | Glu | Val | Thr | Leu | His | Lys | Glu | Gly | Asn |
| 145 | | | | | 150 | | | | | 155 | | | | | 160 |
| Thr | Phe | Gly | Phe | Val | Ile | Arg | Gly | Gly | Ala | His | Asp | Asp | Arg | Asn | Lys |
| | | | | 165 | | | | | 170 | | | | | 175 | |
| Ser | Arg | Pro | Val | Ile | Thr | Cys | Val | Arg | Pro | Gly | Gly | Pro | Ala | Asp |
| | | | 180 | | | | | 185 | | | | | 190 | | |

FIG. 12A-1

Arg Glu Gly Thr Ile Lys Pro Gly Asp Arg Leu Leu Ser Val Asp Gly
         195                 200                 205
Ile Arg Leu Leu Gly Thr Thr His Ala Glu Ala Met Ser Ile Leu Lys
         210                 215                 220
Gln Cys Gly Gln Glu Ala Thr Leu Leu Ile Glu Tyr Asp Val Ser Val
         225                 230                 235                 240
Met Asp Ser Val Ala Thr Ala Ser Gly Pro Leu Leu Val Glu Val Ala
         245                 250                 255
Lys Thr Pro Gly Ala Ser Leu Gly Val Ala Leu Thr Thr Ser Val Cys
         260                 265                 270

FIG. 12A-2

```
Cys Asn Lys Gln Val Ile Val Ile Asp Lys Ile Lys Ser Ala Ser Ile
        275                 280                 285

Ala Asp Arg Cys Gly Ala Leu His Val Gly Asp His Ile Leu Ser Ile
        290                 295                 300

Asp Gly Thr Ser Met Glu Tyr Cys Thr Leu Ala Glu Ala Thr Gln Phe
        305                 310                 315                 320

Leu Ala Asn Thr Thr Asp Gln Val Lys Leu Glu Ile Leu Pro His His
        325                 330                 335

Gln Thr Arg Leu Ala Leu Lys Gly Pro Asp His Val Lys Ile Gln Arg
        340                 345                 350

Ser Asp Arg Gln Leu Pro Trp Asp Pro Trp Ala Ser Ser Gln Cys Ser
        355                 360                 365

Val His Thr Asn His His Asn Pro His His Pro Asp His Cys Arg
        370                 375                 380

Val Pro Ala Leu Gly Phe Pro Lys Ala Leu Thr Pro Asn Ser Pro Pro
        385                 390                 395                 400

Ala Met Val Ser Ser Ser Pro Thr Ser Pro Arg Ser Met Ser Ala Tyr Ser Leu
        405                 410                 415

Ser Ser Leu Asn Met Gly Thr Leu Pro Arg Ser Leu Tyr Ser Thr Ser
        420                 425                 430

Pro Arg Gly Thr Met Met Arg Arg Arg Leu Lys Lys Lys Asp Phe Lys
        435                 440                 445
```

FIG. 12B-1

```
Ser Ser Leu Ser Ser Thr Val Gly Leu Ala Gly Gln Val
450                 455             460
Val His Thr Glu Thr Glu Val Val Leu Thr Ala Asp Pro Val Thr
465                 470             475             480
Gly Phe Gly Ile Gln Leu Gly Ser Val Phe Ala Thr Glu Thr Leu
        485                 490             495
Ser Ser Pro Pro Leu Ile Ser Tyr Ile Gly Asp Ser Pro Ala Glu
            500                 505             510
Arg Cys Gly Val Leu Gln Ile Gly Asp Arg Val Met Ala Ile Asn Gly
        515                 520             525
Ile Pro Thr Glu Asp Ser Thr Phe Glu Glu Ala Asn Gln Leu Leu Arg
        530                 535             540
Asp Ser Ser Ile Thr Ser Lys Val Thr Leu Glu Ile Glu Phe Asp Val
545                 550             555             560
```

FIG. 12B-2

```
Ala Glu Ser Val Ile Pro Ser Ser Gly Thr Phe His Val Lys Leu Pro
            565             570             575

Lys Lys His Ser Val Glu Leu Gly Ile Thr Ile Ser Ser Pro Ser Ser
        580             585             590

Arg Lys Pro Gly Asp Pro Leu Val Ile Ser Asp Ile Lys Lys Gly Ser
        595             600             605

Val Ala His Arg Thr Gly Thr Leu Glu Leu Gly Asp Lys Leu Leu Ala
        610             615             620

Ile Asp Asn Ile Arg Leu Asp Ser Cys Ser Met Glu Asp Ala Val Gln
    625             630             635             640

Ile Leu Gln Gln Cys Glu Asp Leu Val Lys Leu Lys Ile Arg Lys Asp
            645             650             655

Glu Asp Asn Ser Asp Gln Glu Ser Gly Ser Gly Ala Ile Ile Tyr Thr
        660             665             670

Val Glu Leu Lys Arg Tyr Gly Gly Pro Leu Gly Ile Thr Ile Ser Gly
        675             680             685

Thr Glu Glu Pro Phe Asp Pro Ile Ile Ser Ser Leu Thr Lys Gly
        690             695             700

Gly Leu Ala Glu Arg Thr Gly Ala Ile His Ile Gly Asp Arg Ile Leu
705             710             715             720

Ala Ile Asn Ser Ser Ser Leu Lys Gly Lys Pro Leu Ser Glu Ala Ile
            725             730             735
```

FIG. 12C-1

```
His Leu Gln Met Ala Gly Glu Thr Val Thr Leu Lys Ile Lys Lys
                740                 745                 750
Gln Thr Asp Ala Gln Pro Ala Ser Ser Pro Lys Lys Leu Pro Ile Pro
        755                 760                 765
Ser His Ser Ser Asp Leu Gly Asp Gly Glu Glu Asp Pro Ser Pro Ile
        770                 775                 780
Gln Arg Pro Gly Lys Leu Ser Asp Val Tyr Pro Ser Thr Val Pro Ser
785                 790                 795                 800
Val Asp Ser Ala Val Asp Ser Trp Asp Gly Ser Gly Ile Asp Ala Arg
                805                 810                 815
Tyr Gly Ser Gln Gly Thr Thr Phe Gln Thr Ser Gly Tyr Asn Phe Asn
            820                 825                 830
Thr Tyr Asp Trp Arg Ser Pro Lys Arg Ala Ser Leu Ser Pro Val
        835                 840                 845
```

FIG. 12C-2

Pro Lys Pro Arg Ser Gln Thr Tyr Pro Asp Val Gly Leu Ser Asn Glu
850                855                860
Asp Trp Asp Arg Ser Thr Ala Ser Gly Phe Ala Gly Ala Ser Asp Ser
865                870                875                880
Ala Asp Ala Glu Gln Glu Glu Asn Phe Trp Ser Gln Ala Leu Glu Asp
             885                890                895
Leu Glu Thr Cys Gly Gln Ser Gly Ile Ser Leu Arg Glu Leu Glu Ala Thr
        900                905                910
Ile Met Ser Gly Ser Thr Met Ser Leu Asn His Glu Ala Pro Thr Ala
             915                920                925
Arg Ser Gln Leu Gly Arg Gln Ala Ser Phe Gln Glu Gly Arg Ser Asn Ser
        930                935                940
Arg Pro His Tyr Ser Gln Thr Thr Leu Arg Ser Asn Thr Leu Pro Ser Asp
945                950                955                960
Val Gly Arg Lys Ser Val Thr Leu Arg Lys Met Lys Gln Glu Ile Lys
             965                970                975
Glu Ile Met Ser Pro Thr Pro Val Glu Leu His Lys Val Thr Leu Tyr
        980                985                990
Lys Asp Ser Gly Met Glu Asp Phe Gly Phe Ser Val Ala Asp Gly Leu
             995                1000                1005
Leu Glu Lys Gly Val Tyr Val Lys Asn Ile Arg Pro Ala Gly Pro Gly
1010                1015                1020

FIG. 12D-1

```
Asp Leu Gly Gly Leu Lys Pro Tyr Asp Arg Leu Leu Gln Val Asn His
1025                1030                1035                1040
Val Arg Thr Arg Asp Phe Asp Cys Cys Leu Val Val Pro Leu Ile Ala
                1045                1050                1055
Glu Ser Gly Asn Lys Leu Asp Leu Val Ile Ser Arg Asn Pro Leu Ala
                1060                1065                1070
Ser Gln Lys Ser Ile Glu Gln Pro Ala Leu Pro Ser Asp Trp Ser Glu
                1075                1080                1085
Gln Asn Ser Ala Phe Phe Gln Pro Ser His Gly Gly Asn Leu Glu
                1090                1095                1100
Thr Arg Glu Pro Thr Asn Thr Leu
1105                1110
```

JH2493 abs + peptide

JH2493

JH2493

JH2260

```
                10              20              30              40
                 *               *               *               *
    ctg cgg ccg cca gcg caa ang cgc cag ctc ccg gct ccg agg ctg
    gac gcc ggc ggt cgc gtt tnc gcg gtc gag ggc cga ggc tcc gac 50              60              70              80              90
                 *               *               *               *               *
    cgg ggc ggc tgc agg gag gtt gca ggg ctc cgg gtc tgg gac ctg
    gcc ccg ccg acg tcc ctc caa cgt ccc gag gcc cag acc ctg gac 100             100             120             130
                 *               *               *               *
    ccg gcg ggc aaa agt gat gtt ggc ggt gtc act caa ttg gcg gct
    ggc cgc ccg ttt tca cta caa ccg cca cag tga gtt aac cgc cga 140             150             160             170             180
                 *               *               *               *               *
    ggg cgt ggt gag gcg gcg gcc caa aaa cga tgg gcc tta ctc aaa
    ccc gca cca ctc cgc cgc cgg gtt ttt gct acc cgg aat gag ttt 190             200             210             220
                 *               *               *               *
    ggg ggg aaa gga cac agc ggg gac tga tgg ggc cct ggt gtg ccg
    ccc ccc ttt cct gtg tcg ccc ctg act acc ccg gga cca cac ggc 230             240             250             260             270
                 *               *               *               *               *
    ccg cca gag cat tcc aga gga gtt ccg ggg cat cac cat ggt gga
    ggc ggt ctc gta agg tct cct caa ggc ccc gta gtg gta cca cct 280             290             300             310
                 *               *               *               *
    gct gat caa gcg tga ggg cag cac tct ggg cct gac tat ctc agg
    cga cta gtt cgt act ccc gtc gtg aga ccc gga ctg ata gag tcc 320             330             340             350             360
                 *               *               *               *               *
    agg gac tga caa gga cgg gaa gcc cag agt ctc caa cct gag acc
    tcc ctg act gtt cct gcc ctt cgg gtc tca gag gtt gga ctc tgg
```

FIG. 22A-1

```
             370             380             390             400
              *               *               *               *
cgg ggg cct tgc agc cag gag cga tct act gaa tgt ggg cga cta
gcc ccc gga acg tcg gtc ctc gct aga tga ctt aca ccc gct gat 410             420             430             440             450
      *               *               *               *               *
tat ccg ctc agt gaa tgg gat ccg tct gac ccg gct ccg aca tga
ata ggc gag tca ctt acc cta ggc aga ctg ggc cga ggc tgt act 460             470             480             490
              *               *               *               *
cga gat cat cac att gct gaa gaa tgt ggg cga gcg cgt ggt gct
gct cta gta gtg taa cga ctt ctt aca ccc gct cgc gca cca cga 500             510             520             530             540
      *               *               *               *               *
gga ggt gga gta tga gct gcc ccc gcc cgc tcc cga aaa caa ccc
cct cca cct cat act cga cgg ggg cgg gcg agg gct ttt gtt ggg 550             560             570             580
              *               *               *               *
gag gat cat ttc caa gac ggt gga cgt ctc cct cta caa gga agg
```

FIG. 22A-2

```
ctc cta gta aag gtt ctg cca cct gca gag gga gat gtt cct tcc 590           600           610           620           630
      *             *             *             *             *
caa cag ttt tgg ctt tgt cct cag agg agg tgc cca tga gga cct
gtt gtc aaa acc gaa aca gga gtc tcc tcc acg ggt act cct gga 640           650           660           670
            *             *             *             *
gca caa atc ccg ccc att ggt cct gac tta cgt gcg gcc tgg tgg
cgt gtt tag ggc ggg taa cca gga ctg aat gca cgc cgg acc acc 680           690           700           710           720
      *             *             *             *             *
ccc agc aaa cag gga ggg ttc ctt aaa ggt ggg cga cag gct gct
ggg tcg ttt gtc cct ccc aag gaa ttt cca ccc gct gtc cga cga 730           740           750           760
            *             *             *             *
cag cat ana tgg gat ccc act gca cgg ggc cag cca tgc tac cgc
gtc gta tnt acc cta ggg tga cgt gcc ccg gtc ggt acg atg gag 770           780           790           800           810
      *             *             *             *             *
aat agc cac cct gca gca gtg cag cca tga ggc cct ctt cca ggt
tta tcg gtg gga cgt cgt cac gtc ggt act ccg gga gaa ggt cca 820           830           840           850
            *             *             *             *
gga gta cga tgt ggc cac ccc aga cac ggt ggc caa tgc ttc agg
cct cat gct aca ccg gtg ggg tct gtg cca ccg gtt acg aag tcc 860           870           880           890           900
      *             *             *             *             *
ccc ttt ggt ggt aga aat agc caa gac ccc agg atc tgc cct ggg
ggg aaa cca cca tct tta tcg gtt ctg ggg tcc tag acg gga ccc
```

FIG. 22B-1

```
              910            920            930            940
               *              *              *              *
gat ctc tct cac cac tgg ctc cca ccg gaa caa acc agc tat cac
cta gag aga gtg gtg acc gag ggt ggc ctt gtt tgg tcg ata gtg 950            960            970            980            990
       *              *              *              *              *
tat cga ccg cat caa gcc ggc tag cgt ggt gga caa gaa tgg tgc
ata gct ggc gta gtt cgg ccg atc gca cca cct gtt ctt acc acg 1000           1010           1020           1030
            *              *              *              *
cct gca tgc tgg aga aca cat cct ggc cat cga tgg cac cag cac
gga cgt acg acc tct tgt gta gga ccg gta gct acc gtg gtc gtg 1040           1050           1060           1070           1080
        *              *              *              *              *
aga aca ctg ctc tct ggt cga ggc cac gaa gct ctt ggc cag tgt
tct tgt gac gag aga cca gct ccg gtg ctt cga gaa ccg gtc aca 1090           1100           1110           1120
            *              *              *              *
gac cga gaa agt tcg act gga gat ctt gcc tgc acc cca gag tcg
ctg gct ctt tca agc tga cct cta gaa cgg acg tgg ggt ctc agc 1130           1140           1150           1160           1170
```

FIG. 22B-2

```
          *                   *                   *                   *                   *
gcg gcc cct gaa gcc ccc aga ggc agt gag aat aca gag gag tga
cgc cgg gga ctt cgg ggg tct ccg tca ctc tta tgt ctc ctc act 1180                1190                1200                1210
          *                   *                   *                   *
gca act gca cca ctg gga ccc ctg tgt tcc ctc ttg cca tag ccc
cgt tga cgt ggt gac cct ggg gac aca agg gag aac ggt atc ggg 1220                1230                1240                1250                1260
     *                   *                   *                   *                   *
aag gcc aag cca ctg cag ggc acc cac ctg ggc acc tgg agg cca
ttc cgg ttc ggt gac gtc ccg tgg gtg gac ccg tgg acc tcc ggt 1270                1280                1290                1300
          *                   *                   *                   *
gga cca gag ccg atc cgt gtc ctc gac tcc ctt ctc ctc gcc aac
cct ggt ctc ggc tag gca cag gag ctg agg gaa gag gag cgg ttg 1310                1320                1330                1340                1350
     *                   *                   *                   *                   *
tat gaa ccc tgc ctt tcc ctg tgc caa cgc cag cac cct gcc cag
ata ctt ggg acg gaa agg gac acg gtt gcg gtc gtg gga cgg gtc 1360                1370                1380                1390
          *                   *                   *                   *
agg acc cat gag ccc cag aac aac agc ggg gag gag aag gca gcg
tcc tgg gta ctc ggg gtc ttg ttg tcg ccc ctc ctc ttc cgt cgc 1400                1410                1420                1430                1440
     *                   *                   *                   *                   *
aag gaa aga aca cag gag ctc ttt gtc act ggc ctc cag cac ggt
ttc ctt tct tgt gtc ctc gag aaa cag tga ccg gag gtc gtg cca 1450                1460                1470                1480
          *                   *                   *                   *
agg gcc cgg tgg gca gat cgt tca cac gga gac gac gga ggt agt
tcc cgg gcc acc cgt cta gca agt gtg cct ctg ctg cct cca tca
```

FIG. 22C-1

```
          1490            1500            1510            1520            1530
           *               *               *               *               *
gct ctg tgg aga ccc cct cag tgg ctt cgg cct cca gct gca ggg
cga gac acc tct ggg gga gtc acc gaa gcc gga ggt cga cgt ccc 1540            1550            1560            1570
                   *               *               *               *
ggg cat ttt tgc tac cga gac cct gtc ctc ccc acc ctt ggt gcg
ccc gta aaa acg atg gct ctg gga cag gag ggg tgg gaa cca cgc 1580            1590            1600            1610            1620
           *               *               *               *               *
att tat tga acc tga cag ccc tgc tga gag gtg tgg tct gct gca
taa ata act tgg act gtc ggg acg act ctc cac acc aga cga cgt 1630            1640            1650            1660
                   *               *               *               *
ggt ggg gga ccg cgt cct agc cat aaa tgg cat tgc tac tga aga
cca ccc cct ggc gca gga tcg gta ttt acc gta acg atg act tct 1670            1680            1690            1700            1710
           *               *               *               *               *
tgg gac cat gga aga agc caa cca gct gtt gcg gga tgc tgc act
acc ctg gta cct tct tcg gtt ggt cga caa cgc cct acg acg tga
```

FIG. 22C-2

```
                1720            1730            1740            1750
                 *               *               *               *
ggc ccg caa aat tgt ttt gga gat cga gtt tga tgt ggc gga atc
ccg ggc gtt tta aca aaa cct cta gct caa act aca ccg cct tag 1760            1770            1780            1790            1800
         *               *               *               *               *
tgt cat ccc aag cag tgg gac ttt cca cgt gaa gtt acc caa aag
aca gta ggg ttc gtc acc ctg aaa ggt gca ctt caa tgg gtt ttc 1810            1820            1830            1840
                 *               *               *               *
gcg tgg tgt gga gct ggg cat cac cat tag ctc ggc cag cag aaa
cgc acc aca cct cga ccc gta gtg gta atc gag ccg gtc gtc ttt 1850            1860            1870            1880            1890
         *               *               *               *               *
gcg agg gga acc cct gat cat ctc tga cat caa gaa agg cag cgt
cgc tcc cct tgg gga cta gta gag act gta gtt ctt tcc gtc gca 1900            1910            1920            1930
                 *               *               *               *
ggc gca cag gac tgg cac cct cga gcc ggg cga caa gct gct ggc
ccg cgt gtc ctg acc gtg gga gct cgg ccc gct gtt cga cga ccg 1940            1950            1960            1970            1980
         *               *               *               *               *
cat tga caa tat tcg cct gga cca ttg ccc cat gga ata tgc tgt
gta act gtt ata agc gga cct ggt aac ggg gta cct tat acg aca 1990            2000            2010            2020
                 *               *               *               *
gca aat cct gcc cca atg tga gga cct ggt gaa gct gaa gat ccg
cgt tta gga cgg ggt tac act cct gga cca ctt cga ctt cta ggc
```

FIG. 22D-1

```
          2030            2040            2050            2060            2070
           *               *               *               *               *
gaa gga cga gga caa ctc aga tga gca gga gag ctc ggg cgc agt
ctt cct gct cct gtt gag tct act cgt cct ctc gag ccc gag tca 2080            2090            2100            2110
                   *               *               *               *
cag cta cac agt gga act gaa gcg cta tgg cgg acc cct ggg tat
gtc gat gtg tca cct tga ctt cgc gat acc gcc tgg gga ccc ata 2120            2130            2140            2150            2160
           *               *               *               *               *
cac cat ctc cgg tac aga gga acc ttt tga ccc cat cat cat ctc
gtg gta gag gcc atg tct cct tgg aaa act ggg gta gta gta gag 2170            2180            2190            2200
                   *               *               *               *
tgg tct cac caa gcg ggg tct ggc tga aag gac tgg agc atc cat
acc aga gtg gtt cgc ccc aga ccg act ttc ctg acc tcg tag gta 2210            2220            2230            2240            2250
           *               *               *               *               *
gtt ggg gac cgc ata ctg gcc atc aan cag cgt gag cct caa ggg
caa ccc ctg gcg tat gac cgg tag ttn gtc gca ctc gga gtt ccc 2260            2270            2280            2290
                   *               *               *               *
```

FIG. 22D-2

```
ccg gcc cct gag tga ggc cat tca cct tct gca ggt ggc agg gga
ggc cgg gga ctc act ccg gta agt gga aga cgt cca ccg tcc cct 2300        2310        2320        2330        2340
       *           *           *           *           *
gac tgt cac act gaa gat caa gaa gca gct gga ccg tcc cct tct
ctg aca gtg tga ctt cta gtt ctt cgt cga cct ggc agg gga aga 2350        2360        2370        2380
            *           *           *           *
ccc ccg cca gtc agg cag cct cag tga ggc cag tga tgt gga tga
ggg ggc ggt cag tcc gtc gga gtc act ccg gtc act aca cct act 2390        2400        2410        2420        2430
       *           *           *           *           *
gga ccc ccc tga ggc cct caa ggg agg ctt gct gac aac cca ctt
cct ggg ggg act ccg gga gtt ccc tcc gaa cga ctg ttg ggt gaa 2440        2450        2460        2470
            *           *           *           *
ctc acc tgc tgt acc cag cgt gga cag tgc tgt gga gtc ctg ggg
gag tgg acg aca tgg gtc gca cct gtc acg aca cct cag gac ccc 2480        2490        2500        2510        2520
       *           *           *           *           *
cag ctc tgc cac aga ggg tgg ctt tgg ggg ctc agg ctc cta cac
gtc gag acg gtg tct ccc acc gaa acc ccc gag tcc gag gat gtg 2530        2540        2550        2560
            *           *           *           *
tcc gca ggt ggc agt ccg gag tgt gac tcc tca gga gtg gcg ttc
agg cgt cca ccg tca ggc ctc aca ctg agg agt cct cac cgc aag 2570        2580        2590        2600        2610
       *           *           *           *           *
cag cag act gaa gag tag ccc ccc acc cct tga gcc ccg gag gac
gtc gtc tga ctt ctc atc ggg ggg tgg gga act cgg ggc ctc ctg
```

FIG. 22E-1

```
               2620            2630            2640            2650
                *               *               *               *
        gag cta cac acc ggg ccc cac tga cga aag ctt ccc aga gga gga
        ctc gat gtg tgg ccc ggg gtg act gct ttc gaa ggg tct cct cct 2660            2670            2680            2690            2700
            *               *               *               *               *
        aga ggg gga ctg gga gcc acc aat gag ccc agc ccc tgg ccc cgc
        tct ccc cct gac cct cgg tgg tta ctc ggg tcg ggg acc ggg gcg 2710            2720            2730            2740
                *               *               *               *
        ccg aga gga ggg ctt ctg gag agt gct tgg aga ggc cct tga aga
        ggc tct cct ccc gaa gac ctc tca cga acc tct ccg gga act tct 2750            2760            2770            2780            2790
            *               *               *               *               *
        cct gga gtc ctg tgg tca gtc tga act gct aag gga gct gga ggc
        gga cct cag gac acc agt cag act tga cga ttc cct cga cct ccg 2800            2810            2820            2830
                *               *               *               *
        ttc cat cat gac agg cac tgt aca gtc ggt agc tgt gga tgg cag
        aag gta gta ctg tcc gtg aca tgt cag cca tcg aca cct acc gtc
```

FIG. 22E-2

```
              2840          2850          2860          2870          2880
               *             *             *             *             *
          gcc tgg ctc tcg gcc ctg gcg ccg gag ccg gga agt cgg aac atc
          cgg acc gag agc cgg gac cgc ggc ctc ggc cct tca gcc ttg tag 2890          2900          2910          2920
                     *             *             *             *
          ccc gga aga cct gca gga gct gct gtt gcc aac gcc cct gga gat
          ggg cct tct gga cgt cct cga cga caa cgg ttg cgg gga cct cta 2930          2940          2950          2960          2970
               *             *             *             *             *
          gca cag ggt gac cct gca caa aga ccc ggt gag gaa cga ctt tgg
          cgt gtc cca ctg gga cgt gtt tct ggg cca ctc ctt gct gaa acc 2980          2990          3000          3010
                     *             *             *             *
          ttt cag tgt ctc aga tgg cct cct gga gaa ggg tgt cta tgt cca
          aaa gtc aca gag tct acc gga gga cct ctt ccc aca gat aca ggt 3020          3030          3040          3050          3060
               *             *             *             *             *
          cac tgt gcg cat tga tgg gcc agc tca gca cgg agg cct gca gcc
          gtg aca cgc gta act acc cgg tcg agt cgt gcc tcc gga cgt cgg 3070          3080          3090          3100
                     *             *             *             *
          ctt tga ccg tct cct gca ggt caa cca tgt tcg cac tcg gga ctt
          aga act ggc aga gga cgt cca gtt ggt aca agc gtg agc cct gaa 3110          3120          3130          3140          3150
               *             *             *             *             *
          cga ttg ctg tct ggc cgt tcc act cct ggc aga gct ggg ana tcc
          gct aac gac aga ccg gca agg tga gga ccg tct cga ccc tnt agg
```

FIG. 22F-1

```
           3160          3170          3180          3190
            *             *             *             *
ttg agc tgg tgg tca gcc gaa acc ctc tgg cac aga gcc gca gga
aac tcg acc acc agt cgg ctt tgg gag acc gtg tct cgg cgt cct 3200          3210          3220          3230          3240
        *             *             *             *             *
cac cag gag cac cgg gcc cca gta gtc ccc aga tga tct gag gtc
gtg gtc ctc gtg gcc cgg ggt cat cag ggg tct act aga ctc cag 3250          3260          3270          3280
            *             *             *             *
att atg taa gtc agc tgg cgg agt gcc ccc agt cat cga ctt atg
taa tac att cag tcg acc gcc tca cgg ggg tca gta gct gaa tac 3290          3300          3310          3320          3330
        *             *             *             *             *
gcc tgc aga ttt cac atc cgg tag agt ggc atc ttc aag ttg ggt
cgg acg tct aaa gtg tag gcc atc tca ccg tag aag ttc aac cca 3340          3350          3360          3370
            *             *             *             *
ctt cag gat gct cag aga acc cca cag gaa agg ggt cat ccc tgc
gaa gtc cta cga gtc tct tgg ggt gtc ctt tcc cca gta ggg acg 3380          3390          3400          3410          3420
        *             *             *             *             *
                         tgc tca gct agg aga gcc cag ctc cct gtg cag tca tct cag agc
```

FIG. 22F-2

```
                                  acg agt cga tcc tct cgg gtc gag gga cac gtc agt aga gtc tcg 3430                3440                3450                3460
              *                   *                   *                   *
agc gaa cag agt ggg gac ggc cca gct ccg tgt ggt aac tgg act
tcg ctt gtc tca ccc ctg ccg ggt cga ggc aca cca ttg acc tga 3470                3480                3490                3500                3510
         *                   *                   *                   *                   *
gag ctg cca gta ttt ccc atc ctg gga agt taa taa gct gta ggt
ctc gac ggt cat aaa ggg tag gac cct tca att att cga cat cca 3520                3530                3540                3550
              *                   *                   *                   *
cga caa ttc tgc tct gtg aaa aga ggc att tgg cga ccc agc tgt
gct gtt aag acg aga cac ctt tct ccg taa acc gct ggg tcg aca 3560                3570                3580                3590                3600
         *                   *                   *                   *                   *
tca gat ggt acc cag tgc aca ggg acc ctg cca ccg gga aag ata
agt cta cca tgg gtc acg tgt ccc tgg gac ggt ggc cct ttc tat 3610                3620                3630                3640
              *                   *                   *                   *
tgg cac aag aac agt gtc ctc cct tct ccc aaa tga tgg tgt ttt
acc gtg ttc ttg tca cag gag gga aga ggg ttt acc acc aca aaa 3650                3660                3670                3680                3690
         *                   *                   *                   *                   *
gaa gag cct cca gca cct aat tga cca tac tga gga acc cca att
ctt ctc gga ggt cgt gga tta act ggt atg act cct tgg ggt taa 3700                3710                3720                3730
              *                   *                   *                   *
agg gac aat cta ggg tgc cag aga atg ctt gcc cct tcc ttt ggg
tcc ctg tta gat ccc acg gtc tct tac gaa cgg gga agg aaa ccc
```

FIG. 22G-1

```
              3740        3750        3760        3770        3780
               *           *           *           *           *
          ttg gtc ttt caa tta ttt cac ggg tga ttc tga acc tca gag cag
          aac cag aaa gtt aat aaa gtg ccc act aag act tgg agt ctc gtc 3790        3800        3810        3820
                    *           *           *           *
          aac tgt ggc cat caa ccc tcc tgt ccc aca aaa cct tag ccc aag
          ttg aca ccg gta gtt ggg agg aca ggg tgt ttt gga atc ggg ttc 3830        3840        3850        3860        3870
               *           *           *           *           *
          tcc ttg ccc aga gga ggg cac agc tcg ggt caa acg gtc cag gag
          agg aac ggg tct cct ccc gtg tcg agc cca gtt tgc cag gtc ctc 3880        3890        3900        3910
                    *           *           *           *
          cat cca cac acc tgc cat tcc agc aca tat ggt aaa cct tgg gaa
          gta ggt gtg tgg acg gta agg tcg tgt ata cca ttt gga acc ctt 3920        3930        3940        3950        3960
               *           *           *           *           *
          gag act gag cca cag ttc tgc ccc tga ccc cat cag agg aag aga
          ctc tga ctc ggt gtc aag acg ggg act ggg gta gtc tcc ttc tct 3970        3980        3990        4000
```

FIG. 22G-2

```
              *              *              *              *
gga aga nga aag gag ctg aca tgg agg gag gtc agc tga agg atg
cct tct nct ttc ctc gac tgt acc tcc ctc cag tcg act tcc tac 4010         4020         4030         4040         4050
         *            *            *            *            *
aga nag tgg cta act gga gca gtg tcc aag gaa gct att caa gga
tct ntc acc gat tga cct cgt cac agg ttc ctt cga taa gtt cct 4060         4070         4080         4090
            *            *            *            *
ggt ccc cag cat ccc tta act ctg ggc tcc tcc atc tct gct aag
cca ggg gtc gta ggg aat tga gac ccg agg agg tag aga cga ttc 4100         4110         4120         4130         4140
         *            *            *            *            *
cag aac ctt cca gct tca agc aag ant caa gac act tcc ttc cca
gtc ttg gaa ggt cga agt tcg ttc tna gtt ctg tga agg aag ggt 4150         4160         4170         4180
            *            *            *            *
gca gtc tga gct gtt ctg gag act ggc ttc atg ttt gcc cag ctt
cgt cag act cga caa gac ctc tga ccg aag tac aaa cgg gtc gaa 4190         4200         4210         4120         4230
         *            *            *            *            *
aag gtc tca agg acc tgc ggg aag cct cca acc ctg ccc tgt cac
ttc cag agt tcc tgg acg ccc ttc gga ggt tgg gac ggg aca gtg 4240         4250         4260         4270
            *            *            *            *
ccc tct gtg ccc ttg aag ctc act gct aga aag cac tcc ctg ttc
ggg aga cac ggg aac ttc gag tga cga tct ttc gtg agg gac aag 4280         4290         4300         4310         4320
         *            *            *            *            *
aag agg aca gat gag gtc cca gaa gcc att ctt tcc ccg ttc tct
ttc tcc tgt cta ctc cag ggt ctt cgg taa gaa agg ggc aag aga
```

FIG. 22H-1

```
          4330            4340            4350            4360
           *               *               *               *
tct tgg ctg tat aac ctt gag tna agc tga aaa gan aca ggg nga
aga acc gac ata ttg gaa ctc ant tcg act ttt ctn tgt ccc nct 4370            4380            4390            4400            4410
           *               *               *               *               *
gct cca gct gcc cac taa gaa act tca nct ctc tgc ttt tcc taa
cga ggt cga cgg gtg att ctt tga agt nga gag acg aaa agg att 4420            4430            4440            4450
           *               *               *               *
ctt ccc cca tat cct gcc ctt cat gaa ggn ttc ccn ggg aac ctt
gaa ggg ggt ata gga cgg gaa gta ctt ccn aag ggn ccc ttg gaa 4460            4470            4480            4490            4500
           *               *               *               *               *
cag gng acc can tga atc tac ttt cac tgc cca ggg ttg aaa aga
gtc cnc tgg gtn act tag atg aaa gtg acg ggt ccc aac ttt tct 4510            4520            4530            4540
           *               *               *               *
nan tac ccc ccc atc atg ggg gcc caa caa aaa act tcc agc ttc
ntn atg ggg ggg tag tac ccc cgg gtt gta ttt tga agg tcg aag
```

FIG. 22H-2

```
            4550          4560          4570          4580          4590
             *             *             *             *             *
      cta gcc aaa aaa tna atc cta gcc ccn gct cac ctg atc tgt ntt
      gat cgg ttt ttt ant tag gat cgg ggn cga gtg gac tag aca naa 4600          4610          4620          4630
                  *             *             *             *
      aac ttg ggc nga nng gtc anc nct gga att ctg gtt tgt ggn ata
      ttg aac ccg nct nnc cag tng nga cct taa gac caa aca ccn tat 4640          4650          4660          4670          4680
             *             *             *             *             *
      act gaa agt acc cng aaa ggc nct taa cnt ngg gaa atc tgt gtt
      tga ctt tca tgg gnc ttt ccg nga att gna ncc ctt tag aca caa 4690          4700          4710          4720
                  *             *             *             *
      tcn ctt aat gaa acc cgg ctc tga aaa tgg aac ccc cnn aaa ctg
      agn gaa tta ctt tgg gcc gag act ttt acc ttg ggg gnn ttt gac 4730          4740          4750          4760          4770
             *             *             *             *             *
      gcc tnc ccc cgg ggg ngn ngg ggt ccc cnc ccc ccc naa att tnc
      cgg ang ggg gcc ccc ncn ncc cca ggg gng ggg ggg ntt taa ang 4780          4790          4800          4810
                  *             *             *             *
      cac tan ggc caa cng ggt gga can ccn cgg ctg ttg ggc nga agg
      gtg atn ccg gtt gnc cca cct tgn ggn gcc gac aac ccg nct tcc 4820          4830          4840
             *             *             *
      cct ccc nta ttn can att acc ccc cng ggn tt
      gga ggg nat aan gtn taa tgg ggg gnc ccn aa
```

FIG. 22I

```
Sequence Range: 1 to 4847

10                  20                  30                  40
                 *                   *                   *                   *
C  TGC GGC CGC CAG CGC AAA NGC GCC AGC TCC CGG CTC CGA GGC TGC GGG
G  ACG CCG GCG GTC GCG TTT NCG CGG TCG AGG GCC GAG GCT CCG ACG CCC
    C   C   R   Q   R   K   X   A   S   S   R   L   R   G   C   C 50                  60                  70                  80                  90
        *                   *                   *                   *                   *
GCG GCT GCA GGG AGG TTG CAG GGC TCC GGG TCT GGG ACC TGC CGG CGG
CGC CGA CGT CCC TCC AAC GTC CCG AGG CCC AGA CCC TGG ACG GCC GCC
 A>  A   A   G   R   L   Q   G   S   G   S   G   T   C   R   R 100                 110                 120                 130                 140
        *                   *                   *                   *                   *
GCA AAA GTG ATG TTG GCG GTG TCA CTC AAT TGG CGG CTG GGC GTG GTG
CGT TTT CAC TAC AAC CGC CAC AGT GAG TTA ACC GCC GAC CCG CAC CAC
 A   K   V>  M   L   A   V   S   L   N   W   R   L   G   V   V 150                 160                 170                 180                 190
            *                   *                   *                   *                   *
    AGG CGG CGG CCC AAA AAC GAT GGG CCT TAC TCA AAG GGG GGA AAG GAC
    TCC GCC GCC GGG TTT TTG CTA CCC GGA ATG AGT TTC CCC CCT TTC CTG
     R   R   R   P   K>  N   D   G   P   Y   S   K   G   G   K   D 200                 210                 220                 230                 240
           *                   *                   *                   *                   *
   ACA GCG GGG ACT GAT GGG GCC CTG GTG TGC CGC CGC CAG AGC ATT CCA
   TGT CGC CCC TGA CTA CCC CGG GAC CAC ACG GCG GCG GTC TCG TAA GGT
    T   A   G   T   D   G   A>  L   V   C   R   R   Q   S   I   P 250                 260                 270                 280
            *                   *                   *                   *
    GAG GAG TTC CGG GGC ATC ACC ATG GTG GAG CTG ATC AAG CGT GAG GGC
    CTC CTC AAG GCC CCG TAG TGG TAC CAC CTC GAC TAG TTC GCA CTC CCG
     E   E   F   R   G   I   T   M   V>  E   L   I   K   R   E   G
```

FIG. 23A-1

```
     290           300           310           320           330
      *             *             *             *             *
  AGC ACT CTG GGC CTG ACT ATC TCA GGA GGG ACT GAC AAG GAC GGG AAG
  TCG TGA GAC CCG GAC TGA TAG AGT CCT CCC TGA CTG TTC CTG CCC TTC
   S   T   L   G   L   T   I   S   G   G   T>  D   K   D   G   K 340           350           360           370           380
      *             *             *             *             *
  CCC AGA GTC TCC AAC CTG AGA CCC GGG GGC CTT GCA GCC AGG AGC GAT
  GGG TCT CAG AGG TTG GAC TCT CCG CCC CCG GAA CGT CGG TCC TCG CTA
   P   R   V   S   N   L   R   P   G   G   L   A   A>  R   S   D 390           400           410           420           430
          *             *             *             *             *
  CTA CTG AAT GTG GGC GAC TAT ATC CGC TCA GTG AAT GGG ATC CGT CTG
  GAT GAC TTA CAC CCG CTG ATA TAG GCG AGT CAC TTA CCC TAG GCA GAC
   L   L   N   V   G   D   Y   T   R   S   V   N   G   I   R>  L 440           450           460           470           480
              *             *             *             *             *
  ACC CGG CTC CGA CAT GAC GAG ATC ATC ACA TTG CTG AAG AAT GTG GGC
  TGG GCC GAG GCT GTA CTG CTC TAG TAG TGT AAC GAC TTC TTA CAC CCG
   T   R   L   R   H   D   E   I   I   T   L   L   K   N   V   G 490           500           510           520
                  *             *             *             *
  GAG CGC GTG GTG CTG GAG GTG GAG TAT GAG CTG CCC CCG CCC GCT CCC
  CTC GCG CAC CAC GAC CTC CAC CTC ATA CTC GAC GGG GGC GGG CGA GGG
   E>  R   V   V   L   E   V   E   Y   E   L   P   P   P   A   P

530
   *
  GAA AAC AAC
  CTT TTG TTG
   E   N   N>
```

FIG. 23A-2

```
540            550              560             570
 *              *                *               *
CCG AGG ATC ATT TCC AAG ACG GTG GAC GTC TCC CTC TAC
GGC TCC TAG TAA AGG TTC TGC CAC CTG CAG AGG GAG ATG
 P   R   I   I   S   K   T   V   D   V   S   L   Y 580              590              600             610             620
 *                *                *               *               *
AAG GAA GGC AAC AGT TTT GGC TTT GTC CTC AGA GGA GGT GCC CAT GAG
TTC CTT CCG TTG TCA AAA CCG AAA CAG GAG TCT CCT CCA CGG GTA CTC
 K   E   G   M   S>  F   G   F   V   L   R   G   G   A   H   E 630              640              650             660             670
 *                *                *               *               *
GAC CTG CAC AAA TCC CGC CCA TTG GTC CTG ACT TAC GTG CGG CCT GGT
CTG GAC GTG TTT AGG GCG GGT AAC CAG GAC TGA ATG CAC GCC GGA CCA
 D   L   H   K   S   R   P>  L   V   L   T   Y   V   R   P   G 680              690              700             710             720
 *                *                *               *               *
GGC CCA GCA AAC AGG GAG GGT TCC TTA AAG GTG GGC GAC AGG CTG CTC
CCG GGT CGT TTG TCC CTC CCA AGG AAT TTC CAC CCG CTG TCC GAC GAG
 G   P   A   N   R   E   G   S   L>  K   V   G   D   R   L   L 730              740              750             760
 *                *                *               *
AGC ATA NAT GGG ATC CCA CTG CAC GGG GCC AGC CAT GCT ACC GCA ATA
TCG TAT NTA CCC TAG GGT GAC GTG CCC CGG TCG GTA CGA TGG CGT TAT
 S   I   X   G   I   P   L   H   G   A   S>  H   A   T   A   I 770              780              790             800             810
 *                *                *               *               *
GCC ACC CTG CAG CAG TGC AGC CAT GAG GCC CTC TTC CAG GTG GAG TAC
CGG TGG GAC GTC GTC ACG TCG GTA CTC CGG GAG AAG GTC CAC CTC ATG
 A   T   L   Q   Q   C   S   H   E   A   L   F   Q>  V   E   Y
```

FIG. 23B-1

```
          820             830             840             850             860
           *               *               *               *               *
    GAT GTG GCC ACC CCA GAC ACG GTG GCC AAT GCT TCA GGC CCT TTG GTG
    CTA CAC CGG TGG GGT CTG TGC CAC CGG TTA CGA AGT CCG GGA AAC CAC
     D   V   A   T   P   D   T   V   A   N   A   S   G   P   L>  V 870             880             890             900             910
           *               *               *               *               *
    GTA GAA ATA GCC AAG ACC CCA GGA TCT GCC CTG GGG ATC TCT CTC ACC
    CAT CTT TAT CGG TTC TGG GGT CCT AGA CGG GAC CCC TAG AGA GAG TGG
     V   E   I   A   K   T   P   G   S   A   L   G   I   S   L   T 920             930             940             950             960
           *               *               *               *               *
    ACT GGC TCC CAC CGG AAC AAA CCA GCT ATC ACT ATC GAC CGC ATC AAG
    TGA CCG AGG GTG GCC TTG TTT GGT CGA TAG TGA TAG CTG GCG TAG TTC
     T>  G   S   H   R   N   K   P   A   L   T   I   D   R   I   K 970             980             990            1000
           *               *               *               *
    CCG GCT AGC GTG GTG GAC AAG AAT GGT GCC CTG CAT GCT GGA GAA CAC
    GGC CGA TCG CAC CAC CTG TTC TTA CCA CGG GAC GTA CGA CCT CTT GTG
     P   A   S>  V   V   D   K   N   G   A   L   H   A   G   E   H 1010            1020            1030            1040            1050
    *               *               *               *               *
     ATC CTG GCC ATC GAT GGC ACC AGC ACA GAA CAC TGC TCT CTG GTC GAG
     TAG GAC CGG TAG CTA CCG TGG TCG TGT CTT GTG ACG AGA GAC CAG CTC
      I   L   A   I   D>  G   T   S   T   E   H   C   S   L   V   E 1060            1070            1080            1090            1100
    *               *               *               *               *
    GCC ACG AAG CTC TTG GCC AGT GTG ACC GAG AAA GTT CGA CTG GAG ATC
    CGG TGC TTC GAG AAC CGG TCA CAC TGG CTC TTT CAA GCT GAC CTC TAG
     A   T   K   L   L   A   S>  V   T   E   K   V   R   L   E   I
```

FIG. 23B-2

```
         1110              1120              1130              1140              1150
           *                 *                 *                 *                 *
TTG CCT GCA CCC CAG AGT CGG CGG CCC CTG AAG CCC CCA GAG GCA GTG
AAC GGA CGT GGG GTC TCA GCC GCC GGG GAC TTC GGG GGT CTC CGT CAC
 L   P   A   P   Q   S   R   R   P>  L   K   P   P   E   A   V 1160              1170              1180              1190              1200
           *                 *                 *                 *                 *
AGA ATA CAG AGG AGT GAG CAA CTG CAC CAC TGG GAC CCC TGT GTT CCC
TCT TAT GTC TCC TCA CTC GTT GAC GTG GTG ACC CTG GGG ACA CAA GGG
 R   I   Q   R   S   E   Q   L   H   H   W>  D   P   -C  V   P 1210              1220              1230              1240
               *                 *                 *                 *
TCT TGC CAT AGC CCA AGG CCA AGC CAC TGC AGG GCA CCC ACC TGG GCA
AGA ACG GTA TCG GGT TCC GGT TCG GTG ACG TCC CGT GGG TGG ACC CGT
 S   C   H   S   P   R   P   S   H   C   R   A   P>  T   W   A 1250              1260              1270              1280              1290
       *                 *                 *                 *                 *
    CCT GGA GGC CAG GAC CAG AGC CGA TCC GTG TCC TCG ACT CCC TTC TCC
    GGA CCT CCG GTC CTG GTC TCG GCT AGG CAC AGG AGC TGA GGG AAG AGG
     P   G   G   Q   D   Q   S   R   S   V   S   S   T   P   F>  S 1300              1310              1320              1330              1340
           *                 *                 *                 *                 *
TCG CCA ACT ATG AAC CCT GCC TTT CCC TGT GCC AAC GCC AGC ACC CTG
AGC GGT TGA TAC TTG GCA CGG AAA GCG ACA CGG TTG CGG TCG TGG GAC
 S   P   T   M   N   P   A   F   P   C   A   N   A   S   T   L 1350              1360              1370              1380              1390
           *                 *                 *                 *                 *
CCC AGA GGA CCC ATG AGC CCC AGA ACA ACA GCG GGG AGG AGA AGG CAG
GGG TCT CCT GGG TAC TCG GGG TCT TGT TGT CGC CCC TCC TCT TCC GTC
 P>  R   G   P   M   S   P   R   T   T   A   G   R   R   R   Q
```

FIG. 23C-1

```
      1400         1410         1420         1430         1440
       *            *            *            *            *
CGA AGG AAA GAA CAC AGG AGC TCT TTG TCA CTG GCC TCC AGC ACG GTA
GCT TCC TTT CTT GTG TCC TCG AGA AAC AGT GAC CGG AGG TCG TGC CAT
 R   R   K>  E   H   R   S   S   L   S   L   A   S   S   T   V 1450         1460         1470         1480
            *            *            *            *
GGG CCC GGT GGG CAG ATC GTT CAC ACG GAG ACG ACG GAG GTA GTG CTC
CCC GGG CCA CCC GTC TAG CAA GTG TGC CTC TGC TGC CTC CAT CAC GAG
 G   P   G   G   Q>  I   V   H   T   E   T   T   E   V   V   L 1490         1500         1510         1520         1530
   *            *            *            *            *
   TGT GGA GAC CCC CTC AGT GGC TTC GGC CTC CAG CTG CAG GGG GGC ATT
   ACA CCT CTG GGG GAG TCA CCG AAG CCG GAG GTC GAC GTC CCC CCG TAA
    C   G   D   P   L   S   G>  F   G   L   Q   L   Q   G   G   I 1540         1550         1560         1570         1580
   *            *            *            *            *
TTT GCT ACC GAG ACC CTG TCC TCC CCA CCC TTG GTG CGA TTT ATT GAA
AAA CGA TGG CTC TGG GAC AGG AGG GGT GGG AAC CAC GCT AAA TAA CTT
 F   A   T   E   T   L   S   S   P>  P   L   V   R   F   I   E 1590         1600         1610         1620         1630
   *            *            *            *            *
CCT GAC AGC CCT GCT GAG AGG TGT GGT CTG CTG CAG GTG GGG GAC CGC
GGA CTG TCG GGA CGA CTC TCC ACA CCA GAC GAC GTC CAC CCC CTG GCG
 P   D   S   P   A   E   R   C   G   L   L>  Q   V   G   D   R 1640         1650         1660         1670         1680
            *            *            *            *            *
       GTC CTA GCC ATA AAT GGC ATT GCT ACT GAA GAT GGG ACC ATG GAA CAA
       CAG GAT CGG TAT TTA CGC TAA CGA TGA CTT CTA CCC TGG TAC CTT CTT
        V   L   A   I   N   G   I   A   T   E   D   G   T>  M   E   E
```

FIG. 23C-2

```
                1690           1700           1710           1720
                 *              *              *              *
          GCC AAC CAG CTG TTG CGG GAT GCT GCA CTG GCC CGC AAA ATT GTT TTG
          CGG TTG GTC GAC AAC GCC CTA CGA CGT GAC CGG GCG TTT TAA CAA AAC
           A   N   Q   L   L   R   D   A   A   L   A   R   K   I   V>  L 1730           1740           1750           1760           1770
      *              *              *              *              *
         GAG ATC GAG TTT GAT GTG GCG GAA TCT GTC ATC CCA AGC AGT GGG ACT
         CTC TAG CTC AAA CTA CAC CGC CTT AGA CAG TAG GGT TCG TCA CCC TGA
          E   I   E   F   D   V   A   E   S   V   I   P   S   S   G   T 1780           1790           1800           1810           1820
      *              *              *              *              *
     TTC CAC GTG AAG TTA CCC AAA AGG CGT GGT GTG GAG CTG GGC ATC ACC
     AAG CTG CAC TTC AAT GGG TTT TCC GCA CCA CAC CTC GAC CCG TAG TGG
      F>  H   V   K   L   P   K   R   R   G   V   E   L   G   I   T 1830           1840           1850           1860           1870
      *              *              *              *              *
     ATT AGC TCG GCC AGC AGA AAG CGA GGG GAA CCC CTG ATC ATC TCT GAC
     TAA TCG AGC CGG TCG TCT TTC GCT CCC CTT GGG GAC TAG TAG AGA CTG
      I   S   S>  A   S   R   K   R   G   E   P   L   I   I   S   D 1880           1890           1900           1910           1920
              *              *              *              *              *
          ATC AAG AAA GGC AGC GTG GCG CAC AGG ACT GGC ACC CTC GAG CCG GGC
          TAG TTC TTT CCG TCG CAC CGC GTG TCC TGA CCG TGG GAG CTC GCC CCG
           I   K   K   G   S>  V   A   H   R   T   G   T   L   E   P   G 1930           1940           1950           1960
                  *              *              *              *
          GAC AAG CTG CTG GCC ATT GAC AAT ATT CGC CTG GAC CAT TGC CCC ATG
          CTG TTC GAC GAC CGG TAA CTG TTA TAA GCG GAC CTG GTA ACG GGG TAC
           D   K   L   L   A   I   D>  N   I   R   L   D   H   C   P   M

FIG. 23D-1
```

```
    1970            1980            1990            2000            2010
     *               *               *               *               *
  GAA TAT GCT GTG CAA ATC CTG CCC CAA TGT GAG GAC CTG GTG AAG CTG
  CTT ATA CCA CAC GTT TAG CAC GGG GTT ACA CTC CTG GAC CAC TTC GAC
   E   Y   A   V   Q   I   L   P   Q>  C   E   D   L   V   K   L 2020            2030            2040            2050            2060
     *               *               *               *               *
  AAG ATC CGG AAG GAC GAG GAC AAC TCA GAT GAG CAG GAG AGC TCG GGC
  TTC TAG GCC TTC CTG CTC CTG TTG AGT CTA CTC GTC CTC TCG AGC CCG
   K   I   R   K   D   E   D   N   S   D   E>  Q   E   S   S   G 2070            2080            2090            2100            2110
     *               *               *               *               *
 GCA GTC AGC TAC ACA GTG GAA CTG AAG CGC TAT GGC GGA CCC CTG GGT
 CGT CAG TCG ATG TGT CAC CTT GAC TTC GCG ATA CCG CCT GGG GAC CCA
  A   V   S   Y   T   V   E   L   K   R   Y   G   G>  P   L   G 2120            2130            2140            2150            2160
     *               *               *               *               *
 ATC ACC ATC TCC GGT ACA GAG GAA CCT TTT GAC CCC ATC ATC ATC TCT
 TAG TGG TAG AGG CCA TGT CTC CTT GGA AAA CTG GGG TAG TAG TAG AGA
  I   T   I   S   G   T   I   E   P   F   D   P   I   I   I>  S 2170            2180            2190            2200
            *               *               *               *
 GGT CTC ACC AAG CGG GGT CTG GCT GAA AGG ACT GGA GCA TCC ATG TTG
 CCA GAG TGG TTC GCC CCA GAC CGA CTT TCC TGA CCT CGT AGG TAC AAC
  G   L   T   K   R   G   L   A   E   R   T   G   A   S   M   L
```

FIG. 23D-2

```
      2210              2220              2230              2240              2250
       *                 *                 *                 *                 *
   GGG ACC GCA TAC TGG CCA TCA ANC AGC GTG AGC CTC AAG GGC CGG CCC
   CCC TGG CGT ATG ACC GGT AGT TNG TCG CAC TCG GAG TTC CCG GCC GGG
   G>   T   A   Y   W   P   S   X   S   V   S   L   K   G   R   P 2260              2270              2280              2290              2300
       *                 *                 *                 *                 *
   CTG AGT GAG GCC ATT CAC CTT CTG CAG GTG GCA GGG GAG ACT GTC ACA
   GAC TCA CTC CGG TAA GTG GAA GAC GTC CAC CGT CCC CTC TGA CAG TGT
    L   S   E>  A   I   H   L   L   Q   V   A   C   E   T   V   T 2310              2320              2330              2340              2350
       *                 *                 *                 *                 *
   CTG AAG ATC AAG AAG CAG CTG GAC CGT CCC CTT CTC CCC CGC CAG TCA
   GAC TTC TAG TTC TTC GTC GAC CTG GCA GGG GAA GAG GGG GCG GTC AGT CCG TCG
    L   K   I   K   K>  Q   L   D   R   P   L   L   P   R   Q   S 2360              2370              2380              2390              2400
               *                 *                 *                 *                 *
   GGC AGC CTC AGT GAG GCC AGT GAT GTG GAT GAG GAC CCC CCT GAG GCC
   CCG TCG GAG TCA CTC CGG TCA CTA CAC CTA CTC CTG GCC GGA CTC CGG
    G   S   L   S   E   A   S>  D   V   D   E   D   P   P   E   A 2410              2420              2430              2440
                      *                 *                 *                 *
   CTC AAG GGA GGC TTG CTG ACA ACC CAC TTC TCA CCT GCT GTA CCC AGC
   GAG TTC CCT CCG AAC GAC TGT TGG GTG AAG AGT GGA CGA CAT CCC TCG
    L   K   G   G   L   L   I   T   H>  F   S   P   A   V   P   S 2450              2460              2470              2480              2490
      *                 *                 *                 *                 *
   GTG GAC AGT GCT GTG GAG TCC TGG GGC AGC TCT GCC ACA GAG GGT GGC
   CAC CTG TCA CGA CAC CTC AGG ACC CCG TCG AGA CGG TGT CTC CCA CCG
    V   D   S   A   V   E   S   W   G   S   S>  A   T   E   G   G 2500              2510              2520              2530              2540
       *                 *                 *                 *                 *
   TTT GGG GGC TCA GGC TCC TAC ACT CCG CAG GTG GCA GTC CGG AGT GTG
   AAA CCC CCG AGT CCG AGG ATG TGA GGC GTC CAC CGT CAG GCC TCA CAC
    F   G   G   S   G   S   Y   T   P   Q   V   A   V>  R   S   V 2550              2560              2570              2580              2590
       *                 *                 *                 *                 *
   ACT CCT CAG GAG TGG CGT TCC AGC AGA CTG AAG AGT AGC CCC CCA CCC
   TGA GGA GTC CTC ACC GCA AGG TCG TCT GAC TTC TCA TCG GGG GGT GGG
```

FIG. 23E-1

```
        2550            2560            2570            2580            2590
         *               *               *               *               *
ACT CCT CAG GAG TGG CGT TCC AGC AGA CTG AAG AGT AGC CCC CCA CCC
TGA GGA GTC CTC ACC GCA AGG TCG TCT GAC TTC TCA TCG GGG GGT GGG
 T   P   Q   E   W   R   S   S   R   L   K   S   S   P   P>  P 2600            2610            2620            2630            2640
         *               *               *               *               *
CTT GAG CCC CGG AGG ACG AGC TAC ACA CCG GGC CCC ACT GAC GAA AGC
GAA CTC GGG GCC TCC TGC TCG ATG TGT GGC CCG GGG TGA CTG CTT TCG
 L   E   P   R   R   T   S   Y   T   P   G   P   T   D   E   S 2650            2660            2670            2680
         *               *               *               *
TTC CCA GAG GAG GAA GAG GGG GAC TGG GAG CCA CCA ATG AGC CCA GCC
AAG GGT CTC CTC CTT CTC CCC CTG ACC CTC GGT GGT TAC TCG GGT CGG
 F>  P   E   E   E   E   G   D   W   E   P   P   M   S   P   A 2690            2700            2710            2720            2730
 *               *               *               *               *
CCT GGC CCC GCC CGA GAG GAG GGC TTC TGG AGA GTG CTT GGA GAG GCC
GGA CCG GGG CGG GCT CTC CTC CCG AAG ACC TCT CAC GAA CCT CTC CGG
 P   G   P>  A   R   E   E   G   P   W   R   V   L   G   E   A 2740            2750            2760            2770            2780
         *               *               *               *               *
CTT GAA GAC CTG GAG TCC TGT GGT CAG TCT GAA CTG CTA AGG GAG CTG
GAA CTT CTG GAC CTC AGG ACA CCA GTC AGA CTT GAC GAT TCC CTC
 L   E   D   L   E>  S   C   G   Q   S   E   L   L   R   E   L
```

FIG. 23E-2

```
      2790          2800          2810          2820          2830
        *             *             *             *             *
GAG GCT TCC ATC ATG ACA GGC ACT GTA CAG TCG GTA GCT GTG GAT GGC
CTC CGA AGG TAG TAC TGT CCG TGA CAT GTC AGC CAT CGA CAC CTA CCG
 E   A   S   I   M   T   G>  T   V   Q   S   V   A   V   D   G 2840          2850          2860          2870          2880
        *             *             *             *             *
AGG CCT GGC TCT CGG CCC TGG CGC CGG AGC CGG GAA GTC GGA ACA TCC
TCC GGA CCG AGA GCC GGG ACC GCG GCC TCG GCC CTT CAG CCT TGT AGG
 R   P   C   S   R   P   W   F   R>  S   R   E   V   G   T   S 2890          2900          2910          2920
              *             *             *             *
CCG GAA GAC CTG CAG GAG CTG CTG TTG CCA ACG CCC CTG GAG ATG CAC
GGC CTT CTG GAC GTC CTC GAC GAC AAC GGT TGC GGG GAC CTC TAC GTG
 P   E   D   L   Q   E   L   L   L   P   T>  P   L   E   M   H 2930          2940          2950          2960          2970
  *             *             *             *             *
AGG GTG ACC CTG CAC AAA GAC CCG GTG AGG AAC GAC TTT GGT TTC AGT
TCC CAC TGG GAC GTG TTT CTG GGC CAC TCC TTG CTG AAA CCA AAG TCA
 R   V   T   L   H   K   D   P   V   R   N   D   F>  G   F   S 2980          2990          3000          3010          3020
  *             *             *             *             *
GTC TCA GAT GGC CTC CTG GAG AAG GGT GTC TAT GTC CAC ACT GTG CGC
CAG AGT CTA CCG GAG GAC CTC TTC CCA CAG ATA CAG GTG TGA CAC GCG
 V   S   D   G   L   L   E   K   G   V   Y   V   H   T   V>  R 3030          3040          3050          3060          3070
        *             *             *             *             *
ATT GAT GGG CCA GCT CAG CAC GGA GGC CTG CAG CCC TTT GAC CGT CTC
TAA CTA CCC CGT CGA GTC GTG CCT CCG GAC GTC GGG AAA CTG GCA GAG
 I   D   G   P   A   Q   H   G   G   L   Q   P   F   D   R   L 3080          3090          3100          3110          3120
              *             *             *             *             *
CTG CAG GTC AAC CAT GTT CGC ACT CGG GAC TTC GAT TGC TGT CTG GCC
GAC GTC CAG TTG GTA CAA GCG TGA GCC CTG AAG CTA ACG ACA GAC CGG
 L   Q   V   N   H   V   R   T   R   D   F   D   C   C   L   A 3130          3140          3150          3160
              *             *             *             *
GTT CCA CTC CTG GCA GAG CTG GCA NAT CCT TGA GCT GGT GGT CAG CCG
CAA GGT GAG GAC CGT CTC GAC CGT NTA GGA ACT CGA CCA CCA GTC GGC
 V   P   L>  L   A   E   L   G   X   P   *   A   G   C   Q   P
```

FIG. 23F-1

```
              3130            3140            3150            3160
                *               *               *               *
        GTT CCA CTC CTG GCA GAG CTG GGA NAT CCT TGA GCT GGT GGT CAG CCG
        CAA GGT GAG GAC CGT CTC GAC CCT MTA GGA ACT CGA CCA CCA GTC GGC
         V   P   L>  L   A   E   L   G   X   P   *   A   G   C   Q   P 3170            3180            3190            3200            3210
        *               *               *               *               *
        AAA CCC TCT GGC ACA GAG CCG CAG GAC ACC AGG AGC ACC GGG CCC CAG
        TTT GGG AGA CCG TGT CTC GGC GTC CTG TGG TCC TCG TGG CCC GGG GTC
         K   P   S   G   T>  E   P   Q   D   T   R   S   T   G   P   Q 3220            3230            3240            3250            3260
        *               *               *               *               *
        TAG TCC CCA GAT GAT CTG AGG TCA TTA TGT AAG TCA GCT GGC GGA GTG
        ATC AGG GGT CTA CTA GAC TCC AGT AAT ACA TTC AGT CGA CCG CCT CAC
         *   S   P   D   D   L   R>  S   L   C   K   S   A   G   G   V 3270            3280            3290            3300            3310
        *               *               *               *               *
        CCC CCA GTC ATC GAC TTA TGG CCT GCA GAT TTC ACA TCC GGT AGA GTG
        GGG GGT CAG TAG CTG AAT ACC GGA CGT CTA AAG TGT AGG CCA TCT CAC
         P   P   V   I   D   L   W   P   A>  D   F   T   S   G   R   V 3320            3330            3340            3350            3360
        *               *               *               *               *
        GCA TCT TCA AGT TGG GTC TTC AGG ATG CTC AGA GAA CCC CAC AGG AAA
        CGT AGA AGT TCA ACC CAG AAG TCC TAC GAG TCT CTT GGG GTG TCC TTT
         A   S   S   S   W   V   F   R   M   L   R>  E   P   H   R   K
```

FIG. 23F-2

```
           3370              3380              3390              3400
            *                 *                 *                 *
   GGG GTC ATC CCT GCT GCT CAG CTA GGA GAG CCC AGC TCC CTG TGC AGT
   CCC CAG TAG GGA CGA CGA GTC GAT CCT CTC GGG TCG AGG GAC ACG TCA
    G   V   I   P   A   A   Q   L   G   E   P   S   S>  L   C   S 3410              3420              3430              3440              3450
   *                 *                 *                 *                 *
   CAT CTC AGA GCA GCG AAC AGA GTG GGG ACG GCC CAG CTC CGT GTG GTA
   GTA GAG TCT CGT CGC TTG TCT CAC CCC TGC CGG GTC GAG GCA CAC CAT
    H   L   R   A   A   N   R   V   G   T   A   Q   L   R   V>  V 3460              3470              3480              3490              3500
   *                 *                 *                 *                 *
   ACT GGA CTG AGC TGC CAG TAT TTC CCA TCC TGG GAA GTT AAT AAG CTG
   TGA CCT GAC TCG ACG GTC ATA AAG GGT AGG ACC CTT CAA TTA TTC GAC
    T   G   L   S   C   Q   Y   F   P   S   W   E   V   N   K   L 3510              3520              3530              3540              3550
   *                 *                 *                 *                 *
   TAG GTC GAC AAT TCT GCT CTG TGG AAA GAG GCA TTT GGC GAC CCA GCT
   ATC CAG CTG TTA AGA CGA GAC ACC TTT CTC CGT AAA CCG CTG GGT CGA
    *>  V   D   N   S   A   L   W   K   E   A   F   G   D   P   A 3560              3570              3580              3590              3600
            *                 *                 *                 *                 *
   GTT CAG ATG GTA CCC AGT GCA CAG GGA CCC TGC CAC CGG GAA AGA TAT
   CAA GTC TAC CAT GGG TCA CGT GTC CCT GGG ACG GTG GCC CTT TCT ATA
    B   Q   M>  V   P   S   A   Q   G   P   C   H   R   E   R   Y 3610              3620              3630              3640
            *                 *                 *                 *
   GGC ACA AGA ACA GTG TCC TCC CTT CTC CCA AAT GGT GGT GTT TTG AAG
   CCG TGT TCT TGT CAC AGG AGG GAA GAG GGT TTA CCA CCA CAA AAC TTC
    G   T   R   T   V>  S   S   L   L   P   N   G   G   V   L   K
```

FIG. 23G-1

```
       3650           3660           3670           3680           3690
         *              *              *              *              *
    AGC CTC CAG CAC CTA ATT GAC CAT ACT GAG GAA CCC CAA TTA GGG ACA
    TCG GAG GTC GTG GAT TAA CTG GTA TGA CTC CTT GGG GTT AAT CCC TGT
     S   L   Q   G   L   I   D>  H   T   E   E   P   Q   L   C   T 3700           3710           3720           3730           3740
         *              *              *              *              *
    ATC TAG GGT GCC AGA GAA TGC TTG CCC CTT CCT TTG GGT TGG TCT TTC
    TAG ATC CCA CGG TCT CTT ACG AAC GGG GAA GGA AAC CCA ACC AGA AAG
     I   *   G   A   R   E   C   L   P>  L   P   L   G   W   S   F 3750           3760           3770           3780           3790
         *              *              *              *              *
    AAT TAT TTC ACG GGT GAT TCT GAA CCT CAG AGC AGA ACT GTG GCC ATC
    TTA ATA AAG TGC CCA CTA AGA CTT GGA GTC TCG TCT TGA CAC CGG TAG
     N   Y   P   T   C   D   S   E   P   Q   S>  R   T   V   A   I 3800           3810           3820           3830           3840
         *              *              *              *              *
    AAC CCT CCT GTC CCA CAA AAC CTT AGC CCA AGT CCT TGC CCA GAG GAG
    TTG GGA GGA CAG GGT GTT TTG GAA TCG GGT TCA GGA ACG GGT CTC CTC
     N   P   P   V   P   Q   N   L   S   P   S   P   C>  P   E   E 3850           3860           3870           3880
                *              *              *              *
    GGC ACA GCT GTC AAA CGG TCC AGG AGC ATC CAC ACA CCT GCC ATT
    CCG TGT CGA CAG TTT GCC AGG TCC TCG TAG GTG TGT GGA TAA
     G   T   A   R   V   K   R   S   R   S   I   H   T   P   A>
```

FIG. 23G-2

```
                                                              ATT
                                                              TAA
                                                               I 3890           3900          3910          3920          3930
          *              *             *             *             *
      CCA GCA CAT ATG GTA AAC CTT GGG AAG AGA CTG AGC CAC AGT TCT GCC
      GGT CGT GTA TAC CAT TTG GAA CCC TTC TCT GAC TCG GTG TCA AGA CGG
       P   A   H   M   V   N   L   G   K   R   L   S   H   S   S   A 3940           3950          3960          3970          3980
          *              *             *             *             *
      CCT GAC CCC ATC AGA GGA AGA GAG GAA GAN GAA AGG AGC TGA CAT GGA
      GGA CTG GGG TAG TCT CCT TCT CTC CTT CTN CTT TCC TCG ACT GTA CCT
       P>  D   P   I   R   G   R   E   E   X   E   R   S   *   H   G 3990          4000          4010          4020          4030
          *             *             *             *             *
      GGG AGG TCA GCT GAA GGA TGA GAN AGT GGC TAA CTG GAG CAG TGT CCA
      CCC TCC AGT CGA CTT CCT ACT CTN TCA CCG ATT GAC CTC GTC ACA GGT
       G   P   S>  A   E   G   *   L   S   G   *   L   E   Q   C   P 4040          4050          4060          4070          4080
          *             *             *             *             *
      AGG AAG CTA TTC AAG GAG GTC CCC AGC ATC CCT TAA CTC TGG GCT CCT
      TCC TTC GAT AAG TTC CTC CAG GGG TCG TAG GGA ATT GAG ACC CGA GGA
       R   K   L   F   K>  R   V   P   S   I   P   *   L   W   A   P 4090          4100          4110          4120
                 *             *             *             *
      CCA TCT CTG CTA AGC AGA ACC TTC CAG CTT CAA GCA AGA NTC AAG ACA
      GGT AGA GAC GAT TCG TCT TGG AAG GTC GAA GTT CGT TCT MAG TTC TGT
       P   S   L   L   S   R   T>  F   Q   L   Q   A   R   X   K   T 4130          4140          4150          4160          4170
          *             *             *             *             *
      CTT CCT TCC CAG CAG TCT CAG CTG TTC TGG AGA CTG GCT TCA TGT TTG
      GAA GGA AGG GTC GTC AGA GTC GAC AAG ACC TCT GAC CGA AGT ACA AAC
       L   P   S   Q   Q   S   Q   L   F>  W   R   L   A   S   C   L
```

FIG. 23H-1

```
          4180              4190             4200            4210            4220
            *                 *                *               *               *
      CCC AGC TTA AGG TCT CAA GCA CCT GCG GGA AGC CTC CAA CCC TGC CCT
      GGG TCG AAT TCC AGA GTT CGT GGA CGC CCT TCG GAG GTT GGG ACG GGA
       P   S   L   R   S   Q   G   P   A   G   S>  L   Q   P   C   P 4230              4240             4250            4260            4270
            *                 *                *               *               *
      GTC ACC CCT CTG TGC CCT TGA AGC TCA CTG CTA GAA AGC ACT CCC TGT
      CAG TGG GGA GAC ACG GGA ACT TCG AGT GAC GAT CTT TCG TGA GGG ACA
       V   T   P   L   C   P   -   S   S   L   L   E   S>  T   P   C 4280              4290             4300            4310            4320
            *                 *                *               *               *
      TCA AGA GGA CAG ATG AGG TCC CAG AAG CCA TTC TTT CCC CGT TCT CTT
      AGT TCT CCT GTC TAC TCC ACG GTC TTC GGT AAG AAA GGG GCA AGA GAA
       S   R   G   Q   M   R   S   Q   K   P   F   F   P   R   S>  L 4330              4340            4350            4360
                  *                  *               *               *
      CTT GGC TGT ATA ACC TTG AGT NAA GCT GAA AAG ANA CAG GGN GAG CTC
      GAA CCG ACA TAT TGG AAC TCA NTT CGA CTT TTC TNT GTC CCN CTC CAG
       L   G   C   I   T   L   -   X   A   E   K   X   Q   G   E   L 4370          4380             4390            4400            4410
         *             *                                *               *
      CAG CTG CCC ACT AAG AAA CTT CAN CTC TCT GCT TTT CCT AAC TTC CCC
      GTC GAC GGG TGA TTC TTT GAA GTN GAG AGA CGA AAA GGA TTG AAG GGG
       Q>  L   P   T   K   K   L   X   L   S   A   F   P   N   F   P 4420              4430             4440           4450            4460
            *                 *                *              *               *
      CAT ATC CTG CCC TTC ATG AAG GNT TCC CNG GGA ACC TTC AGG NGA CCC
      GTA TAG GAC GGG AAG TAC TTC CNA AGG GNC CCT TGG AAG TCC NCT CCG
       H   I   L>  P   F   M   K   X   S   X   G   T   F   R   X   P
```

FIG. 23H-2

```
        4470           4480           4490           4500           4510
          *              *              *              *              *
ANT GAA TCT ACT TTC ACT GCC CAG GGT TGA AAA GAN ANT ACC CCC CCA
TNA CTT AGA TGA AAG TGA CGG GTC CCA ACT TTT CTN TNA TGG GGG GGT
 X   E   S   T   F>  T   A   Q   G   *   K   X   X   T   P   P 4520           4530           4540           4550           4560
          *              *              *              *              *
TCA TGG GGG CCC AAC AAA AAA CTT CCA GCT TCC TAG CCA AAA AAT NAA
AGT ACC CCC GGG TTG TTT TTT GAA GGT CGA AGG ATC GGT TTT TTA NTT
 S   W   G   P   N   K   K>  L   P   A   S   *   P   K   N   X 4570           4580           4590           4600
          *              *              *              *
TCC TAG CCC CNG CTC ACC TGA TCT GTN TTA ACT TGG GCN GAN NGG TCA
AGG ATC GGG GNC GAG TGG ACT AGA CAN AAT TGA ACC CCN CTN NCC AGT
 S   *   P   X   L   T   *   S   V>  L   T   W   A   X   X   S 4610           4620           4630           4640           4650
  *              *              *              *              *
NCN CTG GAA TTC TGG TTT GTG GNA TAA CTG AAA GTA CCC NGA AAG GCN
NGN GAC CTT AAG ACC AAA CAC CNT ATT GAC TTT CAT GGG NCT TTC CGN
 X   L   E   F   W   F   V   X   *   L   K>  V   P   X   K   A 4660           4670           4680           4690           4700
      *              *              *              *              *
CTT AAC NTN GGG AAA TCT GTG TTT CNC TTA ATG AAA CCC GGC TCT GAA
GAA TTG NAN CCC TTT AGA CAC AAA GNG AAT TAC TTT GGG CCG AGA CTT
 L   N   X   G   K   S   V   F   X   L   M   K   P>  G   S   E 4710           4720           4730           4740           4750
      *              *              *              *              *
AAT GGA ACC CCC NNA AAC TGG CCT NCC CCC GGG GGN GNN GGG GTC CCC
TTA CCT TGG GGG NNT TTG ACC GGA NGG GGG CCC CCN CNN CCC CAG GGG
 N   G   T   P   X   N   W   P   X   P   G   G   X   G   V>  P
```

FIG. 23I-1

```
         4760           4770           4780           4790           4800
           *              *              *              *              *
NCC CCC CCN AAA TTT NCC ACT ANG GCC AAC NGG GTG GAA CNC CNC GGC
NGG GGG GGN TTT AAA NGG TGA TNC CGG TTG NCC CAC CTT GNG GNG CCG
 X   P   P   K   F   X   T   X   A   N   X   V   E   X   X   G 4810           4820           4830           4840
           *              *              *              *
TGT TGG GCN GAA GGC CTC CCN TAT TNC ANA TTA CCC CCC NGG GNT T
ACA ACC CGN CTT CCG GAG GGN ATA ANG TNT AAT GGG GGG NCC CNA A
 C>  W   A   E   G   L   P   Y   X   X   L   P   P   X   X   X>
```

FIG. 23I-2

```
               10             20             30             40             50
                *              *              *              *              *
CGRQR KXASS RLRGC GAAAG RLQGS GSGTC RRAKV MLAVS LNWRL GVVPR 60             70             80             90            100
                *              *              *              *              *
RPKND GPYSK GGKDT AGTDG ALVCR RQSIP EEFRG ITMVE LIKRE GSTLG 110            120            130            140            150
                *              *              *              *              *
LTISG GTDKD GKPRV SNLRP GGLAA RSDLL NVGDY IRSVN GIRLT RLRHD 160            170            180            190            200
                *              *              *              *              *
EIITL LKNVG ERVVL EVEYE LPPPA PENNP RIISK TVDVS LYKEG NSFGF 210            220            230            240            250
                *              *              *              *              *
VLRGG AHEDL HKSRP LVLTY VRPGG PANRE GSLKV GDRLL SIXGI PLHGA 260            270            280            290            300
                *              *              *              *              *
SHATA IATLQ QCSHE ALFQV EYDVA TPDTV ANASG PLVVE IAKTP GSALG
```

FIG. 24A-1

```
           310         320         330         340         350
             *           *           *           *           *
ISLTT GSHRN KPAIT IDRIK PASVV DKNGA LHAGE HILAI DGTST EHCSL 360         370         380         390         400
             *           *           *           *           *
VEATK LLASV TEKVR LEILP APQSR RPLKP PEAVR IQRSE QLHHW DPCVP 410         420         430         440         450
             *           *           *           *           *
SCHSP RPSHC RAPTW APGGQ DQSRS VSSTP FSSPT MNPAF PCANA STLPR 460         470         480         490         500
             *           *           *           *           *
GPMSP RTTAG RRRQR RKEHR SSLSL ASSTV GPGGQ IVHTE TTEVV LCGDP 510         520         530         540         550
             *           *           *           *           *
LSGFG LQLQG GIFAT ETLSS PPLVR FIEPD SPAER CGLLQ VGDRV LAING 560         570         580         590         600
             *           *           *           *           *
IATED GTMEE ANQLL RDAAL ARKIV LEIEF DVAES VIPSS GTFHV KLPKR
```

FIG. 24A-2

```
         610        620        630        640        650
          *          *          *          *          *
RGVEL GITIS SASRK RGEPL IISDI KKGSV AHRTG TLEPG DKLLA IDNIR 660        670        680        690        700
          *          *          *          *          *
LDHCP MEYAV QILPQ CEDLV KLKIR KDEDN SDEQE SSGAV SYTVE LKRYG 710        720        730        740        750
          *          *          *          *          *
GPLGI TISGT EEPFD PIIIS GLTKR GLAER TGASM LGTAY WPSXS VSLKG 760        770        780        790        800
          *          *          *          *          *
RPLSE AIHLL QVAGE TVTLK IKKQL DRPLL PRQSG SLSEA SDVDE DPPEA
```

FIG. 24A-3

```
           810         820         830         840         850
            *           *           *           *           *
     LKGGL LTTHF SPAVP SVDSA VESWG SSATE GGFGG SGSYT PQVAV RSVTP 860         870         880         890         900
            *           *           *           *           *
     QEWRS SRLKS SPPPL EPRRT SYTPG PTDES FPEEE EGDWE PPMSP APGPA 910         920         930         940         950
            *           *           *           *           *
     REEGF WRVLG EALED LESCG QSELL RELEA SIMTG TVQSV AVDGR PGSRP 960         970         980         990         1000
            *           *           *           *           *
     WRRSR EVGTS PEDLQ ELLLP TPLEM HRVTL HKDPV RNDFG FSVSD GLLEK 1010        1020        1030        1040        1050
            *           *           *           *           *
     GVYVH TVRID GPAQH GGLQP FDRLL QVNHV RTRDF DCCLA VPLLA ELGXP
```

FIG. 24B

UNTITLED
ALIGNMENT

| | | |
|---|---|---|
| GRIP  | ---------------------------------MIAVS | 5 |
| GRIP2 | cgrqrkxassrlrgcgaaagrlqgsgsgtcrrakvMIAVS | 40 |
| GRIP  | FKCRCQILRRLTKDESRYTKSASQTKPPDGALAVRRQSTP | 45 |
| GRIP2 | LNWRLGVVRRRPKNDGFESKGGKDTAGTDGALVCRRQSTP | 80 |
| GRIP  | EEFKGSTVVELMKKEGTTLGLTVSGGIDKDGKERVSNLRQ | 85 |
| GRIP2 | EEFRGITMVELIKREGSTLGLTISGGIDKDGKERVSNLRP | 120 |
| GRIP  | GGIAARSDQLDVGEYIKAVDGINLAKFRHDEIISLLKNVG | 125 |
| GRIP2 | GGLAARSDLLNVGEYFRSVNGERLTRDREDEIITLLKNVG | 160 |
| GRIP  | SPVVLEVEKELEF-VSIQGSSVMFRTVEVTLHKEGNTEGE | 160 |
| GRIP2 | EEVVLEVEVELEEpAPENNPRIISKTVDVSLYKEGNSEGE | 200 |
| GRIP  | VIRGGERDDRNRSBFVVITCVERGGPADREGTIKPGDRLL | 160 |
| GRIP2 | VLRGGEEESLERSREIVLTYVREGGEANREGSLKVGDRLL | 200 |
| GRIP  | SVDGIRLLGTTHAEEMSILNQEGQEATLLIEYDVSVMDSV | 244 |
| GRIP2 | SIXGIPLEGASHATAIATLQQCSHEALFQVEYDCATPDTV | 280 |
| GRIP  | ATASGPLLNBVAKTEGASLGVALTISVCCNKQVIVIDKIK | 284 |
| GRIP2 | ANASGPLVVEIARTEGSALGISLTIGSHRNKPAITIERIK | 320 |
| GRIP  | SASIADRCGALRVGDHLLSIDGTSMEYCTLAEATQFLANT | 324 |
| GRIP2 | PASVVDKNGAEDAGEEILAIDGTSTEEESLVEATKLLASV | 360 |
| GRIP  | TDQVKLEILEHHQTRLALKGPDHMKIQPSDRQLPWDPWAS | 364 |
| GRIP2 | TFKVRLETTEAPQSRRPLKPPEAMRIQRSEQLHHWDPCVP | 400 |
| GRIP  | SQCSVHTNHHHNPhhpdhcrvpalgfpkaltpnsppamvs | 404 |
| GRIP2 | SCHSPRPSHCRAPtwapggqdqarsvsstpfssprmnpaf | 440 |
| GRIP  | sssptsmasaysslsslnmgTlprslystSPRGTMMRRRLKK | 444 |
| GRIP2 | pcanastlprgpm---------------SPRTTAGRRRCRR | 466 |

FIG. 25A

UNTITLED

```
GRIP    KDEKSSLSLASSTVGLAEQVHHTETTEVVLTADPVEGFGI        484
GRIP2   KEERSSLSLASSRVGPGEQIVHTETTEEVLCGDEISGFGL        506

GRIP    GLQGSVFRTEILSSEPLISYIEADSEAERCGVLCIGERVM        524
GRIP2   GLQEGIERTEILSSEPLVRFLEPDSEAERCGLLQVGERVL        546

GRIP    NINGLPREDSTEEEANQLLPDSSITSKVILEIEFDVRSSV        564
GRIP2   KINGEATEDGTMEEANQLLRDAALARKIVLEIEEDVAESV        586

GRIP    LPGGGTFIVKLRKKHSVERGITISSPSSRKpGDPLVLSDI        604
GRIP2   IPSSGTEHVKDSKRRGVBLGITISSASRKR-SEPLILSDI        625

GRIP    KKGSVAERTGTLELSDELLAIDNIRLDSCSMEDAVQILQO        644
GRIP2   KKQSVAFRTGTLEPGDELEAIDNIRLDHCPMEYANGELPQ        665

GRIP    GEDLVELFIRKLEDNSDEQESSGAIIMIVELKRVCGFLGI        684
GRIP2   CEDLVKLKIRKDEDNSDEGESSGAVSMIVELKRVGGPIGI        705

GRIP    TESGTEEFEDRIIISSLTKGGLAERTGAIHIGDRIIAINS        724
GRIP2   TISGTEEPEDPIIISGLTKRGLABRIGASMLGTAYWESXS        745

GRIP    SSLKGKPISEAIELLQMAGETVTLKIKKQTDaqpasspkk        764
GRIP2   VSLNGRRLSEVIELLQVAGETVILKIKKQLDrpllprqsg        785

GRIP    IpipshsSDLGDGEEDPSPIQRPGKLSDVYPSTVPSVESA        804
GRIP2   sl-----SEASDVDEDPPEALKGGLLTTHFSPAVPSVDSA        820

GRIP    VDSWDGSGIDARYGSQGITFQTSGYNFNIYDWRSPKKRAS        844
GRIP2   VESWGSSATEGGEGGSGSYTPQVAVRSVIPQEWRSSRLKS        860

GRIP    LSPVPKPRSQTYPDVGLSNEDWDRSTASGFAGASDSADAE        884
GRIP2   SPEPLEPRRTSYTPGPTDESFPEEEEGDWEPPMSPAPGPA        900

GRIP    QEENEWSQAIEDLETCGQSGiIreIeatimscstmslnhe        924
GRIP2   REEGEWRVLGEALEDLESCGcselIreleasimtqtvqsv        940

GRIP    lptarsqlgrqasfqerensrphysqttrsntlpsdvgRK        964
GRIP2   avdgrpgsrpw------------------------RR    953
```

FIG. 25B

UNTITLED

GRIP  SVTLRKMK QFIKEIMSPTBVELHKVTLYKDSGMEDEGFSV
GRIP 2 SREVGTSP EDLQELLLPTBLEMHRVTLHKDPVRNDEGFSV

GRIP  ADGLLEKGV YVKNIBPAGBGDLGGLKBYDRLLQVM HVRTR
GRIP 2 SDGLLEKGV YVETVBIDGBAQHGGLQBFDRLLQVM HVRTR

GRIP  DEDCCLVVPLIRESGnkldlvismplasqksieqpalps
GRIP 2 DEDCCLAVPLLRElGxp-------------------------

GRIP  dwseqnsaffqqpshggnletreptntl
GRIP 2 ----------------------------

FIG. 25C

THERAPEUTIC USES OF GRIP AND GRIP-RELATED MOLECULES

CROSS-REFERENCE TO RELATED APPLICATION

The present application is a continuation-in-part of U.S. Provisional Application Ser. No. 60/041,016, filed Mar. 19, 1997, which is incorporated by reference herein in its entirety.

BACKGROUND OF THE INVENTION

1. Field of the Invention

The present invention generally relates to amino acid sequences that can interact with specified glutamate receptors. In one aspect, the invention features purified polypeptides that can interact with the glutamate receptors. In another aspect, the invention relates to isolated polynucleotides that encode the polypeptides. The present invention has a variety of applications, including use in detecting disorders in the nervous or reproductive system of a subject.

2. Background

The synaptic cytoskeleton plays a critical role in the formation and maintenance of synapses in the nervous system. Recent studies have identified a new protein motif called a PDZ domain which may be important in the targeting of proteins to cell-cell junctions. PDZ domains within cytoskeleton associated proteins mediate the interaction of the cytoskeleton with the C-termini of a variety of membrane proteins.

Synapses are specialized areas of cell-cell contact that are optimized for the efficient transduction of signals between neurons in the brain. Both the pre- and postsynaptic membrane have an elaborate cytoarchitecture that is essential for the functional organization of the synapse. Neurons have many different types of synapses and the synaptic cytoskeleton is likely to play an important role in the localization of different receptors and ion channels to their appropriate synapses. A variety of studies on the neuromuscular junction and inhibitory synapses in spinal cord have shown that the cytoskeleton is intimately involved in the clustering of synaptic components at the postsynaptic membrane [Froehner, *Annul Rev. Neurosci.*, 16:347–368 (1993), Hall et al., *Cell/Neuron*, 72:99–121 (1993), Gautam et al., *Nature*, 377:232–236 (1995), Kirsch et al., *Nature*, 266:745–748 (1993), Meyer et al., *Neuron*, 15:563–572 (1993), Kirsch et al., *J. Neuroscience*, 15:41484156 (1995)] For example, the synaptic peripheral membrane proteins rapsyn and gephryin have been shown to play a critical role in the synaptic targeting of nicotinic acetylcholine receptors and glycine receptors, respectively [Froehner, *Annul Rev. Neurosci.*, 16:347–368 (1993), Hall et al., *Cell/Neuron*, 72:99–121 (1993), Gautam et al., *Nature*, 377:232–236 (1995), Kirsch et al., *Nature*, 266:745–748 (1993), Meyer et al., *Neuron*, 15:563–572 (1995), Kirsch et al., *J. Neuroscience*, 15:41484156 (1995)]. The cytoskeletal proteins involved in the formation of excitatory synapses in the central nervous system, however, have only recently begun to be identified [Kornau et al., *Science*, 269: 1737–1740 (1995), Niethammer et al., *J. Neurosci*, 16:2157–2163 (1996), Ehlers et al., *Curr. Opin. in Cell Biol.*, 8:490495 (1996)].

Ionotropic glutamate receptors mediate the majority of excitatory synaptic transmission in the central nervous system and play important roles in the synaptic plasticity underlying learning and memory and neural development, and in the excitotoxicity associated with stroke and other neurological disorders [Hollmann et al., *Annul Rev. Neurosci.*, 17:31–108 (1994), Seeburg, *The TINS/TIPS Lecture. Trends Neurosci.*, 16:359–365 (1993), Bliss et al., *Nature*, 361:31–39 (1993), Linden, *Neuron*, 12:457472 (1994), Choi, *Trends Neurosci.*, 18:58–60 (1995)]. These receptors can be divided into three different subclasses, AMPA (α-amino-3-hydroxy-5-methyl-isoxazole4-propionic acid), kainate and NMDA (N-methyl-D-aspartate) receptors, based on their physiological and pharmacological properties [Hollmann et al., *Annul Rev. Neurosci.*, 17:31–108 (1994), Seeburg, *The TINS/TIPS Lecture. Trends Neurosci.*, 16:359–365 (1993)]. AMPA and kainate receptors mediate rapid synaptic transmission while NMDA receptors are important in activity-dependent plasticity in the nervous system and in excitotoxicity. These receptors are ligand-gated ion channels consisting of oligomeric complexes of homologous subunits [Hollmann et al., *Annul Rev. Neurosci.*, 17:31–108 (1994), Seeburg., *The TINS/TIPS Lecture. Trends Neurosci.*, 16:359–365 (1993)]. Molecular cloning studies have demonstrated that each receptor subclass is composed of several distinct subunits. The GluR14 subunits belong to the AMPA subclass, the GluR5-7 and KA1-2 subunits belong to the kainate subclass, while the NR1 and NR2A-D subunits belong to the NMDA subclass of ionotropic glutamate receptors [Hollmann et al., *Annul Rev. Neurosci.*, 17:31–108 (1994), Seeburg, *The TINS/TIPS Lecture. Trends Neurosci.*, 16:359–365 (1993)]. These subunits have been proposed to have a large extracellular N-terminal domain, three transmembrane domains, and an intracellular C-terminal domain [Molnar et al., *Neuroscience*, 53:307–326 (1993), Tingley et al., *Nature*, 364:70–73 (1993), Wo et al., *Proc. Natl. Acad. Sci. USA*, 91:7154–7158 (1994), Hollmann et al., *Neuron*, 13:1331–1343 (1994), Stem-Bach et al., *Neuron*, 13:1345–1357 (1994), Bennett et al., *Neuron*, 14:373–384 (1995), Wood et al., *Proc. Natl. Acad. Sci., USA*, 92:48824886 (1995), Roche et al., *Neuron*, 16:1179–1188 (1996)] Glutamate receptor diversity is generated through the differential combination of subunits as well as alternative splicing and editing of glutamate receptor mRNAs [Hollmann et al., *Annul Rev. Neurosci.*, 17:31–108 (1994), Seeburg, *The TINS/TIPS Lecture. Trends Neurosci.*, 16:359–365 (1993)].

Iontophoretic mapping, immunocytochemistry and immunoelectron microscopy studies have demonstrated that ionotropic glutamate receptors are specifically localized to the postsynaptic membranes of CNS neurons [Jones et al., *Neuron*, 7:593–603 (1991), Petralia et al., *Neurol.* 318:329–354 (1992), Craig et al., *Neuron*, 10:1055–1068 (1993)., Huntley et al., *J. Neurosci.*, 14:3603–3619 (1994), Martin et al., *Neuroscience*, 53:327–358 (1993), Petralia et al., *J. Comp. Neurol.*, 349:85–110 (1994a), Petralia et al., *J. Neurosci*, 14:667–696 (1994b), Petralia et al., *J. Neurosci.*, 14:6102–6120 (1994c), Tachibana et al., *J. Comp. Neurol.*, 344:431–454 (1994), Lau et al., *J. Biol. Chem.*, 270:20036–20041 (1995), Roche et al., *Neuroscience*, 69:383–393 (1995), Craig et al., *Proc. Natl. Acad. Sci. USA*, 91:2373–12377 (1994), Nusser et al., *Neuroscience*, 61:421 427 (1994)]. Although both AMPA and NMDA glutamate receptors are clustered at excitatory synapses, neither is present at inhibitory synapses enriched with GABAA receptors [Petralia et al., *J. Neurosci.*, 14:667–696 (1994b), Lau et al., *J. Biol. Chem.*, 270:20036–20041 (1995), Craig et al., *Proc. Natl. Acad. Sci. USA*, 91:2373–12377 (1994)]. This specific concentration and segregation of excitatory and inhibitory neurotransmitter receptor subunits within a neuron requires innervation of the postsynaptic cell but does not require synaptic activity [Craig et al., *Proc. Natl. Acad. Sci.*

USA, 91:2373–12377 (1994)]. Several recent studies have suggested that NMDA receptors directly or indirectly interact with the neuronal cytoskeleton. For example, actin filament stabilization prevents $CA^{2+}$-dependent inactivation of NMDA channels [Rosenmund et al., Neuron, 10:805–816 (1993)], and NMDA receptor responses are sensitive to cytoskeletal strain [Paoletti et al., Neuron, 13:645–655 (1994)]. In addition, NMDA receptor subunits are enriched in the PSD and are resistant to solubilization in nonionic detergents [Lau et al., J. Biol. Chem., 270:20036–20041 (1995), Brose et al., J. Biol. Chem., 268:22663–22671 (1993)]. Recent experiments have shown that the C-termini of NMDA receptors are involved in the subcellular targeting of the receptors and directly interact with synaptic cytoskeletal proteins [Kornau et al., Science, 269:1737–1740 (1995), Niethammer et al., J. Neurosci, 16:2157–2163 (1996), Ehlers et al., Science, 269:1734–1737 (1995)]. Studies on NMDA receptor expression in fibroblasts have demonstrated that the NR1 subunit is clustered into highly concentrated receptor rich domains near the plasma membrane [Ehlers et al., Science, 269:1734–1737 (1995)]. An alternatively spliced region within the C-terminus of the NR1 subunit, the C1 cassette, is both necessary and sufficient for the localization of NR1 to these receptor-enriched domains, suggesting that the C1 cassette directly interacts with cytoskeletal proteins [Ehlers et al., Science, 269:1734–1737 (1995)]. Interestingly the C1 cassette contains several phosphorylation sites [Tingley et al., Nature, 364:70–73 (1993)] and PKC phosphorylation of this region rapidly disperses the NR1 clusters, perhaps by disrupting the association of NR1 with the cytoskeleton [Ehlers et al., Science, 269:1734–1737 (1995). Kornau et al., Science, 269:1737–1740 (1995)] have recently demonstrated that specific subunits of the NMDA receptor directly interact with the synaptic cytoskeletal associated protein PSD-95 or SAP90 [Cho et al., Neuron, 9:929–942 (1992), Kistner et al., J. Biol. Chem., 268:45804583 (1993)]. PSD95/SAP90 specifically binds to the C-termini of the NR2A, NR2B and NR2D subunits and certain splice variants of the NR1 subunit (NR1d, NR1e) [Kornau et al., Science, 269:1737–1740 (1995), Niethammer et al., J. Neurosci., 16:2157–2163 (1996)]. PSD-95/SAP90 is colocalized with the NR2B subunit in excitatory synapses in neurons and is highly enriched in the postsynaptic density [Kornau et al., Science, 269:1737–1740 (1995), Cho et al., Neuron, 9:929–942 (1992)], where it is well-poised to anchor or target NMDA receptors. PSD-95/SAP90 has an intriguing structure which includes three repeats in the N-terminal region of a newly identified protein motif called a PDZ domain [Cho et al., Neuron, 9:929–942 (1992)], named after three proteins containing this motif, PSD-95, Dlg-A and ZO-1 [Cho et al., Neuron, 9:929–942 (1992), Kennedy, Trends in Biochem. Sci., 20:350 (1995), Gomperts, Cell, 84:659–662 (1996)]. These domains have also been called discs-large-homology regions (DHR) or GLGF repeats (referring to a conserved amino acid sequence in the repeat) [Cho et al., Neuron, 9:929–942 (1992), Kennedy, Trends in Biochem. Sci., 20:350 (1995), Gomperts, Cell, 84:659–662 (1996)]. In addition, PSD95/SAP90 has a arc-homology 3 (SH3) domain and a domain homologous to a yeast guanylate kinase in the C-terminal region [Cho et al., Neuron, 9:929–942 (1992), Kistner et al., J. Biol. Chem., 268:45804583 (1993), Kennedy, Trends in Biochem. Sci., 20:350 (1995), Ponting et al., Trends in Biol. Sci., 20:102–103 (1995), Kim, Cell Biol., 7:641–649 (1995), Gomperts, Cell, 84:659–662 (1996)].

PDZ domains are motifs of approximately 90 amino acids [Cho et al., Neuron, 9:929–942 (1992)] present in a number of homologous proteins including the Drosophila septate junction discs-large protein (Dlg-A) [Woods et al., Cell, 66:451464 (1991)], the mammalian tight junction protein ZO-1 [Itoh et al., J. Cell Biol., 121:491–502 (1993)], the C. elegans epithelial cell junction proteins LIN-2A [Hoskins et al., The C. elegans vulval induction gene lin-2 encodes a member of the MAGUK family of cell junction proteins Development, 122:97–111 (1996)] and Lin-7 [Simske et al., Cell, 85:195–204 (1996)] as well as a variety of other proteins including protein tyrosine phosphatases, nitric oxide synthase, and the mammalian neuromuscular junction protein syntrophin [Ponting et al., Trends in Biol. Sci., 20:102–103 (1995)]. PDZ domains are now thought to mediate a variety of protein—protein interactions [Kornau et al., Science, 269:1737–1740 (1995), Gomperts, Cell, 84:659–662 (1996)].

The interaction of NMDA receptor subunits with PSD-95/SAP90 occurs between the final 7 C-terminal amino acids of the NMDA receptor subunits and the first and second domains of PSD-95 [Kornau et al., Science, 269:1737–1740 (1995), Niethammer et al., J. Neurosci, 16:2157–2163 (1996)]. The common motif present in the C-termini of NMDA receptor subunits which interact with the PDZ domains consists of a threonine or serine followed one amino acid later by a valine (referred to as a T/SXV motif) [Kornau et al., Science, 269:1737–1740 (1995), Niethammer et al., J. Neurosci, 16:2157–2163 (1996)]. Interestingly, such motifs are found in a wide variety of cell surface receptors and ion channels [Kornau et al., Science, 269:1737–1740 (1995), Niethammer et al., J. Neurosci, 16:2157–2163 (1996)]. Indeed, Kim et al. [Kim et al., Nature, 378:85–88 (1995)] have shown that such a motif in the Shaker-type K+-channel subunit Kv1.4 interacts with the PDZ1 and PDZ2 domains of PSD-95/SAP90, with mutations of the conserved threonine completely abolishing the interaction.

It has become increasingly clear that PSD-95/SAP90 is but one of a large family of structurally related proteins. In addition to Dlg-A and ZO-1, which share similar overall domain structures, three additional PSD-951SAP90 family members, SAP97 [Muller et al., J. Neurosci, 15:2354–2366 (1995)], SAP102 [Muller et al., Neuron, 17:255–265 (1996), Lau et al., J. Biol. Chem., 271:21622–21628 (1996)] and PSD-93/Chapsyn [Brenman et al., Cell, 84:757–767 (1996), Kim et al., Neuron., 17:103–113 (1996)] have been identified in the mammalian central nervous system. These homologous proteins may serve functions similar to PSD-95/SAP90 [Ehlers et al., Curr. Opin. in Cell Biol, 8:490495 (1996), Gomperts, Cell, 84:659–662 (1996). For example SAP102 has recently been shown to interact with NMDA receptor complexes in rat brain [Muller et al., Neuron, 17:255–265 (1996), Lau et al., J. Biol. Chem., 271:21622–21628 (1996)]. A common feature of these PSD-95/SAP90 family members is that they localize to specialized sites of cell-cell contact including septate junctions in Drosophila (Dlg-A), vertebrate tight junctions (ZO-1), and synapses in the mammalian nervous system (PSD-95/SAP90, SAP97, SAP102) [Ehlers et al., Curr. Opin. in Cell Biol., 8:490495 (1996), Kim, Cell Biol., 7:641–649 (1995), Gomperts, Cell, 84:659–662 (1996)]. Members of this family appear to be involved in both localizing cellular proteins and assisting in the establishment of cell polarity. That PSD-95/SAP90 family members might be important for synaptic organization in the mammalian CNS is suggested by the fact that mutations in the homologous Drosophila protein, Dlg-A, alter the structure of glutamatergic synapses [Lahey et al., Neuron., 13(4):823–35 (1994)].

SUMMARY OF THE INVENTION

The present invention relates to novel GRIP and GRIP-related proteins called (Glutamate Receptor Interacting Proteins). GRIP has been found to bind a specified glutamate receptor. In one aspect, the invention features isolated polynucleotides that encode GRIP or GRIP-related proteins. In another aspect, the invention features isolated GRIP or GRIP-related proteins. Further provided are antibodies that can bind the polypeptides. The present invention has a variety of uses, including detecting and analyzing certain neurological disorders and fertility in a subject.

We have discovered GRIP and GRIP-related proteins. GRIP proteins are new members of the PDZ-containing family of proteins. The GRIP proteins have been found to include multiple PDZ domains and no apparent catalytic domain. GRIP proteins appear to serve as an adapter protein that links AMPA receptors to the synaptic cytoskeleton and may be critical for the clustering of AMPA receptors at excitatory synapses in the brain.

For example, we have found that GRIP is expressed in testes. As will be more fully discussed below, GRIP apparently has important functions in the nervous system and in sperm formation (spermatogenesis).

As will be pointed out below, an exemplary GRIP-related protein is GRIP2: a protein that is substantially equivalent to GRIP.

It is recognized that neurotransmitter receptors mediate signal transduction at the postsynaptic membrane of synaptic connections between neurons in both the central and peripheral nervous systems. It is further recognized that neurotransmitter receptors are highly concentrated at the synaptic membrane and this clustering of the receptors plays an important role in the efficient transduction of signals at synapses. This invention comprises a novel family of proteins involved in neurotransmitter receptor functions, wherein this family of proteins are called GRIPs. More specifically, we have identified a synaptic PDZ domain-containing protein designated as GRIP, that specifically interacts with the non-NMDA glutamate receptors and appears to be involved in the synaptic clustering of these receptors. GRIP has been found to be a cytoskeletal-associated protein that directly binds to the C-termini of the GluR2 and 3 subunits of the non-NMDA glutamate receptors via a new protein motif called a PDZ domain. PDZ domains mediate protein-protein interactions in many proteins and appear to be involved in the proper subcellular targeting of membrane proteins. GRIP contains seven PDZ domains, designated PDZ1 through PDZ7, which appear to crosslink receptors or link them to other synaptic proteins. GRIP may be a critical component in the formation and maintenance of excitatory synapses in the brains.

For example, we describe the isolation of GRIP, a PDZ domain-containing protein. In one aspect, the GRIP protein specifically interacts with the C-terminus of the GluR2 and GluR3 subunits of AMPA receptors, the major excitatory neurotransmitter receptors in brain. GRIP contains seven PDZ domains and no apparent catalytic domain suggesting that it is a member of a new family of PDZ domain containing-proteins that crosslink AMPA receptors or serve as adapter proteins to link the receptors to other proteins. Moreover, GRIP appears to play an important role in the targeting of AMPA receptors to excitatory synapses.

In one embodiment, the present invention provides a novel family of proteins, called GRIPs (e.g., GRIP), that specifically interact with the non-NMDA glutamate receptors and appear to be involved in the synaptic clustering of these receptors.

The present invention also provides isolated nucleic acid molecules that encode proteins that bind the C-termini of an AMPA glutamate receptor. Preferred are nucleic acid molecules encoding GRIP, GRIP2, or fragments and derivatives thereof.

The present invention also provides different forms of GRIP, each of which function similarly and also have substantial sequence homology. As will be shown below, GRIP and GRIP2 show significant sequence homology at the amino acid level.

The present invention also provides an isolated protein which is GRIP or GRIP2.

The present invention also provides vectors (i.e. recombinant vectors) comprising an isolated nucleic acid molecule encoding GRIP, GRIP2, or a fragment thereof.

This invention further provides vectors such as plasmids comprising a DNA molecule encoding GRIP or GRIP2, adapted for expression in a bacterial cell, a yeast cell, an insect cell or a mammalian cell which additionally comprises the regulatory elements necessary for expression of the DNA in the bacterial, yeast, insect or mammalian cells operatively linked to the DNA encoding GRIP or GRIP2 to permit expression thereof. In particular, mammalian cells are provided comprising a DNA molecule encoding GRIP or GRIP2.

This invention also provides nucleic acid probes comprising .a nucleic acid molecule capable of specifically hybridizing with a unique sequence included within the sequence of a nucleic acid molecule encoding GRIP or GRIP2.

This invention also provides a method of detecting expression of GRIP by detecting the presence of mRNA coding for GRIP which comprises obtaining total mRNA from the cell and contacting the mRNA so obtained with a nucleic acid probe comprising a nucleic acid molecule specifically hybridizing with a unique sequence included within the sequence of a nucleic acid molecule encoding GRIP under hybridizing conditions, detecting the presence of mRNA hybridized to the probe, and thereby detecting the expression of GRIP by the cell. Related methods can be used to detect GRIP2 expression at the mRNA level.

This invention provides an antisense oligonucleotide having a sequence capable of binding specifically with any sequences of an mRNA molecule which encodes GRIP or GRIP2 so as to prevent translation of the mRNA molecule. In some embodiments, the antisense oligonucleotide will be capable of specifically binding both GRIP and GRIP2 if desired.

This invention provides a transgenic nonhuman mammal expressing DNA encoding GRIP, GRIP2 or a fragment thereof. Transgenic animals encompass any animal, including, but not limited to, an amphibian, bird, fish, insect, reptile, or mammals, such as mouse, rat, bovine, porcine, and sheep.

This invention farther provides a transgenic nonhuman mammal comprising a homologous recombination knockout of native GRIP or GRIP2.

This invention further provides a transgenic nonhuman mammal whose genome comprises antisense DNA complementary to DNA encoding GRIP or GRIP2 so placed as to be transcribed into antisense mRNA which is complementary to mRNA encoding GRIP and which hybridizes to mRNA encoding GRIP or GRIP2 thereby reducing its translation. The transgenic nonhuman animal may also include suitable GRIP or GRIP2 fragments if desired.

This invention provides antibodies, both polyclonal and monoclonal, directed to GRIP or GRIP2. In some instances, the antibodies will be capable of binding both GRIP and GRIP2.

This invention provides a method of determining the physiological effects of expressing varying levels of human GRIP which comprises producing a transgenic nonhuman animal whose levels of GRIP expression are varied by use of an inducible promoter which regulates GRIP expression. Related methods can be used to detect the effects of expressing varying kinds of human GRIP2.

This invention also provides a method of determining the physiological effects of expressing varying levels of human GRIP or GRIP2 which comprises producing a panel of transgenic nonhuman animals each expressing a different amount of GRIP or GRIP2. Related methods can be performed with GRIP or GRIP2 fragments if desired.

This invention provides a method for diagnosing a predisposition to a disorder associated with the expression of a specific GRIP or GRIP2 allele.

This invention provides a method of preparing isolated GRIP which comprises inducing cells to express GRIP, recovering GRIP from the resultant cells and purifying the protein so recovered. Related methods can be used to prepare isolated GRIP2.

This invention further provides a method of preparing isolated GRIP which comprises inserting nucleic acid encoding GRIP in a suitable vector, inserting the resulting vector in a suitable host cell, recovering the protein produced by the resulting cell, and purifying the protein so recovered. Related methods can be used to prepare isolated GRIP2.

The present invention further relates to methods of treating diseases and disorders, preferably neurological diseases and disorders, in a human or animal through regulating the synaptic targeting of AMPA receptors (e.g., monitoring and controlling excitatory synaptic transmission) by altering the activity and/or the levels of GRIP or GRIP2. For example, altering GRIP or GRIP-related function may involve enhancing or inhibiting excitatory synaptic transmission. Such methods can be used to treat many neurodegenerative diseases, including stroke, ALS, Alzheimer's disease, Parkinson's disease and Huntington's disease. The isolated DNA encoding GRIP and isolated GRIP will also be useful for the treatment of muscular dystrophies such as Duchenne muscular dystrophy and motility disorders such as irritable bowel syndrome. Related methods can be used to treat the neurological disorders altering levels of GRIP2 or using an isolated DNA encoding GRIP2 or a suitable fragment thereof.

The present invention also provides methods of enhancing or otherwise altering memory by using GRIP- or GRIP2-related technology to regulate neurotransmitter receptor function.

Another embodiment of the invention involves a method of screening for infertility, which comprises detecting the presence of antibodies that bind to a polypeptide comprising an amino acid sequence encoded by a nucleic acid sequence from the group consisting of GRIP or GRIP2 in its entirety, specific PDZ binding domains, or any antigenic portion thereof (see FIGS. 2, 3, 11A–11C and 12A–12D). The presence of such antibodies is taken as indicative of infertility.

Polypeptides of the present invention may be used to modulate the behavior of sperm. Agents (antagonists and agonists) may be identified that bind to the sperm, preferably via interaction with a polypeptide comprising an amino acid sequence encoded by a nucleic acid sequence from the group consisting of GRIP or GRIP2 in its entirety, specific PDZ binding domains, or any antigenic portion thereof (see FIGS. 2, 3, 11A–11C and 12A–12D) of the present invention. Further, the means of affecting fertility, or contribution to fertility, can comprise either stimulating or inhibiting the binding of a particular agent to a polypeptide as define herein, (e.g., a polypeptide encoded by a nucleic acid comprising GRIP as defined herein. Such a method may have a practical application as a means of fertility control (e.g., spermicide use, which prevents sperm form migrating towards or fertilizing an egg), but alternately, as a means of enhancing fertility or contributing to fertility.

Another embodiment of the present invention is directed to an antigenic polypeptide, which is useful as an immunocontraceptive agent or for the diagnosis of infertility, as described above. Preferably, the peptide comprises an antigenic fragment of less than about 30 amino acids in length of a polypeptide comprising an amino acid sequence encoded by a nucleic acid comprising a sequence selected from the group consisting of GRIP or GRIP 2 in its entirety, specific PDZ binding domains, or any antigenic portion thereof (see FIGS. 2, 3, 11A–11C and 12A–12D of the drawings).

The invention also provides a method of screening drugs to identify drugs which specifically interact with, bind to, and/or modify the physiological effects of GRIP or GRIP2. This invention also provides a pharmaceutical composition comprising GRIP or GRIP 2 with or without a drug identified by this method.

Additionally provided are kits that include components for detecting and analyzing GRIP or GRIP2 expression in tissue, e.g., specified neurons and reproductive cells. Further provided are kits that include agents capable of modulating sperm formation and particularly fertility in a subject such as a primate, e.g., a mammal (e.g., a domesticated animal such as a cat, dog, or horse) and more particularly a human patient. The agents can include any of the agents described above, e.g., immunological agents and particularly antibodies capable of specifically binding GRIP, a fragment thereof, GRIP2, or a fragment thereof.

Other aspects of the invention are disclosed infra.

BRIEF DESCRIPTION OF THE DRAWINGS

FIG. 3 is an illustration of the amino acid sequence of GRIP (SEQ ID NO. 2). The GRIP cDNA encodes a 1112 amino acid protein that contains seven PDZ domains and no obvious catalytic domain. The PDZ domains are indicated by underlining, the GLGF-like repeats and the conserved arginine/lysine residues are indicated by stippling.

FIGS. 4A–4C depict amino acid sequence alignment of the PDZ domains of GRIP. The PDZ domains of GRIP are aligned with the PDZ domains of dlg, PSD-95/SAP90 and SAP97. The conserved amino acids in PDZ domains are indicated by stippling and the GLGF-like repeats and the conserved arginine/lysine residues are indicated by the asterisks.

FIGS. 8A–8E are representations of Western blots showing distribution of GRIP protein in rat tissues. Antibodies were generated against a GRIP fusion protein and a GRIP peptide was used to identify the GRIP protein in the rat tissues. OLF.-olfactory bulb; CTX-cortex; HPC.-hippocampus; CER.-cerebellum; S.C.-spinal cord.

FIGS. 11A–11C are drawings showing the nucleotide sequence of GRIP (SEQ ID NO: 1). Nucleotides are presented in the 5' to 3' orientation. Numbers represent the nucleotide numbering, starting with the first nucleotide.

FIGS. 12A–12D are drawings showing the deduced amino acid sequence of GRIP (SEQ ID NO: 2). Deduced amino acid sequence by translation of a long open reading frame is shown, along with the 5' and 3' untranslated regions. Numbers represent the amino acid numbering, starting with the first amino acid.

FIGS. 6A–16C are representations of photomicrographs showing immunofluorescence analysis with anti-GRIP antibodies on cryosections of adult rat testis. JH2493 refers to an anti-grip antibody.

FIGS. 22A–22I are drawings showing a GRIP 2 nucleotide sequence (SEQ ID NO. 47). Numbers above the sequence refer to nucleotide numbers.

FIGS. 23A–23I are drawings showing GRIP 2 nucleotide sequence (SEQ ID NO. 48) and conceptual translation (SEQ ID NO. 49) of the GRIP 2 nucleotide sequence.

FIGS. 24A–24B are drawings showing GRIP 2 protein seqeunce (SEQ ID NO. 50).

FIGS. 25A–25C are diagrams illustrating protein sequence comparison between GRIP and GRIP 2. The diagram highlights substantial arnino acid equivalency between GRIP and GRIP 2. Stippled boxes indicate amino acid sequence identity and hatched boxes show amino acid seqeunce similarity. Gaps have been introduced to optimize alignment.

DETAILED DESCRIPTION OF THE INVENTION

Figure 1A:
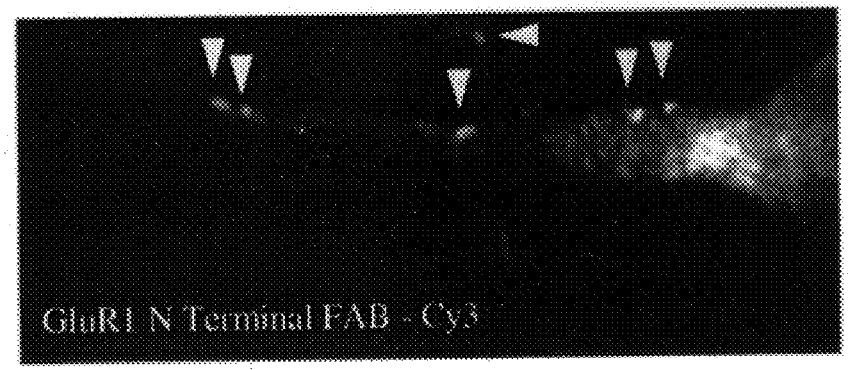
FIGS. 1A–1F are representations of photomicrographs depicting disruption of synaptic AMPA receptor clustering by over expression of the C-terminus of GluR2 in neurons. Transfections with C-terminal GluR1 (FIGS. 1A–1C). Transfections with C-terminal GluR2 (FIGS. 1D–1F).
Figure 1B:
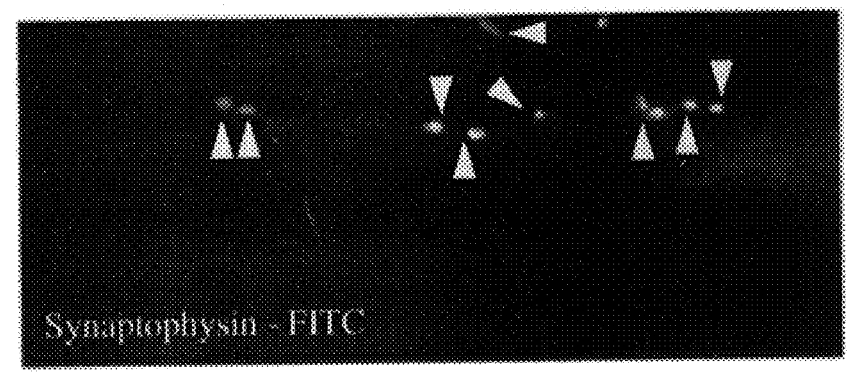
Figure 1C:
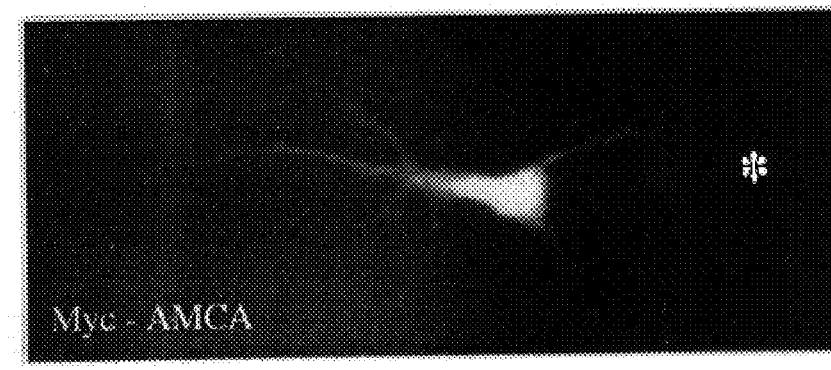
Figure 1D:
Figure 1E:
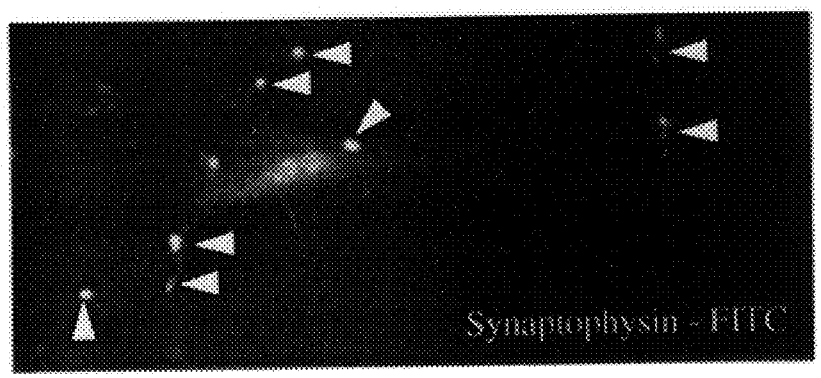
Figure 1F:
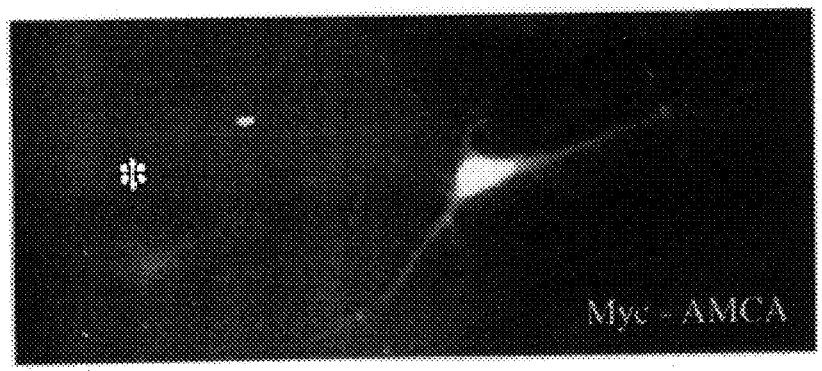

As discussed, the present invention relates to GRIP and fragments thereof, and GRIP2 and fragments thereof. Additionally provided are polynucleotides including sequence encoding GRIP or GRIP fragments, and polynucleotides including sequence encoding GRIP 2 and fragments thereof.

In one aspect, the present invention relates to polynucleotides including sequence that is substantially equivalent to the sequence of FIGS. 11A–11C (SEQ ID NO: 1). In another aspect, the invention relates to polynucleotides including sequence that is substantially equivalent to the sequence of FIGS. 22A–22E (SEQ ID NO. 47).

In another aspect, the invention features amino acid sequences that are substantially equivalent to the GRIP sequence shown in SEQ ID NO: 2. In another aspect, the invention provides amino acid sequences that are substantially equivalent to the GRIP 2 polypeptide sequence shown in SEQ ID. NO. 50. Further provided are molecules capable of detecting or modulating GRIP or GRIP 2 expression in the nervous or reproductive system of a subject.

It has been reported that synaptic clustering of postsynaptic neurotransmitter receptors is important for the efficiency of synaptic transmission. Recent studies on synaptic plasticity have suggested that the regulation of the synaptic targeting of AMPA receptors may be important for the modulation of synaptic function [Liao et al., Nature, 375 (6530):400–4 (1995), Isaac et al., Neuron., 15(2):427–34 (1995), Durand et al., Nature, 381(6577):71–5 (1996)]. Although peripheral membrane proteins involved in the synaptic aggregation of the nicotinic acetylcholine receptor, the glycine receptor, and the NMDA receptor have recently been characterized [Froehner, Annul Rev. Neurosci., 16:347–368 (1993), Hall et al., Cell/Neuron, 72:99–121 (1993), Gautam et al., Nature, 377:232–236 (1995), Kirsch et al., Nature, 266:745–748 (1993), Meyer et al., Neuron, 15:563–572 (1995), Kirsch et al., Neuroscience, 15:41484156 (1995), Kornau et al., Science, 269:1737–1740 (1995), Niethammer et al., J. Neurosci., 16:2157–2163 (1996)], the proteins involved in the clustering of AMPA receptors have yet to be identified.

As noted, the present invention discloses the identification of GRIP, a novel protein that specifically interacts with the GluR2 and GluR3 subunits of AMPA receptors. GRIP is a new member of the PDZ domain-containing protein family and contains seven PDZ domains and no apparent catalytic domain. The 4th and 5th PDZ domains are sufficient to interact with the GluR2 subunit. In contrast, the 1st, 2nd, 3rd and 7th PDZ domains do not appear to interact with the GluR2 subunit. These results indicate the different PDZ domains in GRIP may have distinct specificities for peptide substrates. The C-terminal seven amino acids of the GluR2 subunit appear to be critical for the interaction of GluR2 with GRIP. In addition, although the sequence of the GluR2 C-terminus does not contain the T/SXV consensus sequence that has been shown to be important for the NMDA receptor-PSD95/SAP90 interaction, a serine residue in this region of GluR2 is also important for its interaction with GRIP. The importance of this serine residue in the interaction of GluR2 with GRIP may indicate a potential role for protein phosphorylation in the regulation of GRIP-GluR2 interaction. Interestingly, the C-terminus of the GluR2 subunit has recently been shown to be alternatively spliced to give a variant of GluR2 that has a longer C-terminus with a sequence similar to GluR1 and GluR4 [kohler et al., *J. Biol. Chem.* 269(26): 17367–17370 (1994)]. In addition, the C-terminus of GluR4 has also been shown to be alternatively spliced to give both a long form, like GluR1, and a short for (GluR4c), like GluR2 and GluR3 [llo et al., *J. Neuro.*, 12(3):1010–1023 (1992)]. This suggests that alternative splicing of the C-terminus of AMPA receptor subunits may play a regulatory role in the clustering of AMPA receptors similar to that seen with the NMDA receptor [Ehlers et al., *Science*, 269:1734–1737 (1995)].

Figure 10:
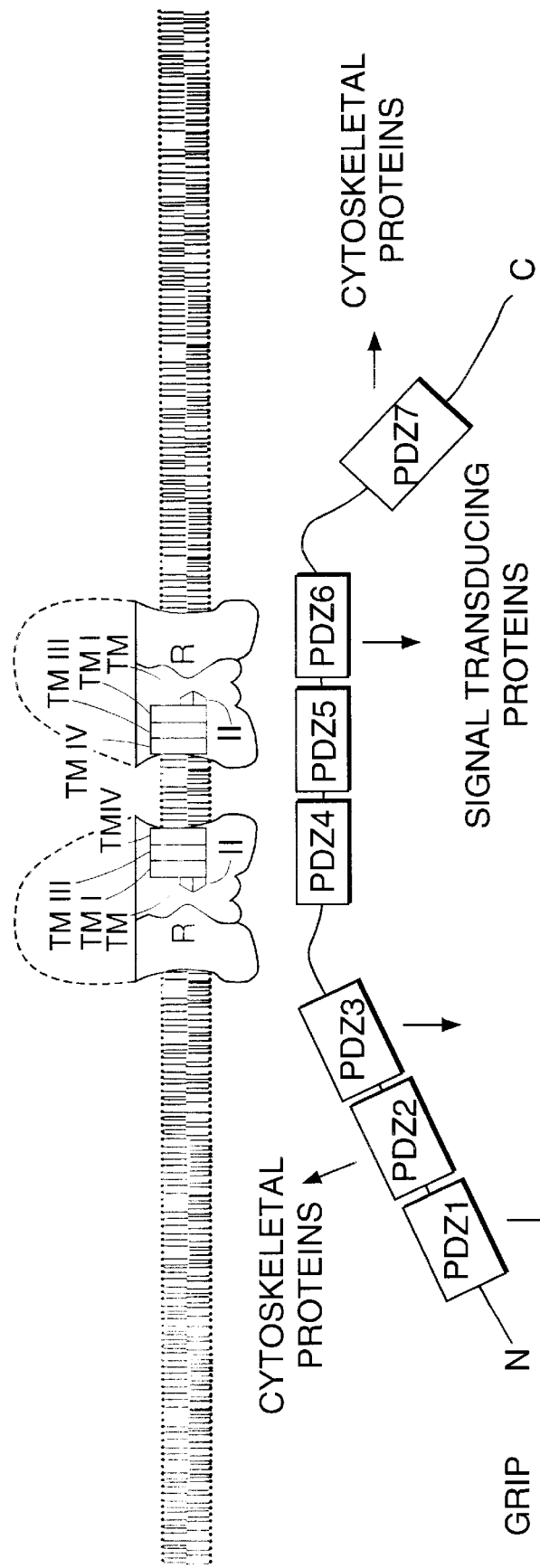
FIG. 10 is a schematic drawing showing a potential role of GRIP in excitatory synaptic function.

FIG. 10 is a schematic showing that GRIP contains seven PDZ domains that are involved in protein-protein interactions at the synapse. The 4th and 5th PDZ domains of GRIP interact with the GluR2 and GluR3 subunits and may crosslink AMPA receptors to form synaptic clusters. In addition, GRIP contains five other PDZ domains that may interact with many different synaptic cytoskeletal proteins or proteins involved in synaptic signal transduction.

In one aspect of the present invention, GRIP mRNA was found to be present in brain suggesting that it plays a role in neuronal function. Immunoblotting of various rat tissues demonstrates that the cytoskeleton associated 130 kDa GRIP protein is also exclusively expressed in brain including the cerebral cortex, olfactory bulb, hippocampus, cerebellum, and spinal cord. Interestingly, an immunologically related soluble protein with an apparent molecular weight of 90 kDa is present in most tissues examined. This protein may be a proteolytic breakdown product of the 130 kDa protein. However, the fact that the mRNA for GRIP is not observed in many non-neuronal tissues suggests that the 90 kDa protein may be the product of a GRIP-related gene. Immunocytochemical staining of hippocampal neurons with the GRIP fusion protein antibody demonstrated that GRIP is localized to neuronal dendrites and clusters at excitatory synapses. Although clustering of GRIP was seen in some neurons, not all AMPA receptor clusters contained high levels of GRIP staining. This may be due to a limited accessibility of the antibody to GRIP in the postsynaptic density, or alternatively, GRIP may be selectively localized at certain excitatory synapses. Antibodies against SAP102, a member of the PSD95/SAP90 family, also selectively label excitatory synapses [Muller et al., *Neuron*, 17:255–265 (1996)]. By analogy with SAP102, it is possible that additional members of the GRIP protein family which also may be involved in excitatory synaptic function.

As will be described in the discussion and examples which follow, over expression of the C-terminal region of GluR2 which interacts with GRIP dramatically decreased the number of AMPA receptor clusters in neurons without significantly effecting the number of synaptophysin positive synapses. Moreover, over expression of the C-terminal truncation mutant GluR2 ΔC, which does not interact with GRIP, did not disrupt AMPA receptor clusters. These results strongly suggest that the interaction of GluR2 with GRIP may be important in AMPA receptor clustering.

The exact role of GRIP in AMPA receptor clustering, however, is not completely understood. Studies on the NMDA receptor and K+-channels have suggested that the three PDZ repeats in the PSD-95/SAP90 family members could provide a mechanism for neurotransmitter receptor clustering by crosslinking receptors or anchoring them to the cytoskeleton [Kornau et al., *Science*, 269:1737–1740 (1995), Niethammer et al., *J. Neurosci.*, 16:2157–2163 (1996), Kim et al., *Nature*, 378:85–88 (1995)]. PSD95/SAP90 family members have also been shown to be involved in co-localizing cellular signal transduction machinery with NMDA receptors near the postsynaptic membrane (Brenrnan et al., *Cell*, 84:757–767 (1996)]. Neuronal nitric oxide synthase (nNOS) possesses a PDZ domain and can interact with PSD-95/SAP90 and PSD-93 through a PDZ-PDZ domain interaction [Brenman et al., *Cell*, 84:757–767 (1996)]. As nNOS is activated by $Ca^{2+}$ influx through NMDA receptors, their coupling via PSD-95/SAP90 could provide a possible mechanism for localized intracellular signaling upon activation of NMDA receptors. GRIP contains seven PDZ domains which may play a similar role to the PDZ domains in the PSD-95/AP90 family by crosslinking AMPA receptors or linking them to the cytoskeleton or to signal transducing enzymes (FIG. 10). Consistent with these ideas, preliminary results have indicated that PDZ7 specifically interacts with a novel brain-specific cytoskeletal protein. The multivalent nature of GRIP with its seven PDZ domains allows for a large diversity of potential interactions.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

One embodiment of the invention comprises isolated nucleic acid molecules which encode a GRIP polypeptide, allelic variant, or analog, including fragments or derivatives thereof. Thus, one aspect of the present invention is isolated polynucleotide operably encoding GRIP, preferably mammalian GRIP, more preferably human. Examples of such an isolated nucleic acid molecule are an RNA, cDNA or isolated genomic DNA molecule encoding GRIP.

Additionally provided are isolated nucleic acid molecules which encode GRIP 2 polypeptide, allelic variant, or analog, including fragments or derivatives thereof In one aspect, the isolated polynucleotide operably encodes GRIP 2, preferably mammalian GRIP 2, more preferably human GRIP 2. Examples of such an isolated nucleic acid molecule are an RNA, cDNA or isolated genomic DNA molecule encoding GRIP 2.

A "fragment" or "derivative" of GRIP or GRIP2 refers to herein 1) a peptide in which one or more amino acid residues are substituted with a conserved or non-conserved amino acid residue (preferably a conserved amino acid residue) and such substituted amino acid residue may or may not be one encoded by the genetic code, or (ii) a peptide in which one or more of the amino acid residues includes a substituent group, or (iii) a peptide in which the mature protein is fused with another compound, such as a compound to increase the half-life of the polypeptide (for example, polyethylene glycol). Thus, a fragment or derivative for use in accordance with the methods of the invention includes a proprotein, which can be activated by cleavage of the proprotein portion to produce an active mature polypeptide. Moreover, GRIP or GRIP2 may have potential for N-linked glycosylation in some settings. Such glycosyl groups, if present, can be partially or completely removed or otherwise modified to provide a GRIP derivative or fragment; or GRIP 2 derivative or fragment.

The GRIP and GRIP2 fragments and derivatives of the invention are of a sufficient length to uniquely identify a region of GRIP or GRIP2. GRIP and GRIP2 fragments thus preferably comprise at least 8 amino acids, usually at least about 12 amino acids, more usually at least about 15 amino acids, still more typically at least about 30 amino acids, even more typically at least about 50 or 70 amino acids. Preferred fragments or derivatives for use in the methods of the invention include those that have at least about 70 percent homology (sequence identity) to SEQ ID NO:2 (amino acid sequence shown in FIG. 3 of the drawings) or SEQ ID NO. 50 (amino acid sequence in FIGS. 24A–24B). More preferably about 80 percent or more homology to SEQ ID NO:2 or to the polypeptide shown in the SEQ ID NO:50, still more preferably about 85 to 90 percent or more homology to SEQ ID NO:2 or the polypeptide shown in the SEQ ID NO:50. Sequence identity or homology with respect to GRIP or GRIP2 refers to herein as the percentage of amino acid sequences of a GRIP protein or fragment or derivative thereof (or GRIP2 protein or fragment or derivative thereof) that are identical with SEQ ID NO:2 or the polypeptide shown in SEQ ID NO:50, after introducing any gaps necessary to achieve the maximum percent homology.

For example, FIGS. 25A–C provide an illustration of suitable gap alignments that serve to highlight substantial sequence equivalency between GRIP and GRIP 2

GRIP, GRIP2, and fragments and derivatives thereof of the invention are "isolated", meaning the protein or peptide constitutes at least about 70%, preferably at least about 85%, more preferably at least about 90% and still more preferably at least about 95% by weight of the total protein in a given sample. A protein or peptide of the invention preferably is also at least 70% free of immunoglobulin contaminants, more preferably at least 85% free, still more preferably at least 90% free and even more preferably at least 95% free of immunoglobulin contaminants. GRIP. GRIP2, and fragments and derivatives thereof may be present in a free state or bound to other components, e.g. blocking groups to chemically insulate reactive groups (e.g. amines, carboxyls, etc.) of the peptide, or fusion peptides or polypeptides (i.e. the peptide may be present as a portion of a larger molecule).

The term "complementary sequence" as it refers to a polynucleotide sequence, relates to the base sequence in another nucleic acid molecule by the base-pairing rules. More particularly, the term or like term refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 95% of the nucleotides of the other strand, usually at least about 98%, and more preferably from about 99 to about 100%. Complementary polynucleotide sequences can be identified by a variety of approaches including use of well-known computer algorithms and software.

A "substantially equivalent" amino acid sequence is a sequence that varies from a GRIP sequence (SEQ ID NO 2) or the GRIP 2 sequence (SEQ ID NO 50) by one or more substitutions, deletions, or additions, the effect of which may or may not result in a difference in the sequence at the amino acid level, and does not result in an undesirable functional dissimilarity between the two sequences, i.e., the polypeptide derived from the substantially equivalent sequence has the functional activity characteristic of unmodified GRIP or GRIP 2.

In particular, the term "substantially equivalent" is meant to point out relationship between two nucleic acid molecules or two polypeptides and generally refers to subunit sequence similarity between two molecules. For example, when the two molecules are polypeptides, and a subunit position in both of the molecules is occupied by the same monomeric subunit, i.e. an amino acid residue, then the molecules are homologous or equivalent at that position. Equivalency between the two sequences is a direct function of the number of matching or homologous positions, egg., if 50% of the subunit positions in the two polypeptide sequences are equivalent then the two sequences are 50% equivalent. By "substantially equivalency" is meant largely but not wholly equivalent.

In particular, the term "substantial equivalency" is meant to denote at least about 60%, 70%, 80%, 90%, 95% or greater equivalency up to about 99% equivalency with respect to amino acid sequences shown in FIG. 3 (SEQ ID NO. 2) or amino acid sequence shown in SEQ ID NO 50. Additionally, the term is meant to define the same or closely related percent of equivalency with respect to a polynucleotide of interest and the GRIP nucleotide sequence shown in FIGS. 11A–C (SEQ ID NO. 1) or the nucleotide sequence shown in FIGS. 22A–22I (SEQ ID NO 47).

Additionally, a difference in a nucleotide sequence, which does not result in a difference at the amino acid level, can include modifications that result in conservative amino acid substitutions, as well as DNA sequence differences due to the degeneracy of the genetic code, i.e., the fact that different nucleic acid sequences can code for the same protein or peptide. A difference in sequence at the amino acid level, i.e., due to a difference in the nucleotide sequence, can include single amino acid substitution (preferably, a conservative substitution), deletion, and/or insertion, or a plurality of amino acid substitutions, deletions, and/or insertions, wherein the resulting polypeptide is still recognizable as related to GRIP as defined by functional activity. Further, a difference in sequence at the amino acid level also can include those amino acid sequence differences that result in a polypeptide of altered size, such as a larger protein, or a truncated protein.

Preferred DNA molecules according to the present invention encode a GRIP polypeptide its entirety and PDZ binding domains having an amino acid sequence as set out in (amino acid positions made in reference to SEQ ID NO:2, FIGS. 12A–12C):

a) amino acids 1 through 1112 (SEQ ID NO:3);
b) amino acids 52 through 135 (SEQ ID NO:4);
c) amino acids 152 through 249 (SEQ ID NO:5);
d) amino acids 252 through 335 (SEQ ID NO:6);
e) amino acids 471 through 558 (SEQ ID NO:7);
f) amino acids 572 through 655 (SEQ ID NO:8);
g) amino acids 672 through 753 (SEQ ID NO:9);
h) amino acids 988 through 1069 (SEQ ID NO:10);
i) amino acids 52 through 249 (SEQ ID NO:11);
j) amino acids 52 through 335 (SEQ ID NO:12);
k) amino acids 52 through 558 (SEQ ID NO:13);
l) amino acids 52 through 655 (SEQ ID NO: 14);
m) amino acids 52 through 753 (SEQ ID NO: 15);
n) amino acids 52 through 1069 (SEQ ID NO:16);
o) amino acids 152 through 335 (SEQ ID NO:17);
p) amino acids 152 through 558 (SEQ ID NO:18);
q) amino acids 152 through 655 (SEQ ID NO:19);

r) amino acids 152 through 753 (SEQ ID NO:20);
s) amino acids 152 through 753 (SEQ ID NO:21);
t) amino acids 252 through 558 (SEQ ID NO:22);
u) amino acids 252 through 655 (SEQ ID NO:23);
v) amino acids 252 through 753 (SEQ ID NO:24);
w) amino acids 252 through 1069 (SEQ ID NO:25);
x) amino acids 471 through 655 (SEQ ID NO:26);
y) amino acids 471 through 753 (SEQ ID NO:27);
z) amino acids 471 through 1069 (SEQ ID NO:28);
aa) amino acids 572 through 753 (SEQ ID NO:29);
bb) amino acids 572 through 1069 (SEQ ID NO:30);
cc) amino acids 672 through 1069 (SEQ ID NO:31);
dd) amino acids 52 through 1112 (SEQ ID NO:2);
ee) amino acids 152 through 1112 (SEQ ID NO:33);
ff) amino acids 252 through 1112 (SEQ ID NO:34);
gg) amino acids 471 through 1112 (SEQ ID NO:35);
hh) amino acids 572 through 1112 (SEQ ID NO:36);
ii) amino acids 672 through 1112 (SEQ ID NO:37); and
jj) amino acids 988 through 1112 (SEQ ID NO:38).

Most preferred DNA molecules according to the present invention encode a GRIP polypeptide in its entirety and PDZ binding domains having an amino acid sequence as set out in a) (SEQ ID NO:3), b) (SEQ ID NO:4), c) (SEQ ID NO:5), d) (SEQ ID NO:6), e) (SEQ ID NO:7), f) (SEQ ID NO:8), g) (SEQ ID NO:9), h) (SEQ ID NO:10), j) (SEQ ID NO:11), and x) (SEQ ID NO:26)as disclosed above.

The enriched or isolated nucleic acid, which comprises the complementary sequence, or the substantially equivalent sequence, can be identified by hybridization under relatively highly stringent conditions to a probe comprising a region GRIP, or a segment thereof, for example, either the entire sequence or a portion of the nucleic acid sequence of FIGS. 11A–C. A "probe" is a molecule, such as a DNA fragment, cDNA fragment or oligonucleotide, that is labeled in some fashion, e.g., with a radioactive isotope, and used to identify or isolate a gene or cDNA, or a fragment thereof. When only a portion of any of these nucleic acid sequences is employed as a probe, preferably that portion comprises a sequence of from about 15 to 500 base pairs, more preferably from about 15 to 100 base pairs, and most preferably from about 15 to about 50 base pairs.

Highly stringent hybridization conditions are known in the field. For example, a stringent hybridization can be performed by use of a hybridization buffer comprising 30% formamide in 0.9M saline/0.09M sodium citrate (SSC) buffer at a temperature of 45° C. and remaining bound when subject to washing twice with that SSC buffer at 45° C. Additionally, use of a suitable GRIP or GRIP2 probe can be performed under moderately stringent hybridization conditions if desired. For example, a moderately stringent hybridization condition would includes use of a hybridization buffer comprising 20% formamide in 0.8M saline/0.08M sodium citrate (SSC) buffer at a temperature of 37° C. and remaining bound when subject to washing once with that SSC buffer at 37° C.

Preferred GRIP and GRIP2 nucleic acid fragments and derivatives of the invention will bind to the sequence of SEQ ID NO:2 or SEQ ID NO 47 under the moderately stringent conditions and more preferably the highly stringent conditions discussed above (referred to herein as "high stringency" conditions).

The GRIP or GRIP2 nucleic acid fragments and derivatives preferably should comprise at least about 20 base pairs, more preferably at least about 50 base pairs, and still more preferably a nucleic acid fragment or derivative of the invention comprises at least about 100, 200, 300 or 400 base pairs. In some preferred embodiments, the nucleic acid fragment or derivative is bound to some moiety which permits ready identification such as a radionucleotide, fluorescent or other chemical identifier.

Particularly preferred GRIP, GRIP2, and fragments and derivatives thereof of the invention have substantial equivalency (sequence identity) to SEQ ID NO: 1 (nucleic acid sequence shown in FIG. 3 of the drawings), or to SEQ ID NO: 47 (nucleic acid sequence shown in FIGS. 22A–22I of the drawings), preferably at least about 70 percent equivalent (sequence identity) to SEQ ID NO:1 are to SEQ ID NO: 47, more preferably about 80 percent or more equivalent to SEQ ID NO:1 or to SEQ ID NO: 47, still more preferably at least about 85, 90 or 95 percent equivalent to SEQ ID NO:1 or to SEQ ID NO: 47.

As noted, substantial sequence equivalency or identity with respect to the nucleic acid sequence of GRIP shown in FIG. 3 of the drawings or to the GRIP2 sequence shown in FIGS. 22A–22I refers to herein as the percentage of base sequences of a GRIP or GRIP2 nucleic acid fragment or derivative thereof that are identical with SEQ ID NO:1 or SEQ ID NO:47, after introducing any gaps necessary to achieve the maximum percent equivalency.

Additionally preferred GRIP and GRIP2 nucleic acid fragments encode polypeptides that are capable of specifically binding the C-terminal end of GluR2. By the term "C-terminal end of GluR2" is meant nearly any amino acid sequence near the C-terminus of the GluR2 with about the final 50 amino acids being generally preferred. Specific binding between the GRIP or GRIP2 polypeptide and the C-terminal end of GluR2 can be determined by a variety of means, e.g., Western blotting, ELISA, RIA, gel mobility shift assay, enzyme immunoassay, competitive assays, saturation assays or other suitable protein binding assays known in the field. By the term "specific binding" or similar term is generally meant polypeptide disclosed herein which binds another polypeptide, thereby forming a specific binding pair, but which does not recognize and bind to other molecules.

A particularly preferred assay for detecting specific binding between the polypeptide encoded by the GRIP or GRIP2 nucleic acid fragment and the C-terminal end of a the GluR2 is what is oftentimes referred to in the field as the two-hybrid system. Typically, the assay is conducted in a suitable yeast strain such as those discussed below. The two-hybrid system registers the specific binding by formation of specific yeast colonies that can be readily detected by inspection of growth plates that include a detectable chromophore. Incidence of the specific yeast colonies with respect to a suitable control is indicative of specific binding between the GRIP or GRIP2 nucleic acid fragment and the C-terminal end of the GluR2. The yeast colonies can be isolated and propagated according to standard techniques to obtain the fragment. Suitable controls generally include performing the same or related two-hybrid system test without the GRIP or GRIP2 nucleic acid fragment. In general, specific binding is readily detectable in the two-hybrid system if the number of "positive" yeast colonies exceeds non-positive control colonies by at least about 5% to about 10% and preferably at least about 20% to about 50%, up to about 100% or more. Preferred yeast two-hybrid systems are discussed more fully in the examples and discussion which follows.

A particularly preferred GRIP nucleic acid fragment encodes at least the following GRIP regions: 1) about 30 amino acids on the N-terminal side of PDZ4; 2) PDZ4 and 3) PDZ5. The preferred GRIP fragment can be readily identified by the yeast two-hybrid system described below in the examples. A related fragment is preferred for the GRIP2 polypeptide.

In addition, GRIP can be identified either from previously unidentified sources or from different species by using a probe under highly or moderately stringent conditions, as desired, using either the entirety or a portion of the nucleic acid sequence of FIGS. 11A–C. Ideally, such a probe is derived from regions of GRIP nucleic acid sequences that demonstrate commonality with GRIP at the amino acid level. A specific example of such a nucleic acid molecule is an isolated nucleic acid molecule having substantially the same nucleotide sequence as the nucleotide sequence shown in SEQ ID NO: 1. One means of isolating nucleic acid molecules encoding GRIP is to probe an organism's genomic library with a natural or artificially designated DNA probe, using methods well known in the art. DNA probes derived from the nucleotides of SEQ ID NO: 1 are particularly useful probes for this purpose. DNA and cDNA molecules which encode GRIP may be used to obtain complementary genomic DNA, cDNA or RNA from human, mammalian or other animal sources, or to isolate related cDNA or genomic clones by the screening of cDNA or genomic libraries, using methods well known to those skilled in the art. Transcriptional regulatory elements from the 5' untranslated region of the isolated clones, and other stability, processing, transcription, translation, and tissue specificity-determining regions from the 3' and 5' untranslated regions of the isolated genes are thereby obtained. Alternatively, the polynucleotide sequence can be an mRNA transcript of SEQ ID NO: 1. Moreover, the invention includes an antisense mRNA sequence to GRIP. The use of antisense technology and gene modification are well known to those skilled in the art. The present invention also provides an enriched or isolated nucleic acid comprising a sequence, which is complementary to, or substantially equivalent to, a sequence selected from the group consisting of FIGS. 11A–C.

GRIP and GRIP2 nucleic acids used in the methods of the invention are typically isolated, meaning the nucleic acids comprise a sequence joined to a nucleotide other than that which it is joined to on a natural chromosome and usually constitute at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

Constructing and screening libraries of polypeptide sequences that specifically bind to a given protein are techniques well known to the skilled artisan and as depicted in an article by Scott et al [Scott et al., *Science*, 249:386–390 (1990)], for example.

Another embodiment of the invention comprises purified GRIP, preferably mammalian GRIP, and more preferably human GRIP. As used herein, the term GRIP encompasses any amino acid sequence, polypeptide or protein having substantially the same properties as the polypeptide or protein that binds to the C-termini of an AMPA glutamate receptor, described herein. As used herein, the term "isolated protein" means a protein molecule essentially free of other cellular components. An example of such a protein is an isolated protein having substantially the same amino acid sequence as the amino acid sequence shown in SEQ ID NO:

2. One means for obtaining isolated GRIP is to express DNA encoding GRIP in a suitable host, such as bacterial, yeast, insect or mammalian cell, using methods well known in the art, and recovering the protein after it has been expressed in such a host, using methods well known in the art.

It is generally preferred that the polypeptides of the present invention, including GRIP and GRIP2, be substantially pure. That is, the polypeptides have been isolated from cell substituents that naturally accompany it so that the polypeptides are present preferably in at least 80% or 90% to 95% homogeneity (w/w). Polypeptides having at least 98 to 99% homogeneity (w/w) are most preferred for many pharmaceutical, clinical and research applications. Once substantially purified the polypeptide should be substantially free of contaminants for therapeutic applications. Once purified partially or to substantial purity, the polypeptides can be used therapeutically, or in performing a desired assay. Substantial purity can be determined by a variety of standard techniques such as chromatography and gel electrophoresis.

This invention also encompasses different forms of GRIP, wherein the different forms of GRIP have a similar function and substantial sequence homology. By the use of the term "substantial sequence homology" it is intended that DNA, RNA, and amino acid sequences which have slight and non-consequential sequence variations from the actual sequences disclosed and claimed herein are within the scope of the present invention. In this regard, the "slight and non-consequential" sequence variations mean that the homologous sequences will function in substantially the same manner to produce substantially the same compositions as the nucleic acid and amino acid compositions disclosed and claimed herein. As one of ordinary skill in the art is aware, conservative substitutions may be made in the amino acid sequence or the disclosed peptides without losing functionality. These substitutions are well known and are based upon the charge and structural properties of each amino acid. Such "functionally equivalent" peptides are also encompassed in the present invention.

Another embodiment of this invention includes vectors comprising an isolated nucleic acid molecule such as DNA, RNA, or cDNA encoding GRIP. Nucleic acid molecules are inserted into vector genomes by methods well known in the art. For example, vectors comprise a nucleic acid molecule encoding GRIP, adapted for expression in a bacterial cell, a yeast cell, insect or a mammalian cell which additionally comprises the regulatory elements necessary for expression of the nucleic acid molecule in a bacterial cell, a yeast cell, insect or a mammalian cell operatively linked to the nucleic acid molecule coding GRIP to permit expression thereof. Any appropriate expression vector (e.g., [Pouwels et al., *Cloning Vectors: A Laboratory Manual* (Elsevior, N.Y. 1985)]) and corresponding suitable host can be employed for production of recombinant proteins. Expression hosts include, but are not limited to, bacterial species within the genera Escherichia, Bacillus, Pseudomas, Salmonella, yeast hosts include, Saccharomyces, Pichia, Candida, Hansenula, and Torulopsis, mammalian, or insect host cell systems including baculovirus systems [Luckow et al., *Bio/Technology*, 6:47 (1988)]. Preferred host cells include bacteria, yeast, mammalian, plant, and insect cells and human cells in tissue culture. Illustratively, such cells are selected from the group consisting of *E. coli*, Pseudomonas, Bacillus, Streptomyces, yeast, CHO, R1.1, B-W, L-M, COS-1, BSC1, BSC40, BMT10, COS 7, C127, 3T3, HeLa, BHK, and Sf9 cells. The choice of expression host has a direct bearing on the type of protein produced. The ordinary skilled artisan is aware, for example, that the glycosylation of proteins produced in yeast or mammalian cells, such as COS-7 cells, will differ from those proteins produced in bacterial cells, such as *Escherichia coli*. As noted, the same or related vectors can be employed to manipulate and express GRIP 2.

The term "vector" or "recombinant vector" as used herein means any nucleic acid sequence of interest capable of being incorporated into a host cell and resulting in the expression of a nucleic acid sequence of interest. Vectors can include, e.g., linear nucleic acid sequences, plasmids, cosmids, phagemids, and extrachromosomal DNA. Specifically, the vector can be a recombinant DNA. Also used herein, the term "expression" or "gene expression", is meant to refer to the production of the protein product of the nucleic acid sequence of interest, including transcription of the DNA and translation of the RNA transcript. Most recombinant vectors will include a "cloning site" which as used herein is intended to encompass at least one restriction endonuclease site. Typically, multiple different restriction endonuclease sites (e.g., a polylinker) are contained within the vector to facilitate cloning. See generally Sambrook et al., *Molecular Cloning* (2d ed. 1989), and Ausubel et al., *Current Protocols in Molecular Biology*, (1989) John Wiley & Sons, New York for examples of suitable vectors and host cells for practicing the present invention.

Also provided in the present invention are mammalian cells containing a GRIP polypeptide encoding DNA sequence and modified in vitro to permit higher expression of GRIP polypeptides by means of a homologous recombinational event consisting of inserting an expression regulating sequence in functional proximity to the GRIP polypeptide encoding sequence. The expression regulating sequence can be a GRIP polypeptide expression sequence or not and can replace a mutant GRIP polypeptide regulating sequence in the cell. Related cells can be made comprising the GRIP 2 polypeptide disclosed herein.

In another embodiment, transgenic nonhuman mammals are provided that express nucleic acid molecules encoding GRIP. In still another embodiment, transgenic nonhuman mammals are provided that express antisense DNA complementary to DNA encoding GRIP. As noted, related mammals can be made that include GRIP 2.

In another embodiment, transgenic nonhuman mammals comprise a homologous recombination knockout of native GRIP. The term "knockout" refers to partial or complete reduction of the expression of at least a portion of a polypeptide encoded by an endogenous gene of a single cell, selected cells, or of all of the cells of a mammal. Included within the scope of this invention is a mammal in which two or more genes have been knocked out. Such mammals can be generated by repeating the procedures set forth in U.S. Pat. Nos. 5,532,158 or 5,557,032, both incorporated by reference herein. Alternatively, the knockout mammals can be produced by breeding mammals, each with a single gene knocked out, to each other, and screening for those mammals with the double knockout genotype. A related non-human animal including GRIP 2 can also be made by these methods.

Conventional abbreviations for amino acids, peptides, and their derivatives are used as generally accepted in the peptide art and as recommended by the IUPAC-UB Commission on Biochemical Nomenclature [*European J. Biochem.*, 138:9–37 (1984)]. A conservative amino acid substitution is defined as a given amino acid is substituted by another amino acid of similar size, charge density, hydrophobicity/hydrophilicity, and/or configuration, without significantly altering the biological or chemical activity of the variant peptide as compared to the original peptide. A nonconservative amino acid substitution is an amino acid substituted by an alternative amino acid of differing charge density, hydrophobicity/hydrophilicity, and/or configuration.

Purified proteins of the invention are also useful as antigens to produce monoclonal or polyclonal antibodies against the protein or specific peptide sequence, using standard methods which are well known to the person skilled in the art. Generally, antibody preparation involves a) conjugating a polypeptide, such as GRIP, to a carrier; b) immunizing a host animal with the polypeptide fragment-carrier protein conjugate and adjuvant; and c) obtaining antibody from the immunized host animal. In particular, anti-peptide and anti-fusion antibodies were generated against GRIP. A GST-fusion protein corresponding to amino acids 798–904 of GRIP (SEQ ID NO. 2) was used to produce antiserum. This antisera was then affinity purified on a fusion protein affinity column. In addition a 20 a.a. peptide (KEDLVKLKIRKDEDNSDEQE; SEQ ID NO. 39) corresponding to amino acids 646–664 of GRIP (SEQ ID NO:2) was synthesized, crosslinked to carrier protein and injected into rabbits to generate antiserum. The resulting antiserum was then affinity purified on a peptide affinity column.

Peptides can be synthesized using standard peptide synthesizing techniques well known to the ordinary artisan, (e.g., [Bodanszky, *Principles of Peptide Synthesis* (1984), (Springer-Verlag, Heidelberg), Merrifield, *Am. Chem. Soc.*, 85:2149–54 (1963), Barany et al., *Int. J. Peptide Protein Res.*, 30:705–739 (1987)] and U.S. Pat. No. 5,424,398). Synthesized peptides may be further purified (e.g., HPLC). Also, it may be preferable to produce fusion proteins using the peptides. Peptides may also be modified by well known chemical and genetic manipulation methods, such as glycosylation, amidation, carboxylation, or phosphorylation, or by the addition of salts, amides, esters, and the like. The may be desirable to manipulate peptides to create peptide derivatives by forming covalent or noncovalent complexes with other moieties. For example, covalently-bound complexes can be prepared by linking the chemical moieties to functional groups on the side chains of amino acids comprising the peptides, or at the N- or C-terminus.

Peptides, variant peptides, or molecules comprising a peptide or a variant peptide of the invention may be conjugated to a reporter group, including, but not limited to, a radiolabel (e.g., $^{32}P$), a fluorescent label, an enzyme, a substrate, a solid matrix, or a carrier (e.g., biotin or avidin) for use in the detection of specific levels of molecules or the specific binding activity of particular molecules.

Derivatives of a GRIP polypeptide or polynucleotide according to the invention have 1 or more chemical moieties attached thereto including, but not limited to, proteins such as serum albumin, heparin, or immunoglobulin, polymers such as natural polymers (dextran), modified natural polymers (carboxymethyl cellulose) and synthetic polymers (Ficoll, polyvinyl alchol, and polyacrylamide). The carrier is preferably a macromolecule which is soluble in the circulatory system and which is physiologically acceptable where physiological acceptance means that those of skill in the art would accept injection of said carrier into a patient as part of a therapeutic regiment. Preferably, the carrier is relatively stable in the circulatory system with an acceptable plasma half life for clearance. Such carriers may be varied in physical structure from the highly cross-linked Ficoll, the branched dextran, to the linear polyacrylamide, carboxymethyl cellulose and polyvinyl alcohol. Polymers such as polyethylene glycol or polyoxyethylated polyols or proteins may be modified to reduce antigenicity by, for example, derivitizing with polyethylene glycol.

The present invention also includes a method of regulating the activity or levels of GRIP in an animal, such as a mammal, but particularly a human, which method comprises administering to a mammal in need of modulation of AMPA receptors a therapeutically effective amount, including a prophylactically-effective amount, of a polypeptide or nucleic acid of the present invention. The polypeptides and nucleic acids of the present invention can be administered as part of a pharmaceutical composition. In addition, the present inventive nucleic acids can be included in a vector and/or a host cell prior to such administration.

The method of the present invention has particular usefulness in the treatment of any disease, disorder, or condition involving AMPA receptors and/or the regulation of GRIP and GRIP-related activity including GRIP 2. Thus, the following disease states and conditions can be treated in accordance with the present invention: Alzheimer's disease, dementia including Alzheimer type dementia and senility, Schziophrenia, Huntington's disease, hypoglycemia, anoxia/hypoxia, modulation of neurotransmitters, (e.g. acetylcholine function), epilepsy, ischemia, ischemia reperfusion, cerebral ischemia (all ischemia-related disorders, including stroke), neurofibromatosis, Parkinson's disease, dystonia, dyskinesia, chores, tics, memory degeneration, cerebral vasospasm, myasthenia gravis and other neuromuscular disorders, including drug-induced neuromuscular disorders and other drug-induced dementia. The polypeptides and the nucleic acids may be acutely administered, (e.g., within about a few minutes to about an hour of the onset or realization of symptoms. The polypeptides and nucleic acids of the present invention also may be used in the treatment of chronic disease states and conditions. In particular, those conditions and disease states wherein chronic polypeptides and nucleic acids of the present invention will treat the disease, prevent the onset of symptoms, or will reduce recovery time. All the methods of this invention can be used in any animal, including, but not limited to, an amphibian, bird, fish, insect, reptile, or mammal. One or more of the methods may have particular utility in humans, domestic animals, such as cow, pigs, sheep, dogs, cats, or horses, and in common pests, such as insects or rodents.

The GRIP protein or nucleic acid encoding GRIP may be admninistered, e.g., to a patient. It is generally more preferred that the GRIP polypeptide be administered to a patient. Nucleic acid coding for GRIP preferably is at least partially pure, i.e. the GRIP nucleic acid constitutes at least about 10%, preferably at least about 30%, and more preferably at least about 60% by weight of nucleic acid present in a given fraction. More typically the GRIP nucleic acid will be substantially pure, i.e. the nucleic acid constitutes at least about 80%, more preferably at least about 90%, and more preferably at least about 95% by weight of total nucleic acid in a given fraction. Related administration methods can be employed with GRIP2 if desired.

The invention furer includes a method of detecting a molecule that enhances or inhibits the binding activity of GRIP polypeptides and nucleic acids or GRIP-related polypeptides and nucleic acids using a yeast two-hybrid assay system. The yeast two-hybrid system is generally known in the art. See e.g., Fields, S and Song, O-K (1989) Nature 340: 245–246; and Chevray, P. M and Nathans, D. (1992) PNAS (USA) 89: 5789–5793. Yeast two-hybrid screening [Fields et al., supra,] was performed using a random primed cDNA library from rat hippocampus subcloned into the Sal I/Not I sites of the pPC86 vector [Chevray et al., supra,], which contains the GAL4 activation domain and a tryptophan selection marker. The final 50 amino acids of GluR2 or mutant forms of the G&uR2 C-terminus were subcloned in-famne into the Sal I/Not I sites of the pPC97 vector, which contains the GAL4 DNA binding domain and a leucine selection marker. The plasmid containing the GAL4 binding domain-GluR2 C-terminus fusion protein (bait vector) was transformed into Y190 yeast cells (Staudinger, J. et al. (1995) J. Cell. Biol. 128 (3) 263–271.) by the lithium acetate method and the transformants selected on the basis of leucine auxotrophy, and subsequently transformed with plasmids 5 containing the GALA activation domain-cDNA library fusion proteins. Positive clones were selected on triple minus plates (Leu-, Trp-, His-) and assayed for β-galactosidase activity. Clones that grew on triple minus plates and turned blue in the presence of X-gal were rescued from yeast and sequenced. Positive clones were also cotransformed with either the bait vector or the original pPC97 vector (backbone) into yeast to confirm the interaction. All the constructs that were used in other mating tests were from PCR products subcloned in-frame into pPC97 or pPC86 vectors and were confirmed by sequencing.

The compositions of the present invention are directed to the use of nucleic acid molecules of the invention, as well as antisense nucleic acid molecules hybridizable to a nucleic acid encoding a GRIP or GRIP-related polypeptide, including GRIP 2, or a polypeptide of the present invention that binds to the C-termini of an AMPA glutamate receptor, or a polypeptide of the present invention that is capable of enhancing or inhibiting excitatory synaptic transmission by interacting with the C-termini of an AMPA glutamate receptor, for the manufacture and administration of a medicament for treatment, (e.g., gene therapy). Preferably, critical regulatory sequences, or binding sequences (e.g., seven PDZ binding domains of the present invention, individual PDZ binding domains, (e.g., PDZ binding domain 6 or 7) or a combination of PDZ binding domains, preferably PDZ binding domains 1, 2, and 3, and PDZ binding domains 4 and 5, which enhance (e.g., agonists) or inhibit (e.g., antagonists) excitatory synaptic transmission involving the C-termini of an AMPA receptor, may be made into pharmaceutical compositions with appropriate pharmaceutically acceptable carriers or diluents. If appropriate, pharmaceutical compositions may be formulated into preparations including, but not limited to, solid, semi-solid, liquid, or gaseous forms, such as tablets, capsules, powders, granules, ointments, solutions, suppositories, injections, inhalants, and aerosols, in the usual ways for their respective route of administration. Methods known in the art can be utilized to prevent release or absorption of the composition until it reaches the target organ or to ensure time-release of the composition. A pharmaceuticahly-acceptable form should be employed which does not in effectuate the compositions of the present invention. In pharmaceutical dosage forms, the compositions may be used alone or in appropriate association, as well as in combination with, other pharmaceutically-active compounds. For example, in applying the method of the present invention for delivery of a nucleic acid comprising a sequence that encodes a GRIP or GRIP-related protein and/or gene-related elements, such delivery may be employed in conjunction with other means of treatment of neurological diseases and disorders, for example.

Accordingly, the pharmaceutical compositions of the present invention can be delivered via various routes and to various sites in an animal body to achieve a particular effect. Local or system delivery can be accomplished by administration comprising application or instillation of the formulation into body cavities, inhalation (e.g. nasal delivery), or insufflation of an aerosol, or by parenteral introduction, comprising intramuscular, intravenous, intraarterial, peritoneal, subcutaneous, intradermal, oral, or pulmonary delivery systems, as well as topical administration.

The composition of the present invention can be provided in unit dosage form, wherein each dosage unit, e.g., a teaspoon, tablet, solution, or suppository, contains a predetermined amount of the composition, alone or in appropriate combination with other pharmaceutically active agents. The term "unit dosage form" refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically-acceptable diluent, carrier (e.g., liquid carrier such as a saline solution, a buffer solution, or other physiological aqueous solution), or vehicle, where appropriate. The specifications for the novel unit dosage forms of the present invention depend on the particular effect to be achieved and the particular pharmacodynamics associated with the pharmaceutical composition in the particular host. Related administration protocols can be used with GRIP 2 polypeptides or polynucleotides as needed.

Additionally, the present invention specifically provides a method of transferring nucleic acids to a host, which comprises administering the composition of the present invention using any of the aforementioned routes of administration or alternative routes known to those skilled in the art and appropriate for the particular application. The "effective amount" of the composition is such as to produce the desired effect in a host which can be monitored using several end-points known to those skilled in the art. For example, one desired effect might comprise effective nucleic acid transfer to a host cell. Such transfer could be monitored in terms of a therapeutic effect, e.g., alleviation of some symptom associated with the disease being treated, or further evidence of the transferred gene or expression of the gene within the host, e.g. using PCR, Northern or Southern hybridization techniques, or transcription assays to detect the nucleic acid in host cells, or using immunoblot analysis, antibody-mediated detection, or particularized assays, as described in the examples, to detect protein or polypeptide encoded by the transferred nucleic acid, or impacted level or function due to such transfer. These methods described are by no means all-inclusive, and furer methods to suit the specific application will be apparent to the ordinary skilled artisan.

Furthermore, the amounts of each active agent included in the compositions employed in the examples described herein, i.e., add range, provide general guidance of the range of each component to be utilized by the practitioner upon optimizing the method of the present invention for practice either in vitro or in vivo. Moreover, such ranges by no means preclude use of a higher or lower amount of a component, as might be warranted in a particular application. For example, the actual dose and schedule may vary depending on whether the compositions are administered in combination with other pharmaceutical compositions, or depending on interindividual differences in pharmacokinetics, drug disposition, and metabolism. Similarly, amounts may vary in vitro applications depending on the particular cell line utilized, e.g., the ability of the plasmid employed for nucleic acid transfer to replicate in that cell line. Furthermore, the amount of nucleic acid to be added per cell or treatment will likely vary with the length and stability of the nucleic acid, as well as the nature of the sequence, and is particularly a parameter which needs to be determined empirically, and may be altered due to factors not inherent to the method of the present invention, e.g., the cost associated with synthesis, for instance One skilled in the art can easily make any necessary adjustments in accordance with the necessities of the particular situation.

It will be apparent from the foregoing that the present invention has a variety of other uses and advantages. For example, the invention can be used to modulate AMPA receptor clustering in primary or immortalized cells of interest. Illustrative of such cells include cultured neurons, e.g., serotonergic or cholinergic neurons, as well as neuronal precursor cells, e.g., chromaffin cells propagated under appropriate conditions. In this example, the invention can be used to increase or decrease AMPA receptor clustering as needed. Thus, synaptic clustering of the receptors can be substantially formed or broken as needed. Accordingly, the present invention is particularly useful for analyzing and modulating synapses in tissue culture. This aspect of the invention lends itself to the design of screens that can be used to detect compounds (agonists or antagonists) that interact with excititory synapses.

As noted, the invention also provides a kit for detecting GRIP or GRIP2 expression. In one embodiment, the kit includes at least one container means which means includes a system for detecting or modulating the expression. In this embodiment, the system comprises at least one of: 1) an antibody (preferably a monoclonal antibody) capable of specifically binding GRIP (SEQ ED NO. 2) or a suitable fragment thereof 2) an antibody (preferably a monoclonal antibody) capable of specifically binding GRIP2 (SEQ ID NO:50) or a suitable fragment thereof; 3) a polynucleotide sequence or fragment of same comprising sequence substantially equivalent or identical to the sequence shown in FIGS. 11A–11C (SEQ ID NO 2) or the complement thereof 4) a polynucleotide sequence or the sequence of SEQ ID NO 47 or the complement thereof; and 3) a GRIP polypeptide or suitable fragment substantially equivalent or identical to the sequence shown in FIG. 3 (SEQ ID NO 1) or a GRIP2 polypeptide or suitable fragment substantially equivalent or identical to the sequence shown in SEQ ID NO 50.

Additionally contemplated is a kit to modulate GRIP or GRIP2 expression. In one embodiment, the kit can be used to monitor or to treat fertility in a subject and particularly a human patient. In a particular embodiment, the kit can be used to monitor or treat spermatogenesis.

The kits of this invention can include any of the components mentioned above, including additional components, as needed, such as suitable buffers, indicators (e.g., fluorophores, chromophores or enzymes providing same), controls (e.g., a suitable polynucleotide or GRIP (or GRIP2) polypeptide of this invention) and directions for using the kit. Kit components can be provided in nearly any acceptable form, including a liquid or solid, e.g, as a lyophilized powder.

Further provided is cDNA library comprising sequence substantially equivalent or identical to the DNA sequence of shown in FIGS. 11A–11C (SEQ ID NO. 1) or SEQ ID NO. 47.

The invention is not intended to be limited to the specific terminology so selected, and it is to be understood that specific elements and specific examples include all technical equivalents which operate in a similar manner to accomplish a similar purpose and aid in the understanding of the invention, and should not be construed in any way limiting its scope.

The following non-limiting examples are illustrative of the invention.

EXAMPLE 1

Involvement of the C-Terminus of the GluR Subunit in AMPA

1. Receptor Clustering Neurons

A variety of studies have demonstrated that the C-terminal region of glutamate receptors is intracellular and appears to be involved in the modulation of glutamate receptor function [Kornau et al., *Science*, 269:1737–1740 (1995), Niethammer et al., *J. Neurosci.*, 16:2157–2163 (1996), Ehlers et al., *Curr. Opin. in Cell Biol.*, 8:490495 (1996), Tingley et al., *Nature*, 364:70–73 91993), Roche et al., *Neuron*, 16:1179–1188 (1996), Ehlers et al., *Science*, 269:1734–1737 (1995), Muller et al., *Neuron*, 17:255–265 (1996), Lau et al., *J. Biol. Chem.*, 271:21622–21628 (1996)]. The C-terminal seven amino acids of the NR2A and NR2B subunits of the NMDA receptor have been shown to directly interact with the synapse associated PSD-95/SAP90 protein and this interaction has been implicated in the clustering of NMDA receptors at excitatory synapses [Kornau et al., *Science*, 269:1737–1740 (1995), Niethammer et al., *J. Neurosci.*, 16:2157–2163 (1996), Ehlers et al., *Curr. Opin. in Cell Biol.*, 8:490495 (1996)]. Although the C-termini of AMPA receptors do not have the consensus site (T/SXV) that has been shown to be important in the interaction of NMDA receptors with the PDZ domains of PSD-95/SAP90 [Kornau et al., *Science*, 269:1737–1740 (1995), Niethammer et al., *J. Neurosci.*, 16:2157–2163 (1996)], the GluR2 and GluR3 subunits do have weak homology to the C-terminus of NMDA receptor subunits (see Table I), suggesting that the C-terminus of GluR2 or GluR3 may directly interact with PDZ domain containing proteins.

TABLE I

Amino Acid Sequence of the C-termini of Glutamate Receptors and K+ –Channels

| PROTEIN | SEQUENCE | SEQ ID NO |
| --- | --- | --- |
| NR2A | PSIESDV | 40 |
| NR2B | SSIESDV | 41 |
| SHAKER A/B | VSIETDV | 42 |
| GLUR2 | GIESVKI | 43 |
| GLUR3 | GTESVKI | 44 |
| GLUR1 | PLGATGL | 45 |
| GLUR4 | VIASDLP | 46 |

To determine whether the C-terminus of the GluR2 subunit is involved in the clustering of AMPA receptors at excitatory synapses, primary neuronal cultures were transfected with constructs containing only the C-terminal region of the GluR2 subunit. Neurons were transfected with myc-tagged cDNA constructs encoding the last 50–226 amino acids of the C-termini of the GluR2 (GluR2C) or GluR1 (GluR1C) subunits of the AMPA receptor or the NR1 subunit of the NMDA receptor (NR1C). The cultures were then fixed and triple stained with: 1) an anti-myc antibody to identify transfected neurons; 2) anti-GluR1 antibodies to identify AMPA receptor clusters within the transfected neurons; and 3) the synapse specific protein synaptophysin to identify synapses. Neurons transfected with GluR1C or NR1C have multiple synaptic AMPA receptor clusters which co-localize with the synaptic protein synaptophysin (FIG. 1 and Table II) similar to that seen in non-tansfected neurons. Table II is shown below.

TABLE II

Disruption of Synaptic AMPA Receptor Clustering by the C-Terminus of the GluR2 Subunit[1].

| | GluR1 Clusters | Synaptophysin Clusters |
| --- | --- | --- |
| R2 C-Terminal (n = 34) | 1.2 +/− 0.29* | 6.9 +/− 0.8 |
| R1 C-Terminal (n = 19) | 3.6 +/− 0.53 | 7.8 +/− 0.9 |
| NR1 C-Terminal (n = 48) | 3.5 +/− 0.38 | |
| R2 C-Term. Mutant (n = 10) | 2.9 +/− 0.48 | |

[1]Values are expressed +/− SEM.
*P < .01 compared with each of the other C-terminal fragments.

Neurons transfected with C-terminal constructs were either fixed and stained with a CY3 labeled C-terminal GluR1 antibody or incubated with CY3 labeled Fab fragment against an extracellular epitope of GluR1 for 1 hour prior to fixation. Synaptophysin clusters were identified with a mouse monoclonal antibody.

In contrast, when GluR2C was transfected into neurons, the number of synaptic ASS receptor clusters dramatically decreased (see FIG. 1 and Table II). Expression of GluR9C, however, had no effect on the number of synaptic contacts detected with the anti-synaptophysin antibody (Table II) or the presence of diffuse surface AMPA receptor staining (FIG. 1). To determine whether this disruption of AMPA receptor clustering by the GluR2 C-teminus was dependent on the C-terminal seven amino acids homologous to the NMDA receptor subunits, we deleted this region of the GluR2 subunit. Transfection of the GluR2 construct of the C-terminus which lacked the last seven amino acids (GluR2C A7) did not disrupt clustering of the AMPA receptor (Table II). These results suggest that expression of the C-terminal tail of GluR2 disrupts the interaction of the GluR2 subunit with a protein important in clustering of AMPA receptors and that the last seven amino acids of GluR2 are required for this interaction.

FIG. 1 is explained in more detail as follows. In an attempt to disrupt the interactions of GluR2 with potential PDZ containing proteins we transfected a myc-tagged construct of the last fifty amino acids of GluR2 (or as a control the C-terminus of GluR1) into primary cultures of spinal cord neurons. The clustering of AMPA receptors was then analyzed by immunocytochemical techniques. The neurons were triple-labeled with: 1) the anti-myc antibody to detect transfected cells; 2) an antibody to synaptophysin to detect synapses; and 3) a Cy3-labeled FAB fragment of an antibody generated against an extracellular epitope of the GluR1 subunit to analyze AMPA receptor clustering. Synapses associated with GluR1 clusters are indicated with arrows while synapses without GluR1 clusters are indicated with arrowheads. Asterisks in FIG. 1 refer to nearby untransfected neurons. Clustering of AMPA receptors was dramatically disrupted by the C-terminus of GluR2 but not GluR 1.

EXAMPLE 2

Figure 2:
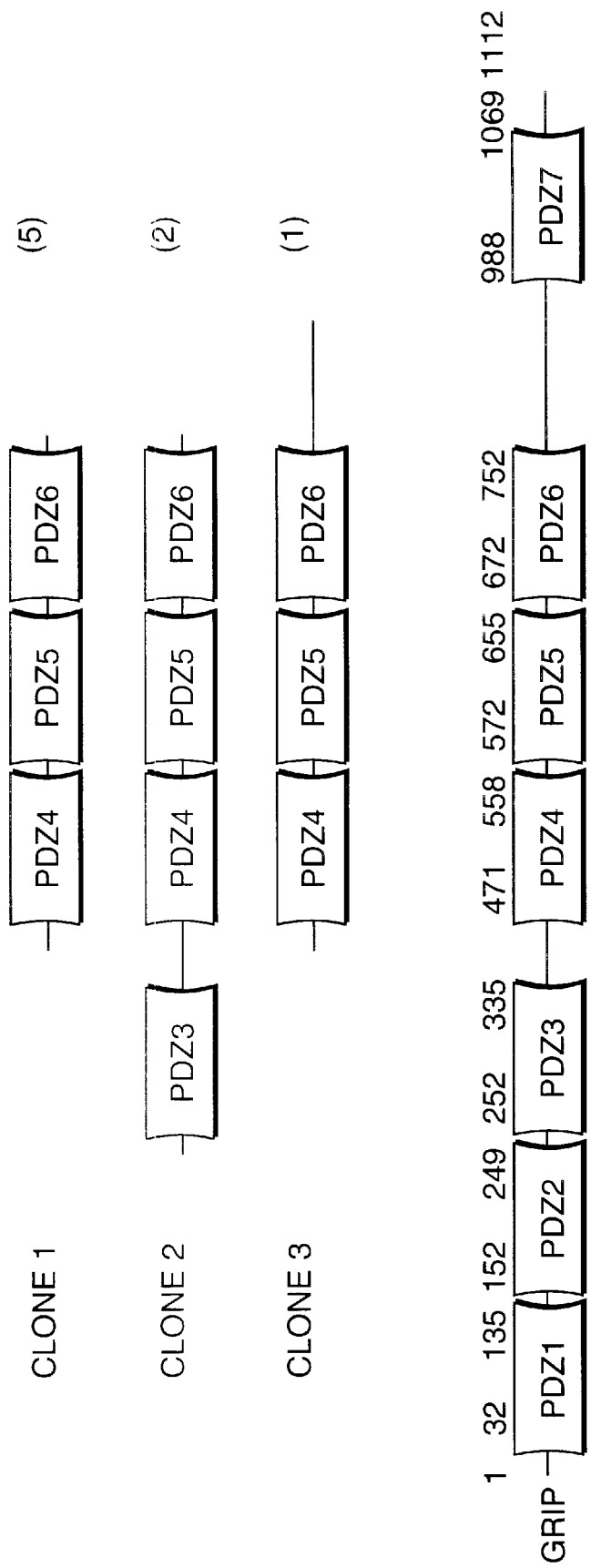
FIG. 2 is a schematic drawing showing isolated GRIP cDNAs.

Isolation of Grip, a Protein Which Specifically Interacts with the C-Terminus of the GluR2 and GluR3 Subunits of AMPA Receptors In order to identify proteins that interact with the C-terminus of the GluR2 subunit, the C-terminal region of GluR2 was used as a probe to screen a rat hippocampal cDNA library using the yeast two-hybrid technique [Fields et al., *Nature*, 340:245–246 (1989), Chevray et al., *Natl. Acacd Sci. USA*, 89:5789–5793 (1992)]. The carboxyl terminal 50 amino acids of the rat GluR2 subunit was fused to the DNA binding domain of the transcription factor Gal4 and used as bait to screen a cDNA library of rat hippocampus fused to the Gal4 activation domain. Eight overlapping clones of a GRIP protein were isolated (see FIG. 2 showing three of such clones). The interaction between GRIP and the GluR2 subunit in the yeast two-hybrid system was specific, since co-transformations of the isolated GRIP cDNAs with the Gal4 DNA binding domain alone, or with the C-terminal tail of GluR1 were not positive. The longest GRIP cDNA encoded a protein that contained four separate regions that were homologous to PDZ domains (FIG. 2).

In particular, FIG. 2 shows three overlapping cDNA clones of a novel protein (GRIP) that was isolated in a yeast two-hybrid screen using the C-terminus of GluR2 as bait. These cDNAs encoded protein that contained three to four PDZ domains. Using these cDNAs a full length cDNA was isolated which encoded seven PDZ domains. The numbers in parentheses indicate how many times each clone was isolated.

With these cDNAs as probes, we obtained a full length GRIP cDNA after repetitive screening of an oligo dt-primed λ-ZAP cDNA library generated from rat hippocampus. This cDNA is nearly 6 kb with a large open reading frame of 3336 bp. The sequence encodes a 1112 amino acid protein with a predicted molecular weight of 120,350 Da (FIG. 3). The start codon was identified by the presence of a Kozak consensus sequence and several upstream in-frame stop codons. In addition to the PDZ domains mentioned above (PDZ3, PDZ4, PDZ5, PDZ6), the full-length GRIP cDNA encodes three additional PDZ domains (PDZ1, PDZ2 and PDZ7). Sequence alignment of GRIP with other proteins that include one or more PDZ domains indicated that each PDZ domain in GRIP contains GLGF-ike repeats, a characteristic of PDZ domains, as well as other amino acids that are conserved in PDZ domains (FIG. 3 and FIG. 4).

Standard computer-assisted database searches showed that GRIP is homologous to many PDZ containing proteins, including members of the PSD-95/SAP90 family, protein tyrosine phosphatases and syntrophin. The regions of GRIP that are homologous to other proteins are limited to the PDZ domains, with the amino acid sequence identity between the GRIP PDZ domains and other PDZ-containing proteins ranging from 35–45%. However, GRIP is a novel PDZ domain-containing protein which, in contrast to PSD-95/SAP90, NOS and the protein tyrosine phosphatases, does not contain any apparent catalytic domains in its C-terminus. Analysis of the translated protein sequence shows no obvious hydrophobic putative transmembrane segments suggesting that GRIP is not a transmembrane protein. These results suggest that GRIP may cross link AMPA receptors or serve as an adaptor protein to attach AMPA receptors to other proteins.

EXAMPLE 3

Figures 5A, 5B:
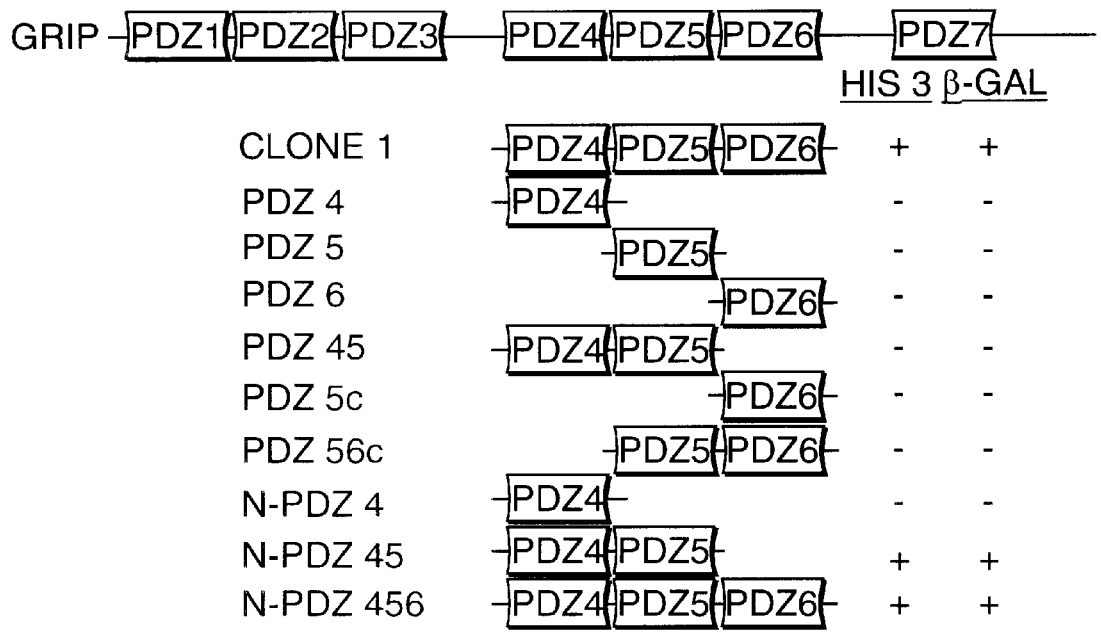
FIGS. 5A and 5B are drawings depicting structural determinants of GRIP and GluR2 required for interaction.

Characterization of the Structural Domains Necessary for the Interaction of Grip with the GluR2 Subunit The yeast two-hybrid system was used to examine the domains of GRIP and GluR2 that are responsible for the GRIP GluR2 interaction. Various constructs of GRIP were made that contained different combinations of PDZ domains 4, 5 and 6 in the yeast pPC86 vector (see FIG. 5A). The shortest construct that was positive when paired with the GluR2 C-terminus contained PDZ4, PDZ5 and about 30 amino acids on the N-terminal side of PDZ4, suggesting that PDZ6 is not necessary for the interaction. Interestingly, PDZ123 and PDZ7 do not interact with the C-terminus of GluR2 in yeast (data not shown), suggesting that the various PDZ domains in GRIP may have different specificities for peptide substrates. GRIP does not interact with the C-terminus of the GluR1 subunit of the AMPA receptor or the C-terminus of the NR2A or NR2B subunit of NMDA receptors in the yeast two-hybrid system (FIG. 5B). These results suggested that the C-terminus of GluR2 may directly interact with the PDZ domains in GRIP with a unique specificity. To analyze whether the C-terminal amino acids of GluR2 were involved in the interaction of GluR2 with GRIP we used the truncation mutant GluR2C Δ7, which deleted the last 7 amino acids (GIESVKI; SEQ ID NO. 42) of the GluR2 C-terminal construct, and two point mutants GluR2C 1878R and GluR2C E879R. Deletion of the last seven amino acids of GluR2 completely disrupted the association of GRIP with GluR2 in this system, while mutating 1878 and E879 had no effect (FIG. 5B).

FIGS. 5A–5B is explained in more detail as follows. The yeast two hybrid system was used to test the domains of GRIP (FIG. 5A) or GluR2 (FIG. 5B) that are required for interaction. Positive selection on His plates and β-Gal activity of each construct is indicated. (GluR2C =the last 50 amino acids of GluR2; GluR1C=the last 82 amino acids of GluR1; NR2A/BC=the last 221 or 226 amino acids, respectively, of the NR2A/B subunits).

EXAMPLE 4

Figure 6A:
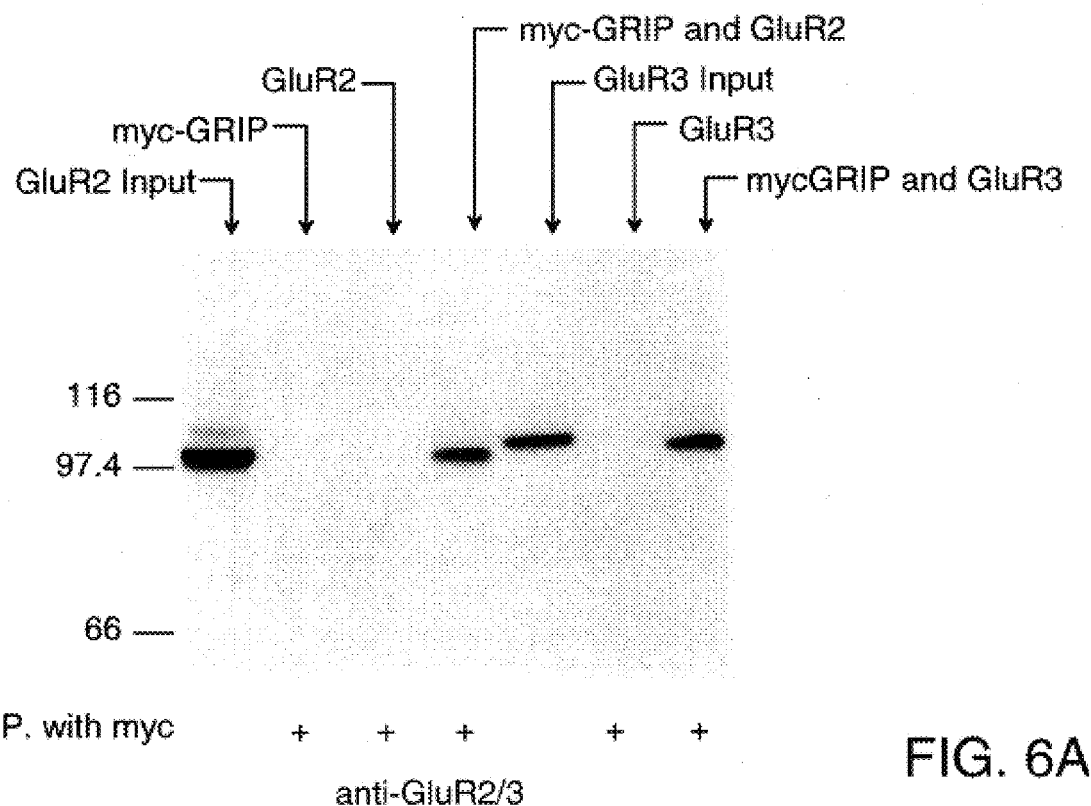
FIGS. 6A–6D are representations of Western blots depicting co-immunoprecipitation of GRIP with GluR2 and GluR3.

Interaction Grip with the GluR2 and GluR3 Subunits in Transfected HEK-293 Cells To examine the interaction between the GluR2 subunit and GRIP in systems other than yeast, we subcloned the cDNA encoding the 4th, 5th and 6th PDZ domains of GRIP into a mammalian expression vector with a myc-tag in the N-terminus (myc-GRIP456) and cotransfected the myc-GRIP456 with the fall length GluR2 subunit into HEK-293 cells. These transfected cells were then solubilized with 1% Triton X-100 and the soluble cell lysate was immunoprecipitated with an anti-myc antibody (anti-myc). The resulting imnmunoprecipitates were then immunoblotted with an amenity purified antiGluR2/3 antibody that recognizes both GluR2 and GluR3. As shown in FIG. 6A, GluR2 could be immunoprecipitated by the anti-myc antibody only when it was co-transfected with GRIP demonstrating that GluR2 associates with GRIP in this system. Interestingly, this co-immunoprecipitation could be inhibited when the extracts were preincubated with a synthetic peptide corresponding to the last 20 amino acids of the C-terminus of GluR2.

Since the GluR3 subunit has a similar carboxyl terminal amino acid sequence to GluR2 (see Table I), we examined whether GluR3 would also associate with GRIP in this system. Co-transfection of GluR3 with myc-GRIP456 also resulted in the coimmunoprecipitation of GluR3 with GRIP (see FIG. 6A). In contrast, the GluR1 subunit which does not have a similar C-terminal amino acid sequence, does not associate with GRIP under these conditions (FIG. 6B).

We also examined the interaction of GRIP with C-termninal mutants of the GluR2 subunit in transfected HBEK-293 cells. The same mutants described above, GluR2 I878R, GluR2E879R and GluR2 Δ7, were generated in the GluR2 subunit cDNA and cotransfected with GRIP into HEK-293T cells. In addition, a mutant in which serine 880 was mutated to an alanine was also tested. All four mutants expressed well and were recognized by the GluR2/3 antibody. As described above for the yeast two-hybrid system. Deletion of the last seven amino acids eliminated the interaction of GRIP with the GluR2 subunit in the HEK-293 cells (FIG. 6C), while mutation of 1878 and E879 did not disrupt the GRIP-GluR2 interaction (FIG. 6C). Interestingly, mutation of serine 880 completely eliminated the GRIP-GluR2 interaction (FIG. 6C), suggesting that similar to the interaction between the PDZ domains of PSD-95/SAP90 and substrate peptides [Kornau et al., Science, 269:1737–1740 (1995), Niethammer et al., J. Neurosci., 16:2157–2163 (1996), Doyle et al., Cell, 85:1067–1076 (1996)], a serine (or threonine) residue is important for the interaction of GRIP PDZ domains with their substrate peptides.

Figure 6B:
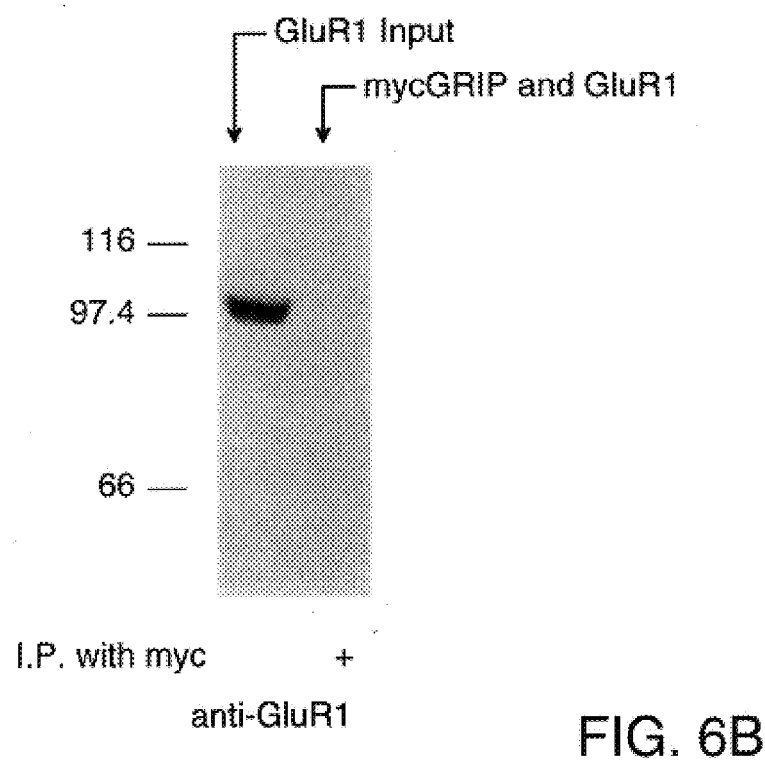
Figure 6C:
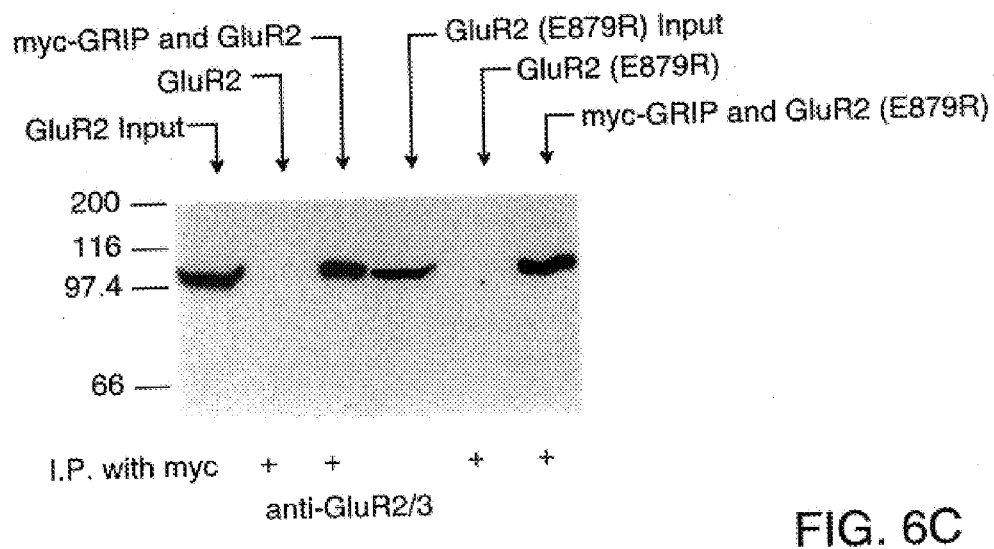
Figure 6D:
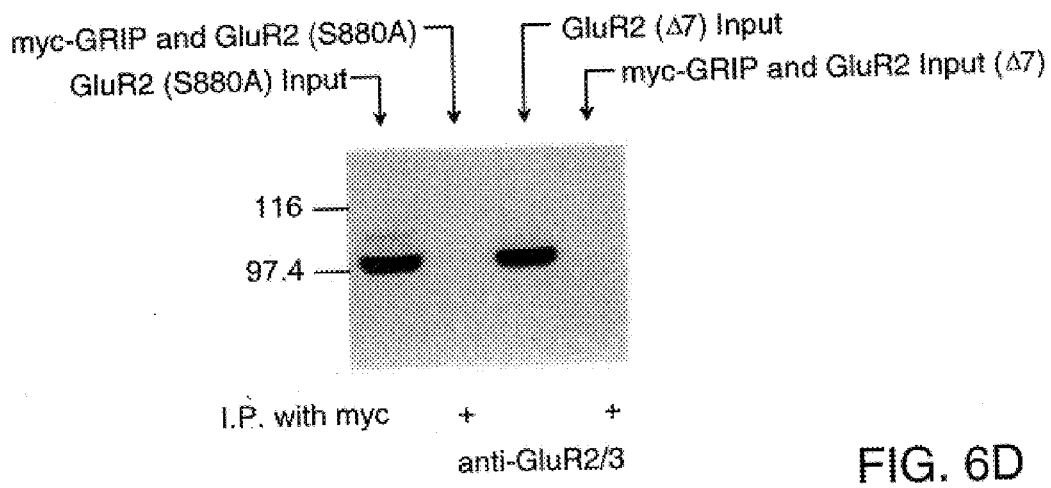

FIGS. 6A–6D are explained in more detail as follows. FIG. 6A and 6B show that full-length GluR2, GluR3 or GluR1 subunits were expressed with or without myc-GRIP456 (as indicated) in QT-6 cells. The cells were then solubilized with Triton X-100 and the myc-GRIP456 immunoprecipitated with an anti-myc antibody. The immunoprecipitates were then analyzed by immunoblot techniques using an antibody that recognizes both GluR2 and GluR3 or GluR1. FIGS. 6C and 6D show various mutants of GluR2 that were also analyzed.

EXAMPLE 5

Tissue Distribution of Grip

Figure 7:
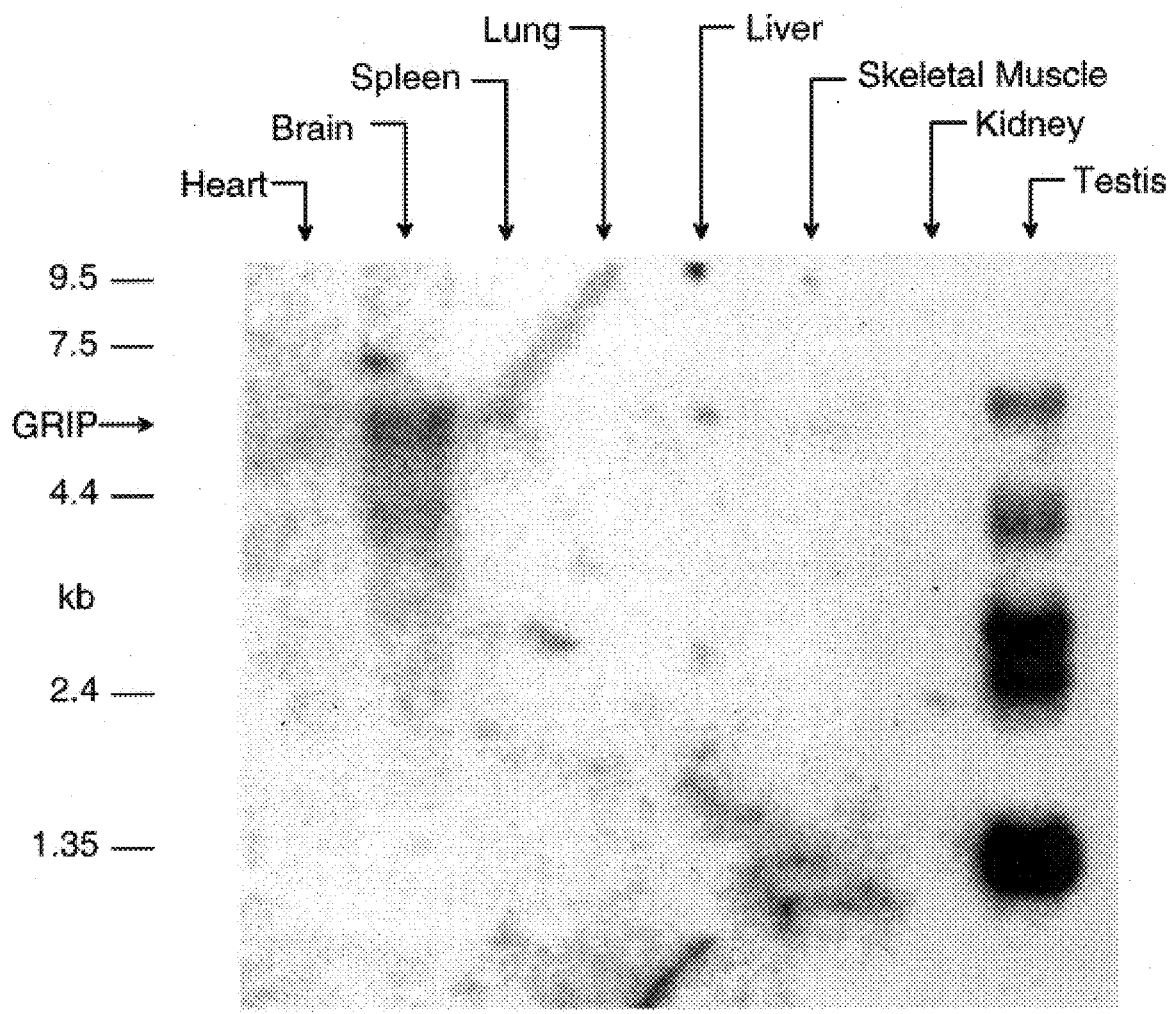
FIG. 7 is a representation of a northern blot of GRIP in rat tissues.

Northern blot analysis was used to examine the expression of GRIP mRNA in various rat tissues. The GRIP mRNA was 6 kb, consistent with the isolated full length cDNA, and was only detected in brain and testes (see FIG. 7). Level of expression in testes was higher than that seen in the brain suggesting an important function for GRIP in testes . The Northern blot shows expression of GRIP a Northern blot of mRNA in various rat tissues that were probed with the GRIP cDNA. The 6 kb GRIP mRNA was only detected in brain and in testes. The results suggest GRIP involvement in localization of receptors in sperm that are required for fertility. The degree of GRIP expression may enhance or prevent fertility.

To analyze the expression of the GRIP protein, an anti-fusion protein (amino acids 798–904) antibody and an antipeptide (amino acids 646–664) antibody were generated against GRIP. The afrinty purified anti-fusion protein antibody recognized a single 130 kDa protein in cells transfected with the fill length GRIP cDNA (see FIG. 8A). The specificity of this antibody was confirmed by blocking the immunoreactivity with the immunogenic fusion protein (FIG. 8A). Interestingly, this antibody specifically recognized a 130 kDa protein as well as an additional protein with an apparent molecular weight of 90 kDa in rat brain (see FIG. 8A). The recognition of both of these proteins by the antibody was blocked by preincubation with the fusion protein (FIG. 8A). These results suggest that the anti-GRIP fusion protein antibody cross reacts with another protein, possibly a GRIP-related protein, or alternatively, it recognizes a proteolytic breakdown product of GRIP. The antipeptide antibody also recognized the 130 kDa protein in cells transfected with full length GRIP cDNA (data not shown) and in rat brain but did not recognize the 90 kDa protein in brain (FIG. 8A). The specificity of this antibody was also confirmed by blocking the immunoreactivity with the immunogenic peptide.

The 130 kDa protein appears to be primarily associated with the membrane, while the 90 kDa is a soluble protein (FIG. 8B). In addition, the 130 kDa protein was resistant to solubilization in non-denaturing detergents in brain and in transfected cells suggesting that it may be associated with the cytoskeleton. Attempts to coimmunoprecipitate GRIP with AMPA receptors from detergent extracts of rat brain have so far been unsuccessful due to the lack of solubility of GRIP in non-denaturing detergents.

Using the anti-GRIP fusion protein antibody, the distribution of GRIP in neuronal and non-neuronal tissues was examined. The 130 kDa protein seems to be brain specific and was widely expressed in various brain regions including the olfactory bulb, cerebral cortex, hippocampus, cerebellum and spinal cord (FIG. 8C). In addition, the 130 kDa protein was observed in testes. In contrast, the 90 kDa protein was expressed in most tissues examined.

Figure 8D:
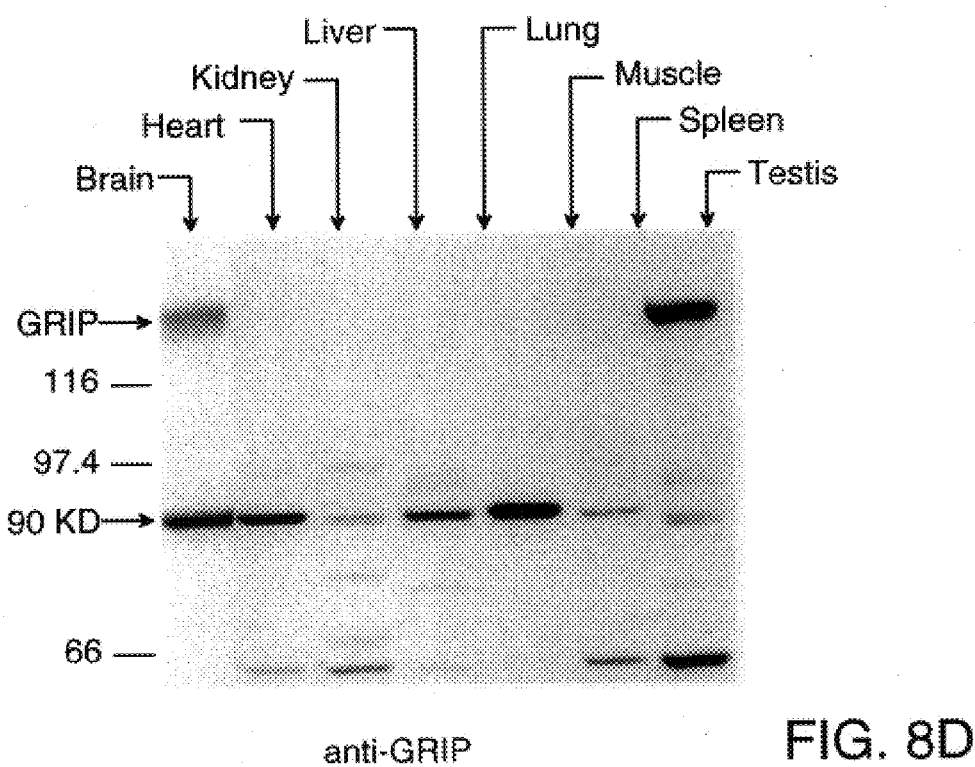

FIGS. 8A–8E are explained in more detail as follows. In FIG. 8A, both the anti-fusion protein and the antipeptide antibody recognized a 130 kDa protein in HEK-293 T cells transfected with the full length GRIP cDNA and in rat hippocampus. The anti-fusion protein also specifically recognized a 90 kDa protein in hippocampus. Inmunorecognition of these proteins by the antibodies was blocked by the immunuogen (+F.P., +Peptide). In FIG. 8C, the 130 kDa protein was mostly associated with the particulate fraction (P), while the 90 kDa protein is present in the soluble fraction (S).

Figure 8E:
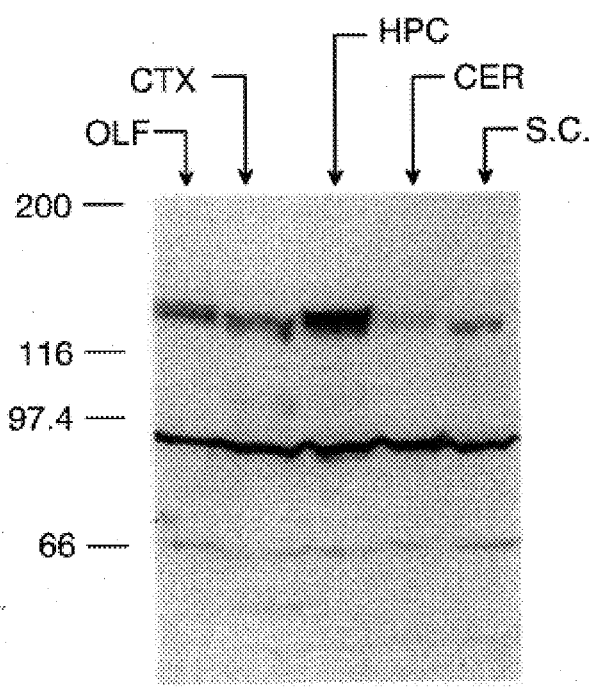

FIGS. 8B–8C show an immunoblot of various brain regions and tissues with the antifusion protein antibody. FIGS. 8D and 8E are Western blots using anti-GRIP antibody, showing that the 130 kDa protein is only expressed in brain and testes while the 90 kDa protein is expressed in most tissues examined.

EXAMPLE 6

Co-localization of Grip with AMPA Receptors in Neurons

Figure 9A:
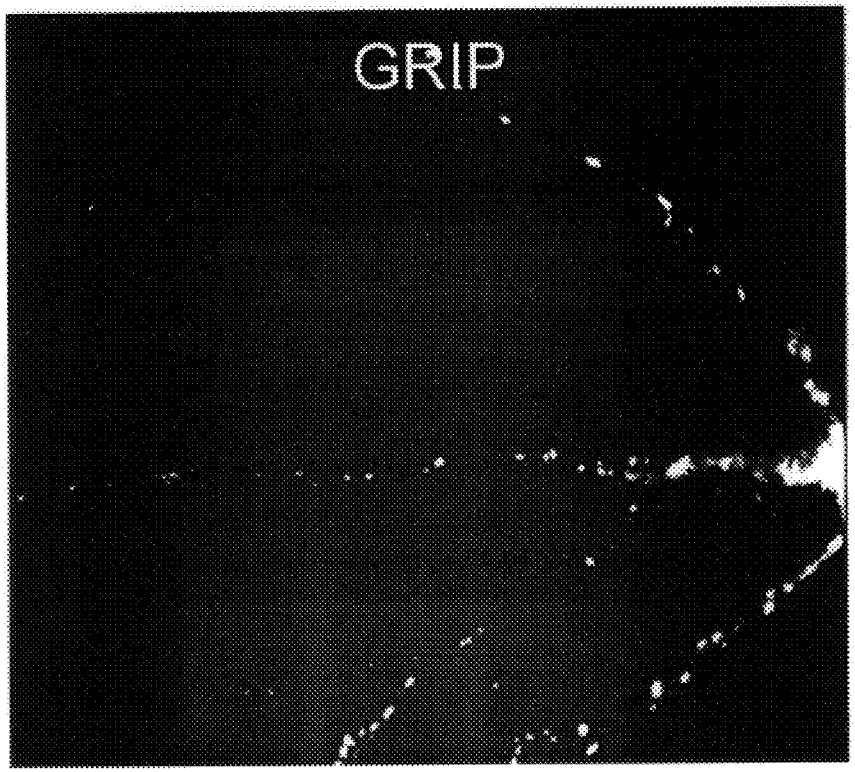
FIGS. 9A–9C are representations of photomicrographs showing co-localization of GRIP with AMPA receptors at excitatory synapses. Primary cultures of hippocampal neurons were double-labeled with anti-GRIP and anti-GluR1 antibodies.
Figure 9B:
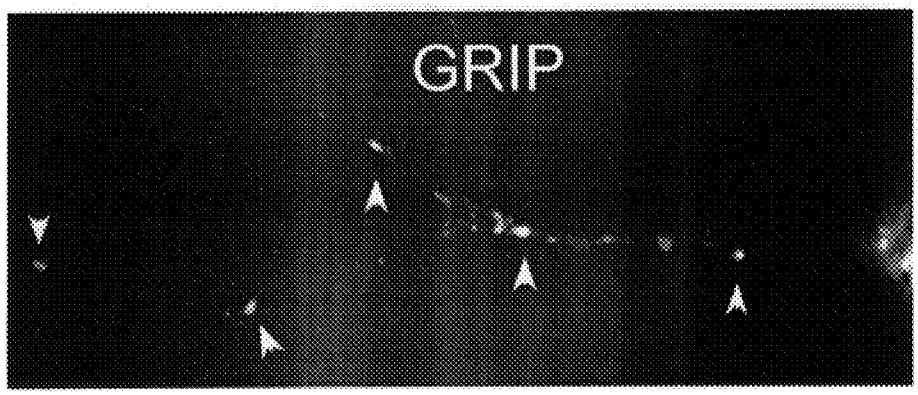
Figure 9C:

To examine the subcellular distribution of GRIP in neurons, primary cultures of rat hippocampal neurons were stained with the anti-GRIP fusion protein antibody and visualized with a FITC-coupled secondary antibody. GRIP was expressed throughout the dendrites of hippocampal neurons and was clustered near the cell surface in many but not all neurons (FIG. 9A). AMPA receptors in hippocampal cultures consist of heteromeric complexes of the GluR1, GluR2 and GluR3 subunits which cluster at excitatory synapses. See Craig, A. M. et al. (1993) Neuron 10: 1055–1068; and Craig, A. M. et al. (1994) PNAS (USA) 91: 12373–12377. Double labeling of the neurons with an antibody to the GluR1 subunit demonstrated that in many cases the clusters of GRIP co-localized with AMPA receptors associated with excitatory synapses (FIGS. 9B and 9C). These results provide supporting evidence that GRIP interacts with AMPA receptors in situ and combined with the results presented in FIG. 1 strongly suggest that GRIP-GluR2 interactions are important for AMPA receptor clustering.

In FIG. 9A, GRIP is present throughout neuronal dendrites and is clustered on dendritic processes. A high power magnification of a neuronal dendrite is shown in FIGS. 9B and 9C with characteristic synaptic AMPA receptor clusters that colocalize with GRIP.

EXAMPLE 7

Grip is Expressed in Rat Sertoli Cells and Germ Cells

The following results show high expression of the GRIP protein in the testis. The results point to a significant role for GRIP in spermatogenesis.

1. Northern and Western blot analysis

For Northern blot analysis on mRNA of adult rat testes, tubules and isolated total germ cells a cDNA probe of 919 bp was generated by PCR using specific primers for GRIP. Proteins of total adult rat testis, seminiferous tubules and isolated germ cells were spearated by SDS-PAGE and analyzed in Western blot analysis by using two affinity purified polyclonal antibodies specific for GRIP (JH2260, JH2493). Furthermore, cryosections of adult rat testis were fixed in 4% paraformaldehyde, as well as in acetone/ethanol, and immunostained with three different anti-GRIP antibodies (JH2260, JH2493, D7).

Figure 13:
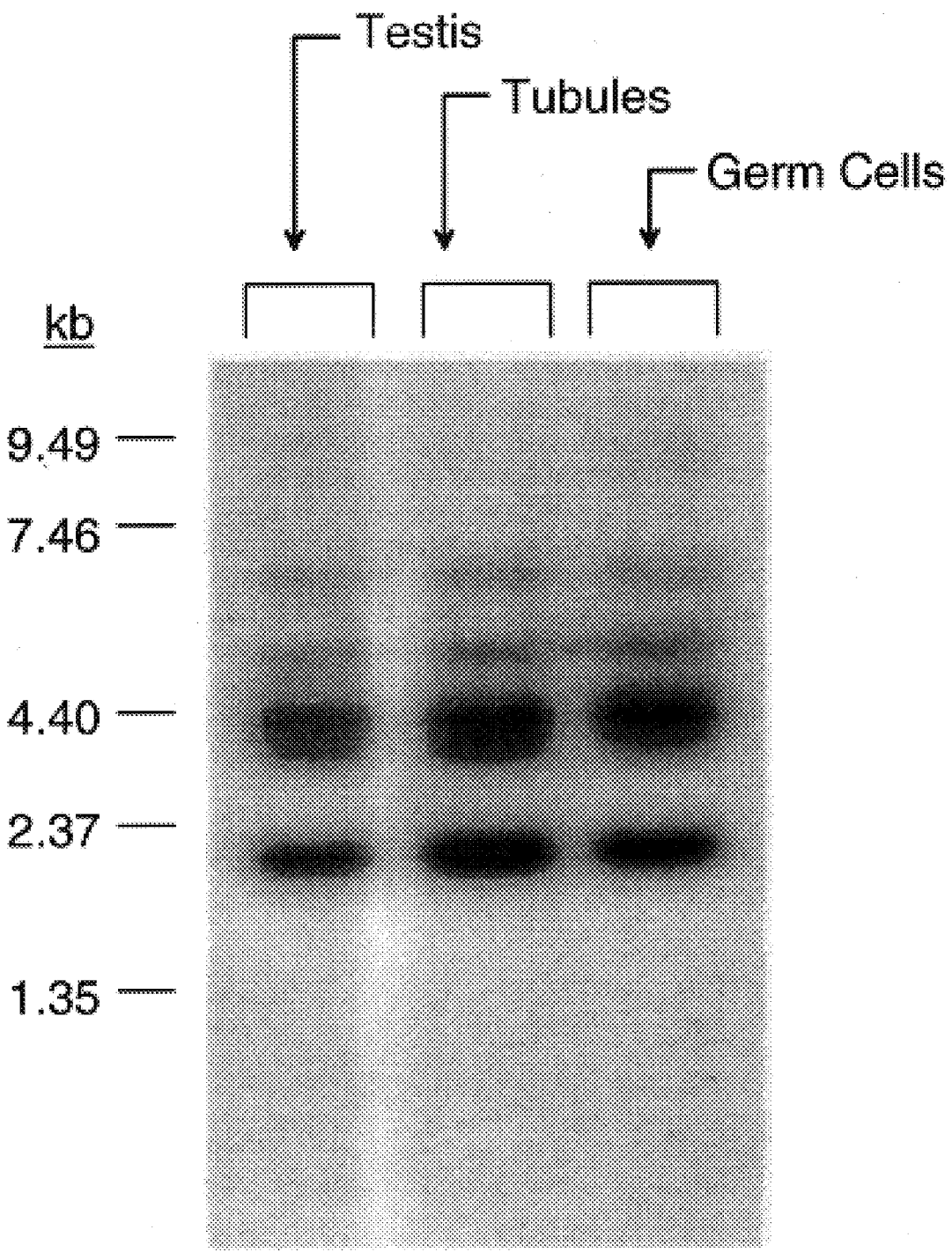
FIG. 13 is a representation of a GRIP Northern blot showing analysis of adult rat testis, isolated seminferous tubules, and germ cells mRNAs.

FIG. 13 shows results of Northern blot analysis of mRNA derived from total testes, seminiferous tubules, or enriched germ cell preparations demonstrated that several different transcripts are present in seminiferous tubule cells.

Figure 14:
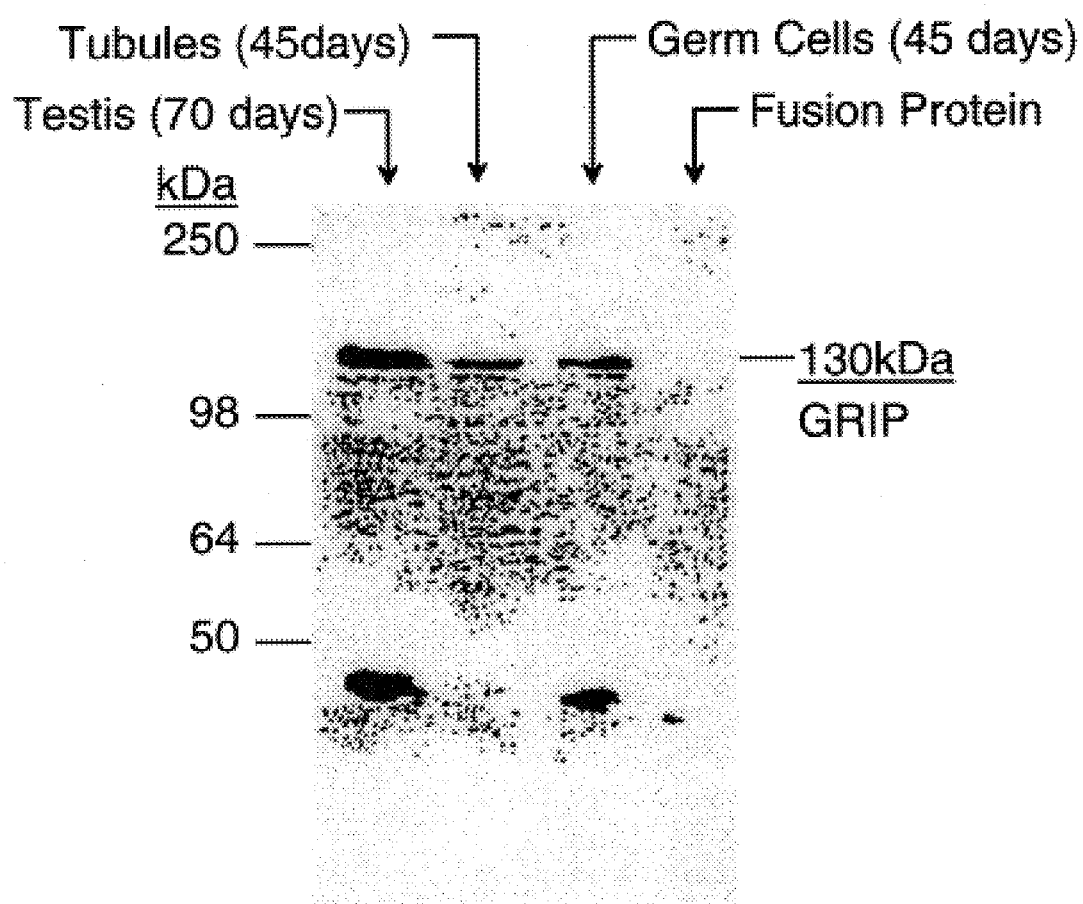
FIG. 14 is a representation of a Western blot showing analysis of GRIP expression in adult rat testis, seminferous tubules and total germ cells.

Western blot analysis with three different antibodies showed that a 130 kDa protein is present in both somatic and germ cells, together with a lower MW protein at 46 kDa (FIG. 14).

2. Immunofluorescence localization of GRIP

Figure 15A:
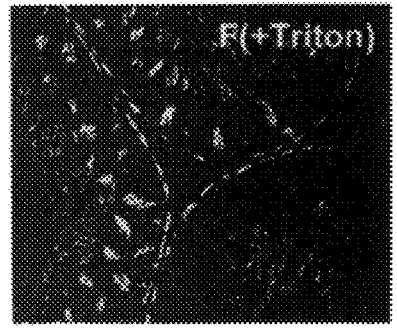
FIGS. 15A–15C are representations of photomicrographs showing immunofluorescence analysis with anti-GRIP antibodies on cryosections of adult rat testis. JH226D refers to an anti-grip antibody.
Figure 15B:
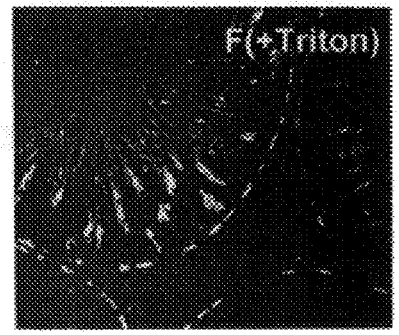
Figure 15C:
Figure 16A:
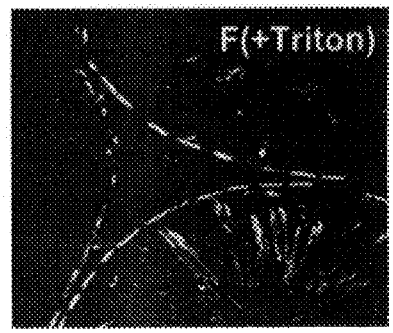
Figure 16B:
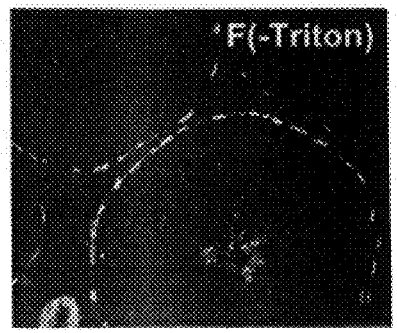
Figure 16C:
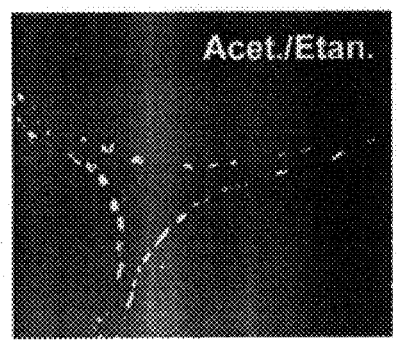
Figure 17A:
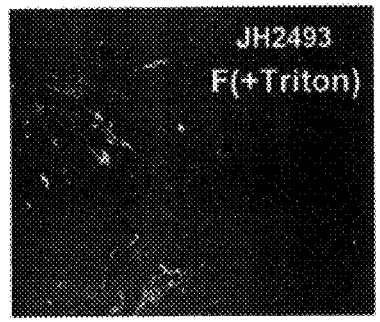
FIGS. 17A–17C are representations of photomicrographs showing hflrnunofluorescence analysis with anti-GRIP antibodies on cryosections of adult rat testis. JH2493 and JH2260 refers to an anti-grip antibody "abs+peptide" refers to a control reaction.
Figure 17B:
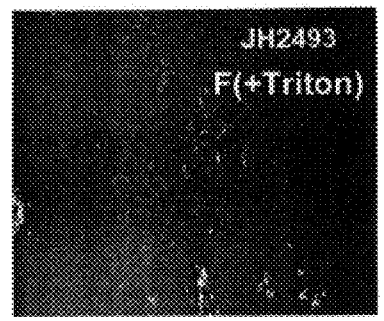
Figure 17C:
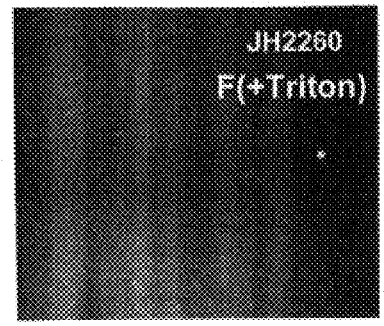

The presence of GRIP in seminiferous epithelium cells was confirmed by immunofluorescence localization. Selected antibodies recognized GRIP antigens at the basal region of Sertoli cells and at Sertoli cell-germ contacts, as well as in maturing germ cells (FIGS. 15A–B; 16A–B, 17A–B).

The data demonstrate that the signal transduction scaffold protein GRIP is expressed in somatic and germ cells of rat testis. The localization observed at the basal compartment of the Sertoli cells suggests that this protein plays a role in the polarization of these cells, as well as in localizing signaling proteins at their interface with the extratubular environment. FSH receptor have been shown to be localized in the same subcellular compartment. Without wishing to be bound to any particular theory, GRIP may be involved in compartinetnalization of the FSH-dependent signaling.

EXAMPLE 8

Immunofluorencence Localization of Grip in Developing Testis

Immunofluorescence localization experiments were performed with adult testis sections using anti-GRIP antibodies described above. It was found that GRIP is localized in the basal membrane of somatic Sertoli cells facing the basal lamina, as well as in specialized junctions that are reported to anchor developing spermatids to these cells. Using Northern blot analysis and reverse transcriptase-polymerase chain reactions (RT-PCR) using GRIP oligonucleotide primers in Sertoli cell cultures essentially devoid of any germ cells, a GRIP signal can be obtained.

Figure 18A:
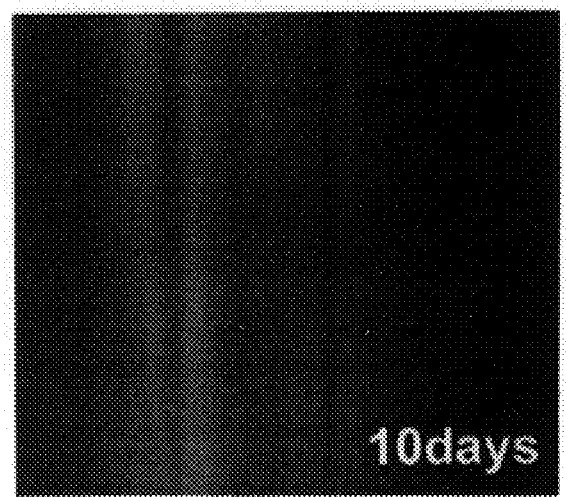
FIGS. 18A and 18B are representations of photomicrographs showing that GRIP is not detectable in immature Sertoli cells prior to organization of blood testis barrier (10 days). JH2493 refers to an anti-GRIP antibody.
Figure 18B:
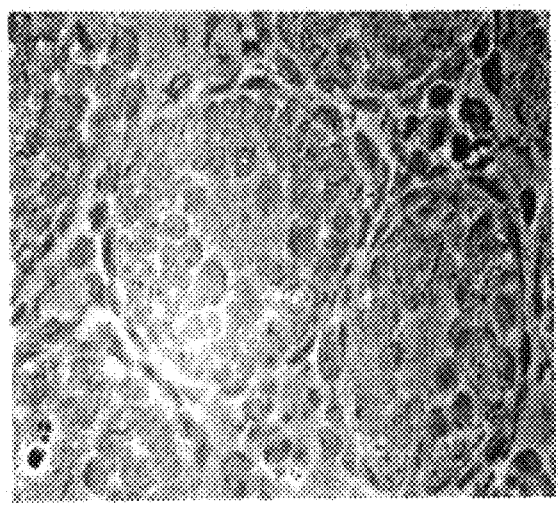
Figure 19A:
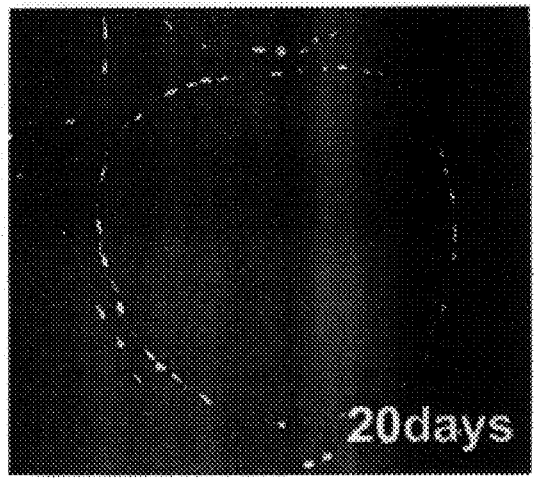
FIGS. 19A and 19B are representations of photomicrographs showing that a GRIP signal appears after tight junctions between Sertoli cells become organized (20 days). JH2493 refers to an anti-GRIP antibody.
Figure 19B:
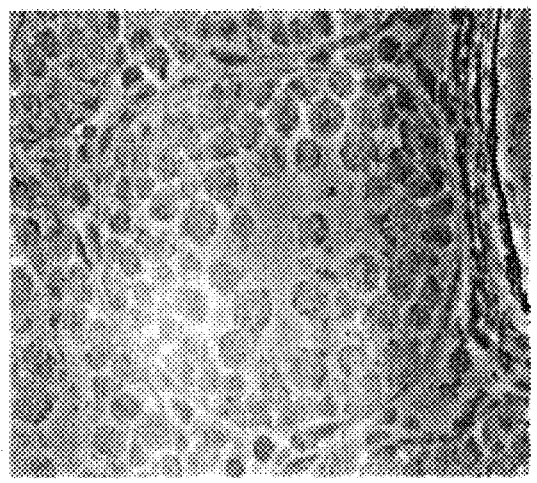
Figure 20A:
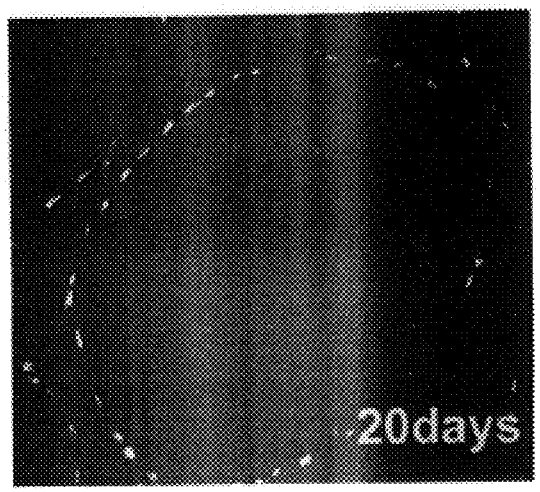
FIG. 20A and 20B are representations of photomicrographs showing that a GRIP expression in Sertoli cells (20 days). JH2260 refers to an anti-GRIP antibody.
Figure 20B:
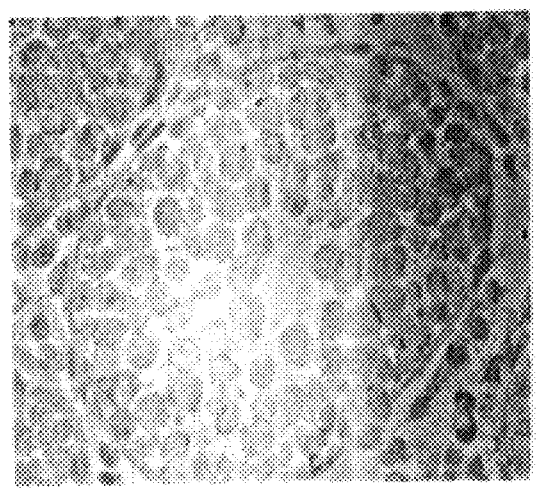
Figure 21:
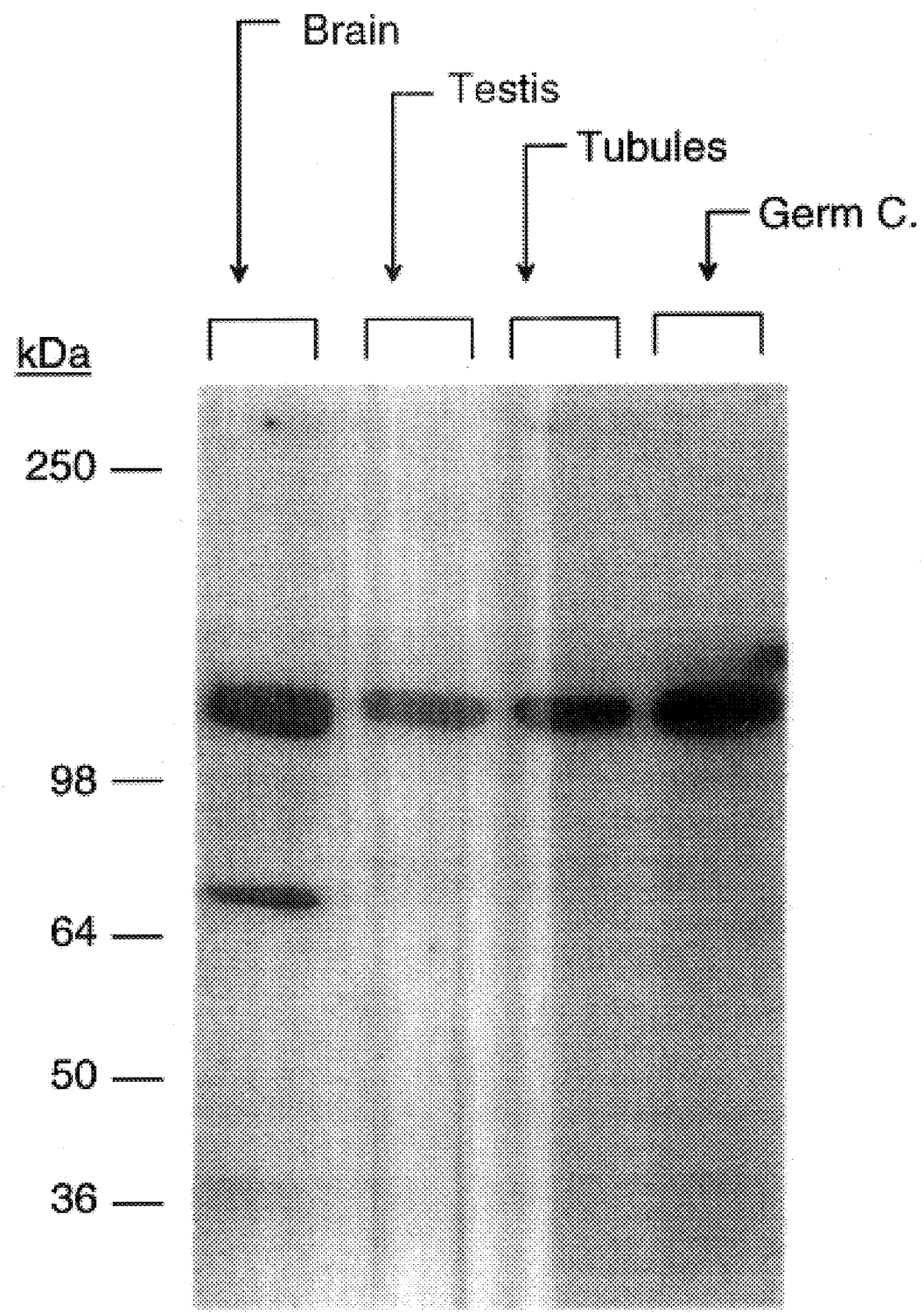
FIG. 21 is a representation of a Western blot showing GRIP expression in germ cells and other cell types.

Additional studies were performed on the developing testis using selected antibodies. FIGS. 18A–18B; 19A–19B show that GRIP is not expressed in the immature Sertoli cell prior to the organization of the blood testis barrier at 10 days (FIGS. 18A–B). The signal appears after the tight junctions between Serrtoli cells become organized at 20 days (FIGS. 19A–B). The data indicate that GRIP expression is coordinated with the polarization of the Sertoli cell.

Oligonucleotide primers have been designed to detect the GluR2 and to determine whether the receptors are expressed in the Sertoli cells. An amplified band (ie. PCR amplified) was seen in brain but not in the testis or Sertoli cells.

EXAMPLE 9

Isolation of PDZ Containing Proteins that Interact with EPH-related RTKs

The (EPH-related RTKs) are thought to be involved in regulating cell movement, axonal pathfinding, typographical neural projections, pattern formation, and have been localized to regions of cell-cell contact. Different studies have converged on a domain (PDZ) that interacts with transmembrane proteins. PDZ-containing proteins are emerging at protein-protein interaction modules that are thought to bring specific multimeric complexes to specialized cell surface sites. PDZ domains were previously shown to interact directly with the cytoplasmic carboxy terminal sequences—T/SXV (SEQ ID NO.41) of transmembrane receptors. Since EPH-family members have a related VXH sequence at their carboxy termini, it was believed that PDZ-containing proteins that interact with the carboxy termini of the EPH-RTKs could be found.

To isolate VXH-interacting proteins, the carboxy terminis of EPH members was employed as bait to screen mouse E11 and E17 libraries in the yeast two-hybrid system. Several PDZ-containing proteins were isolated that specifically interact with the C-terminal tail of EPH receptors.

The following methods were used as needed in the preceeding examples.

1. Immunoprecipitation

Coimmunoprecipitation of GRIP and GluR2/3 the cDNA containing the 4th, 5th and 6th PDZ domains (amino acids 435–969) of GRIP (myc-GRIP456) were directly subcloned into the Sal I/Not I sites of a myc-tagged pRK5 vector. HEK-293 T cells cotransfected with GluR2 (15 µg) and myc-GRIP456 (5 µg) were solubilized with 1% Triton X-100 in I.P. buffer and the supernatant used for immunoprecipitation. Anti-myc antibody was added to about 100 µl protein A Sepharose beads. The cell lysate supernatant was then added to the mixture and rotated slowly at 4° C. for 1–2 hours. After the incubation, the protein A beads were pelleted, and washed once in I.P. buffer containing 1% Triton X-100, twice in I.P. buffer containing 1% Triton X-100 and 0.5M NaCl, and three times in I.P. buffer. The immunoprecipitated proteins were eluted with sample buffer, separated using SDS-PAGE, transferred to PVDF and subjected to immunoblot analysis with anti-GluR2/3 antibodies.

2. Transfection of Spinal Cord Cultures

The C-terminal 50 amino acids of the GluR1 subunit (GluR1C), the GluR2 subunit (GluR2C), the NR1 subunit (NR1C) or a mutant of the GluR2 C-terminus lacking last 7 amino acids (GluR2C Δ7) were subcloned into the Sal I/Not I sites of the myc-tagged pRK5 vector, amplified and the plasmid purified with a Qiagen column (Qiagen Co.). Spinal cord neurons were taken from the ventral lumbar spinal cord of E 19 rat embryos using papain digestion. The cells were grown at low density (40 neurons/mm$^2$) on a feeder layer of spinal cord glia. The media was 75% MEM, 25% Neurobasal Media (Gibco) supplemented with N2 supplements [Banker, G and Goslin K. (1991). *Culturing Nerve Cells*. MIT Press, Cambridge, Mass.], 2% horse serum, and 15 µg/ml chick leg extract. On day 2 in culture the neurons were pretreated for 30 minutes with DMEM adjusted to an Osm of 280 and supplemented with 1 mM kynurenate. Neuronal cell transfection was performed using a modification of a previously published method [Xia et al. *J. Neuro.* 16(17) :5425–5436 (1996)]. The cDNA precipitate was prepared by adding 8 µg of DNA to 85.5 µl H$_2$O and then mixed with 12.5 µl of 2.0 M CaCl$_2$ and 2 µl Cal-Phos Maximizer (Clontech). The above solution was gently vortexed and then added 10 µl at a time to a 100 µl solution of 2× HBS (pH 7.0) with vortexing after every addition. After the entire solution was added it was sucked up and down several times through a yellow tip and allowed to stand for 25 minutes. The coverslips were added to a 12 well dish with 2ml of the DMEM solution and 100 µl of the DNA solution was added.

The neurons were incubated with DNA for two hours and then the coverslips were washed for two hours with multiple changes of DMEM alternating with standard growth media This procedure transfected from 1 to 2% of the neurons (and glia) and maximal expression appeared at 72 hours but was still strong at 96 hours. The neurons were triple labeled with: 1) anti-myc antibody to detect neurons transfecte with the myc-tagged proteins; 2) anti-synaptophysin antibodies to label synapses; and 3) anti-GluR1 antibodies to identify endogenous AMPA receptor clusters. Surface staining of GluR1 was performed using a Cy3 labeled FAB fragment of an antibody raised against a synthetic peptide corresponding to amino acids 251–269 in the N-terminal region of GluR1. Live neurons were incubated for one hour with 10 µg/ml Cy3 labeled FAB fragment in growth media, rinsed with MEM three times and fixed in 4% paraformaldehyde. Neurons were then labeled with a mouse monoclonal synaptophysin antibody (Boehringer Mannheim) followed by FITC coupled anti-mouse secondary antibody. Finally, the cells were labeled with the anti-myc antibody and AMCA coupled anti-mouse secondary antibody.

3. HEK-293 Cell Transfection

HEK-293 T cells were maintained in MEM medium (Gibco) with 10% fetal bovine serum (FBS, Gibco), 0.5% sodium pyrophosphate (Gibco), 0.5% streptomycin-penicillin (Gibco) and 0.5% L-glutamine. cDNAs subcloned into the pBKCMV vector or in the pRK5 vector with or without a N-terminal 16 amino acid myc-tag were used. cDNA (20 µg) was transfected into one 10 cm culture dish of HEK-293 cells using calcium phosphate co-precipitation as described (Ehlers, M D (1995) *Science* 269: 1743–1737). After transfection (36–48 hours), HEK-293 cells were harvested in immunoprecipitation (I.P.) buffer (25 mM TRISHC1 buffered saline (pH 7.4), containing 10 units/ml Trasylol, 0.1 mM phenylmethylsulfonyl fluoride (PMSF), 5 mM EDTA and 5 mM EGTA) and 1% Triton X100. Cell lysates were either centrifuged at 14,000 rpm for 10 min at 4° C. and the supernatant used for immunoprecipitation, or the whole lysate was diluted into sample buffer (125 mM Tris (pH 6.8), 5.0% β-mercaptoethanol. 2.0% SDS, with pyronin Y dye) for SDS-PAGE-.

4. Northern Blot Hybridization

One example of a northern blot hybridation was performed as follows. A nitrocellulose blot containing total RNA (10 µg) from various tissues (Clontech) was prehybridized in hybridization buffer (5× SSPE, Sx Denhards' solution, 50% formamide, 100–200µg/ml denatured salmon sperm DNA (ssDNA), 0.2% SDS) at 42° C. overnight. The blot was then incubated in fresh hybridization buffer with denatured cDNA probe (5–10×10$^6$ cpm/ml buffer) at 42° C. for 2 days. Blots were then subjected to wash in 1× SSC, 1% SDS at room temperature for 30–60 minutes, with 2–3 changes of washing buffer, and then further washed in more stringent conditions (0.5× SSC, 2% SDS, 55° C.) for 1–4 hours, with 2–3 changes of washing buffer and subjected to autoradiography at −70° C.

5. GRIP Immunocytochemistry

Cultured Hippocampal neurons were fixed in 4% paraformaldehyde, 4% sucrose for 30' at room temperature, permeabilized for 5' with 0.5% triton and blocked with 10% normal goat serum (NGS). Affinity purified anti-GRIP fusion protein antibody (0.2 µg/ml) was added overnight in 3% NGS followed by incubation for 1 hour with FITC anti-rabbit antibody at room temperature. Cells were then rinsed for 1 hour in PBS and incubated in 5% normal rabbit serum for 30'. Cy3 labeled anti-GluR1 antibody in 5% normal rabbit serum was then incubated with the neurons overnight. Cultures were then rinsed, mounted in Permafluor (Immunon) with 20 mg/ml Dabco and viewed at 100× Images were collected with a SIT Camera and digitized using Image 1 (Universal Imaging). Appropriate controls using fusion protein and peptide blocking of the anti-GRIP or anti-GluR1 antibodies showed no staining of the neurons.

EXAMPLE 10

Isolation of Grip 2 cDNA

A blast search of rat GRIP DNA sequence yielded one mouse homologue AA003555. The clone AA003555 was purchased from the Genome system, and sequenced. A 300 bp region which shows the least homology with GRIP was amplified by PCR, and used as a probe to screen the lambda zap cDNA library constructed from the rat hippocampus. After high stringency screening, a 4.5 Kb clone was obtained. Nucleic acid sequences and amino acid sequences were analyzed using the MacVector program, and the homology with GRIP was analyzed by the Blast search and the MACAW program.

All publications and patent applications herein are incorporated by reference to the same extent as if each individual publication or patent application was specifically and individually indicated to be incorporated by reference.

The invention has been described in detail with particular reference to the preferred embodiments thereof. However, it will be appreciated that modifications and improvements within the spirit and teachings of the invention may be made by those in the art upon considering the present disclosure.

What is claimed is:

1. An isolated and purified nucleic acid molecule encoding a 130 kDa GRIP protein, said protein having the ability to bind the C-terminal amino acids of the GluR2 and GluR3 subunits of AMPA receptors.

2. The nucleic acid molecule of claim 1, wherein said protein comprises seven PDZ binding domains.

3. The nucleic acid molecule of claim 1, wherein said protein comprises the amino acid sequence depicted in SEQ ID NO:2.

4. The nucleic acid molecule of claim 1, wherein said nucleic acid molecule comprises the nucleotide sequence depicted in SEQ ID NO:1.

5. An isolated and purified nucleic acid molecule encoding a PDZ binding domain containing fragment of a 130 kDa GRIP protein, said GRIP protein having the ability to bind the C-terminal amino acids of GluR2 and GluR3 subunits of AMPA receptors.

6. The nucleic acid molecule of claim 5, wherein said PDZ binding domain containing fragment includes the PDZ1 binding domain consisting of amino acids Thr52-Glu135 of SEQ ID NO:2 (SEQ ID NO:4).

7. The nucleic acid molecule of claim 6, wherein said nucleic acid molecule comprises nucleotides 339–591 of SEQ ID NO:1.

8. The nucleic acid molecule of claim 5, wherein said PDZ binding domain containing fragment includes the PDZ2 binding domain consisting of amino acids Glu152-Gly249 of SEQ ID NO:2 (SEQ ID NO:5).

9. The nucleic acid molecule of claim 8, wherein said nucleic acid molecule comprises nucleotides 640–933 of SEQ ID NO:1.

10. The nucleic acid molecule of claim 5, wherein said PDZ binding domain containing fragment includes the PDZ3 binding domain consisting of amino acids Leu252-His335 of SEQ ID NO:2 (SEQ ID NO:6).

11. The nucleic acid molecule of claim 10, wherein said nucleic acid molecule comprises nucleotides 940–1191 of SEQ ID NO:1.

12. The nucleic acid molecule of claim 5, wherein said PDZ binding domain containing fragment includes the PDZ4 binding domain consisting of amino acids Glu471-Phe558 of SEQ ID NO:2 (SEQ ID NO:7).

13. The nucleic acid molecule of claim 12, wherein said nucleic acid molecule comprises nucleotides 1597–1860 of SEQ ID NO:1.

14. The nucleic acid molecule of claim 5, wherein said PDZ binding domain containing fragment includes the PDZ5 binding domain consisting of amino acids His572-Lys655 of SEQ ID NO:2 (SEQ ID NO:8).

15. The nucleic acid molecule of claim 14, wherein said nucleic acid molecule comprises nucleotides 1900–2151 of SEQ ID NO:1.

16. The nucleic acid molecule of claim 5, wherein said PDZ binding domain containing fragment includes the PDZ6 binding domain consisting of amino acids Thr672-Gln753 of SEQ ID NO:2 (SEQ ID NO:9).

17. The nucleic acid molecule of claim 16, wherein said nucleic acid molecule comprises nucleotides 2200–2445 of SEQ ID NO:1.

18. The nucleic acid molecule of claim 5, wherein said PDZ binding domain containing fragment includes the PDZ7 binding domain consisting of amino acids Leu252-His335 of SEQ ID NO:2 (SEQ ID NO:6).

19. The nucleic acid molecule of claim 18, wherein said nucleic acid molecule comprises nucleotides 3148–3393 of SEQ ID NO:1.

20. The nucleic acid molecule of claim 5, wherein the PDZ binding domain containing fragment is selected from the group consisting of Thr52-Gly249 (SEQ ID NO:11), Thr52-His335 (SEQ ID NO:12), Thr52-Phe558 (SEQ ID NO:13), Thr52-Lys655 (SEQ ID NO:14), Thr52-Gln753 (SEQ ID NO:15), Thr52-Asn1069 (SEQ ID NO:16), Thr52-Leu1112 (SEQ ID NO:32), Glu152-His335 (SEQ ID NO:17), Glu152-Phe558 (SEQ ID NO:18), Glu152-Lys655 (SEQ ID NO:19), Glu152-Gln753 (SEQ ID NO:20), Glu152-Asn1069 (SEQ ID NO:21), and Glu152-Leu1112 (SEQ ID NO:33), Leu252-Phe558 (SEQ ID NO:22), Leu252-Lys655 (SEQ ID NO:23) Leu252-Gln753 (SEQ ID NO:24), Leu252-Asn1069 (SEQ ID NO:25), Leu252-Leu1112 (SEQ ID NO:34), Glu471-Lys655 (SEQ ID NO:26), Glu471-Gln753 (SEQ ID NO:27), Glu471-Asn1069 (SEQ ID NO:28), Glu471-Leu1112 (SEQ ID NO:35), His572-Gln753 (SEQ ID NO:29), His572-Asn1069 (SEQ ID NO:30), His572-Leu1112 (SEQ ID NO:36), Thr672-Asn1069 (SEQ ID NO:31), Thr672-Leu1112 (SEQ ID NO:37), and Lys988-Leu1112 (SEQ ID NO:38) of SEQ ID NO:2.

21. The nucleic acid molecule of claim 20, wherein the nucleic acid molecule is selected from the group consisting of nucleotides 339–933, 339–1191, 339–1860, 339–2151, 339–2445, 339–3393, 339–3522, 640–1191, 640–1860, 640–2151, 640–2445, 640–3393, 640–3522, 940–1860, 940–2151, 940–2445, 940– 3393, 940–3522, 1597–2151, 1597–2445, 1597–3393, 1597–3522, 1900–2445, 1900–3393, 1900–3522, 2200–3393, 2200–3522, and 3148–3522 of SEQ ID NO:1.

22. An isolated and purified nucleic acid molecule encoding an antigenic peptide fragment of a 130 kDa GRIP protein, wherein said GRIP protein has the ability to bind the C-terminal amino acids of GluR2 and GluR3 subunits of AMPA receptors.

23. The nucleic acid molecule of claim 22, wherein the antigenic peptide comprises the amino acid sequence SEQ ID NO:39.

24. The nucleic acid molecule of claim 22, wherein the antigenic peptide comprises amino acid residues 798 to 904 of SEQ ID NO:2.

25. The nucleic acid molecule of claim 1, wherein the molecule is cDNA.

26. The nucleic acid molecule of claim 1, wherein the molecule is RNA.

27. An isolated and purified nucleic acid molecule encoding a GRIP protein, wherein said nucleic acid molecule is capable of hybridizing to the nucleotides depicted in SEQ ID NO:1 under the high stringent conditions using a hybridization buffer comprising 30% formamide in 0.9M saline/0.9M sodium citrate (SSC) buffer at a temperature of 45° C. and remaining bound when subject to washing twice with that SSC buffer at 45° C., said protein having the ability to bind the C-terminal amino acids of the GluR2 and GluR3 subunits of AMPA receptors.

28. A composition comprising the nucleic acid molecule of any one of claims 1 to 24.

29. An expression vector comprising the nucleic acid molecule of any one of claims 1–24.

30. A host cell comprising the expression vector of claim 29.

31. A method of producing a GRIP protein or PDZ binding domain containing fragment thereof, said method comprising culturing the host cell of claim 30 under conditions wherein the GRIP protein or PDZ binding domain containing fragment thereof is expressed and isolating the GRIP protein or PDZ binding domain containing fragment thereof from the host cell.

32. A method for obtaining the isolated and purified nucleic acid molecule of claim 1, 5 or 22, the method comprising contacting a cDNA or genomic library with the nucleotide sequence of SEQ ID NO:2 or a portion thereof and isolating a vector comprising the nucleic acid molecule from the cDNA or genomic library.

33. A method for obtaining the isolated and purified nucleic acid molecule of claim 1, 5, or 22, the method comprising obtaining one or more oligonucleotide primers from a portion of the nucleotide sequence of SEQ ID NO:2, contacting a cDNA library with the primers, and performing a polymerase chain reaction (PCR) with the cDNA library sufficient to obtain the nucleic acid molecule.

34. A kit for detecting the expression of a 130 kDa GRIP protein, said kit comprising at least one of the isolated and purified nucleic acid molecules of claim 1, 5, or 22, said GRIP protein has the ability to bind the C-terminal amino acids of GluR2 and GluR3 subunits of AMPA receptors.

* * * * *

SEQUENCE LISTING (1) GENERAL INFORMATION:

(iii) NUMBER OF SEQUENCES: 105

(2) INFORMATION FOR SEQ ID NO:1:

(i) SEQUENCE CHARACTERISTICS:
      (A) LENGTH: 4527 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
AGCTCCACCA GATGACATGT AGCGCGCGGG ACCTCTGCAT CAGCCAAGAG GAATTAAGCT      60
TTGTCACTCC CCACTGGGAC TACCTTCCTC CTGGTATGTG CGCAAGGAAT TCATATACTG     120
CTGCTCGCCG CCGCAGGCAC CAGAGCAGAG CCCTGTGTGC ACTTTGGCAG AGATCAGGGA     180
GCAAGAATGA TAGCTGTCTC TTTTAAATGC CGCTGTCAGA TTCTAAGGCG ACTTACCAAA     240
GATGAGAGTC CCTACACTAA ATCTGCCAGC CAGACAAAGC CGCCCGATGG AGCATTGGCT     300
GTGAGGAGAC AGAGCATCCC AGAGGAATTC AAGGGCTCCA CCGTGGTGGA GCTGATGAAG     360
AAGGAGGGAA CCACTCTTGG CCTGACGGTA TCAGGAGGAA TCGATAAAGA TGGAAAGCCA     420
AGAGTGTCCA ACCTGCGGCA GGGAGGGATT GCTGCCAGAA GTGACCAGCT GGATGTGGGC     480
GACTACATCA AGCGGTGAA TGGGATCAAC CTGGCCAAAT TCCGCCATGA TGAGATCATC     540
AGCCTGCTGA AAAATGTTGG GGAAAGAGTG GTCCTGGAGG TCGAGTATGA GCTTCCACCG     600
GTCTCTATCC AAGGATCGAG TGTTATGTTC CGAACAGTGG AGGTCACCTT GCACAAAGAA     660
GGCAACACCT TTGGTTTTGT CATCCGAGGG GGAGCGCATG ATGACAGAAA TAAGTCCCGT     720
CCAGTTGTGA TAACCTGTGT TCGTCCTGGA GGGCCTGCTG ACAGAGAGGG CACCATCAAA     780
CCTGGAGACA GGTTGCTCAG TGTGGATGGA ATTCGGCTTC TGGGAACCAC CCATGCTGAG     840
GCCATGAGCA TCCTTAAACA GTGCGGACAA GAAGCAACGC TGCTGATAGA ATATGATGTC     900
TCCGTGATGG ATTCTGTAGC AACAGCATCC GGGCCACTAC TAGTTGAAGT TGCCAAAACT     960
CCCGGTGCAA GCCTTGGGGT TGCACTAACT ACCTCCGTGT GCTGTAACAA CAAGTCATC    1020
GTCATAGACA AAATCAAATC TGCAAGCATT GCGGACAGGT GCGGGCGCT ACATGTGGGA    1080
GACCACATCC TCTCCATCGA CGGCACGAGC ATGGAGTACT GTACCCTCGC AGAAGCAACC    1140
CAGTTCCTGG CCAACACCAC TGACCAGGTC AAGCTGGAGA TTCTCCCACA CCATCAGACC    1200
CGCCTGGCCC TGAAGGGACC TGACCATGTG AAAATTCAGA GGAGCGACAG ACAGCTTCCC    1260
TGGGATCCCT GGGCCAGCAG CCAGTGCAGC GTTCATACCA ACCATCACCA TAACCCGCAC    1320
CACCCAGACC ATTGCCGAGT ACCAGCCCTG GGTTTTCCGA AAGCGCTTAC TCCAAACAGC    1380
CCTCCGGCTA TGGTGTCCTC GTCCTCTCCT ACCTCTATGA GTGCGTACAG CCTGAGTTCC    1440
CTGAACATGG GGACTTTACC TCGAAGCCTC TACTCTACTA GTCCACGAGG AACCATGATG    1500
AGGAGGAGAC TGAAAAAGAA GGACTTCAAA AGCTCACTGT CTTTAGCTTC TAGCACTGTG    1560
GGATTGGCTG ACAGGTTGT TCACACTGAA ACCACAGAGG TTGTGCTGAC GGCTGATCCT    1620
GTCACTGGCT TTGGAATCCA ACTGCAGGGC AGCGTGTTTG CCACAGAGAC TCTCTCCTCC    1680
CCACCTCTGA TTTCCTATAT TGAAGCTGAC AGCCCAGCAG AGAGATGTGG TGTGCTGCAG    1740
ATTGGAGACA GAGTCATGGC CATTAATGGA ATCCCAACAG AAGACAGCAC CTTTGAGGAA    1800
GCCAATCAGC TCCTTCGAGA CTCTTCCATC ACGAGCAAAG TCACACTGGA AATCGAGTTT    1860
GATGTTGCAG AATCTGTCAT CCCAAGTAGT GGAACATTTC ATGTAAAACT GCCTAAGAAG    1920
CACAGCGTGG AGCTTGGAAT AACCATCAGT TCGCCATCCA GTAGAAAACC AGGGGACCCT    1980
CTCGTCATTT CAGATATCAA GAAAGGCAGT GTGGCACACA GAACTGGAAC TCTGGAACTT    2040
GGAGATAAAT TGCTCGCCAT AGATAACATC CGGTTGGACA GCTGTTCCAT GGAAGATGCA    2100
GTCCAGATCC TCCAGCAGTG TGAAGACCTG GTGAAGCTCA AAATCCGCAA AGATGAAGAT    2160
AACTCAGATG AGCAAGAGAG TTCCGGGGCG ATTATTTACA CGGTGGAGCT GAAGCGCTAT    2220
GGGGGGCCCC TTGGCATCAC CATTTCTGGA ACGGAAGAGC CCTTTGATCC TATTATCATC    2280
TCGAGCCTCA CTAAAGGGGG ATTAGCTGAA AGGACTGGAG CGATCCACAT CGGAGATCGA    2340
```

```
ATCCTAGCCA TCAATAGCAG TAGCTTGAAG GGGAAGCCTC TGAGTGAAGC CATCCACTTG      2400

CTACAGATGG CGGGAGAGAC TGTCACCCTG AAAATTAAGA AGCAGACAGA TGCTCAACCT      2460

GCCTCAAGTC CCAAGAAGCT GCCCATCCCC AGCCACTCAA GTGACCTAGG AGATGGTGAG      2520

GAGGACCCCT CCCCAATACA AAGGCCTGGC AAGCTCTCTG ACGTGTACCC CTCCACAGTA      2580

CCCAGCGTGG ACAGTGCTGT GGACTCCTGG GACGGATCTG GAATAGATGC CAGGTATGGG      2640

AGTCAAGGCA CGACTTTTCA GACTTCAGGG TACAATTTCA ACACCTATGA CTGGAGGAGT      2700

CCGAAGAAAA GAGCCAGCCT GTCCCCGGTC CCCAAGCCTC GAAGCCAGAC ATACCCAGAT      2760

GTGGGCTTGA GTAATGAAGA CTGGGACCGG TCCACAGCCA GTGGCTTCGC CGGGGCTTCT      2820

GACAGTGCAG ACGCTGAACA AGAGGAAAAC TTCTGGTCTC AAGCATTGGA GGACCTGGAG      2880

ACCTGCGGCC AGTCGGGAAT CCTGAGAGAG CTCGAGGCAA CAATCATGTC GGGGAGCACT      2940

ATGAGTTTGA ATCATGAGGC TCCAACGGCT CGCAGTCAGC TGGGGCGACA GGCCAGCTTC      3000

CAGGAACGGA GCAATTCGAG GCCACACTAT AGCCAAACGA CTCGCAGCAA CACTCTGCCC      3060

TCGGATGTGG GCAGAAAGTC TGTGACCCTG CGGAAAATGA AGCAAGAAAT CAAGGAGATT      3120

ATGTCCCCAA CTCCCGTGGA GCTTCACAAG GTGACCTTAT ACAAAGACTC TGGCATGGAG      3180

GACTTTGGGT TCAGTGTGGC AGATGGCCTG CTGGAGAAAG GGGTGTATGT CAAAAATATC      3240

CGCCCAGCTG GGCCAGGTGA TCTTGGAGGC TTGAAGCCTT ATGACAGGCT CTTACAGGTT      3300

AACCACGTCC GAACGAGAGA CTTCGACTGC TGCCTGGTGG TGCCCCTCAT AGCCGAATCC      3360

GGTAACAAGC TGGACCTGGT TATTAGCAGA AACCCGCTGG CCTCCCAGAA GTCGATAGAA      3420

CAGCCGGCTC TGCCCAGTGA CTGGAGCGAA CAGAACAGCG CTTTCTTCCA GCAGCCCAGC      3480

CACGGTGGTA ACCTAGAGAC ACGAGAACCC ACTAACACAT TATAGCATTA CTTTTATAAA      3540

GCAGGACGAA AGACGATATC TACATGGTGC TAAAACAAAA CAGAACAGAA CAGAACAGAA      3600

CAGAACAGAA CAGAACAGAA CAGAACAGAA CAACCCTTTA AGATTTCTTG TGACAGCTTG      3660

AAGCACAGAG AATCACCGTG GCATTAATTG CAAAGCACAG GGGTCTTTTA AATCTCCCTC      3720

ATAGCTCATG TTCTCATCCC TTCCCAACTA GAAGAGGTTT CTTTTAGGAT GACCACTCTG      3780

TTAACTGGCG GGTCCTCCTC TGCCGGGGGT GGGGAGGCCC CTTCGGTAGA CAATAAAGAG      3840

GAAGGCAGCC CACCCCTTCC CCCACCCCAA TCAAGATCAG AGGAAACTTT TTACAATTCA      3900

CCTTACTGTC ACTTTTAACA GAGAGAAACA TCCCTTTGAA AATATTCTCT ATGGTAATTT      3960

CCTGAATGGA GTAAGTTTCT TACTATAACG TCATTAGTGT AAGAACACGA TCAATATGGA      4020

TTTACACATA GCTGGCCCTG CTAGGGGAGC TAGGATGGGT GAATGGCTAG GCCTGCCGCG      4080

GTGGGAGGGG CACAGGTATA ACATTAGGTT TTCTTAAAAT ATTTCAGCAA CAGTGCACGT      4140

TGGAGACCAT AATAGGTGGT GGTAAATGTT TCGCCCAAAT ATAGGAATGA TTTTAACTAA      4200

GATGTATGCT ATTCCCTATG CAACAGATGA TCAAACAGGA TATGTCTTGT GACCTGTTTT      4260

TTTTTTTCCT TAAGGACACA TTCTTTTTTT TTTTTTTAAT AGCTGAAAAA AATCTCTGGT      4320

AATGAATTAG AGTGTGTGGT AACACTGAGC ATTAGTGATA TGACCCTATT TTTAAAATCC      4380

AAGACTAAGA ATTTAAGGAG TGAAGAGTCT AATGAAATGA GATTCACTTT CTGGGTAGGC      4440

AAACAGAACT CATGCAGCTC AGAAGTCTGC AGACTGCTAC ACCGAGGGGT GCACAGCACA      4500

ATGACTTAAG GACGACGACG ATTTGGT                                        4527
```

(2) INFORMATION FOR SEQ ID NO:2:

(i) SEQUENCE CHARACTERISTICS:
        (A) LENGTH: 1112 amino acids
        (B) TYPE: amino acid (C) STRANDEDNESS:
        (D) TOPOLOGY: linear (ii) MOLECULE TYPE: protein (xi) SEQUENCE DESCRIPTION: SEQ ID NO:2:

```
Met Ile Ala Val Ser Phe Lys Cys Arg Cys Gln Ile Leu Arg Arg Leu
1               5                   10                  15

Thr Lys Asp Glu Ser Pro Tyr Thr Lys Ser Ala Ser Gln Thr Lys Pro
            20                  25                  30

Pro Asp Gly Ala Leu Ala Val Arg Arg Gln Ser Ile Pro Glu Glu Phe
        35                  40                  45

Lys Gly Ser Thr Val Val Glu Leu Met Lys Lys Glu Gly Thr Thr Leu
    50                  55                  60

Gly Cys Thr Val Ser Gly Gly Ile Asp Lys Asp Gly Lys Pro Arg Val
65                  70                  75                  80

Ser Asn Leu Arg Gln Gly Gly Ile Ala Ala Arg Ser Asp Gln Leu Asp
                85                  90                  95

Val Gly Asp Tyr Ile Lys Ala Val Asn Gly Ile Asn Leu Ala Lys Phe
            100                 105                 110

Arg His Asp Glu Ile Ile Ser Leu Leu Lys Asn Val Gly Glu Arg Val
        115                 120                 125

Val Leu Glu Val Glu Tyr Glu Leu Pro Pro Val Ser Ile Gln Gly Ser
    130                 135                 140

Ser Val Met Phe Arg Thr Val Glu Val Thr Leu His Lys Glu Gly Asn
145                 150                 155                 160

Thr Phe Gly Phe Val Ile Arg Gly Gly Ala His Asp Asp Arg Asn Lys
                165                 170                 175

Ser Arg Pro Val Val Ile Thr Cys Val Arg Pro Gly Gly Pro Asp Asp
            180                 185                 190

Arg Glu Gly Thr Ile Lys Pro Gly Asp Arg Leu Leu Ser Val Asp Gly
        195                 200                 205

Ile Arg Leu Leu Gly Thr Thr His Ala Glu Ala Met Ser Ile Leu Lys
210                 215                 220

Gln Cys Gly Gln Glu Ala Thr Leu Leu Ile Glu Tyr Asp Val Ser Ala
225                 230                 235                 240

Met Asp Ser Val Ala Thr Ala Ser Gly Pro Leu Leu Val Glu Val Ala
                245                 250                 255

Lys Thr Pro Gly Ala Ser Leu Gly Val Ala Leu Thr Thr Ser Val Cys
            260                 265                 270

Cys Asn Lys Gln Val Ile Val Ile Asp Lys Ile Lys Ser Ala Ser Ile
        275                 280                 285

Ala Asp Arg Cys Gly Ala Leu His Val Gly Asp His Ile Leu Ser Ile
    290                 295                 300

Asp Gly Thr Ser Met Glu Tyr Cys Thr Leu Ala Glu Ala Thr Gln Phe
305                 310                 315                 320

Leu Gly Asn Thr Thr Asp Gln Val Lys Leu Glu Ile Leu Pro His His
                325                 330                 335

Gln Thr Arg Leu Ala Leu Lys Gly Pro Asp His Val Lys Ile Gln Arg
            340                 345                 350

Ser Asp Arg Gln Leu Pro Trp Asp Pro Trp Ala Ser Ser Gln Cys Ser
        355                 360                 365

Val His Thr Asn His His Asn Pro His Pro Asp His Cys Arg
    370                 375                 380

Val Pro Ala Leu Gly Phe Pro Lys Ala Leu Thr Pro Asn Ser Pro Pro
```

-continued

```
            385                 390                 395                 400
Ala Met Val Ser Ser Ser Pro Thr Ser Met Ala Tyr Ser Leu
                    405                 410                 415
Ser Ser Leu Asn Met Gly Thr Leu Pro Arg Ser Leu Tyr Ser Thr Ser
                420                 425                 430
Pro Arg Gly Thr Met Met Arg Arg Arg Leu Lys Lys Lys Asp Phe Lys
            435                 440                 445
Ser Ser Leu Ser Leu Ala Ser Ser Thr Val Gly Leu Ala Gly Gln Val
            450                 455                 460
Val His Thr Glu Thr Thr Glu Val Val Leu Thr Ala Asp Pro Val Thr
465                 470                 475                 480
Gly Phe Gly Ile Gln Leu Gln Gly Ser Val Phe Ala Thr Glu Thr Leu
                            485                 490                 495
Ser Ser Pro Pro Leu Ile Ser Tyr Ile Glu Ala Asp Ser Pro Ala Glu
                500                 505                 510
Arg Cys Gly Val Leu Gln Ile Gly Asp Arg Val Met Ala Ile Asn Gly
                515                 520                 525
Ile Pro Thr Glu Asp Ser Thr Phe Glu Glu Ala Asn Gln Leu Leu Arg
            530                 535                 540
Asp Ser Ser Ile Thr Ser Lys Val Thr Leu Glu Ile Glu Phe Asp Val
545                 550                 555                 560
Ala Glu Ser Val Ile Pro Ser Ser Gly Thr Phe His Val Lys Leu Pro
                            565                 570                 575
Lys Lys His Ser Val Glu Leu Gly Ile Thr Ile Ser Ser Pro Ser Ser
                        580                 585                 590
Arg Lys Pro Gly Asp Pro Leu Val Ile Ser Asp Ile Lys Lys Gly Ser
                    595                 600                 605
Val Ala His Arg Thr Gly Thr Leu Glu Leu Gly Asp Lys Leu Leu Ala
610                 615                 620
Ile Asp Asn Ile Arg Leu Asp Ser Cys Ser Met Glu Asp Ala Val Gln
625                         630                 635                 640
Ile Leu Gln Gln Cys Glu Asp Leu Val Lys Leu Lys Ile Arg Lys Asp
                        645                 650                 655
Glu Asp Asn Ser Asp Glu Gln Glu Ser Ser Gly Ala Ile Ile Tyr Thr
                    660                 665                 670
Val Glu Leu Lys Arg Tyr Gly Gly Pro Leu Gly Ile Thr Ile Ser Gly
                675                 680                 685
Thr Glu Glu Pro Phe Asp Pro Ile Ile Ile Ser Ser Leu Thr Lys Gly
            690                 695                 700
Gly Leu Ala Glu Arg Thr Gly Ala Ile His Ile Gly Asp Arg Ile Leu
705                 710                 715                 720
Ala Ile Asn Ser Ser Ser Leu Lys Gly Lys Pro Leu Ser Glu Asp Ile
                    725                 730                 735
His Leu Leu Gln Met Ala Gly Glu Thr Val Thr Leu Lys Ile Lys Lys
                740                 745                 750
Gln Thr Asp Ala Gln Pro Ala Ser Ser Pro Lys Lys Leu Pro Ile Pro
            755                 760                 765
Ser His Ser Ser Asp Leu Gly Asp Gly Glu Glu Asp Pro Ser Pro Ile
    770                 775                 780
Gln Arg Pro Gly Lys Leu Ser Asp Val Tyr Pro Ser Thr Val Pro Ser
785                 790                 795                 800
Val Asp Ser Ala Val Asp Ser Trp Asp Gly Ser Gly Ile Asp Ala Arg
                        805                 810                 815
```

-continued

```
Tyr Gly Ser Gln Gly Thr Thr Phe Gln Thr Ser Gly Tyr Asn Phe Asn
            820                 825                 830

Thr Tyr Asp Trp Arg Ser Pro Lys Lys Arg Ala Ser Leu Ser Pro Val
            835                 840                 845

Pro Lys Pro Arg Ser Gln Thr Tyr Pro Asp Val Gly Leu Ser Asn Glu
            850                 855                 860

Asp Trp Asp Arg Ser Thr Ala Ser Gly Phe Ala Gly Ala Ser Asp Ser
865                 870                 875                 880

Ala Asp Ala Glu Gln Glu Glu Asn Phe Trp Ser Gln Ala Leu Glu Asp
            885                 890                 895

Leu Glu Thr Cys Gly Gln Ser Gly Ile Leu Arg Glu Leu Glu Ala Thr
            900                 905                 910

Ile Met Ser Gly Ser Thr Met Ser Leu Asn His Glu Ala Pro Thr Ala
            915                 920                 925

Arg Ser Gln Leu Gly Arg Gln Ala Ser Phe Gln Glu Arg Ser Asn Ser
            930                 935                 940

Arg Pro His Tyr Ser Gln Thr Thr Arg Ser Asn Thr Leu Pro Ser Asp
945                 950                 955                 960

Val Gly Arg Lys Ser Val Thr Leu Arg Lys Met Lys Gln Glu Ile Lys
            965                 970                 975

Glu Ile Met Ser Pro Thr Pro Val Glu Leu His Lys Val Thr Leu Tyr
            980                 985                 990

Lys Asp Ser Gly Met Glu Asp Phe Gly Phe Ser Val Ala Asp Gly Leu
            995                 1000                1005

Leu Glu Lys Gly Val Tyr Val Lys Asn Ile Arg Pro Ala Gly Pro Gly
       1010                1015                1020

Asp Leu Gly Gly Leu Lys Pro Tyr Asp Arg Leu Leu Gln Val Asn His
1025                1030                1035                1040

Val Arg Thr Arg Asp Phe Asp Cys Cys Leu Val Val Pro Leu Ile Ala
            1045                1050                1055

Glu Ser Gly Asn Lys Leu Asp Leu Val Ile Ser Arg Asn Pro Leu Ala
            1060                1065                1070

Ser Gln Lys Ser Ile Glu Gln Pro Ala Leu Pro Ser Asp Trp Ser Glu
       1075                1080                1085

Gln Asn Ser Ala Phe Phe Gln Gln Pro Ser His Gly Gly Asn Leu Glu
       1090                1095                1100

Thr Arg Glu Pro Thr Asn Thr Leu
1105                1110
```

(2) INFORMATION FOR SEQ ID NO:3:

(i) SEQUENCE CHARACTERISTICS:
        (A) LENGTH: 1112 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

```
Met Ile Ala Val Ser Phe Lys Cys Arg Cys Gln Ile Leu Arg Arg Leu
1               5                   10                  15

Thr Lys Asp Glu Ser Pro Tyr Thr Lys Ser Ala Ser Gln Thr Lys Pro
            20                  25                  30

Pro Asp Gly Ala Leu Ala Val Arg Gln Ser Ile Pro Glu Glu Phe
            35                  40                  45

Lys Gly Ser Thr Val Val Glu Leu Met Lys Lys Glu Gly Thr Thr Leu
```

```
                    50                      55                      60
Gly Cys Thr Val Ser Gly Ile Asp Lys Gly Lys Pro Arg Val
 65                  70                      75                      80

Ser Asn Leu Arg Gln Gly Ile Ala Ala Arg Ser Asp Gln Leu Asp
                 85                      90                      95

Val Gly Asp Tyr Ile Lys Ala Val Asn Gly Ile Asn Leu Ala Lys Phe
                100                     105                     110

Arg His Asp Glu Ile Ile Ser Leu Leu Lys Asn Val Gly Glu Arg Val
            115                     120                     125

Val Leu Glu Val Glu Tyr Glu Leu Pro Pro Val Ser Ile Gln Gly Ser
    130                     135                     140

Ser Val Met Phe Arg Thr Val Glu Val Thr Leu His Lys Glu Gly Asn
145                     150                     155                     160

Thr Phe Gly Phe Val Ile Arg Gly Gly Ala His Asp Asp Arg Asn Lys
                    165                     170                     175

Ser Arg Pro Val Val Ile Thr Cys Val Arg Pro Gly Gly Pro Asp Asp
                180                     185                     190

Arg Glu Gly Thr Ile Lys Pro Gly Asp Arg Leu Leu Ser Val Asp Gly
            195                     200                     205

Ile Arg Leu Leu Gly Thr Thr His Ala Glu Ala Met Ser Ile Leu Lys
210                     215                     220

Gln Cys Gly Gln Glu Ala Thr Leu Leu Ile Glu Tyr Asp Val Ser Ala
225                     230                     235                     240

Met Asp Ser Val Ala Thr Ala Ser Gly Pro Leu Leu Val Glu Val Ala
                    245                     250                     255

Lys Thr Pro Gly Ala Ser Leu Gly Val Ala Leu Thr Thr Ser Val Cys
                260                     265                     270

Cys Asn Lys Gln Val Ile Val Ile Asp Lys Ile Lys Ser Ala Ser Ile
            275                     280                     285

Ala Asp Arg Cys Gly Ala Leu His Val Gly Asp His Ile Leu Ser Ile
290                     295                     300

Asp Gly Thr Ser Met Glu Tyr Cys Thr Leu Ala Glu Ala Thr Gln Phe
305                     310                     315                     320

Leu Gly Asn Thr Thr Asp Gln Val Lys Leu Glu Ile Leu Pro His His
                    325                     330                     335

Gln Thr Arg Leu Ala Leu Lys Gly Pro Asp His Val Lys Ile Gln Arg
                340                     345                     350

Ser Asp Arg Gln Leu Pro Trp Asp Pro Trp Ala Ser Ser Gln Cys Ser
            355                     360                     365

Val His Thr Asn His His Asn Pro His Pro Asp His Cys Arg
370                     375                     380

Val Pro Ala Leu Gly Phe Pro Lys Ala Leu Thr Pro Asn Ser Pro
385                     390                     395                     400

Ala Met Val Ser Ser Ser Pro Thr Ser Met Ser Ala Tyr Ser Leu
                    405                     410                     415

Ser Ser Leu Asn Met Gly Thr Leu Pro Arg Ser Leu Tyr Ser Thr Ser
                420                     425                     430

Pro Arg Gly Thr Met Met Arg Arg Arg Leu Lys Lys Lys Asp Phe Lys
            435                     440                     445

Ser Ser Leu Ser Leu Ala Ser Ser Thr Val Gly Leu Ala Gly Gln Val
    450                     455                     460

Val His Thr Glu Thr Thr Glu Val Val Leu Thr Ala Asp Pro Val Thr
465                     470                     475                     480
```

```
Gly Phe Gly Ile Gln Leu Gln Gly Ser Val Phe Ala Thr Glu Thr Leu
                485                 490                 495

Ser Ser Pro Pro Leu Ile Ser Tyr Ile Glu Ala Asp Ser Pro Ala Glu
            500                 505                 510

Arg Cys Gly Val Leu Gln Ile Gly Asp Arg Val Met Ala Ile Asn Gly
            515                 520                 525

Ile Pro Thr Glu Asp Ser Thr Phe Glu Glu Ala Asn Gln Leu Leu Arg
        530                 535                 540

Asp Ser Ser Ile Thr Ser Lys Val Thr Leu Glu Ile Glu Phe Asp Val
545                 550                 555                 560

Ala Glu Ser Val Ile Pro Ser Ser Gly Thr Phe His Val Lys Leu Pro
                565                 570                 575

Lys Lys His Ser Val Glu Leu Gly Ile Thr Ile Ser Ser Pro Ser Ser
            580                 585                 590

Arg Lys Pro Gly Asp Pro Leu Val Ile Ser Asp Ile Lys Lys Gly Ser
        595                 600                 605

Val Ala His Arg Thr Gly Thr Leu Glu Leu Gly Asp Lys Leu Leu Ala
610                 615                 620

Ile Asp Asn Ile Arg Leu Asp Ser Cys Ser Met Glu Asp Ala Val Gln
625                 630                 635                 640

Ile Leu Gln Gln Cys Glu Asp Leu Val Lys Leu Lys Ile Arg Lys Asp
            645                 650                 655

Glu Asp Asn Ser Asp Glu Gln Glu Ser Ser Gly Ala Ile Ile Tyr Thr
        660                 665                 670

Val Glu Leu Lys Arg Tyr Gly Gly Pro Leu Gly Ile Thr Ile Ser Gly
                675                 680                 685

Thr Glu Glu Pro Phe Asp Pro Ile Ile Ile Ser Ser Leu Thr Lys Gly
        690                 695                 700

Gly Leu Ala Glu Arg Thr Gly Ala Ile His Ile Gly Asp Arg Ile Leu
705                 710                 715                 720

Ala Ile Asn Ser Ser Ser Leu Lys Gly Lys Pro Leu Ser Glu Asp Ile
            725                 730                 735

His Leu Leu Gln Met Ala Gly Glu Thr Val Thr Leu Lys Ile Lys Lys
        740                 745                 750

Gln Thr Asp Ala Gln Pro Ala Ser Ser Pro Lys Lys Leu Pro Ile Pro
            755                 760                 765

Ser His Ser Ser Asp Leu Gly Asp Gly Glu Glu Asp Pro Ser Pro Ile
    770                 775                 780

Gln Arg Pro Gly Lys Leu Ser Asp Val Tyr Pro Ser Thr Val Pro Ser
785                 790                 795                 800

Val Asp Ser Ala Val Asp Ser Trp Asp Gly Ser Gly Ile Asp Ala Arg
                805                 810                 815

Tyr Gly Ser Gln Gly Thr Thr Phe Gln Thr Ser Gly Tyr Asn Phe Asn
            820                 825                 830

Thr Tyr Asp Trp Arg Ser Pro Lys Lys Arg Ala Ser Leu Ser Pro Val
        835                 840                 845

Pro Lys Pro Arg Ser Gln Thr Tyr Pro Asp Val Gly Leu Ser Asn Glu
    850                 855                 860

Asp Trp Asp Arg Ser Thr Ala Ser Gly Phe Ala Gly Ala Ser Asp Ser
865                 870                 875                 880

Ala Asp Ala Glu Gln Glu Glu Asn Phe Trp Ser Gln Ala Leu Glu Asp
                885                 890                 895

Leu Glu Thr Cys Gly Gln Ser Gly Ile Leu Arg Glu Leu Glu Ala Thr
            900                 905                 910
```

```
Ile Met Ser Gly Ser Thr Met Ser Leu Asn His Glu Ala Pro Thr Ala
        915                 920                 925
Arg Ser Gln Leu Gly Arg Gln Ala Ser Phe Gln Glu Arg Ser Asn Ser
        930                 935                 940
Arg Pro His Tyr Ser Gln Thr Thr Arg Ser Asn Thr Leu Pro Ser Asp
945                 950                 955                 960
Val Gly Arg Lys Ser Val Thr Leu Arg Lys Met Lys Gln Glu Ile Lys
                965                 970                 975
Glu Ile Met Ser Pro Thr Pro Val Glu Leu His Lys Val Thr Leu Tyr
            980                 985                 990
Lys Asp Ser Gly Met Glu Asp Phe Gly Phe Ser Val Ala Asp Gly Leu
            995                 1000                1005
Leu Glu Lys Gly Val Tyr Val Lys Asn Ile Arg Pro Ala Gly Pro Gly
        1010                1015                1020
Asp Leu Gly Gly Leu Lys Pro Tyr Asp Arg Leu Leu Gln Val Asn His
1025                1030                1035                1040
Val Arg Thr Arg Asp Phe Asp Cys Cys Leu Val Val Pro Leu Ile Ala
            1045                1050                1055
Glu Ser Gly Asn Lys Leu Asp Leu Val Ile Ser Arg Asn Pro Leu Ala
            1060                1065                1070
Ser Gln Lys Ser Ile Glu Gln Pro Ala Leu Pro Ser Asp Trp Ser Glu
            1075                1080                1085
Gln Asn Ser Ala Phe Phe Gln Gln Pro Ser His Gly Gly Asn Leu Glu
            1090                1095                1100
Thr Arg Glu Pro Thr Asn Thr Leu
1105                1110

(2) INFORMATION FOR SEQ ID NO:4:

(i) SEQUENCE CHARACTERISTICS:
        (A) LENGTH: 84 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

Thr Val Val Glu Leu Met Lys Lys Glu Gly Thr Thr Leu Gly Cys Thr
1               5                   10                  15
Val Ser Gly Gly Ile Asp Lys Asp Gly Lys Pro Arg Val Ser Asn Leu
            20                  25                  30
Arg Gln Gly Gly Ile Ala Ala Arg Ser Asp Gln Leu Asp Val Gly Asp
        35                  40                  45
Tyr Ile Lys Ala Val Asn Gly Ile Asn Leu Ala Lys Phe Arg His Asp
    50                  55                  60
Glu Ile Ile Ser Leu Leu Lys Asn Val Gly Glu Arg Val Val Leu Glu
65                  70                  75                  80
Val Glu Tyr Glu (2) INFORMATION FOR SEQ ID NO:5:

(i) SEQUENCE CHARACTERISTICS:
        (A) LENGTH: 98 amino acids
        (B) TYPE: amino acid
        (C) STRANDEDNESS:
        (D) TOPOLOGY: linear (ii) MOLECULE TYPE: protein
```

(xi) SEQUENCE DESCRIPTION: SEQ ID NO:5:

Glu Val Thr Leu His Lys Glu Gly Asn Thr Phe Gly Phe Val Ile Arg
1               5                   10                  15

Gly Gly Ala His Asp Asp Arg Asn Lys Ser Arg Pro Val Val Ile Thr
                20                  25                  30

Cys Val Arg Pro Gly Gly Pro Asp Asp Arg Glu Gly Thr Ile Lys Pro
            35                  40                  45

Gly Asp Arg Leu Leu Ser Val Asp Gly Ile Arg Leu Leu Gly Thr Thr
        50                  55                  60

His Ala Glu Ala Met Ser Ile Leu Lys Gln Cys Gly Gln Glu Ala Thr
65                  70                  75                  80

Leu Leu Ile Glu Tyr Asp Val Ser Ala Met Asp Ser Val Ala Thr Ala
                85                  90                  95

Ser Gly (2) INFORMATION FOR SEQ ID NO:6:

(i) SEQUENCE CHARACTERISTICS:
        (A) LENGTH: 84 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Leu Val Glu Val Ala Lys Thr Pro Gly Ala Ser Leu Gly Val Ala Leu
1               5                   10                  15

Thr Thr Ser Val Cys Cys Asn Lys Gln Val Ile Val Ile Asp Lys Ile
                20                  25                  30

Lys Ser Ala Ser Ile Ala Asp Arg Cys Gly Ala Leu His Val Gly Asp
            35                  40                  45

His Ile Leu Ser Ile Asp Gly Thr Ser Met Glu Tyr Cys Thr Leu Ala
        50                  55                  60

Glu Ala Thr Gln Phe Leu Gly Asn Thr Thr Asp Gln Val Lys Leu Glu
65                  70                  75                  80

Ile Leu Pro His (2) INFORMATION FOR SEQ ID NO:7:

(i) SEQUENCE CHARACTERISTICS:
        (A) LENGTH: 88 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

Glu Val Val Leu Thr Ala Asp Pro Val Thr Gly Phe Gly Ile Gln Leu
1               5                   10                  15

Gln Gly Ser Val Phe Ala Thr Glu Thr Leu Ser Ser Pro Pro Leu Ile
                20                  25                  30

Ser Tyr Ile Glu Ala Asp Ser Pro Ala Glu Arg Cys Gly Val Leu Gln
            35                  40                  45

Ile Gly Asp Arg Val Met Ala Ile Asn Gly Ile Pro Thr Glu Asp Ser
        50                  55                  60

Thr Phe Glu Glu Ala Asn Gln Leu Leu Arg Asp Ser Ser Ile Thr Ser
65                  70                  75                  80

Lys Val Thr Leu Glu Ile Glu Phe
              85

(2) INFORMATION FOR SEQ ID NO:8:

(i) SEQUENCE CHARACTERISTICS:
        (A) LENGTH: 84 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

His Val Lys Leu Pro Lys Lys His Ser Val Glu Leu Gly Ile Thr Ile
1               5                   10                  15

Ser Ser Pro Ser Ser Arg Lys Pro Gly Asp Pro Leu Val Ile Ser Asp
                20                  25                  30

Ile Lys Lys Gly Ser Val Ala His Arg Thr Gly Thr Leu Glu Leu Gly
                35                  40                  45

Asp Lys Leu Leu Ala Ile Asp Asn Ile Arg Leu Asp Ser Cys Ser Met
            50                  55                  60

Glu Asp Ala Val Gln Ile Leu Gln Gln Cys Glu Asp Leu Val Lys Leu
65                  70                  75                  80

Lys Ile Arg Lys (2) INFORMATION FOR SEQ ID NO:9:

(i) SEQUENCE CHARACTERISTICS:
        (A) LENGTH: 82 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

Thr Val Glu Leu Lys Arg Tyr Gly Gly Pro Leu Gly Ile Thr Ile Ser
1               5                   10                  15

Gly Thr Glu Glu Pro Phe Asp Pro Ile Ile Ile Ser Ser Leu Thr Lys
                20                  25                  30

Gly Gly Leu Ala Glu Arg Thr Gly Ala Ile His Ile Gly Asp Arg Ile
                35                  40                  45

Leu Ala Ile Asn Ser Ser Ser Leu Lys Gly Lys Pro Leu Ser Glu Asp
            50                  55                  60

Ile His Leu Leu Gln Met Ala Gly Glu Thr Val Thr Leu Lys Ile Lys
65                  70                  75                  80

Lys Gln (2) INFORMATION FOR SEQ ID NO:10:

(i) SEQUENCE CHARACTERISTICS:
        (A) LENGTH: 82 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

Lys Val Thr Leu Tyr Lys Asp Ser Gly Met Glu Asp Phe Gly Phe Ser
1               5                   10                  15

```
Val Ala Asp Gly Leu Leu Glu Lys Gly Val Tyr Val Lys Asn Ile Arg
         20                  25                  30

Pro Ala Gly Pro Gly Asp Leu Gly Gly Leu Lys Pro Tyr Asp Arg Leu
         35                  40                  45

Leu Gln Val Asn His Val Arg Thr Arg Asp Phe Asp Cys Cys Leu Val
 50                  55                  60

Val Pro Leu Ile Ala Glu Ser Gly Asn Lys Leu Asp Leu Val Ile Ser
 65                  70                  75                  80

Arg Asn
```

(2) INFORMATION FOR SEQ ID NO:11:

(i) SEQUENCE CHARACTERISTICS:
        (A) LENGTH: 198 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

```
Thr Val Val Glu Leu Met Lys Lys Glu Gly Thr Thr Leu Gly Cys Thr
 1               5                  10                  15

Val Ser Gly Gly Ile Asp Lys Asp Gly Lys Pro Arg Val Ser Asn Leu
         20                  25                  30

Arg Gln Gly Gly Ile Ala Ala Arg Ser Asp Gln Leu Asp Val Gly Asp
         35                  40                  45

Tyr Ile Lys Ala Val Asn Gly Ile Asn Leu Ala Lys Phe Arg His Asp
 50                  55                  60

Glu Ile Ile Ser Leu Leu Lys Asn Val Gly Glu Arg Val Val Leu Glu
65                   70                  75                  80

Val Glu Tyr Glu Leu Pro Pro Val Ser Ile Gln Gly Ser Ser Val Met
         85                  90                  95

Phe Arg Thr Val Glu Val Thr Leu His Lys Glu Gly Asn Thr Phe Gly
         100                 105                 110

Phe Val Ile Arg Gly Gly Ala His Asp Asp Arg Asn Lys Ser Arg Pro
         115                 120                 125

Val Val Ile Thr Cys Val Arg Pro Gly Gly Pro Asp Asp Arg Glu Gly
         130                 135                 140

Thr Ile Lys Pro Gly Asp Arg Leu Leu Ser Val Asp Gly Ile Arg Leu
145                 150                 155                 160

Leu Gly Thr Thr His Ala Glu Ala Met Ser Ile Leu Lys Gln Cys Gly
                165                 170                 175

Gln Glu Ala Thr Leu Leu Ile Glu Tyr Asp Val Ser Ala Met Asp Ser
                180                 185                 190

Val Ala Thr Ala Ser Gly
                195
```

(2) INFORMATION FOR SEQ ID NO:12:

(i) SEQUENCE CHARACTERISTICS:
        (A) LENGTH: 284 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

Thr Val Val Glu Leu Met Lys Lys Glu Gly Thr Thr Leu Gly Cys Thr

```
            1               5                  10                  15
Val Ser Gly Gly Ile Asp Lys Asp Gly Lys Pro Arg Val Ser Asn Leu
                    20                  25                  30

Arg Gln Gly Gly Ile Ala Ala Arg Ser Asp Gln Leu Asp Val Gly Asp
                35                  40                  45

Tyr Ile Lys Ala Val Asn Gly Ile Asn Leu Ala Lys Phe Arg His Asp
            50                  55                  60

Glu Ile Ile Ser Leu Leu Lys Asn Val Gly Glu Arg Val Val Leu Glu
65                  70                  75                  80

Val Glu Tyr Glu Leu Pro Pro Val Ser Ile Gln Gly Ser Ser Val Met
                    85                  90                  95

Phe Arg Thr Val Glu Val Thr Leu His Lys Glu Gly Asn Thr Phe Gly
                100                 105                 110

Phe Val Ile Arg Gly Gly Ala His Asp Asp Arg Asn Lys Ser Arg Pro
            115                 120                 125

Val Val Ile Thr Cys Val Arg Pro Gly Gly Pro Asp Asp Arg Glu Gly
            130                 135                 140

Thr Ile Lys Pro Gly Asp Arg Leu Leu Ser Val Asp Gly Ile Arg Leu
145                 150                 155                 160

Leu Gly Thr Thr His Ala Glu Ala Met Ser Ile Leu Lys Gln Cys Gly
                165                 170                 175

Gln Glu Ala Thr Leu Leu Ile Glu Tyr Asp Val Ser Ala Met Asp Ser
                180                 185                 190

Val Ala Thr Ala Ser Gly Pro Leu Leu Val Glu Val Ala Lys Thr Pro
                195                 200                 205

Gly Ala Ser Leu Gly Val Ala Leu Thr Thr Ser Val Cys Cys Asn Lys
            210                 215                 220

Gln Val Ile Val Ile Asp Lys Ile Lys Ser Ala Ser Ile Ala Asp Arg
225                 230                 235                 240

Cys Gly Ala Leu His Val Gly Asp His Ile Leu Ser Ile Asp Gly Thr
                245                 250                 255

Ser Met Glu Tyr Cys Thr Leu Ala Glu Ala Thr Gln Phe Leu Gly Asn
                260                 265                 270

Thr Thr Asp Gln Val Lys Leu Glu Ile Leu Pro His
            275                 280

(2) INFORMATION FOR SEQ ID NO:13:

(i) SEQUENCE CHARACTERISTICS:
        (A) LENGTH: 507 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

Thr Val Val Glu Leu Met Lys Lys Glu Gly Thr Thr Leu Gly Cys Thr
1               5                   10                  15

Val Ser Gly Gly Ile Asp Lys Asp Gly Lys Pro Arg Val Ser Asn Leu
                    20                  25                  30

Arg Gln Gly Gly Ile Ala Ala Arg Ser Asp Gln Leu Asp Val Gly Asp
                35                  40                  45

Tyr Ile Lys Ala Val Asn Gly Ile Asn Leu Ala Lys Phe Arg His Asp
            50                  55                  60

Glu Ile Ile Ser Leu Leu Lys Asn Val Gly Glu Arg Val Val Leu Glu
65                  70                  75                  80
```

-continued

Val Glu Tyr Glu Leu Pro Pro Val Ser Ile Gln Gly Ser Ser Val Met
                85                  90                  95

Phe Arg Thr Val Glu Val Thr Leu His Lys Glu Gly Asn Thr Phe Gly
               100                 105                 110

Phe Val Ile Arg Gly Gly Ala His Asp Asp Arg Asn Lys Ser Arg Pro
               115                 120                 125

Val Val Ile Thr Cys Val Arg Pro Gly Gly Pro Asp Asp Arg Glu Gly
               130                 135                 140

Thr Ile Lys Pro Gly Asp Arg Leu Leu Ser Val Asp Gly Ile Arg Leu
145                 150                 155                 160

Leu Gly Thr Thr His Ala Glu Ala Met Ser Ile Leu Lys Gln Cys Gly
               165                 170                 175

Gln Glu Ala Thr Leu Leu Ile Glu Tyr Asp Val Ser Ala Met Asp Ser
               180                 185                 190

Val Ala Thr Ala Ser Gly Pro Leu Leu Val Glu Val Ala Lys Thr Pro
               195                 200                 205

Gly Ala Ser Leu Gly Val Ala Leu Thr Thr Ser Val Cys Cys Asn Lys
               210                 215                 220

Gln Val Ile Val Ile Asp Lys Ile Lys Ser Ala Ser Ile Ala Asp Arg
225                 230                 235                 240

Cys Gly Ala Leu His Val Gly Asp His Ile Leu Ser Ile Asp Gly Thr
               245                 250                 255

Ser Met Glu Tyr Cys Thr Leu Ala Glu Ala Thr Gln Phe Leu Gly Asn
               260                 265                 270

Thr Thr Asp Gln Val Lys Leu Glu Ile Leu Pro His His Gln Thr Arg
               275                 280                 285

Leu Ala Leu Lys Gly Pro Asp His Val Lys Ile Gln Arg Ser Asp Arg
               290                 295                 300

Gln Leu Pro Trp Asp Pro Trp Ala Ser Ser Gln Cys Ser Val His Thr
305                 310                 315                 320

Asn His His His Asn Pro His His Pro Asp His Cys Arg Val Pro Ala
               325                 330                 335

Leu Gly Phe Pro Lys Ala Leu Thr Pro Asn Ser Pro Ala Met Val
               340                 345                 350

Ser Ser Ser Ser Pro Thr Ser Met Ser Ala Tyr Ser Leu Ser Ser Leu
               355                 360                 365

Asn Met Gly Thr Leu Pro Arg Ser Leu Tyr Ser Thr Ser Pro Arg Gly
               370                 375                 380

Thr Met Met Arg Arg Leu Lys Lys Lys Asp Phe Lys Ser Ser Leu
385                 390                 395                 400

Ser Leu Ala Ser Ser Thr Val Gly Leu Ala Gly Gln Val Val His Thr
               405                 410                 415

Glu Thr Thr Glu Val Val Leu Thr Ala Asp Pro Val Thr Gly Phe Gly
               420                 425                 430

Ile Gln Leu Gln Gly Ser Val Phe Ala Thr Glu Thr Leu Ser Ser Pro
               435                 440                 445

Pro Leu Ile Ser Tyr Ile Glu Ala Asp Ser Pro Ala Glu Arg Cys Gly
               450                 455                 460

Val Leu Gln Ile Gly Asp Arg Val Met Ala Ile Asn Gly Ile Pro Thr
465                 470                 475                 480

Glu Asp Ser Thr Phe Glu Glu Ala Asn Gln Leu Leu Arg Asp Ser Ser
               485                 490                 495

Ile Thr Ser Lys Val Thr Leu Glu Ile Glu Phe 500                 505

(2) INFORMATION FOR SEQ ID NO:14:

(i) SEQUENCE CHARACTERISTICS:
        (A) LENGTH: 604 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:

Thr Val Val Glu Leu Met Lys Lys Glu Gly Thr Thr Leu Gly Cys Thr
1               5                   10                  15

Val Ser Gly Gly Ile Asp Lys Asp Gly Lys Pro Arg Val Ser Asn Leu
            20                  25                  30

Arg Gln Gly Gly Ile Ala Ala Arg Ser Asp Gln Leu Asp Val Gly Asp
        35                  40                  45

Tyr Ile Lys Ala Val Asn Gly Ile Asn Leu Ala Lys Phe Arg His Asp
    50                  55                  60

Glu Ile Ile Ser Leu Leu Lys Asn Val Gly Glu Arg Val Val Leu Glu
65                  70                  75                  80

Val Glu Tyr Glu Leu Pro Pro Val Ser Ile Gln Gly Ser Ser Val Met
                85                  90                  95

Phe Arg Thr Val Glu Val Thr Leu His Lys Glu Gly Asn Thr Phe Gly
            100                 105                 110

Phe Val Ile Arg Gly Gly Ala His Asp Asp Arg Asn Lys Ser Arg Pro
        115                 120                 125

Val Val Ile Thr Cys Val Arg Pro Gly Gly Pro Asp Asp Arg Glu Gly
    130                 135                 140

Thr Ile Lys Pro Gly Asp Arg Leu Leu Ser Val Asp Gly Ile Arg Leu
145                 150                 155                 160

Leu Gly Thr Thr His Ala Glu Ala Met Ser Ile Leu Lys Gln Cys Gly
                165                 170                 175

Gln Glu Ala Thr Leu Leu Ile Glu Tyr Asp Val Ser Ala Met Asp Ser
            180                 185                 190

Val Ala Thr Ala Ser Gly Pro Leu Leu Val Glu Val Ala Lys Thr Pro
        195                 200                 205

Gly Ala Ser Leu Gly Val Ala Leu Thr Thr Ser Val Cys Cys Asn Lys
    210                 215                 220

Gln Val Ile Val Ile Asp Lys Ile Lys Ser Ala Ser Ile Ala Asp Arg
225                 230                 235                 240

Cys Gly Ala Leu His Val Gly Asp His Ile Leu Ser Ile Asp Gly Thr
                245                 250                 255

Ser Met Glu Tyr Cys Thr Leu Ala Glu Ala Thr Gln Phe Leu Gly Asn
            260                 265                 270

Thr Thr Asp Gln Val Lys Leu Glu Ile Leu Pro His His Gln Thr Arg
        275                 280                 285

Leu Ala Leu Lys Gly Pro Asp His Val Lys Ile Gln Arg Ser Asp Arg
    290                 295                 300

Gln Leu Pro Trp Asp Pro Trp Ala Ser Ser Gln Cys Ser Val His Thr
305                 310                 315                 320

Asn His His His Asn Pro His His Pro Asp His Cys Arg Val Pro Ala
                325                 330                 335

Leu Gly Phe Pro Lys Ala Leu Thr Pro Asn Ser Pro Pro Ala Met Val
            340                 345                 350

```
Ser Ser Ser Ser Pro Thr Ser Met Ser Ala Tyr Ser Leu Ser Ser Leu
            355                 360                 365

Asn Met Gly Thr Leu Pro Arg Ser Leu Tyr Ser Thr Ser Pro Arg Gly
            370                 375                 380

Thr Met Met Arg Arg Arg Leu Lys Lys Lys Asp Phe Lys Ser Ser Leu
385                 390                 395                 400

Ser Leu Ala Ser Ser Thr Val Gly Leu Ala Gly Gln Val Val His Thr
                405                 410                 415

Glu Thr Thr Glu Val Val Leu Thr Ala Asp Pro Val Thr Gly Phe Gly
            420                 425                 430

Ile Gln Leu Gln Gly Ser Val Phe Ala Thr Glu Thr Leu Ser Ser Pro
            435                 440                 445

Pro Leu Ile Ser Tyr Ile Glu Ala Asp Ser Pro Ala Glu Arg Cys Gly
            450                 455                 460

Val Leu Gln Ile Gly Asp Arg Val Met Ala Ile Asn Gly Ile Pro Thr
465                 470                 475                 480

Glu Asp Ser Thr Phe Glu Glu Ala Asn Gln Leu Leu Arg Asp Ser Ser
                485                 490                 495

Ile Thr Ser Lys Val Thr Leu Glu Ile Glu Phe Asp Val Ala Glu Ser
            500                 505                 510

Val Ile Pro Ser Ser Gly Thr Phe His Val Lys Leu Pro Lys Lys His
            515                 520                 525

Ser Val Glu Leu Gly Ile Thr Ile Ser Ser Pro Ser Ser Arg Lys Pro
            530                 535                 540

Gly Asp Pro Leu Val Ile Ser Asp Ile Lys Lys Gly Ser Val Ala His
545                 550                 555                 560

Arg Thr Gly Thr Leu Glu Leu Gly Asp Lys Leu Leu Ala Ile Asp Asn
                565                 570                 575

Ile Arg Leu Asp Ser Cys Ser Met Glu Asp Ala Val Gln Ile Leu Gln
            580                 585                 590

Gln Cys Glu Asp Leu Val Lys Leu Lys Ile Arg Lys
            595                 600

(2) INFORMATION FOR SEQ ID NO:15:

(i) SEQUENCE CHARACTERISTICS:
        (A) LENGTH: 702 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:15:

Thr Val Val Glu Leu Met Lys Lys Glu Gly Thr Thr Leu Gly Cys Thr
1               5                   10                  15

Val Ser Gly Gly Ile Asp Lys Asp Gly Lys Pro Arg Val Ser Asn Leu
            20                  25                  30

Arg Gln Gly Gly Ile Ala Ala Arg Ser Asp Gln Leu Asp Val Gly Asp
            35                  40                  45

Tyr Ile Lys Ala Val Asn Gly Ile Asn Leu Ala Lys Phe Arg His Asp
            50                  55                  60

Glu Ile Ile Ser Leu Leu Lys Asn Val Gly Glu Arg Val Val Leu Glu
65                  70                  75                  80

Val Glu Tyr Glu Leu Pro Pro Val Ser Ile Gln Gly Ser Ser Val Met
            85                  90                  95
```

-continued

```
Phe Arg Thr Val Glu Val Thr Leu His Lys Glu Gly Asn Thr Phe Gly
            100                 105                 110

Phe Val Ile Arg Gly Gly Ala His Asp Asp Arg Asn Lys Ser Arg Pro
            115                 120                 125

Val Val Ile Thr Cys Val Arg Pro Gly Gly Pro Asp Asp Arg Glu Gly
            130                 135                 140

Thr Ile Lys Pro Gly Asp Arg Leu Leu Ser Val Asp Gly Ile Arg Leu
145                 150                 155                 160

Leu Gly Thr Thr His Ala Glu Ala Met Ser Ile Leu Lys Gln Cys Gly
                    165                 170                 175

Gln Glu Ala Thr Leu Leu Ile Glu Tyr Asp Val Ser Ala Met Asp Ser
                180                 185                 190

Val Ala Thr Ala Ser Gly Pro Leu Leu Val Glu Val Ala Lys Thr Pro
            195                 200                 205

Gly Ala Ser Leu Gly Val Ala Leu Thr Thr Ser Val Cys Cys Asn Lys
            210                 215                 220

Gln Val Ile Val Ile Asp Lys Ile Lys Ser Ala Ser Ile Ala Asp Arg
225                 230                 235                 240

Cys Gly Ala Leu His Val Gly Asp His Ile Leu Ser Ile Asp Gly Thr
                    245                 250                 255

Ser Met Glu Tyr Cys Thr Leu Ala Glu Ala Thr Gln Phe Leu Gly Asn
                260                 265                 270

Thr Thr Asp Gln Val Lys Leu Glu Ile Leu Pro His His Gln Thr Arg
            275                 280                 285

Leu Ala Leu Lys Gly Pro Asp His Val Lys Ile Gln Arg Ser Asp Arg
290                 295                 300

Gln Leu Pro Trp Asp Pro Trp Ala Ser Ser Gln Cys Ser Val His Thr
305                 310                 315                 320

Asn His His His Asn Pro His His Pro Asp His Cys Arg Val Pro Ala
                    325                 330                 335

Leu Gly Phe Pro Lys Ala Leu Thr Pro Asn Ser Pro Ala Met Val
                340                 345                 350

Ser Ser Ser Ser Pro Thr Ser Met Ser Ala Tyr Ser Leu Ser Ser Leu
            355                 360                 365

Asn Met Gly Thr Leu Pro Arg Ser Leu Tyr Ser Thr Ser Pro Arg Gly
370                 375                 380

Thr Met Met Arg Arg Leu Lys Lys Lys Asp Phe Lys Ser Ser Leu
385                 390                 395                 400

Ser Leu Ala Ser Ser Thr Val Gly Leu Ala Gly Gln Val Val His Thr
                    405                 410                 415

Glu Thr Thr Glu Val Val Leu Thr Ala Asp Pro Val Thr Gly Phe Gly
                420                 425                 430

Ile Gln Leu Gln Gly Ser Val Phe Ala Thr Glu Thr Leu Ser Ser Pro
            435                 440                 445

Pro Leu Ile Ser Tyr Ile Glu Ala Asp Ser Pro Ala Glu Arg Cys Gly
            450                 455                 460

Val Leu Gln Ile Gly Asp Arg Val Met Ala Ile Asn Gly Ile Pro Thr
465                 470                 475                 480

Glu Asp Ser Thr Phe Glu Glu Ala Asn Gln Leu Leu Arg Asp Ser Ser
                    485                 490                 495

Ile Thr Ser Lys Val Thr Leu Glu Ile Glu Phe Asp Val Ala Glu Ser
                500                 505                 510

Val Ile Pro Ser Ser Gly Thr Phe His Val Lys Leu Pro Lys Lys His
            515                 520                 525
```

```
Ser Val Glu Leu Gly Ile Thr Ile Ser Ser Pro Ser Arg Lys Pro
    530                 535                 540

Gly Asp Pro Leu Val Ile Ser Asp Ile Lys Lys Gly Ser Val Ala His
545                 550                 555                 560

Arg Thr Gly Thr Leu Glu Leu Gly Asp Lys Leu Leu Ala Ile Asp Asn
                565                 570                 575

Ile Arg Leu Asp Ser Cys Ser Met Glu Asp Ala Val Gln Ile Leu Gln
                580                 585                 590

Gln Cys Glu Asp Leu Val Lys Leu Lys Ile Arg Lys Asp Glu Asp Asn
        595                 600                 605

Ser Asp Glu Gln Glu Ser Ser Gly Ala Ile Ile Tyr Thr Val Glu Leu
    610                 615                 620

Lys Arg Tyr Gly Gly Pro Leu Gly Ile Thr Ile Ser Gly Thr Glu Glu
625                 630                 635                 640

Pro Phe Asp Pro Ile Ile Ile Ser Ser Leu Thr Lys Gly Gly Leu Ala
                645                 650                 655

Glu Arg Thr Gly Ala Ile His Ile Gly Asp Arg Ile Leu Ala Ile Asn
                660                 665                 670

Ser Ser Ser Leu Lys Gly Lys Pro Leu Ser Glu Asp Ile His Leu Leu
        675                 680                 685

Gln Met Ala Gly Glu Thr Val Thr Leu Lys Ile Lys Lys Gln
    690                 695                 700

(2) INFORMATION FOR SEQ ID NO:16:

(i) SEQUENCE CHARACTERISTICS:
        (A) LENGTH: 1018 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:16:

Thr Val Val Glu Leu Met Lys Lys Glu Gly Thr Thr Leu Gly Cys Thr
1               5                   10                  15

Val Ser Gly Gly Ile Asp Lys Asp Gly Lys Pro Arg Val Ser Asn Leu
                20                  25                  30

Arg Gln Gly Gly Ile Ala Ala Arg Ser Asp Gln Leu Asp Val Gly Asp
            35                  40                  45

Tyr Ile Lys Ala Val Asn Gly Ile Asn Leu Ala Lys Phe Arg His Asp
    50                  55                  60

Glu Ile Ile Ser Leu Leu Lys Asn Val Gly Glu Arg Val Val Leu Glu
65                  70                  75                  80

Val Glu Tyr Glu Leu Pro Pro Val Ser Ile Gln Gly Ser Ser Val Met
                85                  90                  95

Phe Arg Thr Val Glu Val Thr Leu His Lys Glu Gly Asn Thr Phe Gly
                100                 105                 110

Phe Val Ile Arg Gly Gly Ala His Asp Asp Arg Asn Lys Ser Arg Pro
            115                 120                 125

Val Val Ile Thr Cys Val Arg Pro Gly Gly Pro Asp Asp Arg Glu Gly
            130                 135                 140

Thr Ile Lys Pro Gly Asp Arg Leu Leu Ser Val Asp Gly Ile Arg Leu
145                 150                 155                 160

Leu Gly Thr Thr His Ala Glu Ala Met Ser Ile Leu Lys Gln Cys Gly
                165                 170                 175
```

```
Gln Glu Ala Thr Leu Leu Ile Glu Tyr Asp Val Ser Ala Met Asp Ser
                180                 185                 190

Val Ala Thr Ala Ser Gly Pro Leu Val Glu Val Ala Lys Thr Pro
            195                 200                 205

Gly Ala Ser Leu Gly Val Ala Leu Thr Thr Ser Val Cys Cys Asn Lys
            210                 215                 220

Gln Val Ile Val Ile Asp Lys Ile Lys Ser Ala Ser Ile Ala Asp Arg
225                 230                 235                 240

Cys Gly Ala Leu His Val Gly Asp His Ile Leu Ser Ile Asp Gly Thr
                245                 250                 255

Ser Met Glu Tyr Cys Thr Leu Ala Glu Ala Thr Gln Phe Leu Gly Asn
                260                 265                 270

Thr Thr Asp Gln Val Lys Leu Glu Ile Leu Pro His His Gln Thr Arg
            275                 280                 285

Leu Ala Leu Lys Gly Pro Asp His Val Lys Ile Gln Arg Ser Asp Arg
            290                 295                 300

Gln Leu Pro Trp Asp Pro Trp Ala Ser Ser Gln Cys Ser Val His Thr
305                 310                 315                 320

Asn His His His Asn Pro His His Pro Asp His Cys Arg Val Pro Ala
                325                 330                 335

Leu Gly Phe Pro Lys Ala Leu Thr Pro Asn Ser Pro Pro Ala Met Val
                340                 345                 350

Ser Ser Ser Ser Pro Thr Ser Met Ser Ala Tyr Ser Leu Ser Ser Leu
            355                 360                 365

Asn Met Gly Thr Leu Pro Arg Ser Leu Tyr Ser Thr Ser Pro Arg Gly
            370                 375                 380

Thr Met Met Arg Arg Arg Leu Lys Lys Lys Asp Phe Lys Ser Ser Leu
385                 390                 395                 400

Ser Leu Ala Ser Ser Thr Val Gly Leu Ala Gly Gln Val Val His Thr
                405                 410                 415

Glu Thr Thr Glu Val Val Leu Thr Ala Asp Pro Val Thr Gly Phe Gly
                420                 425                 430

Ile Gln Leu Gln Gly Ser Val Phe Ala Thr Glu Thr Leu Ser Ser Pro
            435                 440                 445

Pro Leu Ile Ser Tyr Ile Glu Ala Asp Ser Pro Ala Glu Arg Cys Gly
            450                 455                 460

Val Leu Gln Ile Gly Asp Arg Val Met Ala Ile Asn Gly Ile Pro Thr
465                 470                 475                 480

Glu Asp Ser Thr Phe Glu Glu Ala Asn Gln Leu Leu Arg Asp Ser Ser
                485                 490                 495

Ile Thr Ser Lys Val Thr Leu Glu Ile Glu Phe Asp Val Ala Glu Ser
                500                 505                 510

Val Ile Pro Ser Ser Gly Thr Phe His Val Lys Leu Pro Lys Lys His
            515                 520                 525

Ser Val Glu Leu Gly Ile Thr Ile Ser Ser Pro Ser Arg Lys Pro
            530                 535                 540

Gly Asp Pro Leu Val Ile Ser Asp Ile Lys Lys Gly Ser Val Ala His
545                 550                 555                 560

Arg Thr Gly Thr Leu Glu Leu Gly Asp Lys Leu Leu Ala Ile Asp Asn
                565                 570                 575

Ile Arg Leu Asp Ser Cys Ser Met Glu Asp Ala Val Gln Ile Leu Gln
                580                 585                 590

Gln Cys Glu Asp Leu Val Lys Leu Lys Ile Arg Lys Asp Glu Asp Asn
            595                 600                 605
```

-continued

```
Ser Asp Glu Gln Glu Ser Ser Gly Ala Ile Ile Tyr Thr Val Glu Leu
    610             615                 620
Lys Arg Tyr Gly Gly Pro Leu Gly Ile Thr Ile Ser Gly Thr Glu Glu
625             630                 635                 640
Pro Phe Asp Pro Ile Ile Ser Ser Leu Thr Lys Gly Gly Leu Ala
                645                 650                 655
Glu Arg Thr Gly Ala Ile His Ile Gly Asp Arg Ile Leu Ala Ile Asn
                660                 665                 670
Ser Ser Ser Leu Lys Gly Lys Pro Leu Ser Glu Asp Ile His Leu Leu
            675                 680                 685
Gln Met Ala Gly Glu Thr Val Thr Leu Lys Ile Lys Lys Gln Thr Asp
    690                 695                 700
Ala Gln Pro Ala Ser Ser Pro Lys Lys Leu Pro Ile Pro Ser His Ser
705                 710                 715                 720
Ser Asp Leu Gly Asp Gly Glu Glu Asp Pro Ser Pro Ile Gln Arg Pro
                725                 730                 735
Gly Lys Leu Ser Asp Val Tyr Pro Ser Thr Val Pro Ser Val Asp Ser
                740                 745                 750
Ala Val Asp Ser Trp Asp Gly Ser Gly Ile Asp Ala Arg Tyr Gly Ser
            755                 760                 765
Gln Gly Thr Thr Phe Gln Thr Ser Gly Tyr Asn Phe Asn Thr Tyr Asp
    770                 775                 780
Trp Arg Ser Pro Lys Lys Arg Ala Ser Leu Ser Pro Val Pro Lys Pro
785                 790                 795                 800
Arg Ser Gln Thr Tyr Pro Asp Val Gly Leu Ser Asn Glu Asp Trp Asp
                805                 810                 815
Arg Ser Thr Ala Ser Gly Phe Ala Gly Ala Ser Asp Ser Ala Asp Ala
                820                 825                 830
Glu Gln Glu Glu Asn Phe Trp Ser Gln Ala Leu Glu Asp Leu Glu Thr
            835                 840                 845
Cys Gly Gln Ser Gly Ile Leu Arg Glu Leu Ala Thr Ile Met Ser
    850                 855                 860
Gly Ser Thr Met Ser Leu Asn His Glu Ala Pro Thr Ala Arg Ser Gln
865                 870                 875                 880
Leu Gly Arg Gln Ala Ser Phe Gln Glu Arg Ser Asn Ser Arg Pro His
                885                 890                 895
Tyr Ser Gln Thr Thr Arg Ser Asn Thr Leu Pro Ser Asp Val Gly Arg
                900                 905                 910
Lys Ser Val Thr Leu Arg Lys Met Lys Gln Glu Ile Lys Glu Ile Met
            915                 920                 925
Ser Pro Thr Pro Val Glu Leu His Lys Val Thr Leu Tyr Lys Asp Ser
    930                 935                 940
Gly Met Glu Asp Phe Gly Phe Ser Val Ala Asp Gly Leu Leu Glu Lys
945                 950                 955                 960
Gly Val Tyr Val Lys Asn Ile Arg Pro Ala Gly Pro Gly Asp Leu Gly
                965                 970                 975
Gly Leu Lys Pro Tyr Asp Arg Leu Leu Gln Val Asn His Val Arg Thr
                980                 985                 990
Arg Asp Phe Asp Cys Cys Leu Val Val Pro Leu Ile Ala Glu Ser Gly
            995                 1000                1005
Asn Lys Leu Asp Leu Val Ile Ser Arg Asn
    1010                1015
```

(2) INFORMATION FOR SEQ ID NO:17:

(i) SEQUENCE CHARACTERISTICS:
        (A) LENGTH: 184 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:17:

```
Glu Val Thr Leu His Lys Glu Gly Asn Thr Phe Gly Phe Val Ile Arg
 1               5                  10                  15

Gly Gly Ala His Asp Asp Arg Asn Lys Ser Arg Pro Val Val Ile Thr
             20                  25                  30

Cys Val Arg Pro Gly Gly Pro Asp Asp Arg Glu Gly Thr Ile Lys Pro
         35                  40                  45

Gly Asp Arg Leu Leu Ser Val Asp Gly Ile Arg Leu Leu Gly Thr Thr
 50                  55                  60

His Ala Glu Ala Met Ser Ile Leu Lys Gln Cys Gly Gln Glu Ala Thr
 65                  70                  75                  80

Leu Leu Ile Glu Tyr Asp Val Ser Ala Met Asp Ser Val Ala Thr Ala
                 85                  90                  95

Ser Gly Pro Leu Leu Val Glu Val Ala Lys Thr Pro Gly Ala Ser Leu
             100                 105                 110

Gly Val Ala Leu Thr Thr Ser Val Cys Cys Asn Lys Gln Val Ile Val
         115                 120                 125

Ile Asp Lys Ile Lys Ser Ala Ser Ile Ala Asp Arg Cys Gly Ala Leu
130                 135                 140

His Val Gly Asp His Ile Leu Ser Ile Asp Gly Thr Ser Met Glu Tyr
145                 150                 155                 160

Cys Thr Leu Ala Glu Ala Thr Gln Phe Leu Gly Asn Thr Thr Asp Gln
                 165                 170                 175

Val Lys Leu Glu Ile Leu Pro His
             180
```

(2) INFORMATION FOR SEQ ID NO:18:

(i) SEQUENCE CHARACTERISTICS:
        (A) LENGTH: 407 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:18:

```
Glu Val Thr Leu His Lys Glu Gly Asn Thr Phe Gly Phe Val Ile Arg
 1               5                  10                  15

Gly Gly Ala His Asp Asp Arg Asn Lys Ser Arg Pro Val Val Ile Thr
             20                  25                  30

Cys Val Arg Pro Gly Gly Pro Asp Asp Arg Glu Gly Thr Ile Lys Pro
         35                  40                  45

Gly Asp Arg Leu Leu Ser Val Asp Gly Ile Arg Leu Leu Gly Thr Thr
 50                  55                  60

His Ala Glu Ala Met Ser Ile Leu Lys Gln Cys Gly Gln Glu Ala Thr
 65                  70                  75                  80

Leu Leu Ile Glu Tyr Asp Val Ser Ala Met Asp Ser Val Ala Thr Ala
                 85                  90                  95

Ser Gly Pro Leu Leu Val Glu Val Ala Lys Thr Pro Gly Ala Ser Leu
```

-continued

```
                    100                 105                 110
Gly Val Ala Leu Thr Thr Ser Val Cys Cys Asn Lys Gln Val Ile Val
                115                 120                 125

Ile Asp Lys Ile Lys Ser Ala Ser Ile Ala Asp Arg Cys Gly Ala Leu
130                 135                 140

His Val Gly Asp His Ile Leu Ser Ile Asp Gly Thr Ser Met Glu Tyr
145                 150                 155                 160

Cys Thr Leu Ala Glu Ala Thr Gln Phe Leu Gly Asn Thr Thr Asp Gln
                165                 170                 175

Val Lys Leu Glu Ile Leu Pro His His Gln Thr Arg Leu Ala Leu Lys
            180                 185                 190

Gly Pro Asp His Val Lys Ile Gln Arg Ser Asp Arg Gln Leu Pro Trp
        195                 200                 205

Asp Pro Trp Ala Ser Ser Gln Cys Ser Val His Thr Asn His His His
    210                 215                 220

Asn Pro His His Pro Asp His Cys Arg Val Pro Ala Leu Gly Phe Pro
225                 230                 235                 240

Lys Ala Leu Thr Pro Asn Ser Pro Ala Met Val Ser Ser Ser
                245                 250                 255

Pro Thr Ser Met Ser Ala Tyr Ser Leu Ser Ser Leu Asn Met Gly Thr
                260                 265                 270

Leu Pro Arg Ser Leu Tyr Ser Thr Ser Pro Arg Gly Thr Met Met Arg
            275                 280                 285

Arg Arg Leu Lys Lys Lys Asp Phe Lys Ser Ser Leu Ser Leu Ala Ser
        290                 295                 300

Ser Thr Val Gly Leu Ala Gly Gln Val Val His Thr Glu Thr Glu
305                 310                 315                 320

Val Val Leu Thr Ala Asp Pro Val Thr Gly Phe Gly Ile Gln Leu Gln
                325                 330                 335

Gly Ser Val Phe Ala Thr Glu Thr Leu Ser Ser Pro Leu Ile Ser
                340                 345                 350

Tyr Ile Glu Ala Asp Ser Pro Ala Glu Arg Cys Gly Val Leu Gln Ile
            355                 360                 365

Gly Asp Arg Val Met Ala Ile Asn Gly Ile Pro Thr Glu Asp Ser Thr
370                 375                 380

Phe Glu Glu Ala Asn Gln Leu Leu Arg Asp Ser Ser Ile Thr Ser Lys
385                 390                 395                 400

Val Thr Leu Glu Ile Glu Phe
                405

(2) INFORMATION FOR SEQ ID NO:19:

(i) SEQUENCE CHARACTERISTICS:
        (A) LENGTH: 504 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:19:

Glu Val Thr Leu His Lys Glu Gly Asn Thr Phe Gly Phe Val Ile Arg
1               5                   10                  15

Gly Gly Ala His Asp Asp Arg Asn Lys Ser Arg Pro Val Val Ile Thr
            20                  25                  30

Cys Val Arg Pro Gly Gly Pro Asp Asp Arg Glu Gly Thr Ile Lys Pro
        35                  40                  45
```

```
Gly Asp Arg Leu Leu Ser Val Asp Gly Ile Arg Leu Leu Gly Thr Thr
    50                  55                  60

His Ala Glu Ala Met Ser Ile Leu Lys Gln Cys Gly Gln Ala Thr
65                  70                  75                  80

Leu Leu Ile Glu Tyr Asp Val Ser Ala Met Asp Ser Val Ala Thr Ala
                85                  90                  95

Ser Gly Pro Leu Leu Val Glu Val Ala Lys Thr Pro Gly Ala Ser Leu
            100                 105                 110

Gly Val Ala Leu Thr Thr Ser Val Cys Cys Asn Lys Gln Val Ile Val
        115                 120                 125

Ile Asp Lys Ile Lys Ser Ala Ser Ile Ala Asp Arg Cys Gly Ala Leu
    130                 135                 140

His Val Gly Asp His Ile Leu Ser Ile Asp Gly Thr Ser Met Glu Tyr
145                 150                 155                 160

Cys Thr Leu Ala Glu Ala Thr Gln Phe Leu Gly Asn Thr Thr Asp Gln
                165                 170                 175

Val Lys Leu Glu Ile Leu Pro His His Gln Thr Arg Leu Ala Leu Lys
            180                 185                 190

Gly Pro Asp His Val Lys Ile Gln Arg Ser Asp Arg Gln Leu Pro Trp
        195                 200                 205

Asp Pro Trp Ala Ser Ser Gln Cys Ser Val His Thr Asn His His His
    210                 215                 220

Asn Pro His His Pro Asp His Cys Arg Val Pro Ala Leu Gly Phe Pro
225                 230                 235                 240

Lys Ala Leu Thr Pro Asn Ser Pro Ala Met Val Ser Ser Ser Ser
                245                 250                 255

Pro Thr Ser Met Ser Ala Tyr Ser Leu Ser Ser Leu Asn Met Gly Thr
                260                 265                 270

Leu Pro Arg Ser Leu Tyr Ser Thr Ser Pro Arg Gly Thr Met Met Arg
            275                 280                 285

Arg Arg Leu Lys Lys Lys Asp Phe Lys Ser Ser Leu Ser Leu Ala Ser
        290                 295                 300

Ser Thr Val Gly Leu Ala Gly Gln Val Val His Thr Glu Thr Thr Glu
305                 310                 315                 320

Val Val Leu Thr Ala Asp Pro Val Thr Gly Phe Gly Ile Gln Leu Gln
                325                 330                 335

Gly Ser Val Phe Ala Thr Glu Thr Leu Ser Ser Pro Leu Ile Ser
                340                 345                 350

Tyr Ile Glu Ala Asp Ser Pro Ala Glu Arg Cys Gly Val Leu Gln Ile
            355                 360                 365

Gly Asp Arg Val Met Ala Ile Asn Gly Ile Pro Thr Glu Asp Ser Thr
        370                 375                 380

Phe Glu Glu Ala Asn Gln Leu Leu Arg Asp Ser Ser Ile Thr Ser Lys
385                 390                 395                 400

Val Thr Leu Glu Ile Glu Phe Asp Val Ala Glu Ser Val Ile Pro Ser
                405                 410                 415

Ser Gly Thr Phe His Val Lys Leu Pro Lys Lys His Ser Val Glu Leu
            420                 425                 430

Gly Ile Thr Ile Ser Ser Pro Ser Ser Arg Lys Pro Gly Asp Pro Leu
        435                 440                 445

Val Ile Ser Asp Ile Lys Lys Gly Ser Val Ala His Arg Thr Gly Thr
    450                 455                 460

Leu Glu Leu Gly Asp Lys Leu Leu Ala Ile Asp Asn Ile Arg Leu Asp
```

```
                 465                 470                 475                 480
Ser Cys Ser Met Glu Asp Ala Val Gln Ile Leu Gln Gln Cys Glu Asp
                485                 490                 495

Leu Val Lys Leu Lys Ile Arg Lys
                500
```

(2) INFORMATION FOR SEQ ID NO:20:

(i) SEQUENCE CHARACTERISTICS:
        (A) LENGTH: 602 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:20:

```
Glu Val Thr Leu His Lys Glu Gly Asn Thr Phe Gly Phe Val Ile Arg
1               5                   10                  15

Gly Gly Ala His Asp Asp Arg Asn Lys Ser Arg Pro Val Val Ile Thr
                20                  25                  30

Cys Val Arg Pro Gly Gly Pro Asp Arg Glu Gly Thr Ile Lys Pro
            35                  40                  45

Gly Asp Arg Leu Leu Ser Val Asp Gly Ile Arg Leu Leu Gly Thr Thr
        50                  55                  60

His Ala Glu Ala Met Ser Ile Leu Lys Gln Cys Gly Gln Glu Ala Thr
65                  70                  75                  80

Leu Leu Ile Glu Tyr Asp Val Ser Ala Met Asp Ser Val Ala Thr Ala
                85                  90                  95

Ser Gly Pro Leu Leu Val Glu Val Ala Lys Thr Pro Gly Ala Ser Leu
                100                 105                 110

Gly Val Ala Leu Thr Thr Ser Val Cys Cys Asn Lys Gln Val Ile Val
            115                 120                 125

Ile Asp Lys Ile Lys Ser Ala Ser Ile Ala Asp Arg Cys Gly Ala Leu
130                 135                 140

His Val Gly Asp His Ile Leu Ser Ile Asp Gly Thr Ser Met Glu Tyr
145                 150                 155                 160

Cys Thr Leu Ala Glu Ala Thr Gln Phe Leu Gly Asn Thr Thr Asp Gln
                165                 170                 175

Val Lys Leu Glu Ile Leu Pro His His Gln Thr Arg Leu Ala Leu Lys
                180                 185                 190

Gly Pro Asp His Val Lys Ile Gln Arg Ser Asp Arg Gln Leu Pro Trp
            195                 200                 205

Asp Pro Trp Ala Ser Ser Gln Cys Ser Val His Thr Asn His His His
        210                 215                 220

Asn Pro His His Pro Asp His Cys Arg Val Pro Ala Leu Gly Phe Pro
225                 230                 235                 240

Lys Ala Leu Thr Pro Asn Ser Pro Ala Met Val Ser Ser Ser Ser
                245                 250                 255

Pro Thr Ser Met Ser Ala Tyr Ser Leu Ser Ser Leu Asn Met Gly Thr
                260                 265                 270

Leu Pro Arg Ser Leu Tyr Ser Thr Ser Pro Arg Gly Thr Met Met Arg
            275                 280                 285

Arg Arg Leu Lys Lys Lys Asp Phe Lys Ser Ser Leu Ser Leu Ala Ser
        290                 295                 300

Ser Thr Val Gly Leu Ala Gly Gln Val Val His Thr Glu Thr Thr Glu
305                 310                 315                 320
```

```
Val Val Leu Thr Ala Asp Pro Val Thr Gly Phe Gly Ile Gln Leu Gln
            325                 330                 335

Gly Ser Val Phe Ala Thr Glu Thr Leu Ser Ser Pro Pro Leu Ile Ser
            340                 345                 350

Tyr Ile Glu Ala Asp Ser Pro Ala Glu Arg Cys Gly Val Leu Gln Ile
            355                 360                 365

Gly Asp Arg Val Met Ala Ile Asn Gly Ile Pro Thr Glu Asp Ser Thr
            370                 375                 380

Phe Glu Glu Ala Asn Gln Leu Leu Arg Asp Ser Ser Ile Thr Ser Lys
385                 390                 395                 400

Val Thr Leu Glu Ile Glu Phe Asp Val Ala Glu Ser Val Ile Pro Ser
            405                 410                 415

Ser Gly Thr Phe His Val Lys Leu Pro Lys Lys His Ser Val Glu Leu
            420                 425                 430

Gly Ile Thr Ile Ser Ser Pro Ser Ser Arg Lys Pro Gly Asp Pro Leu
            435                 440                 445

Val Ile Ser Asp Ile Lys Lys Gly Ser Val Ala His Arg Thr Gly Thr
            450                 455                 460

Leu Glu Leu Gly Asp Lys Leu Leu Ala Ile Asp Asn Ile Arg Leu Asp
465                 470                 475                 480

Ser Cys Ser Met Glu Asp Ala Val Gln Ile Leu Gln Cys Glu Asp
            485                 490                 495

Leu Val Lys Leu Lys Ile Arg Lys Asp Glu Asp Asn Ser Asp Glu Gln
            500                 505                 510

Glu Ser Ser Gly Ala Ile Ile Tyr Thr Val Glu Leu Lys Arg Tyr Gly
            515                 520                 525

Gly Pro Leu Gly Ile Thr Ile Ser Gly Thr Glu Glu Pro Phe Asp Pro
            530                 535                 540

Ile Ile Ile Ser Ser Leu Thr Lys Gly Gly Leu Ala Glu Arg Thr Gly
545                 550                 555                 560

Ala Ile His Ile Gly Asp Arg Ile Leu Ala Ile Asn Ser Ser Ser Leu
            565                 570                 575

Lys Gly Lys Pro Leu Ser Glu Asp Ile His Leu Leu Gln Met Ala Gly
            580                 585                 590

Glu Thr Val Thr Leu Lys Ile Lys Lys Gln
            595                 600
```

(2) INFORMATION FOR SEQ ID NO:21:

(i) SEQUENCE CHARACTERISTICS:
        (A) LENGTH: 918 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:21:

```
Glu Val Thr Leu His Lys Glu Gly Asn Thr Phe Gly Phe Val Ile Arg
1               5                   10                  15

Gly Gly Ala His Asp Asp Arg Asn Lys Ser Arg Pro Val Val Ile Thr
            20                  25                  30

Cys Val Arg Pro Gly Gly Pro Asp Asp Arg Glu Gly Thr Ile Lys Pro
            35                  40                  45

Gly Asp Arg Leu Leu Ser Val Asp Gly Ile Arg Leu Leu Gly Thr Thr
            50                  55                  60
```

-continued

His Ala Glu Ala Met Ser Ile Leu Lys Gln Cys Gly Gln Ala Thr
65                  70                  75                  80

Leu Leu Ile Glu Tyr Asp Val Ser Ala Met Asp Ser Val Ala Thr Ala
            85                  90                  95

Ser Gly Pro Leu Leu Val Glu Val Ala Lys Thr Pro Gly Ala Ser Leu
            100                 105                 110

Gly Val Ala Leu Thr Thr Ser Val Cys Cys Asn Lys Gln Val Ile Val
        115                 120                 125

Ile Asp Lys Ile Lys Ser Ala Ser Ile Ala Asp Arg Cys Gly Ala Leu
130                 135                 140

His Val Gly Asp His Ile Leu Ser Ile Asp Gly Thr Ser Met Glu Tyr
145                 150                 155                 160

Cys Thr Leu Ala Glu Ala Thr Gln Phe Leu Gly Asn Thr Thr Asp Gln
                165                 170                 175

Val Lys Leu Glu Ile Leu Pro His His Gln Thr Arg Leu Ala Leu Lys
        180                 185                 190

Gly Pro Asp His Val Lys Ile Gln Arg Ser Asp Arg Gln Leu Pro Trp
            195                 200                 205

Asp Pro Trp Ala Ser Ser Gln Cys Ser Val His Thr Asn His His His
    210                 215                 220

Asn Pro His His Pro Asp His Cys Arg Val Pro Ala Leu Gly Phe Pro
225                 230                 235                 240

Lys Ala Leu Thr Pro Asn Ser Pro Ala Met Val Ser Ser Ser Ser
                245                 250                 255

Pro Thr Ser Met Ser Ala Tyr Ser Leu Ser Ser Leu Asn Met Gly Thr
                260                 265                 270

Leu Pro Arg Ser Leu Tyr Ser Thr Ser Pro Arg Gly Thr Met Met Arg
        275                 280                 285

Arg Arg Leu Lys Lys Lys Asp Phe Lys Ser Ser Leu Ser Leu Ala Ser
    290                 295                 300

Ser Thr Val Gly Leu Ala Gly Gln Val Val His Thr Glu Thr Thr Glu
305                 310                 315                 320

Val Val Leu Thr Ala Asp Pro Val Thr Gly Phe Gly Ile Gln Leu Gln
                325                 330                 335

Gly Ser Val Phe Ala Thr Glu Thr Leu Ser Ser Pro Leu Ile Ser
            340                 345                 350

Tyr Ile Glu Ala Asp Ser Pro Ala Glu Arg Cys Gly Val Leu Gln Ile
        355                 360                 365

Gly Asp Arg Val Met Ala Ile Asn Gly Ile Pro Thr Glu Asp Ser Thr
    370                 375                 380

Phe Glu Glu Ala Asn Gln Leu Leu Arg Asp Ser Ser Ile Thr Ser Lys
385                 390                 395                 400

Val Thr Leu Glu Ile Glu Phe Asp Val Ala Glu Ser Val Ile Pro Ser
                405                 410                 415

Ser Gly Thr Phe His Val Lys Leu Pro Lys Lys His Ser Val Glu Leu
            420                 425                 430

Gly Ile Thr Ile Ser Ser Pro Ser Arg Lys Pro Gly Asp Pro Leu
        435                 440                 445

Val Ile Ser Asp Ile Lys Lys Gly Ser Val Ala His Arg Thr Gly Thr
    450                 455                 460

Leu Glu Leu Gly Asp Lys Leu Leu Ala Ile Asp Asn Ile Arg Leu Asp
465                 470                 475                 480

Ser Cys Ser Met Glu Asp Ala Val Gln Ile Leu Gln Gln Cys Glu Asp
                485                 490                 495

-continued

Leu Val Lys Leu Lys Ile Arg Lys Asp Glu Asp Asn Ser Asp Glu Gln
        500                 505                 510

Glu Ser Ser Gly Ala Ile Ile Tyr Thr Val Glu Leu Lys Arg Tyr Gly
        515                 520                 525

Gly Pro Leu Gly Ile Thr Ile Ser Gly Thr Glu Glu Pro Phe Asp Pro
        530                 535                 540

Ile Ile Ile Ser Ser Leu Thr Lys Gly Gly Leu Ala Glu Arg Thr Gly
545                 550                 555                 560

Ala Ile His Ile Gly Asp Arg Ile Leu Ala Ile Asn Ser Ser Ser Leu
                565                 570                 575

Lys Gly Lys Pro Leu Ser Glu Asp Ile His Leu Leu Gln Met Ala Gly
            580                 585                 590

Glu Thr Val Thr Leu Lys Ile Lys Lys Gln Thr Asp Ala Gln Pro Ala
        595                 600                 605

Ser Ser Pro Lys Lys Leu Pro Ile Pro Ser His Ser Ser Asp Leu Gly
    610                 615                 620

Asp Gly Glu Glu Asp Pro Ser Pro Ile Gln Arg Pro Gly Lys Leu Ser
625                 630                 635                 640

Asp Val Tyr Pro Ser Thr Val Pro Ser Val Asp Ser Ala Val Asp Ser
                645                 650                 655

Trp Asp Gly Ser Gly Ile Asp Ala Arg Tyr Gly Ser Gln Gly Thr Thr
            660                 665                 670

Phe Gln Thr Ser Gly Tyr Asn Phe Asn Thr Tyr Asp Trp Arg Ser Pro
        675                 680                 685

Lys Lys Arg Ala Ser Leu Ser Pro Val Pro Lys Pro Arg Ser Gln Thr
    690                 695                 700

Tyr Pro Asp Val Gly Leu Ser Asn Glu Asp Trp Asp Arg Ser Thr Ala
705                 710                 715                 720

Ser Gly Phe Ala Gly Ala Ser Asp Ser Ala Asp Ala Glu Gln Glu Glu
                725                 730                 735

Asn Phe Trp Ser Gln Ala Leu Glu Asp Leu Glu Thr Cys Gly Gln Ser
            740                 745                 750

Gly Ile Leu Arg Glu Leu Glu Ala Thr Ile Met Ser Gly Ser Thr Met
        755                 760                 765

Ser Leu Asn His Glu Ala Pro Thr Ala Arg Ser Gln Leu Gly Arg Gln
    770                 775                 780

Ala Ser Phe Gln Glu Arg Ser Asn Ser Arg Pro His Tyr Ser Gln Thr
785                 790                 795                 800

Thr Arg Ser Asn Thr Leu Pro Ser Asp Val Gly Arg Lys Ser Val Thr
                805                 810                 815

Leu Arg Lys Met Lys Gln Glu Ile Lys Glu Ile Met Ser Pro Thr Pro
            820                 825                 830

Val Glu Leu His Lys Val Thr Leu Tyr Lys Asp Ser Gly Met Glu Asp
        835                 840                 845

Phe Gly Phe Ser Val Ala Asp Gly Leu Leu Glu Lys Gly Val Tyr Val
    850                 855                 860

Lys Asn Ile Arg Pro Ala Gly Pro Gly Asp Leu Gly Gly Leu Lys Pro
865                 870                 875                 880

Tyr Asp Arg Leu Leu Gln Val Asn His Val Arg Thr Arg Asp Phe Asp
                885                 890                 895

Cys Cys Leu Val Val Pro Leu Ile Ala Glu Ser Gly Asn Lys Leu Asp
            900                 905                 910

Leu Val Ile Ser Arg Asn

915

(2) INFORMATION FOR SEQ ID NO:22:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:22:

```
Leu Val Glu Val Ala Lys Thr Pro Gly Ala Ser Leu Gly Val Ala Leu
  1               5                  10                  15

Thr Thr Ser Val Cys Cys Asn Lys Gln Val Ile Val Ile Asp Lys Ile
             20                  25                  30

Lys Ser Ala Ser Ile Ala Asp Arg Cys Gly Ala Leu His Val Gly Asp
         35                  40                  45

His Ile Leu Ser Ile Asp Gly Thr Ser Met Glu Tyr Cys Thr Leu Ala
     50                  55                  60

Glu Ala Thr Gln Phe Leu Gly Asn Thr Thr Asp Gln Val Lys Leu Glu
 65                  70                  75                  80

Ile Leu Pro His His Gln Thr Arg Leu Ala Leu Lys Gly Pro Asp His
                 85                  90                  95

Val Lys Ile Gln Arg Ser Asp Arg Gln Leu Pro Trp Asp Pro Trp Ala
            100                 105                 110

Ser Ser Gln Cys Ser Val His Thr Asn His His Asn Pro His His
            115                 120                 125

Pro Asp His Cys Arg Val Pro Ala Leu Gly Phe Pro Lys Ala Leu Thr
        130                 135                 140

Pro Asn Ser Pro Pro Ala Met Val Ser Ser Ser Pro Thr Ser Met
145                 150                 155                 160

Ser Ala Tyr Ser Leu Ser Ser Leu Asn Met Gly Thr Leu Pro Arg Ser
                165                 170                 175

Leu Tyr Ser Thr Ser Pro Arg Gly Thr Met Met Arg Arg Leu Lys
            180                 185                 190

Lys Lys Asp Phe Lys Ser Ser Leu Ser Leu Ala Ser Ser Thr Val Gly
        195                 200                 205

Leu Ala Gly Gln Val Val His Thr Glu Thr Thr Glu Val Val Leu Thr
210                 215                 220

Ala Asp Pro Val Thr Gly Phe Gly Ile Gln Leu Gln Gly Ser Val Phe
225                 230                 235                 240

Ala Thr Glu Thr Leu Ser Ser Pro Pro Leu Ile Ser Tyr Ile Glu Ala
                245                 250                 255

Asp Ser Pro Ala Glu Arg Cys Gly Val Leu Gln Ile Gly Asp Arg Val
            260                 265                 270

Met Ala Ile Asn Gly Ile Pro Thr Glu Asp Ser Thr Phe Glu Glu Ala
        275                 280                 285

Asn Gln Leu Leu Arg Asp Ser Ser Ile Thr Ser Lys Val Thr Leu Glu
290                 295                 300

Ile Glu Phe
305
```

(2) INFORMATION FOR SEQ ID NO:23:

(i) SEQUENCE CHARACTERISTICS:
        (A) LENGTH: 404 amino acids (B) TYPE: amino acid
(C) STRANDEDNESS:
(D) TOPOLOGY: linear (ii) MOLECULE TYPE: protein (xi) SEQUENCE DESCRIPTION: SEQ ID NO:23:

```
Leu Val Glu Val Ala Lys Thr Pro Gly Ala Ser Leu Gly Val Ala Leu
1               5                   10                  15

Thr Thr Ser Val Cys Cys Asn Lys Gln Val Ile Val Ile Asp Lys Ile
            20                  25                  30

Lys Ser Ala Ser Ile Ala Asp Arg Cys Gly Ala Leu His Val Gly Asp
        35                  40                  45

His Ile Leu Ser Ile Asp Gly Thr Ser Met Glu Tyr Cys Thr Leu Ala
    50                  55                  60

Glu Ala Thr Gln Phe Leu Gly Asn Thr Thr Asp Gln Val Lys Leu Glu
65                  70                  75                  80

Ile Leu Pro His His Gln Thr Arg Leu Ala Leu Lys Gly Pro Asp His
                85                  90                  95

Val Lys Ile Gln Arg Ser Asp Arg Gln Leu Pro Trp Asp Pro Trp Ala
            100                 105                 110

Ser Ser Gln Cys Ser Val His Thr Asn His His Asn Pro His His
        115                 120                 125

Pro Asp His Cys Arg Val Pro Ala Leu Gly Phe Pro Lys Ala Leu Thr
130                 135                 140

Pro Asn Ser Pro Pro Ala Met Val Ser Ser Ser Pro Thr Ser Met
145                 150                 155                 160

Ser Ala Tyr Ser Leu Ser Ser Leu Asn Met Gly Thr Leu Pro Arg Ser
                165                 170                 175

Leu Tyr Ser Thr Ser Pro Arg Gly Thr Met Met Arg Arg Leu Lys
            180                 185                 190

Lys Lys Asp Phe Lys Ser Ser Leu Ser Leu Ala Ser Ser Thr Val Gly
        195                 200                 205

Leu Ala Gly Gln Val Val His Thr Glu Thr Thr Glu Val Val Leu Thr
    210                 215                 220

Ala Asp Pro Val Thr Gly Phe Gly Ile Gln Leu Gln Gly Ser Val Phe
225                 230                 235                 240

Ala Thr Glu Thr Leu Ser Ser Pro Pro Leu Ile Ser Tyr Ile Glu Ala
                245                 250                 255

Asp Ser Pro Ala Glu Arg Cys Gly Val Leu Gln Ile Gly Asp Arg Val
            260                 265                 270

Met Ala Ile Asn Gly Ile Pro Thr Glu Asp Ser Thr Phe Glu Glu Ala
        275                 280                 285

Asn Gln Leu Leu Arg Asp Ser Ser Ile Thr Ser Lys Val Thr Leu Glu
    290                 295                 300

Ile Glu Phe Asp Val Ala Glu Ser Val Ile Pro Ser Ser Gly Thr Phe
305                 310                 315                 320

His Val Lys Leu Pro Lys Lys His Ser Val Glu Leu Gly Ile Thr Ile
                325                 330                 335

Ser Ser Pro Ser Ser Arg Lys Pro Gly Asp Pro Leu Val Ile Ser Asp
            340                 345                 350

Ile Lys Lys Gly Ser Val Ala His Arg Thr Gly Thr Leu Glu Leu Gly
        355                 360                 365

Asp Lys Leu Leu Ala Ile Asp Asn Ile Arg Leu Asp Ser Cys Ser Met
    370                 375                 380
```

-continued

Glu Asp Ala Val Gln Ile Leu Gln Gln Cys Glu Asp Leu Val Lys Leu
385                 390                 395                 400

Lys Ile Arg Lys (2) INFORMATION FOR SEQ ID NO:24:

(i) SEQUENCE CHARACTERISTICS:
        (A) LENGTH: 502 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:24:

Leu Val Glu Val Ala Lys Thr Pro Gly Ala Ser Leu Gly Val Ala Leu
1               5                   10                  15

Thr Thr Ser Val Cys Cys Asn Lys Gln Val Ile Val Ile Asp Lys Ile
                20                  25                  30

Lys Ser Ala Ser Ile Ala Asp Arg Cys Gly Ala Leu His Val Gly Asp
            35                  40                  45

His Ile Leu Ser Ile Asp Gly Thr Ser Met Glu Tyr Cys Thr Leu Ala
        50                  55                  60

Glu Ala Thr Gln Phe Leu Gly Asn Thr Thr Asp Gln Val Lys Leu Glu
65                  70                  75                  80

Ile Leu Pro His His Gln Thr Arg Leu Ala Leu Lys Gly Pro Asp His
                85                  90                  95

Val Lys Ile Gln Arg Ser Asp Arg Gln Leu Pro Trp Asp Pro Trp Ala
                100                 105                 110

Ser Ser Gln Cys Ser Val His Thr Asn His His Asn Pro His His
            115                 120                 125

Pro Asp His Cys Arg Val Pro Ala Leu Gly Phe Pro Lys Ala Leu Thr
        130                 135                 140

Pro Asn Ser Pro Pro Ala Met Val Ser Ser Ser Pro Thr Ser Met
145                 150                 155                 160

Ser Ala Tyr Ser Leu Ser Ser Leu Asn Met Gly Thr Leu Pro Arg Ser
                165                 170                 175

Leu Tyr Ser Thr Ser Pro Arg Gly Thr Met Met Arg Arg Arg Leu Lys
                180                 185                 190

Lys Lys Asp Phe Lys Ser Ser Leu Ser Leu Ala Ser Ser Thr Val Gly
            195                 200                 205

Leu Ala Gly Gln Val Val His Thr Glu Thr Thr Glu Val Val Leu Thr
        210                 215                 220

Ala Asp Pro Val Thr Gly Phe Gly Ile Gln Leu Gln Gly Ser Val Phe
225                 230                 235                 240

Ala Thr Glu Thr Leu Ser Ser Pro Pro Leu Ile Ser Tyr Ile Glu Ala
                245                 250                 255

Asp Ser Pro Ala Glu Arg Cys Gly Val Leu Gln Ile Gly Asp Arg Val
                260                 265                 270

Met Ala Ile Asn Gly Ile Pro Thr Glu Asp Ser Thr Phe Glu Glu Ala
            275                 280                 285

Asn Gln Leu Leu Arg Asp Ser Ser Ile Thr Ser Lys Val Thr Leu Glu
        290                 295                 300

Ile Glu Phe Asp Val Ala Glu Ser Val Ile Pro Ser Ser Gly Thr Phe
305                 310                 315                 320

His Val Lys Leu Pro Lys Lys His Ser Val Glu Leu Gly Ile Thr Ile
                325                 330                 335

```
Ser Ser Pro Ser Ser Arg Lys Pro Gly Asp Pro Leu Val Ile Ser Asp
            340                 345                 350

Ile Lys Lys Gly Ser Val Ala His Arg Thr Gly Thr Leu Glu Leu Gly
            355                 360                 365

Asp Lys Leu Leu Ala Ile Asp Asn Ile Arg Leu Asp Ser Cys Ser Met
            370                 375                 380

Glu Asp Ala Val Gln Ile Leu Gln Gln Cys Glu Asp Leu Val Lys Leu
385                 390                 395                 400

Lys Ile Arg Lys Asp Glu Asp Asn Ser Asp Glu Gln Glu Ser Ser Gly
            405                 410                 415

Ala Ile Ile Tyr Thr Val Glu Leu Lys Arg Tyr Gly Gly Pro Leu Gly
            420                 425                 430

Ile Thr Ile Ser Gly Thr Glu Glu Pro Phe Asp Pro Ile Ile Ile Ser
            435                 440                 445

Ser Leu Thr Lys Gly Gly Leu Ala Glu Arg Thr Gly Ala Ile His Ile
            450                 455                 460

Gly Asp Arg Ile Leu Ala Ile Asn Ser Ser Ser Leu Lys Gly Lys Pro
465                 470                 475                 480

Leu Ser Glu Asp Ile His Leu Leu Gln Met Ala Gly Glu Thr Val Thr
            485                 490                 495

Leu Lys Ile Lys Lys Gln
            500
```

(2) INFORMATION FOR SEQ ID NO:25:

(i) SEQUENCE CHARACTERISTICS:
        (A) LENGTH: 818 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:25:

```
Leu Val Glu Val Ala Lys Thr Pro Gly Ala Ser Leu Gly Val Ala Leu
1               5                   10                  15

Thr Thr Ser Val Cys Cys Asn Lys Gln Val Ile Val Ile Asp Lys Ile
            20                  25                  30

Lys Ser Ala Ser Ile Ala Asp Arg Cys Gly Ala Leu His Val Gly Asp
            35                  40                  45

His Ile Leu Ser Ile Asp Gly Thr Ser Met Glu Tyr Cys Thr Leu Ala
            50                  55                  60

Glu Ala Thr Gln Phe Leu Gly Asn Thr Thr Asp Gln Val Lys Leu Glu
65                  70                  75                  80

Ile Leu Pro His His Gln Thr Arg Leu Ala Leu Lys Gly Pro Asp His
            85                  90                  95

Val Lys Ile Gln Arg Ser Asp Arg Gln Leu Pro Trp Asp Pro Trp Ala
            100                 105                 110

Ser Ser Gln Cys Ser Val His Thr Asn His His Asn Pro His His
            115                 120                 125

Pro Asp His Cys Arg Val Pro Ala Leu Gly Phe Pro Lys Ala Leu Thr
            130                 135                 140

Pro Asn Ser Pro Pro Ala Met Val Ser Ser Ser Pro Thr Ser Met
145                 150                 155                 160

Ser Ala Tyr Ser Leu Ser Ser Leu Asn Met Gly Thr Leu Pro Arg Ser
            165                 170                 175
```

```
Leu Tyr Ser Thr Ser Pro Arg Gly Thr Met Met Arg Arg Arg Leu Lys
            180                 185                 190

Lys Lys Asp Phe Lys Ser Ser Leu Ser Leu Ala Ser Ser Thr Val Gly
        195                 200                 205

Leu Ala Gly Gln Val Val His Thr Glu Thr Thr Glu Val Val Leu Thr
    210                 215                 220

Ala Asp Pro Val Thr Gly Phe Gly Ile Gln Leu Gln Gly Ser Val Phe
225                 230                 235                 240

Ala Thr Glu Thr Leu Ser Ser Pro Pro Leu Ile Ser Tyr Ile Glu Ala
                245                 250                 255

Asp Ser Pro Ala Glu Arg Cys Gly Val Leu Gln Ile Gly Asp Arg Val
            260                 265                 270

Met Ala Ile Asn Gly Ile Pro Thr Glu Asp Ser Thr Phe Glu Glu Ala
            275                 280                 285

Asn Gln Leu Leu Arg Asp Ser Ser Ile Thr Ser Lys Val Thr Leu Glu
        290                 295                 300

Ile Glu Phe Asp Val Ala Glu Ser Val Ile Pro Ser Ser Gly Thr Phe
305                 310                 315                 320

His Val Lys Leu Pro Lys Lys His Ser Val Glu Leu Gly Ile Thr Ile
                325                 330                 335

Ser Ser Pro Ser Ser Arg Lys Pro Gly Asp Pro Leu Val Ile Ser Asp
            340                 345                 350

Ile Lys Lys Gly Ser Val Ala His Arg Thr Gly Thr Leu Glu Leu Gly
        355                 360                 365

Asp Lys Leu Leu Ala Ile Asp Asn Ile Arg Leu Asp Ser Cys Ser Met
    370                 375                 380

Glu Asp Ala Val Gln Ile Leu Gln Gln Cys Glu Asp Leu Val Lys Leu
385                 390                 395                 400

Lys Ile Arg Lys Asp Glu Asp Asn Ser Asp Glu Gln Glu Ser Ser Gly
                405                 410                 415

Ala Ile Ile Tyr Thr Val Glu Leu Lys Arg Tyr Gly Gly Pro Leu Gly
            420                 425                 430

Ile Thr Ile Ser Gly Thr Glu Glu Pro Phe Asp Pro Ile Ile Ile Ser
        435                 440                 445

Ser Leu Thr Lys Gly Gly Leu Ala Glu Arg Thr Gly Ala Ile His Ile
    450                 455                 460

Gly Asp Arg Ile Leu Ala Ile Asn Ser Ser Ser Leu Lys Gly Lys Pro
465                 470                 475                 480

Leu Ser Glu Asp Ile His Leu Leu Gln Met Ala Gly Glu Thr Val Thr
                485                 490                 495

Leu Lys Ile Lys Lys Gln Thr Asp Ala Gln Pro Ala Ser Ser Pro Lys
            500                 505                 510

Lys Leu Pro Ile Pro Ser His Ser Ser Asp Leu Gly Asp Gly Glu Glu
        515                 520                 525

Asp Pro Ser Pro Ile Gln Arg Pro Gly Lys Leu Ser Asp Val Tyr Pro
    530                 535                 540

Ser Thr Val Pro Ser Val Asp Ser Ala Val Asp Ser Trp Asp Gly Ser
545                 550                 555                 560

Gly Ile Asp Ala Arg Tyr Gly Ser Gln Gly Thr Thr Phe Gln Thr Ser
                565                 570                 575

Gly Tyr Asn Phe Asn Thr Tyr Asp Trp Arg Ser Pro Lys Lys Arg Ala
            580                 585                 590

Ser Leu Ser Pro Val Pro Lys Pro Arg Ser Gln Thr Tyr Pro Asp Val
        595                 600                 605
```

```
Gly Leu Ser Asn Glu Asp Trp Asp Arg Ser Thr Ala Ser Gly Phe Ala
        610                 615                 620

Gly Ala Ser Asp Ser Ala Asp Ala Glu Gln Glu Asn Phe Trp Ser
625                 630                 635                 640

Gln Ala Leu Glu Asp Leu Glu Thr Cys Gly Gln Ser Gly Ile Leu Arg
                    645                 650                 655

Glu Leu Glu Ala Thr Ile Met Ser Gly Ser Thr Met Ser Leu Asn His
                660                 665                 670

Glu Ala Pro Thr Ala Arg Ser Gln Leu Gly Arg Gln Ala Ser Phe Gln
            675                 680                 685

Glu Arg Ser Asn Ser Arg Pro His Tyr Ser Gln Thr Thr Arg Ser Asn
        690                 695                 700

Thr Leu Pro Ser Asp Val Gly Arg Lys Ser Val Thr Leu Arg Lys Met
705                 710                 715                 720

Lys Gln Glu Ile Lys Glu Ile Met Ser Pro Thr Pro Val Glu Leu His
                    725                 730                 735

Lys Val Thr Leu Tyr Lys Asp Ser Gly Met Glu Asp Phe Gly Phe Ser
                740                 745                 750

Val Ala Asp Gly Leu Leu Glu Lys Gly Val Tyr Val Lys Asn Ile Arg
            755                 760                 765

Pro Ala Gly Pro Gly Asp Leu Gly Gly Leu Lys Pro Tyr Asp Arg Leu
        770                 775                 780

Leu Gln Val Asn His Val Arg Thr Arg Asp Phe Asp Cys Cys Leu Val
785                 790                 795                 800

Val Pro Leu Ile Ala Glu Ser Gly Asn Lys Leu Asp Leu Val Ile Ser
                    805                 810                 815

Arg Asn (2) INFORMATION FOR SEQ ID NO:26:

(i) SEQUENCE CHARACTERISTICS:
        (A) LENGTH: 185 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:26:

Glu Val Val Leu Thr Ala Asp Pro Val Thr Gly Phe Gly Ile Gln Leu
1               5                   10                  15

Gln Gly Ser Val Phe Ala Thr Glu Thr Leu Ser Ser Pro Pro Leu Ile
                20                  25                  30

Ser Tyr Ile Glu Ala Asp Ser Pro Ala Glu Arg Cys Gly Val Leu Gln
            35                  40                  45

Ile Gly Asp Arg Val Met Ala Ile Asn Gly Ile Pro Thr Glu Asp Ser
50                  55                  60

Thr Phe Glu Glu Ala Asn Gln Leu Leu Arg Asp Ser Ser Ile Thr Ser
65                  70                  75                  80

Lys Val Thr Leu Glu Ile Glu Phe Asp Val Ala Glu Ser Val Ile Pro
                85                  90                  95

Ser Ser Gly Thr Phe His Val Lys Leu Pro Lys Lys His Ser Val Glu
                100                 105                 110

Leu Gly Ile Thr Ile Ser Ser Pro Ser Ser Arg Lys Pro Gly Asp Pro
            115                 120                 125

Leu Val Ile Ser Asp Ile Lys Lys Gly Ser Val Ala His Arg Thr Gly
```

```
            130                 135                 140
Thr Leu Glu Leu Gly Asp Lys Leu Leu Ala Ile Asp Asn Ile Arg Leu
145                 150                 155                 160

Asp Ser Cys Ser Met Glu Asp Ala Val Gln Ile Leu Gln Gln Cys Glu
                165                 170                 175

Asp Leu Val Lys Leu Lys Ile Arg Lys
                180                 185
```

(2) INFORMATION FOR SEQ ID NO:27:

(i) SEQUENCE CHARACTERISTICS:
        (A) LENGTH: 283 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:27:

```
Glu Val Val Leu Thr Ala Asp Pro Val Thr Gly Phe Gly Ile Gln Leu
1               5                   10                  15

Gln Gly Ser Val Phe Ala Thr Glu Thr Leu Ser Ser Pro Pro Leu Ile
                20                  25                  30

Ser Tyr Ile Glu Ala Asp Ser Pro Ala Glu Arg Cys Gly Val Leu Gln
                35                  40                  45

Ile Gly Asp Arg Val Met Ala Ile Asn Gly Ile Pro Thr Glu Asp Ser
50                  55                  60

Thr Phe Glu Glu Ala Asn Gln Leu Leu Arg Asp Ser Ser Ile Thr Ser
65                  70                  75                  80

Lys Val Thr Leu Glu Ile Glu Phe Asp Val Ala Glu Ser Val Ile Pro
                85                  90                  95

Ser Ser Gly Thr Phe His Val Lys Leu Pro Lys Lys His Ser Val Glu
                100                 105                 110

Leu Gly Ile Thr Ile Ser Ser Pro Ser Ser Arg Lys Pro Gly Asp Pro
                115                 120                 125

Leu Val Ile Ser Asp Ile Lys Lys Gly Ser Val Ala His Arg Thr Gly
130                 135                 140

Thr Leu Glu Leu Gly Asp Lys Leu Leu Ala Ile Asp Asn Ile Arg Leu
145                 150                 155                 160

Asp Ser Cys Ser Met Glu Asp Ala Val Gln Ile Leu Gln Gln Cys Glu
                165                 170                 175

Asp Leu Val Lys Leu Lys Ile Arg Lys Asp Glu Asn Ser Asp Glu
                180                 185                 190

Gln Glu Ser Ser Gly Ala Ile Ile Tyr Thr Val Glu Leu Lys Arg Tyr
                195                 200                 205

Gly Gly Pro Leu Gly Ile Thr Ile Ser Gly Thr Glu Glu Pro Phe Asp
210                 215                 220

Pro Ile Ile Ile Ser Ser Leu Thr Lys Gly Gly Leu Ala Glu Arg Thr
225                 230                 235                 240

Gly Ala Ile His Ile Gly Asp Arg Ile Leu Ala Ile Asn Ser Ser Ser
                245                 250                 255

Leu Lys Gly Lys Pro Leu Ser Glu Asp Ile His Leu Leu Gln Met Ala
                260                 265                 270

Gly Glu Thr Val Thr Leu Lys Ile Lys Lys Gln
                275                 280
```

(2) INFORMATION FOR SEQ ID NO:28:

(i) SEQUENCE CHARACTERISTICS:
    (A) LENGTH: 599 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO:28:

```
Glu Val Val Leu Thr Ala Asp Pro Val Thr Gly Phe Gly Ile Gln Leu
1               5                   10                  15

Gln Gly Ser Val Phe Ala Thr Glu Thr Leu Ser Ser Pro Pro Leu Ile
            20                  25                  30

Ser Tyr Ile Glu Ala Asp Ser Pro Ala Glu Arg Cys Gly Val Leu Gln
        35                  40                  45

Ile Gly Asp Arg Val Met Ala Ile Asn Gly Ile Pro Thr Glu Asp Ser
    50                  55                  60

Thr Phe Glu Glu Ala Asn Gln Leu Leu Arg Asp Ser Ser Ile Thr Ser
65                  70                  75                  80

Lys Val Thr Leu Glu Ile Glu Phe Asp Val Ala Glu Ser Val Ile Pro
                85                  90                  95

Ser Ser Gly Thr Phe His Val Lys Leu Pro Lys Lys His Ser Val Glu
            100                 105                 110

Leu Gly Ile Thr Ile Ser Ser Pro Ser Ser Arg Lys Pro Gly Asp Pro
        115                 120                 125

Leu Val Ile Ser Asp Ile Lys Lys Gly Ser Val Ala His Arg Thr Gly
    130                 135                 140

Thr Leu Glu Leu Gly Asp Lys Leu Leu Ala Ile Asp Asn Ile Arg Leu
145                 150                 155                 160

Asp Ser Cys Ser Met Glu Asp Ala Val Gln Ile Leu Gln Gln Cys Glu
                165                 170                 175

Asp Leu Val Lys Leu Lys Ile Arg Lys Asp Glu Asp Asn Ser Asp Glu
            180                 185                 190

Gln Glu Ser Ser Gly Ala Ile Ile Tyr Thr Val Glu Leu Lys Arg Tyr
        195                 200                 205

Gly Gly Pro Leu Gly Ile Thr Ile Ser Gly Thr Glu Glu Pro Phe Asp
    210                 215                 220

Pro Ile Ile Ile Ser Ser Leu Thr Lys Gly Gly Leu Ala Glu Arg Thr
225                 230                 235                 240

Gly Ala Ile His Ile Gly Asp Arg Ile Leu Ala Ile Asn Ser Ser Ser
                245                 250                 255

Leu Lys Gly Lys Pro Leu Ser Glu Asp Ile His Leu Leu Gln Met Ala
            260                 265                 270

Gly Glu Thr Val Thr Leu Lys Ile Lys Lys Gln Thr Asp Ala Gln Pro
        275                 280                 285

Ala Ser Ser Pro Lys Lys Leu Pro Ile Pro Ser His Ser Ser Asp Leu
    290                 295                 300

Gly Asp Gly Glu Glu Asp Pro Ser Pro Ile Gln Arg Pro Gly Lys Leu
305                 310                 315                 320

Ser Asp Val Tyr Pro Ser Thr Val Pro Ser Val Asp Ser Ala Val Asp
                325                 330                 335

Ser Trp Asp Gly Ser Gly Ile Asp Ala Arg Tyr Gly Ser Gln Gly Thr
            340                 345                 350

Thr Phe Gln Thr Ser Gly Tyr Asn Phe Asn Thr Tyr Asp Trp Arg Ser
        355                 360                 365
```

```
Pro Lys Lys Arg Ala Ser Leu Ser Pro Val Pro Lys Pro Arg Ser Gln
    370                 375                 380

Thr Tyr Pro Asp Val Gly Leu Ser Asn Glu Asp Trp Asp Arg Ser Thr
385                 390                 395                 400

Ala Ser Gly Phe Ala Gly Ala Ser Asp Ser Ala Asp Ala Glu Gln Glu
                405                 410                 415

Glu Asn Phe Trp Ser Gln Ala Leu Glu Asp Leu Glu Thr Cys Gly Gln
            420                 425                 430

Ser Gly Ile Leu Arg Glu Leu Glu Ala Thr Ile Met Ser Gly Ser Thr
        435                 440                 445

Met Ser Leu Asn His Glu Ala Pro Thr Ala Arg Ser Gln Leu Gly Arg
    450                 455                 460

Gln Ala Ser Phe Gln Glu Arg Ser Asn Ser Arg Pro His Tyr Ser Gln
465                 470                 475                 480

Thr Thr Arg Ser Asn Thr Leu Pro Ser Asp Val Gly Arg Lys Ser Val
                485                 490                 495

Thr Leu Arg Lys Met Lys Gln Glu Ile Lys Glu Ile Met Ser Pro Thr
            500                 505                 510

Pro Val Glu Leu His Lys Val Thr Leu Tyr Lys Asp Ser Gly Met Glu
        515                 520                 525

Asp Phe Gly Phe Ser Val Ala Asp Gly Leu Leu Glu Lys Gly Val Tyr
    530                 535                 540

Val Lys Asn Ile Arg Pro Ala Gly Pro Gly Asp Leu Gly Gly Leu Lys
545                 550                 555                 560

Pro Tyr Asp Arg Leu Leu Gln Val Asn His Val Arg Thr Arg Asp Phe
                565                 570                 575

Asp Cys Cys Leu Val Val Pro Leu Ile Ala Glu Ser Gly Asn Lys Leu
            580                 585                 590

Asp Leu Val Ile Ser Arg Asn
        595

(2) INFORMATION FOR SEQ ID NO:29:

(i) SEQUENCE CHARACTERISTICS:
        (A) LENGTH: 182 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:29:

His Val Lys Leu Pro Lys Lys His Ser Val Glu Leu Gly Ile Thr Ile
1               5                   10                  15

Ser Ser Pro Ser Ser Arg Lys Pro Gly Asp Pro Leu Val Ile Ser Asp
            20                  25                  30

Ile Lys Lys Gly Ser Val Ala His Arg Thr Gly Thr Leu Glu Leu Gly
        35                  40                  45

Asp Lys Leu Leu Ala Ile Asp Asn Ile Arg Leu Asp Ser Cys Ser Met
    50                  55                  60

Glu Asp Ala Val Gln Ile Leu Gln Gln Cys Glu Asp Leu Val Lys Leu
65                  70                  75                  80

Lys Ile Arg Lys Asp Glu Asp Asn Ser Asp Glu Gln Glu Ser Ser Gly
                85                  90                  95

Ala Ile Ile Tyr Thr Val Glu Leu Lys Arg Tyr Gly Gly Pro Leu Gly
            100                 105                 110

Ile Thr Ile Ser Gly Thr Glu Glu Pro Phe Asp Pro Ile Ile Ile Ser
```

```
                    115                 120                 125
Ser Leu Thr Lys Gly Gly Leu Ala Glu Arg Thr Gly Ala Ile His Ile
    130                 135                 140

Gly Asp Arg Ile Leu Ala Ile Asn Ser Ser Leu Lys Gly Lys Pro
145                 150                 155                 160

Leu Ser Glu Asp Ile His Leu Leu Gln Met Ala Gly Glu Thr Val Thr
                165                 170                 175

Leu Lys Ile Lys Lys Gln
                180

(2) INFORMATION FOR SEQ ID NO:30:

(i) SEQUENCE CHARACTERISTICS:
        (A) LENGTH: 498 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:30:

His Val Lys Leu Pro Lys Lys His Ser Val Glu Leu Gly Ile Thr Ile
1               5                   10                  15

Ser Ser Pro Ser Ser Arg Lys Pro Gly Asp Pro Leu Val Ile Ser Asp
                20                  25                  30

Ile Lys Lys Gly Ser Val Ala His Arg Thr Gly Thr Leu Glu Leu Gly
            35                  40                  45

Asp Lys Leu Leu Ala Ile Asp Asn Ile Arg Leu Asp Ser Cys Ser Met
        50                  55                  60

Glu Asp Ala Val Gln Ile Leu Gln Gln Cys Glu Asp Leu Val Lys Leu
65                  70                  75                  80

Lys Ile Arg Lys Asp Glu Asp Asn Ser Asp Glu Gln Glu Ser Ser Gly
                85                  90                  95

Ala Ile Ile Tyr Thr Val Glu Leu Lys Arg Tyr Gly Gly Pro Leu Gly
            100                 105                 110

Ile Thr Ile Ser Gly Thr Glu Glu Pro Phe Asp Pro Ile Ile Ile Ser
        115                 120                 125

Ser Leu Thr Lys Gly Gly Leu Ala Glu Arg Thr Gly Ala Ile His Ile
    130                 135                 140

Gly Asp Arg Ile Leu Ala Ile Asn Ser Ser Leu Lys Gly Lys Pro
145                 150                 155                 160

Leu Ser Glu Asp Ile His Leu Leu Gln Met Ala Gly Glu Thr Val Thr
                165                 170                 175

Leu Lys Ile Lys Lys Gln Thr Asp Ala Gln Pro Ala Ser Ser Pro Lys
                180                 185                 190

Lys Leu Pro Ile Pro Ser His Ser Ser Asp Leu Gly Asp Gly Glu Glu
                195                 200                 205

Asp Pro Ser Pro Ile Gln Arg Pro Gly Lys Leu Ser Asp Val Tyr Pro
            210                 215                 220

Ser Thr Val Pro Ser Val Asp Ser Ala Val Asp Ser Trp Asp Gly Ser
225                 230                 235                 240

Gly Ile Asp Ala Arg Tyr Gly Ser Gln Gly Thr Thr Phe Gln Thr Ser
                245                 250                 255

Gly Tyr Asn Phe Asn Thr Tyr Asp Trp Arg Ser Pro Lys Lys Arg Ala
                260                 265                 270

Ser Leu Ser Pro Val Pro Lys Pro Arg Ser Gln Thr Tyr Pro Asp Val
    275                 280                 285
```

```
Gly Leu Ser Asn Glu Asp Trp Asp Arg Ser Thr Ala Ser Gly Phe Ala
            290                 295                 300

Gly Ala Ser Asp Ser Ala Asp Ala Glu Gln Glu Asn Phe Trp Ser
305                 310                 315                 320

Gln Ala Leu Glu Asp Leu Glu Thr Cys Gly Gln Ser Gly Ile Leu Arg
                325                 330                 335

Glu Leu Glu Ala Thr Ile Met Ser Gly Ser Thr Met Ser Leu Asn His
                340                 345                 350

Glu Ala Pro Thr Ala Arg Ser Gln Leu Gly Arg Gln Ala Ser Phe Gln
                355                 360                 365

Glu Arg Ser Asn Ser Arg Pro His Tyr Ser Gln Thr Thr Arg Ser Asn
370                 375                 380

Thr Leu Pro Ser Asp Val Gly Arg Lys Ser Val Thr Leu Arg Lys Met
385                 390                 395                 400

Lys Gln Glu Ile Lys Glu Ile Met Ser Pro Thr Pro Val Glu Leu His
                405                 410                 415

Lys Val Thr Leu Tyr Lys Asp Ser Gly Met Glu Asp Phe Gly Phe Ser
                420                 425                 430

Val Ala Asp Gly Leu Leu Glu Lys Gly Val Tyr Val Lys Asn Ile Arg
                435                 440                 445

Pro Ala Gly Pro Gly Asp Leu Gly Gly Leu Lys Pro Tyr Asp Arg Leu
450                 455                 460

Leu Gln Val Asn His Val Arg Thr Arg Asp Phe Asp Cys Cys Leu Val
465                 470                 475                 480

Val Pro Leu Ile Ala Glu Ser Gly Asn Lys Leu Asp Leu Val Ile Ser
                485                 490                 495

Arg Asn (2) INFORMATION FOR SEQ ID NO:31:

(i) SEQUENCE CHARACTERISTICS:
        (A) LENGTH: 398 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:31:

Thr Val Glu Leu Lys Arg Tyr Gly Gly Pro Leu Gly Ile Thr Ile Ser
1               5                   10                  15

Gly Thr Glu Glu Pro Phe Asp Pro Ile Ile Ile Ser Ser Leu Thr Lys
                20                  25                  30

Gly Gly Leu Ala Glu Arg Thr Gly Ala Ile His Ile Gly Asp Arg Ile
            35                  40                  45

Leu Ala Ile Asn Ser Ser Ser Leu Lys Gly Lys Pro Leu Ser Glu Asp
        50                  55                  60

Ile His Leu Leu Gln Met Ala Gly Glu Thr Val Thr Leu Lys Ile Lys
65                  70                  75                  80

Lys Gln Thr Asp Ala Gln Pro Ala Ser Ser Pro Lys Lys Leu Pro Ile
                85                  90                  95

Pro Ser His Ser Ser Asp Leu Gly Asp Gly Glu Asp Pro Ser Pro
                100                 105                 110

Ile Gln Arg Pro Gly Lys Leu Ser Asp Val Tyr Pro Ser Thr Val Pro
                115                 120                 125

Ser Val Asp Ser Ala Val Asp Ser Trp Asp Gly Ser Gly Ile Asp Ala
```

```
                130             135             140
Arg Tyr Gly Ser Gln Gly Thr Thr Phe Gln Thr Ser Gly Tyr Asn Phe
145                 150                 155                 160

Asn Thr Tyr Asp Trp Arg Ser Pro Lys Lys Arg Ala Ser Leu Ser Pro
                165                 170                 175

Val Pro Lys Pro Arg Ser Gln Thr Tyr Pro Asp Val Gly Leu Ser Asn
                180                 185                 190

Glu Asp Trp Asp Arg Ser Thr Ala Ser Gly Phe Ala Gly Ala Ser Asp
                195                 200                 205

Ser Ala Asp Ala Glu Gln Glu Glu Asn Phe Trp Ser Gln Ala Leu Glu
210                 215                 220

Asp Leu Glu Thr Cys Gly Gln Ser Gly Ile Leu Arg Glu Leu Glu Ala
225                 230                 235                 240

Thr Ile Met Ser Gly Ser Thr Met Ser Leu Asn His Glu Ala Pro Thr
                245                 250                 255

Ala Arg Ser Gln Leu Gly Arg Gln Ala Ser Phe Gln Glu Arg Ser Asn
                260                 265                 270

Ser Arg Pro His Tyr Ser Gln Thr Thr Arg Ser Asn Thr Leu Pro Ser
                275                 280                 285

Asp Val Gly Arg Lys Ser Val Thr Leu Arg Lys Met Lys Gln Glu Ile
290                 295                 300

Lys Glu Ile Met Ser Pro Thr Pro Val Glu Leu His Lys Val Thr Leu
305                 310                 315                 320

Tyr Lys Asp Ser Gly Met Glu Asp Phe Gly Phe Ser Val Ala Asp Gly
                325                 330                 335

Leu Leu Glu Lys Gly Val Tyr Val Lys Asn Ile Arg Pro Ala Gly Pro
                340                 345                 350

Gly Asp Leu Gly Gly Leu Lys Pro Tyr Asp Arg Leu Leu Gln Val Asn
                355                 360                 365

His Val Arg Thr Arg Asp Phe Asp Cys Cys Leu Val Val Pro Leu Ile
                370                 375                 380

Ala Glu Ser Gly Asn Lys Leu Asp Leu Val Ile Ser Arg Asn
385                 390                 395

(2) INFORMATION FOR SEQ ID NO:32:

(i) SEQUENCE CHARACTERISTICS:
        (A) LENGTH: 1061 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:32:

Thr Val Val Glu Leu Met Lys Lys Glu Gly Thr Thr Leu Gly Cys Thr
1               5                   10                  15

Val Ser Gly Gly Ile Asp Lys Asp Gly Lys Pro Arg Val Ser Asn Leu
                20                  25                  30

Arg Gln Gly Gly Ile Ala Ala Arg Ser Asp Gln Leu Asp Val Gly Asp
                35                  40                  45

Tyr Ile Lys Ala Val Asn Gly Ile Asn Leu Ala Lys Phe Arg His Asp
                50                  55                  60

Glu Ile Ile Ser Leu Leu Lys Asn Val Gly Glu Arg Val Val Leu Glu
65                  70                  75                  80

Val Glu Tyr Glu Leu Pro Pro Val Ser Ile Gln Gly Ser Ser Val Met
                85                  90                  95
```

-continued

```
Phe Arg Thr Val Glu Val Thr Leu His Lys Glu Gly Asn Thr Phe Gly
            100                 105                 110
Phe Val Ile Arg Gly Gly Ala His Asp Asp Arg Asn Lys Ser Arg Pro
            115                 120                 125
Val Val Ile Thr Cys Val Arg Pro Gly Gly Pro Asp Asp Arg Glu Gly
            130                 135                 140
Thr Ile Lys Pro Gly Asp Arg Leu Leu Ser Val Asp Gly Ile Arg Leu
145                 150                 155                 160
Leu Gly Thr Thr His Ala Glu Ala Met Ser Ile Leu Lys Gln Cys Gly
            165                 170                 175
Gln Glu Ala Thr Leu Leu Ile Glu Tyr Asp Val Ser Ala Met Asp Ser
            180                 185                 190
Val Ala Thr Ala Ser Gly Pro Leu Leu Val Glu Val Ala Lys Thr Pro
            195                 200                 205
Gly Ala Ser Leu Gly Val Ala Leu Thr Thr Ser Val Cys Cys Asn Lys
            210                 215                 220
Gln Val Ile Val Ile Asp Lys Ile Lys Ser Ala Ser Ile Ala Asp Arg
225                 230                 235                 240
Cys Gly Ala Leu His Val Gly Asp His Ile Leu Ser Ile Asp Gly Thr
            245                 250                 255
Ser Met Glu Tyr Cys Thr Leu Ala Glu Ala Thr Gln Phe Leu Gly Asn
            260                 265                 270
Thr Thr Asp Gln Val Lys Leu Glu Ile Leu Pro His His Gln Thr Arg
            275                 280                 285
Leu Ala Leu Lys Gly Pro Asp His Val Lys Ile Gln Arg Ser Asp Arg
            290                 295                 300
Gln Leu Pro Trp Asp Pro Trp Ala Ser Ser Gln Cys Ser Val His Thr
305                 310                 315                 320
Asn His His His Asn Pro His Pro Asp His Cys Arg Val Pro Ala
            325                 330                 335
Leu Gly Phe Pro Lys Ala Leu Thr Pro Asn Ser Pro Pro Ala Met Val
            340                 345                 350
Ser Ser Ser Ser Pro Thr Ser Met Ser Ala Tyr Ser Leu Ser Ser Leu
            355                 360                 365
Asn Met Gly Thr Leu Pro Arg Ser Leu Tyr Ser Thr Ser Pro Arg Gly
            370                 375                 380
Thr Met Met Arg Arg Leu Lys Lys Lys Asp Phe Lys Ser Ser Leu
385                 390                 395                 400
Ser Leu Ala Ser Ser Thr Val Gly Leu Ala Gly Gln Val Val His Thr
            405                 410                 415
Glu Thr Thr Glu Val Val Leu Thr Ala Asp Pro Val Thr Gly Phe Gly
            420                 425                 430
Ile Gln Leu Gln Gly Ser Val Phe Ala Thr Glu Thr Leu Ser Ser Pro
            435                 440                 445
Pro Leu Ile Ser Tyr Ile Glu Ala Asp Ser Pro Ala Glu Arg Cys Gly
            450                 455                 460
Val Leu Gln Ile Gly Asp Arg Val Met Ala Ile Asn Gly Ile Pro Thr
465                 470                 475                 480
Glu Asp Ser Thr Phe Glu Glu Ala Asn Gln Leu Leu Arg Asp Ser Ser
            485                 490                 495
Ile Thr Ser Lys Val Thr Leu Glu Ile Glu Phe Asp Val Ala Glu Ser
            500                 505                 510
Val Ile Pro Ser Ser Gly Thr Phe His Val Lys Leu Pro Lys Lys His
```

-continued

```
            515                 520                 525
Ser Val Glu Leu Gly Ile Thr Ile Ser Ser Pro Ser Arg Lys Pro
        530                 535                 540
Gly Asp Pro Leu Val Ile Ser Asp Ile Lys Lys Gly Ser Val Ala His
545                 550                 555                 560
Arg Thr Gly Thr Leu Glu Leu Gly Asp Lys Leu Leu Ala Ile Asp Asn
                565                 570                 575
Ile Arg Leu Asp Ser Cys Ser Met Glu Asp Ala Val Gln Ile Leu Gln
                580                 585                 590
Gln Cys Glu Asp Leu Val Lys Leu Lys Ile Arg Lys Asp Glu Asp Asn
        595                 600                 605
Ser Asp Glu Gln Glu Ser Ser Gly Ala Ile Ile Tyr Thr Val Glu Leu
        610                 615                 620
Lys Arg Tyr Gly Gly Pro Leu Gly Ile Thr Ile Ser Gly Thr Glu Glu
625                 630                 635                 640
Pro Phe Asp Pro Ile Ile Ile Ser Ser Leu Thr Lys Gly Gly Leu Ala
                645                 650                 655
Glu Arg Thr Gly Ala Ile His Ile Gly Asp Arg Ile Leu Ala Ile Asn
                660                 665                 670
Ser Ser Ser Leu Lys Gly Lys Pro Leu Ser Glu Asp Ile His Leu Leu
        675                 680                 685
Gln Met Ala Gly Glu Thr Val Thr Leu Lys Ile Lys Lys Gln Thr Asp
690                 695                 700
Ala Gln Pro Ala Ser Ser Pro Lys Lys Leu Pro Ile Pro Ser His Ser
705                 710                 715                 720
Ser Asp Leu Gly Asp Gly Glu Glu Asp Pro Ser Pro Ile Gln Arg Pro
                725                 730                 735
Gly Lys Leu Ser Asp Val Tyr Pro Ser Thr Val Pro Ser Val Asp Ser
                740                 745                 750
Ala Val Asp Ser Trp Asp Gly Ser Gly Ile Asp Ala Arg Tyr Gly Ser
                755                 760                 765
Gln Gly Thr Thr Phe Gln Thr Ser Gly Tyr Asn Phe Asn Thr Tyr Asp
        770                 775                 780
Trp Arg Ser Pro Lys Lys Arg Ala Ser Leu Ser Pro Val Pro Lys Pro
785                 790                 795                 800
Arg Ser Gln Thr Tyr Pro Asp Val Gly Leu Ser Asn Glu Asp Trp Asp
                805                 810                 815
Arg Ser Thr Ala Ser Gly Phe Ala Gly Ser Asp Ser Ala Asp Ala
                820                 825                 830
Glu Gln Glu Glu Asn Phe Trp Ser Gln Ala Leu Glu Asp Leu Glu Thr
        835                 840                 845
Cys Gly Gln Ser Gly Ile Leu Arg Glu Leu Glu Ala Thr Ile Met Ser
850                 855                 860
Gly Ser Thr Met Ser Leu Asn His Glu Ala Pro Thr Ala Arg Ser Gln
865                 870                 875                 880
Leu Gly Arg Gln Ala Ser Phe Gln Glu Arg Ser Asn Ser Arg Pro His
                885                 890                 895
Tyr Ser Gln Thr Thr Arg Ser Asn Thr Leu Pro Ser Asp Val Gly Arg
                900                 905                 910
Lys Ser Val Thr Leu Arg Lys Met Lys Gln Glu Ile Lys Glu Ile Met
        915                 920                 925
Ser Pro Thr Pro Val Glu Leu His Lys Val Thr Leu Tyr Lys Asp Ser
        930                 935                 940
```

```
Gly Met Glu Asp Phe Gly Phe Ser Val Ala Asp Gly Leu Leu Glu Lys
945                 950                 955                 960

Gly Val Tyr Val Lys Asn Ile Arg Pro Ala Gly Pro Gly Asp Leu Gly
            965                 970                 975

Gly Leu Lys Pro Tyr Asp Arg Leu Leu Gln Val Asn His Val Arg Thr
            980                 985                 990

Arg Asp Phe Asp Cys Cys Leu Val Val Pro Leu Ile Ala Glu Ser Gly
            995                 1000                1005

Asn Lys Leu Asp Leu Val Ile Ser Arg Asn Pro Leu Ala Ser Gln Lys
            1010                1015                1020

Ser Ile Glu Gln Pro Ala Leu Pro Ser Asp Trp Ser Glu Gln Asn Ser
1025                1030                1035                1040

Ala Phe Phe Gln Gln Pro Ser His Gly Gly Asn Leu Glu Thr Arg Glu
                1045                1050                1055

Pro Thr Asn Thr Leu
                1060

(2) INFORMATION FOR SEQ ID NO:33:

(i) SEQUENCE CHARACTERISTICS:
        (A) LENGTH: 961 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:33:

Glu Val Thr Leu His Lys Glu Gly Asn Thr Phe Gly Phe Val Ile Arg
1               5                   10                  15

Gly Gly Ala His Asp Asp Arg Asn Lys Ser Arg Pro Val Val Ile Thr
            20                  25                  30

Cys Val Arg Pro Gly Gly Pro Asp Asp Arg Glu Gly Thr Ile Lys Pro
            35                  40                  45

Gly Asp Arg Leu Leu Ser Val Asp Gly Ile Arg Leu Leu Gly Thr Thr
50                  55                  60

His Ala Glu Ala Met Ser Ile Leu Lys Gln Cys Gly Gln Glu Ala Thr
65                  70                  75                  80

Leu Leu Ile Glu Tyr Asp Val Ser Ala Met Asp Ser Val Ala Thr Ala
                85                  90                  95

Ser Gly Pro Leu Leu Val Glu Val Ala Lys Thr Pro Gly Ala Ser Leu
            100                 105                 110

Gly Val Ala Leu Thr Thr Ser Val Cys Cys Asn Lys Gln Val Ile Val
            115                 120                 125

Ile Asp Lys Ile Lys Ser Ala Ser Ile Ala Asp Arg Cys Gly Ala Leu
130                 135                 140

His Val Gly Asp His Ile Leu Ser Ile Asp Gly Thr Ser Met Glu Tyr
145                 150                 155                 160

Cys Thr Leu Ala Glu Ala Thr Gln Phe Leu Gly Asn Thr Thr Asp Gln
            165                 170                 175

Val Lys Leu Glu Ile Leu Pro His His Gln Thr Arg Leu Ala Leu Lys
            180                 185                 190

Gly Pro Asp His Val Lys Ile Gln Arg Ser Asp Arg Gln Leu Pro Trp
            195                 200                 205

Asp Pro Trp Ala Ser Ser Gln Cys Ser Val His Thr Asn His His His
            210                 215                 220

Asn Pro His His Pro Asp His Cys Arg Val Pro Ala Leu Gly Phe Pro
```

```
            225                 230                 235                 240
Lys Ala Leu Thr Pro Asn Ser Pro Ala Met Val Ser Ser Ser
                245                 250                 255

Pro Thr Ser Met Ser Ala Tyr Ser Leu Ser Ser Leu Asn Met Gly Thr
                260                 265                 270

Leu Pro Arg Ser Leu Tyr Ser Thr Ser Pro Arg Gly Thr Met Met Arg
                275                 280                 285

Arg Arg Leu Lys Lys Asp Phe Lys Ser Ser Leu Ser Leu Ala Ser
                290                 295                 300

Ser Thr Val Gly Leu Ala Gly Gln Val Val His Thr Glu Thr Thr Glu
305                 310                 315                 320

Val Val Leu Thr Ala Asp Pro Val Thr Gly Phe Gly Ile Gln Leu Gln
                325                 330                 335

Gly Ser Val Phe Ala Thr Glu Thr Leu Ser Ser Pro Pro Leu Ile Ser
                340                 345                 350

Tyr Ile Glu Ala Asp Ser Pro Ala Glu Arg Cys Gly Val Leu Gln Ile
                355                 360                 365

Gly Asp Arg Val Met Ala Ile Asn Gly Ile Pro Thr Glu Asp Ser Thr
370                 375                 380

Phe Glu Glu Ala Asn Gln Leu Leu Arg Asp Ser Ser Ile Thr Ser Lys
385                 390                 395                 400

Val Thr Leu Glu Ile Glu Phe Asp Val Ala Glu Ser Val Ile Pro Ser
                405                 410                 415

Ser Gly Thr Phe His Val Lys Leu Pro Lys Lys His Ser Val Glu Leu
                420                 425                 430

Gly Ile Thr Ile Ser Ser Pro Ser Ser Arg Lys Pro Gly Asp Pro Leu
                435                 440                 445

Val Ile Ser Asp Ile Lys Lys Gly Ser Val Ala His Arg Thr Gly Thr
450                 455                 460

Leu Glu Leu Gly Asp Lys Leu Leu Ala Ile Asp Asn Ile Arg Leu Asp
465                 470                 475                 480

Ser Cys Ser Met Glu Asp Ala Val Gln Ile Leu Gln Gln Cys Glu Asp
                485                 490                 495

Leu Val Lys Leu Lys Ile Arg Lys Asp Glu Asp Asn Ser Asp Glu Gln
                500                 505                 510

Glu Ser Ser Gly Ala Ile Ile Tyr Thr Val Glu Leu Lys Arg Tyr Gly
                515                 520                 525

Gly Pro Leu Gly Ile Thr Ile Ser Gly Thr Glu Glu Pro Phe Asp Pro
                530                 535                 540

Ile Ile Ile Ser Ser Leu Thr Lys Gly Gly Leu Ala Glu Arg Thr Gly
545                 550                 555                 560

Ala Ile His Ile Gly Asp Arg Ile Leu Ala Ile Asn Ser Ser Ser Leu
                565                 570                 575

Lys Gly Lys Pro Leu Ser Glu Asp Ile His Leu Leu Gln Met Ala Gly
                580                 585                 590

Glu Thr Val Thr Leu Lys Ile Lys Lys Gln Thr Asp Ala Gln Pro Ala
                595                 600                 605

Ser Ser Pro Lys Lys Leu Pro Ile Pro Ser His Ser Ser Asp Leu Gly
                610                 615                 620

Asp Gly Glu Glu Asp Pro Ser Pro Ile Gln Arg Pro Gly Lys Leu Ser
625                 630                 635                 640

Asp Val Tyr Pro Ser Thr Val Pro Ser Val Asp Ser Ala Val Asp Ser
                645                 650                 655
```

-continued

```
Trp Asp Gly Ser Gly Ile Asp Ala Arg Tyr Gly Ser Gln Gly Thr Thr
            660                 665                 670

Phe Gln Thr Ser Gly Tyr Asn Phe Asn Thr Tyr Asp Trp Arg Ser Pro
        675                 680                 685

Lys Lys Arg Ala Ser Leu Ser Pro Val Pro Lys Pro Arg Ser Gln Thr
690                 695                 700

Tyr Pro Asp Val Gly Leu Ser Asn Glu Asp Trp Asp Arg Ser Thr Ala
705                 710                 715                 720

Ser Gly Phe Ala Gly Ala Ser Asp Ser Ala Asp Ala Glu Gln Glu Glu
                725                 730                 735

Asn Phe Trp Ser Gln Ala Leu Glu Asp Leu Glu Thr Cys Gly Gln Ser
            740                 745                 750

Gly Ile Leu Arg Glu Leu Glu Ala Thr Ile Met Ser Gly Ser Thr Met
        755                 760                 765

Ser Leu Asn His Glu Ala Pro Thr Ala Arg Ser Gln Leu Gly Arg Gln
770                 775                 780

Ala Ser Phe Gln Glu Arg Ser Asn Ser Arg Pro His Tyr Ser Gln Thr
785                 790                 795                 800

Thr Arg Ser Asn Thr Leu Pro Ser Asp Val Gly Arg Lys Ser Val Thr
                805                 810                 815

Leu Arg Lys Met Lys Gln Glu Ile Lys Glu Ile Met Ser Pro Thr Pro
            820                 825                 830

Val Glu Leu His Lys Val Thr Leu Tyr Lys Asp Ser Gly Met Glu Asp
        835                 840                 845

Phe Gly Phe Ser Val Ala Asp Gly Leu Leu Glu Lys Gly Val Tyr Val
850                 855                 860

Lys Asn Ile Arg Pro Ala Gly Pro Gly Asp Leu Gly Gly Leu Lys Pro
865                 870                 875                 880

Tyr Asp Arg Leu Leu Gln Val Asn His Val Arg Thr Arg Asp Phe Asp
                885                 890                 895

Cys Cys Leu Val Val Pro Leu Ile Ala Glu Ser Gly Asn Lys Leu Asp
            900                 905                 910

Leu Val Ile Ser Arg Asn Pro Leu Ala Ser Gln Lys Ser Ile Glu Gln
        915                 920                 925

Pro Ala Leu Pro Ser Asp Trp Ser Glu Gln Asn Ser Ala Phe Phe Gln
930                 935                 940

Gln Pro Ser His Gly Gly Asn Leu Glu Thr Arg Glu Pro Thr Asn Thr
945                 950                 955                 960

Leu
```

(2) INFORMATION FOR SEQ ID NO:34:

(i) SEQUENCE CHARACTERISTICS:
        (A) LENGTH: 861 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:34:

```
Leu Val Glu Val Ala Lys Thr Pro Gly Ala Ser Leu Gly Val Ala Leu
1               5                   10                  15

Thr Thr Ser Val Cys Cys Asn Lys Gln Val Ile Val Ile Asp Lys Ile
                20                  25                  30

Lys Ser Ala Ser Ile Ala Asp Arg Cys Gly Ala Leu His Val Gly Asp
            35                  40                  45
```

```
His Ile Leu Ser Ile Asp Gly Thr Ser Met Glu Tyr Cys Thr Leu Ala
         50                  55                  60
Glu Ala Thr Gln Phe Leu Gly Asn Thr Thr Asp Gln Val Lys Leu Glu
 65                  70                  75                  80
Ile Leu Pro His His Gln Thr Arg Leu Ala Leu Lys Gly Pro Asp His
                 85                  90                  95
Val Lys Ile Gln Arg Ser Asp Arg Gln Leu Pro Trp Asp Pro Trp Ala
            100                 105                 110
Ser Ser Gln Cys Ser Val His Thr Asn His His Asn Pro His His
            115                 120                 125
Pro Asp His Cys Arg Val Pro Ala Leu Gly Phe Pro Lys Ala Leu Thr
        130                 135                 140
Pro Asn Ser Pro Pro Ala Met Val Ser Ser Ser Pro Thr Ser Met
145                 150                 155                 160
Ser Ala Tyr Ser Leu Ser Ser Leu Asn Met Gly Thr Leu Pro Arg Ser
                165                 170                 175
Leu Tyr Ser Thr Ser Pro Arg Gly Thr Met Met Arg Arg Leu Lys
            180                 185                 190
Lys Lys Asp Phe Lys Ser Ser Leu Ser Leu Ala Ser Ser Thr Val Gly
        195                 200                 205
Leu Ala Gly Gln Val Val His Thr Glu Thr Thr Glu Val Val Leu Thr
        210                 215                 220
Ala Asp Pro Val Thr Gly Phe Gly Ile Gln Leu Gln Gly Ser Val Phe
225                 230                 235                 240
Ala Thr Glu Thr Leu Ser Ser Pro Pro Leu Ile Ser Tyr Ile Glu Ala
                245                 250                 255
Asp Ser Pro Ala Glu Arg Cys Gly Val Leu Gln Ile Gly Asp Arg Val
            260                 265                 270
Met Ala Ile Asn Gly Ile Pro Thr Glu Asp Ser Thr Phe Glu Glu Ala
        275                 280                 285
Asn Gln Leu Leu Arg Asp Ser Ser Ile Thr Ser Lys Val Thr Leu Glu
290                 295                 300
Ile Glu Phe Asp Val Ala Glu Ser Val Ile Pro Ser Ser Gly Thr Phe
305                 310                 315                 320
His Val Lys Leu Pro Lys Lys His Ser Val Glu Leu Gly Ile Thr Ile
                325                 330                 335
Ser Ser Pro Ser Ser Arg Lys Pro Gly Asp Pro Leu Val Ile Ser Asp
            340                 345                 350
Ile Lys Lys Gly Ser Val Ala His Arg Thr Gly Thr Leu Glu Leu Gly
        355                 360                 365
Asp Lys Leu Leu Ala Ile Asp Asn Ile Arg Leu Asp Ser Cys Ser Met
        370                 375                 380
Glu Asp Ala Val Gln Ile Leu Gln Gln Cys Glu Asp Leu Val Lys Leu
385                 390                 395                 400
Lys Ile Arg Lys Asp Glu Asp Asn Ser Asp Glu Gln Glu Ser Ser Gly
                405                 410                 415
Ala Ile Ile Tyr Thr Val Glu Leu Lys Arg Tyr Gly Gly Pro Leu Gly
            420                 425                 430
Ile Thr Ile Ser Gly Thr Glu Glu Pro Phe Asp Pro Ile Ile Ile Ser
        435                 440                 445
Ser Leu Thr Lys Gly Gly Leu Ala Glu Arg Thr Gly Ala Ile His Ile
450                 455                 460
Gly Asp Arg Ile Leu Ala Ile Asn Ser Ser Ser Leu Lys Gly Lys Pro
```

-continued

```
              465                 470                 475                 480
Leu Ser Glu Asp Ile His Leu Leu Gln Met Ala Gly Glu Thr Val Thr
                    485                 490                 495
Leu Lys Ile Lys Lys Gln Thr Asp Ala Gln Pro Ala Ser Ser Pro Lys
                500                 505                 510
Lys Leu Pro Ile Pro Ser His Ser Ser Asp Leu Gly Asp Gly Glu Glu
                515                 520                 525
Asp Pro Ser Pro Ile Gln Arg Pro Gly Lys Leu Ser Asp Val Tyr Pro
                530                 535                 540
Ser Thr Val Pro Ser Val Asp Ser Ala Val Asp Ser Trp Asp Gly Ser
545                 550                 555                 560
Gly Ile Asp Ala Arg Tyr Gly Ser Gln Gly Thr Thr Phe Gln Thr Ser
                565                 570                 575
Gly Tyr Asn Phe Asn Thr Tyr Asp Trp Arg Ser Pro Lys Lys Arg Ala
                580                 585                 590
Ser Leu Ser Pro Val Pro Lys Pro Arg Ser Gln Thr Tyr Pro Asp Val
                595                 600                 605
Gly Leu Ser Asn Glu Asp Trp Asp Arg Ser Thr Ala Ser Gly Phe Ala
                610                 615                 620
Gly Ala Ser Asp Ser Ala Asp Ala Glu Gln Glu Glu Asn Phe Trp Ser
625                 630                 635                 640
Gln Ala Leu Glu Asp Leu Glu Thr Cys Gly Gln Ser Gly Ile Leu Arg
                645                 650                 655
Glu Leu Glu Ala Thr Ile Met Ser Gly Ser Thr Met Ser Leu Asn His
                660                 665                 670
Glu Ala Pro Thr Ala Arg Ser Gln Leu Gly Arg Gln Ala Ser Phe Gln
                675                 680                 685
Glu Arg Ser Asn Ser Arg Pro His Tyr Ser Gln Thr Thr Arg Ser Asn
                690                 695                 700
Thr Leu Pro Ser Asp Val Gly Arg Lys Ser Val Thr Leu Arg Lys Met
705                 710                 715                 720
Lys Gln Glu Ile Lys Glu Ile Met Ser Pro Thr Pro Val Glu Leu His
                725                 730                 735
Lys Val Thr Leu Tyr Lys Asp Ser Gly Met Glu Asp Phe Gly Phe Ser
                740                 745                 750
Val Ala Asp Gly Leu Leu Glu Lys Gly Val Tyr Val Lys Asn Ile Arg
                755                 760                 765
Pro Ala Gly Pro Gly Asp Leu Gly Gly Leu Lys Pro Tyr Asp Arg Leu
                770                 775                 780
Leu Gln Val Asn His Val Arg Thr Arg Asp Phe Asp Cys Cys Leu Val
785                 790                 795                 800
Val Pro Leu Ile Ala Glu Ser Gly Asn Lys Leu Asp Leu Val Ile Ser
                    805                 810                 815
Arg Asn Pro Leu Ala Ser Gln Lys Ser Ile Glu Gln Pro Ala Leu Pro
                820                 825                 830
Ser Asp Trp Ser Glu Gln Asn Ser Ala Phe Phe Gln Gln Pro Ser His
                835                 840                 845
Gly Gly Asn Leu Glu Thr Arg Glu Pro Thr Asn Thr Leu
850                 855                 860
```

(2) INFORMATION FOR SEQ ID NO:35:

(i) SEQUENCE CHARACTERISTICS:
        (A) LENGTH: 642 amino acids
        (B) TYPE: amino acid (C) STRANDEDNESS:
(D) TOPOLOGY: linear (ii) MOLECULE TYPE: protein (xi) SEQUENCE DESCRIPTION: SEQ ID NO:35:

```
Glu Val Val Leu Thr Ala Asp Pro Val Thr Gly Phe Gly Ile Gln Leu
 1               5                  10                  15

Gln Gly Ser Val Phe Ala Thr Glu Thr Leu Ser Ser Pro Pro Leu Ile
            20                  25                  30

Ser Tyr Ile Glu Ala Asp Ser Pro Ala Glu Arg Cys Gly Val Leu Gln
        35                  40                  45

Ile Gly Asp Arg Val Met Ala Ile Asn Gly Ile Pro Thr Glu Asp Ser
    50                  55                  60

Thr Phe Glu Glu Ala Asn Gln Leu Leu Arg Asp Ser Ser Ile Thr Ser
65                  70                  75                  80

Lys Val Thr Leu Glu Ile Glu Phe Asp Val Ala Glu Ser Val Ile Pro
                85                  90                  95

Ser Ser Gly Thr Phe His Val Lys Leu Pro Lys Lys His Ser Val Glu
            100                 105                 110

Leu Gly Ile Thr Ile Ser Ser Pro Ser Ser Arg Lys Pro Gly Asp Pro
        115                 120                 125

Leu Val Ile Ser Asp Ile Lys Lys Gly Ser Val Ala His Arg Thr Gly
    130                 135                 140

Thr Leu Glu Leu Gly Asp Lys Leu Leu Ala Ile Asp Asn Ile Arg Leu
145                 150                 155                 160

Asp Ser Cys Ser Met Glu Asp Ala Val Gln Ile Leu Gln Gln Cys Glu
                165                 170                 175

Asp Leu Val Lys Leu Lys Ile Arg Lys Asp Glu Asp Asn Ser Asp Glu
            180                 185                 190

Gln Glu Ser Ser Gly Ala Ile Ile Tyr Thr Val Glu Leu Lys Arg Tyr
        195                 200                 205

Gly Gly Pro Leu Gly Ile Thr Ile Ser Gly Thr Glu Glu Pro Phe Asp
    210                 215                 220

Pro Ile Ile Ile Ser Ser Leu Thr Lys Gly Gly Leu Ala Glu Arg Thr
225                 230                 235                 240

Gly Ala Ile His Ile Gly Asp Arg Ile Leu Ala Ile Asn Ser Ser Ser
                245                 250                 255

Leu Lys Gly Lys Pro Leu Ser Glu Asp Ile His Leu Leu Gln Met Ala
            260                 265                 270

Gly Glu Thr Val Thr Leu Lys Ile Lys Lys Gln Thr Asp Ala Gln Pro
        275                 280                 285

Ala Ser Ser Pro Lys Lys Leu Pro Ile Pro Ser His Ser Ser Asp Leu
    290                 295                 300

Gly Asp Gly Glu Glu Asp Pro Ser Pro Ile Gln Arg Pro Gly Lys Leu
305                 310                 315                 320

Ser Asp Val Tyr Pro Ser Thr Val Pro Ser Val Asp Ser Ala Val Asp
                325                 330                 335

Ser Trp Asp Gly Ser Gly Ile Asp Ala Arg Tyr Gly Ser Gln Gly Thr
            340                 345                 350

Thr Phe Gln Thr Ser Gly Tyr Asn Phe Asn Thr Tyr Asp Trp Arg Ser
        355                 360                 365

Pro Lys Lys Arg Ala Ser Leu Ser Pro Val Pro Lys Pro Arg Ser Gln
    370                 375                 380

Thr Tyr Pro Asp Val Gly Leu Ser Asn Glu Asp Trp Asp Arg Ser Thr
```

```
385                 390                 395                 400
Ala Ser Gly Phe Ala Gly Ala Ser Asp Ser Ala Asp Ala Glu Gln Glu
                405                 410                 415
Glu Asn Phe Trp Ser Gln Ala Leu Glu Asp Leu Glu Thr Cys Gly Gln
                420                 425                 430
Ser Gly Ile Leu Arg Glu Leu Glu Ala Thr Ile Met Ser Gly Ser Thr
                435                 440                 445
Met Ser Leu Asn His Glu Ala Pro Thr Ala Arg Ser Gln Leu Gly Arg
            450                 455                 460
Gln Ala Ser Phe Gln Glu Arg Ser Asn Ser Arg Pro His Tyr Ser Gln
465                 470                 475                 480
Thr Thr Arg Ser Asn Thr Leu Pro Ser Asp Val Gly Arg Lys Ser Val
                485                 490                 495
Thr Leu Arg Lys Met Lys Gln Glu Ile Lys Glu Ile Met Ser Pro Thr
                500                 505                 510
Pro Val Glu Leu His Lys Val Thr Leu Tyr Lys Asp Ser Gly Met Glu
                515                 520                 525
Asp Phe Gly Phe Ser Val Ala Asp Gly Leu Leu Glu Lys Gly Val Tyr
            530                 535                 540
Val Lys Asn Ile Arg Pro Ala Gly Pro Gly Asp Leu Gly Gly Leu Lys
545                 550                 555                 560
Pro Tyr Asp Arg Leu Leu Gln Val Asn His Val Arg Thr Arg Asp Phe
                565                 570                 575
Asp Cys Cys Leu Val Val Pro Leu Ile Ala Glu Ser Gly Asn Lys Leu
                580                 585                 590
Asp Leu Val Ile Ser Arg Asn Pro Leu Ala Ser Gln Lys Ser Ile Glu
            595                 600                 605
Gln Pro Ala Leu Pro Ser Asp Trp Ser Glu Gln Asn Ser Ala Phe Phe
610                 615                 620
Gln Gln Pro Ser His Gly Gly Asn Leu Glu Thr Arg Glu Pro Thr Asn
625                 630                 635                 640
Thr Leu (2) INFORMATION FOR SEQ ID NO:36:

(i) SEQUENCE CHARACTERISTICS:
        (A) LENGTH: 541 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:36:

His Val Lys Leu Pro Lys Lys His Ser Val Glu Leu Gly Ile Thr Ile
1               5                   10                  15
Ser Ser Pro Ser Ser Arg Lys Pro Gly Asp Pro Leu Val Ile Ser Asp
                20                  25                  30
Ile Lys Lys Gly Ser Val Ala His Arg Thr Gly Thr Leu Glu Leu Gly
                35                  40                  45
Asp Lys Leu Leu Ala Ile Asp Asn Ile Arg Leu Asp Ser Cys Ser Met
            50                  55                  60
Glu Asp Ala Val Gln Ile Leu Gln Gln Cys Glu Asp Leu Val Lys Leu
65                  70                  75                  80
Lys Ile Arg Lys Asp Glu Asp Asn Ser Asp Glu Gln Glu Ser Ser Gly
                85                  90                  95
```

-continued

```
Ala Ile Ile Tyr Thr Val Glu Leu Lys Arg Tyr Gly Gly Pro Leu Gly
                100                 105                 110

Ile Thr Ile Ser Gly Thr Glu Glu Pro Phe Asp Pro Ile Ile Ile Ser
            115                 120                 125

Ser Leu Thr Lys Gly Gly Leu Ala Glu Arg Thr Gly Ala Ile His Ile
        130                 135                 140

Gly Asp Arg Ile Leu Ala Ile Asn Ser Ser Leu Lys Gly Lys Pro
145                 150                 155                 160

Leu Ser Glu Asp Ile His Leu Leu Gln Met Ala Gly Glu Thr Val Thr
                165                 170                 175

Leu Lys Ile Lys Lys Gln Thr Asp Ala Gln Pro Ala Ser Ser Pro Lys
            180                 185                 190

Lys Leu Pro Ile Pro Ser His Ser Ser Asp Leu Gly Asp Gly Glu Glu
        195                 200                 205

Asp Pro Ser Pro Ile Gln Arg Pro Gly Lys Leu Ser Asp Val Tyr Pro
210                 215                 220

Ser Thr Val Pro Ser Val Asp Ser Ala Val Asp Ser Trp Asp Gly Ser
225                 230                 235                 240

Gly Ile Asp Ala Arg Tyr Gly Ser Gln Gly Thr Thr Phe Gln Thr Ser
                245                 250                 255

Gly Tyr Asn Phe Asn Thr Tyr Asp Trp Arg Ser Pro Lys Lys Arg Ala
            260                 265                 270

Ser Leu Ser Pro Val Pro Lys Pro Arg Ser Gln Thr Tyr Pro Asp Val
        275                 280                 285

Gly Leu Ser Asn Glu Asp Trp Asp Arg Ser Thr Ala Ser Gly Phe Ala
    290                 295                 300

Gly Ala Ser Asp Ser Ala Asp Ala Glu Gln Glu Asn Phe Trp Ser
305                 310                 315                 320

Gln Ala Leu Glu Asp Leu Glu Thr Cys Gly Gln Ser Gly Ile Leu Arg
                325                 330                 335

Glu Leu Glu Ala Thr Ile Met Ser Gly Ser Thr Met Ser Leu Asn His
            340                 345                 350

Glu Ala Pro Thr Ala Arg Ser Gln Leu Gly Arg Gln Ala Ser Phe Gln
        355                 360                 365

Glu Arg Ser Asn Ser Arg Pro His Tyr Ser Gln Thr Thr Arg Ser Asn
    370                 375                 380

Thr Leu Pro Ser Asp Val Gly Arg Lys Ser Val Thr Leu Arg Lys Met
385                 390                 395                 400

Lys Gln Glu Ile Lys Glu Ile Met Ser Pro Thr Pro Val Glu Leu His
                405                 410                 415

Lys Val Thr Leu Tyr Lys Asp Ser Gly Met Glu Asp Phe Gly Phe Ser
            420                 425                 430

Val Ala Asp Gly Leu Leu Glu Lys Gly Val Tyr Val Lys Asn Ile Arg
        435                 440                 445

Pro Ala Gly Pro Gly Asp Leu Gly Gly Leu Lys Pro Tyr Asp Arg Leu
    450                 455                 460

Leu Gln Val Asn His Val Arg Thr Arg Asp Phe Asp Cys Cys Leu Val
465                 470                 475                 480

Val Pro Leu Ile Ala Glu Ser Gly Asn Lys Leu Asp Leu Val Ile Ser
                485                 490                 495

Arg Asn Pro Leu Ala Ser Gln Lys Ser Ile Glu Gln Pro Ala Leu Pro
            500                 505                 510

Ser Asp Trp Ser Glu Gln Asn Ser Ala Phe Phe Gln Gln Pro Ser His
        515                 520                 525
```

```
Gly Gly Asn Leu Glu Thr Arg Glu Pro Thr Asn Thr Leu
    530                 535                 540
```

(2) INFORMATION FOR SEQ ID NO:37:

(i) SEQUENCE CHARACTERISTICS:
        (A) LENGTH: 441 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:37:

```
Thr Val Glu Leu Lys Arg Tyr Gly Gly Pro Leu Gly Ile Thr Ile Ser
1               5                   10                  15

Gly Thr Glu Glu Pro Phe Asp Pro Ile Ile Ile Ser Ser Leu Thr Lys
                20                  25                  30

Gly Gly Leu Ala Glu Arg Thr Gly Ala Ile His Ile Gly Asp Arg Ile
            35                  40                  45

Leu Ala Ile Asn Ser Ser Leu Lys Gly Lys Pro Leu Ser Glu Asp
50                  55                  60

Ile His Leu Leu Gln Met Ala Gly Glu Thr Val Thr Leu Lys Ile Lys
65                  70                  75                  80

Lys Gln Thr Asp Ala Gln Pro Ala Ser Ser Pro Lys Lys Leu Pro Ile
                85                  90                  95

Pro Ser His Ser Ser Asp Leu Gly Asp Gly Glu Asp Pro Ser Pro
                100                 105                 110

Ile Gln Arg Pro Gly Lys Leu Ser Asp Val Tyr Pro Ser Thr Val Pro
            115                 120                 125

Ser Val Asp Ser Ala Val Asp Ser Trp Asp Gly Ser Gly Ile Asp Ala
130                 135                 140

Arg Tyr Gly Ser Gln Gly Thr Thr Phe Gln Thr Ser Gly Tyr Asn Phe
145                 150                 155                 160

Asn Thr Tyr Asp Trp Arg Ser Pro Lys Lys Arg Ala Ser Leu Ser Pro
                165                 170                 175

Val Pro Lys Pro Arg Ser Gln Thr Tyr Pro Asp Val Gly Leu Ser Asn
                180                 185                 190

Glu Asp Trp Asp Arg Ser Thr Ala Ser Gly Phe Ala Gly Ala Ser Asp
            195                 200                 205

Ser Ala Asp Ala Glu Gln Glu Glu Asn Phe Trp Ser Gln Ala Leu Glu
210                 215                 220

Asp Leu Glu Thr Cys Gly Gln Ser Gly Ile Leu Arg Glu Leu Glu Ala
225                 230                 235                 240

Thr Ile Met Ser Gly Ser Thr Met Ser Leu Asn His Glu Ala Pro Thr
                245                 250                 255

Ala Arg Ser Gln Leu Gly Arg Gln Ala Ser Phe Gln Glu Arg Ser Asn
                260                 265                 270

Ser Arg Pro His Tyr Ser Gln Thr Thr Arg Ser Asn Thr Leu Pro Ser
            275                 280                 285

Asp Val Gly Arg Lys Ser Val Thr Leu Arg Lys Met Lys Gln Glu Ile
290                 295                 300

Lys Glu Ile Met Ser Pro Thr Pro Val Glu Leu His Lys Val Thr Leu
305                 310                 315                 320

Tyr Lys Asp Ser Gly Met Glu Asp Phe Gly Phe Ser Val Ala Asp Gly
                325                 330                 335
```

```
Leu Leu Glu Lys Gly Val Tyr Val Lys Asn Ile Arg Pro Ala Gly Pro
            340                 345                 350

Gly Asp Leu Gly Gly Leu Lys Pro Tyr Asp Arg Leu Leu Gln Val Asn
        355                 360                 365

His Val Arg Thr Arg Asp Phe Asp Cys Cys Leu Val Val Pro Leu Ile
    370                 375                 380

Ala Glu Ser Gly Asn Lys Leu Asp Leu Val Ile Ser Arg Asn Pro Leu
385                 390                 395                 400

Ala Ser Gln Lys Ser Ile Glu Gln Pro Ala Leu Pro Ser Asp Trp Ser
                405                 410                 415

Glu Gln Asn Ser Ala Phe Phe Gln Gln Pro Ser His Gly Gly Asn Leu
                420                 425                 430

Glu Thr Arg Glu Pro Thr Asn Thr Leu
                435                 440
```

(2) INFORMATION FOR SEQ ID NO:38:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:38:

```
Lys Val Thr Leu Tyr Lys Asp Ser Gly Met Glu Asp Phe Gly Phe Ser
1               5                   10                  15

Val Ala Asp Gly Leu Leu Glu Lys Gly Val Tyr Val Lys Asn Ile Arg
            20                  25                  30

Pro Ala Gly Pro Gly Asp Leu Gly Gly Leu Lys Pro Tyr Asp Arg Leu
        35                  40                  45

Leu Gln Val Asn His Val Arg Thr Arg Asp Phe Asp Cys Cys Leu Val
    50                  55                  60

Val Pro Leu Ile Ala Glu Ser Gly Asn Lys Leu Asp Leu Val Ile Ser
65                  70                  75                  80

Arg Asn Pro Leu Ala Ser Gln Lys Ser Ile Glu Gln Pro Ala Leu Pro
                85                  90                  95

Ser Asp Trp Ser Glu Gln Asn Ser Ala Phe Phe Gln Gln Pro Ser His
            100                 105                 110

Gly Gly Asn Leu Glu Thr Arg Glu Pro Thr Asn Thr Leu
            115                 120                 125
```

(2) INFORMATION FOR SEQ ID NO:39:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

```
Lys Glu Asp Leu Val Lys Leu Lys Ile Arg Lys Asp Glu Asp Asn Ser
1               5                   10                  15

Asp Glu Gln Glu
            20
```

(2) INFORMATION FOR SEQ ID NO:40:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

Pro Ser Ile Glu Ser Asp Val
1               5

(2) INFORMATION FOR SEQ ID NO:41:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

Ser Ser Ile Glu Ser Asp Val
1               5

(2) INFORMATION FOR SEQ ID NO:42:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

Val Ser Ile Glu Thr Asp Val
1               5

(2) INFORMATION FOR SEQ ID NO:43:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

Gly Ile Glu Ser Val Lys Ile
1               5

(2) INFORMATION FOR SEQ ID NO:44:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

Gly Thr Glu Ser Val Lys Ile
1               5

(2) INFORMATION FOR SEQ ID NO:45:

```
    (i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:45:

Pro Leu Gly Ala Thr Gly Leu
1               5

(2) INFORMATION FOR SEQ ID NO:46:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:46:

Val Ile Ala Ser Asp Leu Pro
1               5

(2) INFORMATION FOR SEQ ID NO:47:

(i) SEQUENCE CHARACTERISTICS:
        (A) LENGTH: 4847 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:47:

CTGCGGCCGC CAGCGCAAAN GCGCCAGCTC CCGGCTCCGA GGCTGCGGGG CGGCTGCAGG        60

GAGGTTGCAG GGCTCCGGGT CTGGGACCTG CCGGCGGGCA AAAGTGATGT TGGCGGTGTC       120

ACTCAATTGG CGGCTGGGCG TGGTGAGGCG GCGGCCCAAA AACGATGGGC CTTACTCAAA       180

GGGGGGAAAG GACACAGCGG GGACTGATGG GGCCCTGGTG TGCCGCCGCC AGAGCATTCC       240

AGAGGAGTTC CGGGGCATCA CCATGGTGGA GCTGATCAAG CGTGAGGGCA GCACTCTGGG       300

CCTGACTATC TCAGGAGGGA CTGACAAGGA CGGGAAGCCC AGAGTCTCCA ACCTGAGACC       360

CGGGGGCCTT GCAGCCAGGA GCGATCTACT GAATGTGGGC GACTATATCC GCTCAGTGAA       420

TGGGATCCGT CTGACCCGGC TCCGACATGA CGAGATCATC ACATTGCTGA AGAATGTGGG       480

CGAGCGCGTG GTGCTGGAGG TGGAGTATGA GCTGCCCCCG CCCGCTCCCG AAAACAACCC       540

GAGGATCATT TCCAAGACGG TGGACGTCTC CCTCTACAAG GAAGGCAACA GTTTTGGCTT       600

TGTCCTCAGA GGAGGTGCCC ATGAGGACCT GCACAAATCC CGCCCATTGG TCCTGACTTA       660

CGTGCGGCCT GGTGGCCCAG CAAACAGGGA GGGTTCCTTA AAGGTGGGCG ACAGGCTGCT       720

CAGCATANAT GGGATCCCAC TGCACGGGGC CAGCCATGCT ACCGCAATAG CCACCCTGCA       780

GCAGTGCAGC CATGAGGCCC TCTTCCAGGT GGAGTACGAT GTGCCACCC CAGACACGGT       840

GGCCAATGCT TCAGGCCCTT TGGTGGTAGA AATAGCCAAG ACCCCAGGAT CTGCCCTGGG       900

GATCTCTCTC ACCACTGGCT CCCACCGGAA CAAACCAGCT ATCACTATCG ACCGCATCAA       960

GCCGGCTAGC GTGGTGGACA AGAATGGTGC CCTGCATGCT GGAGAACACA TCCTGGCCAT      1020

CGATGGCACC AGCACAGAAC ACTGCTCTCT GGTCGAGGCC ACGAAGCTCT TGGCCAGTGT      1080

GACCGAGAAA GTTCGACTGG AGATCTTGCC TGCACCCCAG AGTCGGCGGC CCCTGAAGCC      1140
```

```
CCCAGAGGCA GTGAGAATAC AGAGGAGTGA GCAACTGCAC CACTGGGACC CCTGTGTTCC    1200

CTCTTGCCAT AGCCCAAGGC CAAGCCACTG CAGGGCACCC ACCTGGGCAC CTGGAGGCCA    1260

GGACCAGAGC CGATCCGTGT CCTCGACTCC CTTCTCCTCG CCAACTATGA ACCCTGCCTT    1320

TCCCTGTGCC AACGCCAGCA CCCTGCCCAG AGGACCCATG AGCCCAGAA CAACAGCGGG     1380

GAGGAGAAGG CAGCGAAGGA AAGAACACAG GAGCTCTTTG TCACTGGCCT CCAGCACGGT    1440

AGGGCCCGGT GGGCAGATCG TTCACACGGA GACGACGGAG GTAGTGCTCT GTGGAGACCC    1500

CCTCAGTGGC TTCGGCCTCC AGCTGCAGGG GGGCATTTTT GCTACCGAGA CCCTGTCCTC    1560

CCCACCCTTG GTGCGATTTA TTGAACCTGA CAGCCCTGCT GAGAGGTGTG GTCTGCTGCA    1620

GGTGGGGGAC CGCGTCCTAG CCATAAATGG CATTGCTACT GAAGATGGGA CCATGGAAGA    1680

AGCCAACCAG CTGTTGCGGG ATGCTGCACT GGCCCGCAAA ATTGTTTTGG AGATCGAGTT    1740

TGATGTGGCG GAATCTGTCA TCCCAAGCAG TGGGACTTTC CACGTGAAGT TACCCAAAAG    1800

GCGTGGTGTG GAGCTGGGCA TCACCATTAG CTCGGCCAGC AGAAAGCGAG GGGAACCCCT    1860

GATCATCTCT GACATCAAGA AAGGCAGCGT GGCGCACAGG ACTGGCACCC TCGAGCCGGG    1920

CGACAAGCTG CTGGCCATTG ACAATATTCG CCTGGACCAT TGCCCCATGG AATATGCTGT    1980

GCAAATCCTG CCCCAATGTG AGGACCTGGT GAAGCTGAAG ATCCGGAAGG ACGAGGACAA    2040

CTCAGATGAG CAGGAGAGCT CGGGCGCAGT CAGCTACACA GTGGAACTGA AGCGCTATGG    2100

CGGACCCCTG GGTATCACCA TCTCCGGTAC AGAGGAACCT TTTGACCCCA TCATCATCTC    2160

TGGTCTCACC AAGCGGGGTC TGGCTGAAAG GACTGGAGCA TCCATGTTGG GACCGCATA    2220

CTGGCCATCA ANCAGCGTGA GCCTCAAGGG CCGGCCCCTG AGTGAGGCCA TTCACCTTCT    2280

GCAGGTGGCA GGGGAGACTG TCACACTGAA GATCAAGAAG CAGCTGGACC GTCCCCTTCT    2340

CCCCCGCCAG TCAGGCAGCC TCAGTGAGGC CAGTGATGTG GATGAGGACC CCCTGAGGC    2400

CCTCAAGGGA GGCTTGCTGA CAACCCACTT CTCACCTGCT GTACCCAGCG TGGACAGTGC    2460

TGTGGAGTCC TGGGGCAGCT CTGCCACAGA GGGTGGCTTT GGGGGCTCAG GCTCCTACAC    2520

TCCGCAGGTG GCAGTCCGGA GTGTGACTCC TCAGGAGTGG CGTTCCAGCA GACTGAAGAG    2580

TAGCCCCCCA CCCCTTGAGC CCCGGAGGAC GAGCTACACA CCGGGCCCCA CTGACGAAAG    2640

CTTCCCAGAG GAGGAAGAGG GGGACTGGGA GCCACCAATG AGCCCAGCCC CTGGCCCCGC    2700

CCGAGAGGAG GGCTTCTGGA GAGTGCTTGG AGAGGCCCTT GAAGACCTGG AGTCCTGTGG    2760

TCAGTCTGAA CTGCTAAGGG AGCTGGAGGC TTCCATCATG ACAGGCACTG TACAGTCGGT    2820

AGCTGTGGAT GGCAGGCCTG GCTCTCGGCC CTGGCGCCGG AGCCGGGAAG TCGGAACATC    2880

CCCGGAAGAC CTGCAGGAGC TGCTGTTGCC AACGCCCCTG GAGATGCACA GGGTGACCCT    2940

GCACAAAGAC CCGGTGAGGA ACGACTTTGG TTTCAGTGTC TCAGATGGCC TCCTGGAGAA    3000

GGGTGTCTAT GTCCACACTG TGCGCATTGA TGGGCCAGCT CAGCACGGAG GCCTGCAGCC    3060

CTTTGACCGT CTCCTGCAGG TCAACCATGT TCGCACTCGG GACTTCGATT GCTGTCTGGC    3120

CGTTCCACTC CTGGCAGAGC TGGGANATCC TTGAGCTGGT GGTCAGCCGA AACCCTCTGG    3180

CACAGAGCCG CAGGACACCA GGAGCACCGG GCCCCAGTAG TCCCCAGATG ATCTGAGGTC    3240

ATTATGTAAG TCAGCTGGCG GAGTGCCCCC AGTCATCGAC TTATGGCCTG CAGATTTCAC    3300

ATCCGGTAGA GTGGCATCTT CAAGTTGGGT CTTCAGGATG CTCAGAGAAC CCCACAGGAA    3360

AGGGGTCATC CCTGCTGCTC AGCTAGGAGA GCCCAGCTCC CTGTGCAGTC ATCTCAGAGC    3420

AGCGAACAGA GTGGGACGG CCCAGCTCCG TGTGGTAACT GGACTGAGCT GCCAGTATTT     3480

CCCATCCTGG GAAGTTAATA AGCTGTAGGT CGACAATTCT GCTCTGTGGA AAGAGGCATT    3540
```

-continued

```
TGGCGACCCA GCTGTTCAGA TGGTACCCAG TGCACAGGGA CCCTGCCACC GGGAAAGATA    3600

TGGCACAAGA ACAGTGTCCT CCCTTCTCCC AAATGATGGT GTTTTGAAGA GCCTCCAGCA    3660

CCTAATTGAC CATACTGAGG AACCCCAATT AGGGACAATC TAGGGTGCCA GAGAATGCTT    3720

GCCCCTTCCT TTGGGTTGGT CTTTCAATTA TTTCACGGGT GATTCTGAAC CTCAGAGCAG    3780

AACTGTGGCC ATCAACCCTC CTGTCCCACA AAACCTTAGC CCAAGTCCTT GCCCAGAGGA    3840

GGGCACAGCT CGGGTCAAAC GGTCCAGGAG CATCCACACA CCTGCCATTC CAGCACATAT    3900

GGTAAACCTT GGGAAGAGAC TGAGCCACAG TTCTGCCCCT GACCCCATCA GAGGAAGAGA    3960

GGAAGANGAA AGGAGCTGAC ATGGAGGGAG GTCAGCTGAA GGATGAGANA GTGGCTAACT    4020

GGAGCAGTGT CCAAGGAAGC TATTCAAGGA GGTCCCCAGC ATCCCTTAAC TCTGGGCTCC    4080

TCCATCTCTG CTAAGCAGAA CCTTCCAGCT TCAAGCAAGA NTCAAGACAC TTCCTTCCCA    4140

GCAGTCTGAG CTGTTCTGGA GACTGGCTTC ATGTTTGCCC AGCTTAAGGT CTCAAGGACC    4200

TGCGGGAAGC CTCCAACCCT GCCCTGTCAC CCCTCTGTGC CCTTGAAGCT CACTGCTAGA    4260

AAGCACTCCC TGTTCAAGAG GACAGATGAG GTCCCAGAAG CCATTCTTTC CCCGTTCTCT    4320

TCTTGGCTGT ATAACCTTGA GTNAAGCTGA AAAGANACAG GGNGAGCTCC AGCTGCCCAC    4380

TAAGAAACTT CANCTCTCTG CTTTTCCTAA CTTCCCCCAT ATCCTGCCCT TCATGAAGGN    4440

TTCCCNGGGA ACCTTCAGGN GACCCANTGA ATCTACTTTC ACTGCCCAGG GTTGAAAAGA    4500

NANTACCCCC CCATCATGGG GGCCCAACAA AAAACTTCCA GCTTCCTAGC CAAAAAATNA    4560

ATCCTAGCCC CNGCTCACCT GATCTGTNTT AACTTGGGCN GANNGGTCAN CNCTGGAATT    4620

CTGGTTTGTG GNATAACTGA AAGTACCCNG AAAGGCNCTT AACNTNGGGA AATCTGTGTT    4680

TCNCTTAATG AAACCCGGCT CTGAAAATGG AACCCCCNNA AACTGGCCTN CCCCCGGGGG    4740

NGNNGGGGTC CCCNCCCCCC CNAAATTTNC CACTANGGCC AACNGGGTGG ACANCCNCGG    4800

CTGTTGGGCN GAAGGCCTCC CNTATTNCAN ATTACCCCCC NGGGNTT                 4847
```

(2) INFORMATION FOR SEQ ID NO:48:

(i) SEQUENCE CHARACTERISTICS:
        (A) LENGTH: 4847 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 2..3151

(xi) SEQUENCE DESCRIPTION: SEQ ID NO:48:

```
C TGC GGC CGC CAG CGC AAA NGC GCC AGC TCC CGG CTC CGA GGC TGC         46
  Cys Gly Arg Gln Arg Lys Xaa Ala Ser Ser Arg Leu Arg Gly Cys
  1               5                  10                  15

GGG GCG GCT GCA GGG AGG TTG CAG GGC TCC GGG TCT GGG ACC TGC CGG       94
Gly Ala Ala Ala Gly Arg Leu Gln Gly Ser Gly Ser Gly Thr Cys Arg
                20                  25                  30

CGG GCA AAA GTG ATG TTG GCG GTG TCA CTC AAT TGG CGG CTG GGC GTG      142
Arg Ala Lys Val Met Leu Ala Val Ser Leu Asn Trp Arg Leu Gly Val
                    35                  40                  45

GTG AGG CGG CGG CCC AAA AAC GAT GGG CCT TAC TCA AAG GGG GGA AAG      190
Val Arg Arg Arg Pro Lys Asn Asp Gly Pro Tyr Ser Lys Gly Gly Lys
        50                  55                  60

GAC ACA GCG GGG ACT GAT GGG GCC CTG GTG TGC CGC CGC CAG AGC ATT      238
Asp Thr Ala Gly Thr Asp Gly Ala Leu Val Cys Arg Arg Gln Ser Ile
65                  70                  75
```

```
CCA GAG GAG TTC CGG GGC ATC ACC ATG GTG GAG CTG ATC AAG CGT GAG      286
Pro Glu Glu Phe Arg Gly Ile Thr Met Val Glu Leu Ile Lys Arg Glu
 80              85                  90                  95

GGC AGC ACT CTG GGC CTG ACT ATC TCA GGA GGG ACT GAC AAG GAC GGG      334
Gly Ser Thr Leu Gly Leu Thr Ile Ser Gly Gly Thr Asp Lys Asp Gly
                100                 105                 110

AAG CCC AGA GTC TCC AAC CTG AGA CCC GGG GGC CTT GCA GCC AGG AGC      382
Lys Pro Arg Val Ser Asn Leu Arg Pro Gly Gly Leu Ala Ala Arg Ser
            115                 120                 125

GAT CTA CTG AAT GTG GGC GAC TAT ATC CGC TCA GTG AAT GGG ATC CGT      430
Asp Leu Leu Asn Val Gly Asp Tyr Ile Arg Ser Val Asn Gly Ile Arg
        130                 135                 140

CTG ACC CGG CTC CGA CAT GAC GAG ATC ATC ACA TTG CTG AAG AAT GTG      478
Leu Thr Arg Leu Arg His Asp Glu Ile Ile Thr Leu Leu Lys Asn Val
    145                 150                 155

GGC GAG CGC GTG GTG CTG GAG GTG GAG TAT GAG CTG CCC CCG CCC GCT      526
Gly Glu Arg Val Val Leu Glu Val Glu Tyr Glu Leu Pro Pro Pro Ala
160                 165                 170                 175

CCC GAA AAC AAC CCG AGG ATC ATT TCC AAG ACG GTG GAC GTC TCC CTC      574
Pro Glu Asn Asn Pro Arg Ile Ile Ser Lys Thr Val Asp Val Ser Leu
                180                 185                 190

TAC AAG GAA GGC AAC AGT TTT GGC TTT GTC CTC AGA GGA GGT GCC CAT      622
Tyr Lys Glu Gly Asn Ser Phe Gly Phe Val Leu Arg Gly Gly Ala His
            195                 200                 205

GAG GAC CTG CAC AAA TCC CGC CCA TTG GTC CTG ACT TAC GTG CGG CCT      670
Glu Asp Leu His Lys Ser Arg Pro Leu Val Leu Thr Tyr Val Arg Pro
        210                 215                 220

GGT GGC CCA GCA AAC AGG GAG GGT TCC TTA AAG GTG GGC GAC AGG CTG      718
Gly Gly Pro Ala Asn Arg Glu Gly Ser Leu Lys Val Gly Asp Arg Leu
    225                 230                 235

CTC AGC ATA NAT GGG ATC CCA CTG CAC GGG GCC AGC CAT GCT ACC GCA      766
Leu Ser Ile Xaa Gly Ile Pro Leu His Gly Ala Ser His Ala Thr Ala
240                 245                 250                 255

ATA GCC ACC CTG CAG CAG TGC AGC CAT GAG GCC CTC TTC CAG GTG GAG      814
Ile Ala Thr Leu Gln Gln Cys Ser His Glu Ala Leu Phe Gln Val Glu
                260                 265                 270

TAC GAT GTG GCC ACC CCA GAC ACG GTG GCC AAT GCT TCA GGC CCT TTG      862
Tyr Asp Val Ala Thr Pro Asp Thr Val Ala Asn Ala Ser Gly Pro Leu
            275                 280                 285

GTG GTA GAA ATA GCC AAG ACC CCA GGA TCT GCC CTG GGG ATC TCT CTC      910
Val Val Glu Ile Ala Lys Thr Pro Gly Ser Ala Leu Gly Ile Ser Leu
        290                 295                 300

ACC ACT GGC TCC CAC CGG AAC AAA CCA GCT ATC ACT ATC GAC CGC ATC      958
Thr Thr Gly Ser His Arg Asn Lys Pro Ala Ile Thr Ile Asp Arg Ile
    305                 310                 315

AAG CCG GCT AGC GTG GTG GAC AAG AAT GGT GCC CTG CAT GCT GGA GAA     1006
Lys Pro Ala Ser Val Val Asp Lys Asn Gly Ala Leu His Ala Gly Glu
320                 325                 330                 335

CAC ATC CTG GCC ATC GAT GGC ACC AGC ACA GAA CAC TGC TCT CTG GTC     1054
His Ile Leu Ala Ile Asp Gly Thr Ser Thr Glu His Cys Ser Leu Val
                340                 345                 350

GAG GCC ACG AAG CTC TTG GCC AGT GTG ACC GAG AAA GTT CGA CTG GAG     1102
Glu Ala Thr Lys Leu Leu Ala Ser Val Thr Glu Lys Val Arg Leu Glu
            355                 360                 365

ATC TTG CCT GCA CCC CAG AGT CGG CGG CCC CTG AAG CCC CCA GAG GCA     1150
Ile Leu Pro Ala Pro Gln Ser Arg Arg Pro Leu Lys Pro Pro Glu Ala
        370                 375                 380

GTG AGA ATA CAG AGG AGT GAG CAA CTG CAC CAC TGG GAC CCC TGT GTT     1198
Val Arg Ile Gln Arg Ser Glu Gln Leu His His Trp Asp Pro Cys Val
    385                 390                 395
```

```
CCC TCT TGC CAT AGC CCA AGG CCA AGC CAC TGC AGG GCA CCC ACC TGG       1246
Pro Ser Cys His Ser Pro Arg Pro Ser His Cys Arg Ala Pro Thr Trp
400                 405                 410                 415

GCA CCT GGA GGC CAG GAC CAG AGC CGA TCC GTG TCC TCG ACT CCC TTC       1294
Ala Pro Gly Gly Gln Asp Gln Ser Arg Ser Val Ser Ser Thr Pro Phe
                420                 425                 430

TCC TCG CCA ACT ATG AAC CCT GCC TTT CCC TGT GCC AAC GCC AGC ACC       1342
Ser Ser Pro Thr Met Asn Pro Ala Phe Pro Cys Ala Asn Ala Ser Thr
            435                 440                 445

CTG CCC AGA GGA CCC ATG AGC CCC AGA ACA ACA GCG GGG AGG AGA AGG       1390
Leu Pro Arg Gly Pro Met Ser Pro Arg Thr Thr Ala Gly Arg Arg Arg
        450                 455                 460

CAG CGA AGG AAA GAA CAC AGG AGC TCT TTG TCA CTG GCC TCC AGC ACG       1438
Gln Arg Arg Lys Glu His Arg Ser Ser Leu Ser Leu Ala Ser Ser Thr
    465                 470                 475

GTA GGG CCC GGT GGG CAG ATC GTT CAC ACG GAG ACG ACG GAG GTA GTG       1486
Val Gly Pro Gly Gly Gln Ile Val His Thr Glu Thr Thr Glu Val Val
480                 485                 490                 495

CTC TGT GGA GAC CCC CTC AGT GGC TTC GGC CTC CAG CTG CAG GGG GGC       1534
Leu Cys Gly Asp Pro Leu Ser Gly Phe Gly Leu Gln Leu Gln Gly Gly
                500                 505                 510

ATT TTT GCT ACC GAG ACC CTG TCC TCC CCA CCC TTG GTG CGA TTT ATT       1582
Ile Phe Ala Thr Glu Thr Leu Ser Ser Pro Pro Leu Val Arg Phe Ile
            515                 520                 525

GAA CCT GAC AGC CCT GCT GAG AGG TGT GGT CTG CTG CAG GTG GGG GAC       1630
Glu Pro Asp Ser Pro Ala Glu Arg Cys Gly Leu Leu Gln Val Gly Asp
        530                 535                 540

CGC GTC CTA GCC ATA AAT GGC ATT GCT ACT GAA GAT GGG ACC ATG GAA       1678
Arg Val Leu Ala Ile Asn Gly Ile Ala Thr Glu Asp Gly Thr Met Glu
    545                 550                 555

CAA GCC AAC CAG CTG TTG CGG GAT GCT GCA CTG GCC CGC AAA ATT GTT       1726
Gln Ala Asn Gln Leu Leu Arg Asp Ala Ala Leu Ala Arg Lys Ile Val
560                 565                 570                 575

TTG GAG ATC GAG TTT GAT GTG GCG GAA TCT GTC ATC CCA AGC AGT GGG       1774
Leu Glu Ile Glu Phe Asp Val Ala Glu Ser Val Ile Pro Ser Ser Gly
                580                 585                 590

ACT TTC CAC GTG AAG TTA CCC AAA AGG CGT GGT GTG GAG CTG GGC ATC       1822
Thr Phe His Val Lys Leu Pro Lys Arg Arg Gly Val Glu Leu Gly Ile
            595                 600                 605

ACC ATT AGC TCG GCC AGC AGA AAG CGA GGG GAA CCC CTG ATC ATC TCT       1870
Thr Ile Ser Ser Ala Ser Arg Lys Arg Gly Glu Pro Leu Ile Ile Ser
        610                 615                 620

GAC ATC AAG AAA GGC AGC GTG GCG CAC AGG ACT GGC ACC CTC GAG CCG       1918
Asp Ile Lys Lys Gly Ser Val Ala His Arg Thr Gly Thr Leu Glu Pro
    625                 630                 635

GGC GAC AAG CTG CTG GCC ATT GAC AAT ATT CGC CTG GAC CAT TGC CCC       1966
Gly Asp Lys Leu Leu Ala Ile Asp Asn Ile Arg Leu Asp His Cys Pro
640                 645                 650                 655

ATG GAA TAT GCT GTG CAA ATC CTG CCC CAA TGT GAG GAC CTG GTG AAG       2014
Met Glu Tyr Ala Val Gln Ile Leu Pro Gln Cys Glu Asp Leu Val Lys
                660                 665                 670

CTG AAG ATC CGG AAG GAC GAG GAC AAC TCA GAT GAG CAG GAG AGC TCG       2062
Leu Lys Ile Arg Lys Asp Glu Asp Asn Ser Asp Glu Gln Glu Ser Ser
            675                 680                 685

GGC GCA GTC AGC TAC ACA GTG GAA CTG AAG CGC TAT GGC GGA CCC CTG       2110
Gly Ala Val Ser Tyr Thr Val Glu Leu Lys Arg Tyr Gly Gly Pro Leu
        690                 695                 700

GGT ATC ACC ATC TCC GGT ACA GAG GAA CCT TTT GAC CCC ATC ATC ATC       2158
Gly Ile Thr Ile Ser Gly Thr Glu Glu Pro Phe Asp Pro Ile Ile Ile
    705                 710                 715
```

```
TCT GGT CTC ACC AAG CGG GGT CTG GCT GAA AGG ACT GGA GCA TCC ATG          2206
Ser Gly Leu Thr Lys Arg Gly Leu Ala Glu Arg Thr Gly Ala Ser Met
720             725                 730                 735

TTG GGG ACC GCA TAC TGG CCA TCA ANC AGC GTG AGC CTC AAG GGC CGG          2254
Leu Gly Thr Ala Tyr Trp Pro Ser Xaa Ser Val Ser Leu Lys Gly Arg
            740                 745                 750

CCC CTG AGT GAG GCC ATT CAC CTT CTG CAG GTG GCA GGG GAG ACT GTC          2302
Pro Leu Ser Glu Ala Ile His Leu Leu Gln Val Ala Gly Glu Thr Val
                755                 760                 765

ACA CTG AAG ATC AAG AAG CAG CTG GAC CGT CCC CTT CTC CCC CGC CAG          2350
Thr Leu Lys Ile Lys Lys Gln Leu Asp Arg Pro Leu Leu Pro Arg Gln
            770                 775                 780

TCA GGC AGC CTC AGT GAG GCC AGT GAT GTG GAT GAG GAC CCC CCT GAG          2398
Ser Gly Ser Leu Ser Glu Ala Ser Asp Val Asp Glu Asp Pro Pro Glu
                785                 790                 795

GCC CTC AAG GGA GGC TTG CTG ACA ACC CAC TTC TCA CCT GCT GTA CCC          2446
Ala Leu Lys Gly Gly Leu Leu Thr Thr His Phe Ser Pro Ala Val Pro
800             805                 810                 815

AGC GTG GAC AGT GCT GTG GAG TCC TGG GGC AGC TCT GCC ACA GAG GGT          2494
Ser Val Asp Ser Ala Val Glu Ser Trp Gly Ser Ser Ala Thr Glu Gly
            820                 825                 830

GGC TTT GGG GGC TCA GGC TCC TAC ACT CCG CAG GTG GCA GTC CGG AGT          2542
Gly Phe Gly Gly Ser Gly Ser Tyr Thr Pro Gln Val Ala Val Arg Ser
                835                 840                 845

GTG ACT CCT CAG GAG TGG CGT TCC AGC AGA CTG AAG AGT AGC CCC CCA          2590
Val Thr Pro Gln Glu Trp Arg Ser Ser Arg Leu Lys Ser Ser Pro Pro
            850                 855                 860

CCC CTT GAG CCC CGG AGG ACG AGC TAC ACA CCG GGC CCC ACT GAC GAA          2638
Pro Leu Glu Pro Arg Arg Thr Ser Tyr Thr Pro Gly Pro Thr Asp Glu
                865                 870                 875

AGC TTC CCA GAG GAG GAA GAG GGG GAC TGG GAG CCA CCA ATG AGC CCA          2686
Ser Phe Pro Glu Glu Glu Glu Gly Asp Trp Glu Pro Pro Met Ser Pro
880             885                 890                 895

GCC CCT GGC CCC GCC CGA GAG GAG GGC TTC TGG AGA GTG CTT GGA GAG          2734
Ala Pro Gly Pro Ala Arg Glu Glu Gly Phe Trp Arg Val Leu Gly Glu
            900                 905                 910

GCC CTT GAA GAC CTG GAG TCC TGT GGT CAG TCT GAA CTG CTA AGG GAG          2782
Ala Leu Glu Asp Leu Glu Ser Cys Gly Gln Ser Glu Leu Leu Arg Glu
                915                 920                 925

CTG GAG GCT TCC ATC ATG ACA GGC ACT GTA CAG TCG GTA GCT GTG GAT          2830
Leu Glu Ala Ser Ile Met Thr Gly Thr Val Gln Ser Val Ala Val Asp
            930                 935                 940

GGC AGG CCT GGC TCT CGG CCC TGG CGC CGG AGC CGG GAA GTC GGA ACA          2878
Gly Arg Pro Gly Ser Arg Pro Trp Arg Arg Ser Arg Glu Val Gly Thr
945             950                 955

TCC CCG GAA GAC CTG CAG GAG CTG CTG TTG CCA ACG CCC CTG GAG ATG          2926
Ser Pro Glu Asp Leu Gln Glu Leu Leu Leu Pro Thr Pro Leu Glu Met
960             965                 970                 975

CAC AGG GTG ACC CTG CAC AAA GAC CCG GTG AGG AAC GAC TTT GGT TTC          2974
His Arg Val Thr Leu His Lys Asp Pro Val Arg Asn Asp Phe Gly Phe
            980                 985                 990

AGT GTC TCA GAT GGC CTC CTG GAG AAG GGT GTC TAT GTC CAC ACT GTG          3022
Ser Val Ser Asp Gly Leu Leu Glu Lys Gly Val Tyr Val His Thr Val
                995                 1000                1005

CGC ATT GAT GGG CCA GCT CAG CAC GGA GGC CTG CAG CCC TTT GAC CGT          3070
Arg Ile Asp Gly Pro Ala Gln His Gly Gly Leu Gln Pro Phe Asp Arg
            1010                1015                1020

CTC CTG CAG GTC AAC CAT GTT CGC ACT CGG GAC TTC GAT TGC TGT CTG          3118
Leu Leu Gln Val Asn His Val Arg Thr Arg Asp Phe Asp Cys Cys Leu
        1025                1030                1035
```

```
GCC GTT CCA CTC CTG GCA GAG CTG GGA NAT CCT TGAGCTGGTG GTCAGCCGAA      3171
Ala Val Pro Leu Leu Ala Glu Leu Gly Xaa Pro
1040              1045                1050

ACCCTCTGGC ACAGAGCCGC AGGACACCAG GAGCACCGGG CCCCAGTAGT CCCCAGATGA      3231

TCTGAGGTCA TTATGTAAGT CAGCTGGCGG AGTGCCCCCA GTCATCGACT TATGGCCTGC      3291

AGATTTCACA TCCGGTAGAG TGGCATCTTC AAGTTGGGTC TTCAGGATGC TCAGAGAACC      3351

CCACAGGAAA GGGGTCATCC CTGCTGCTCA GCTAGGAGAG CCCAGCTCCC TGTGCAGTCA      3411

TCTCAGAGCA GCGAACAGAG TGGGACGGC CCAGCTCCGT GTGGTAACTG GACTGAGCTG      3471

CCAGTATTTC CCATCCTGGG AAGTTAATAA GCTGTAGGTC GACAATTCTG CTCTGTGGAA      3531

AGAGGCATTT GGCGACCCAG CTGTTCAGAT GGTACCCAGT GCACAGGGAC CCTGCCACCG      3591

GGAAAGATAT GGCACAAGAA CAGTGTCCTC CCTTCTCCCA AATGGTGGTG TTTTGAAGAG      3651

CCTCCAGCAC CTAATTGACC ATACTGAGGA ACCCCAATTA GGGACAATCT AGGGTGCCAG      3711

AGAATGCTTG CCCCTTCCTT TGGGTTGGTC TTTCAATTAT TTCACGGGTG ATTCTGAACC      3771

TCAGAGCAGA ACTGTGGCCA TCAACCCTCC TGTCCCACAA AACCTTAGCC CAAGTCCTTG      3831

CCCAGAGGAG GGCACAGCTC GGGTCAAACG GTCCAGGAGC ATCCACACAC CTGCCATTCC      3891

AGCACATATG GTAAACCTTG GAAGAGACT GAGCCACAGT TCTGCCCCTG ACCCCATCAG      3951

AGGAAGAGAG GAAGANGAAA GGAGCTGACA TGGAGGGAGG TCAGCTGAAG GATGAGANAG      4011

TGGCTAACTG GAGCAGTGTC CAAGGAAGCT ATTCAAGGAG GTCCCCAGCA TCCCTTAACT      4071

CTGGGCTCCT CCATCTCTGC TAAGCAGAAC CTTCCAGCTT CAAGCAAGAN TCAAGACACT      4131

TCCTTCCCAG CAGTCTGAGC TGTTCTGGAG ACTGGCTTCA TGTTTGCCCA GCTTAAGGTC      4191

TCAAGGACCT GCGGGAAGCC TCCAACCCTG CCCTGTCACC CCTCTGTGCC CTTGAAGCTC      4251

ACTGCTAGAA AGCACTCCCT GTTCAAGAGG ACAGATGAGG TCCCAGAAGC CATTCTTTCC      4311

CCGTTCTCTT CTTGGCTGTA TAACCTTGAG TNAAGCTGAA AAGANACAGG GNGAGCTCCA      4371

GCTGCCCACT AAGAAACTTC ANCTCTCTGC TTTTCCTAAC TTCCCCCATA TCCTGCCCTT      4431

CATGAAGGNT TCCCNGGGAA CCTTCAGGNG ACCCANTGAA TCTACTTTCA CTGCCCAGGG      4491

TTGAAAAGAN ANTACCCCCC CATCATGGGG GCCCAACAAA AAACTTCCAG CTTCCTAGCC      4551

AAAAAATNAA TCCTAGCCCC NGCTCACCTG ATCTGTNTTA ACTTGGGCNG ANNGGTCANC      4611

NCTGGAATTC TGGTTTGTGG NATAACTGAA AGTACCCNGA AAGGCNCTTA ACNTNGGGAA      4671

ATCTGTGTTT CNCTTAATGA AACCCGGCTC TGAAAATGGA ACCCCCNNAA ACTGGCCTNC      4731

CCCCGGGGGN GNNGGGGTCC CCNCCCCCCC NAAATTTNCC ACTANGGCCA ACNGGGTGGA      4791

ACNCCNCGGC TGTTGGGCNG AAGGCCTCCC NTATTNCANA TTACCCCCCN GGGNTT         4847

(2) INFORMATION FOR SEQ ID NO:49:

(i) SEQUENCE CHARACTERISTICS:
        (A) LENGTH: 1050 amino acids
        (B) TYPE: amino acid
        (D) TOPOLOGY: linear (ii) MOLECULE TYPE: protein (xi) SEQUENCE DESCRIPTION: SEQ ID NO:49:

Cys Gly Arg Gln Arg Lys Xaa Ala Ser Ser Arg Leu Arg Gly Cys Gly
  1               5                  10                  15

Ala Ala Ala Gly Arg Leu Gln Gly Ser Gly Ser Gly Thr Cys Arg Arg
             20                  25                  30

Ala Lys Val Met Leu Ala Val Ser Leu Asn Trp Arg Leu Gly Val Val
```

```
                    35                  40                  45
Arg Arg Arg Pro Lys Asn Asp Gly Pro Tyr Ser Lys Gly Gly Lys Asp
         50                  55                  60
Thr Ala Gly Thr Asp Gly Ala Leu Val Cys Arg Arg Gln Ser Ile Pro
 65                  70                  75                  80
Glu Glu Phe Arg Gly Ile Thr Met Val Glu Leu Ile Lys Arg Glu Gly
                     85                  90                  95
Ser Thr Leu Gly Leu Thr Ile Ser Gly Gly Thr Asp Lys Asp Gly Lys
                100                 105                 110
Pro Arg Val Ser Asn Leu Arg Pro Gly Gly Leu Ala Ala Arg Ser Asp
            115                 120                 125
Leu Leu Asn Val Gly Asp Tyr Ile Arg Ser Val Asn Gly Ile Arg Leu
130                 135                 140
Thr Arg Leu Arg His Asp Glu Ile Ile Thr Leu Leu Lys Asn Val Gly
145                 150                 155                 160
Glu Arg Val Val Leu Glu Val Glu Tyr Glu Leu Pro Pro Pro Ala Pro
                165                 170                 175
Glu Asn Asn Pro Arg Ile Ile Ser Lys Thr Val Asp Val Ser Leu Tyr
                180                 185                 190
Lys Glu Gly Asn Ser Phe Gly Phe Val Leu Arg Gly Gly Ala His Glu
            195                 200                 205
Asp Leu His Lys Ser Arg Pro Leu Val Leu Thr Tyr Val Arg Pro Gly
210                 215                 220
Gly Pro Ala Asn Arg Glu Gly Ser Leu Lys Val Gly Asp Arg Leu Leu
225                 230                 235                 240
Ser Ile Xaa Gly Ile Pro Leu His Gly Ala Ser His Ala Thr Ala Ile
                245                 250                 255
Ala Thr Leu Gln Gln Cys Ser His Glu Ala Leu Phe Gln Val Glu Tyr
            260                 265                 270
Asp Val Ala Thr Pro Asp Thr Val Ala Asn Ala Ser Gly Pro Leu Val
        275                 280                 285
Val Glu Ile Ala Lys Thr Pro Gly Ser Ala Leu Gly Ile Ser Leu Thr
290                 295                 300
Thr Gly Ser His Arg Asn Lys Pro Ala Ile Thr Ile Asp Arg Ile Lys
305                 310                 315                 320
Pro Ala Ser Val Val Asp Lys Asn Gly Ala Leu His Ala Gly Glu His
                325                 330                 335
Ile Leu Ala Ile Asp Gly Thr Ser Thr Glu His Cys Ser Leu Val Glu
                340                 345                 350
Ala Thr Lys Leu Leu Ala Ser Val Thr Glu Lys Val Arg Leu Glu Ile
            355                 360                 365
Leu Pro Ala Pro Gln Ser Arg Arg Pro Leu Lys Pro Pro Glu Ala Val
370                 375                 380
Arg Ile Gln Arg Ser Glu Gln Leu His His Trp Asp Pro Cys Val Pro
385                 390                 395                 400
Ser Cys His Ser Pro Arg Pro Ser His Cys Arg Ala Pro Thr Trp Ala
                405                 410                 415
Pro Gly Gly Gln Asp Gln Ser Arg Ser Val Ser Ser Thr Pro Phe Ser
            420                 425                 430
Ser Pro Thr Met Asn Pro Ala Phe Pro Cys Ala Asn Ala Ser Thr Leu
        435                 440                 445
Pro Arg Gly Pro Met Ser Pro Arg Thr Thr Ala Gly Arg Arg Arg Gln
450                 455                 460
```

-continued

```
Arg Arg Lys Glu His Arg Ser Ser Leu Ser Leu Ala Ser Ser Thr Val
465                 470                 475                 480

Gly Pro Gly Gly Gln Ile Val His Thr Glu Thr Thr Glu Val Val Leu
            485                 490                 495

Cys Gly Asp Pro Leu Ser Gly Phe Gly Leu Gln Leu Gln Gly Gly Ile
        500                 505                 510

Phe Ala Thr Glu Thr Leu Ser Ser Pro Pro Leu Val Arg Phe Ile Glu
    515                 520                 525

Pro Asp Ser Pro Ala Glu Arg Cys Gly Leu Leu Gln Val Gly Asp Arg
530                 535                 540

Val Leu Ala Ile Asn Gly Ile Ala Thr Glu Asp Gly Thr Met Glu Gln
545                 550                 555                 560

Ala Asn Gln Leu Leu Arg Asp Ala Ala Leu Ala Arg Lys Ile Val Leu
                565                 570                 575

Glu Ile Glu Phe Asp Val Ala Glu Ser Val Ile Pro Ser Ser Gly Thr
            580                 585                 590

Phe His Val Lys Leu Pro Lys Arg Arg Gly Val Glu Leu Gly Ile Thr
        595                 600                 605

Ile Ser Ser Ala Ser Arg Lys Arg Gly Glu Pro Leu Ile Ile Ser Asp
    610                 615                 620

Ile Lys Lys Gly Ser Val Ala His Arg Thr Gly Thr Leu Glu Pro Gly
625                 630                 635                 640

Asp Lys Leu Leu Ala Ile Asp Asn Ile Arg Leu Asp His Cys Pro Met
                645                 650                 655

Glu Tyr Ala Val Gln Ile Leu Pro Gln Cys Glu Asp Leu Val Lys Leu
            660                 665                 670

Lys Ile Arg Lys Asp Glu Asp Asn Ser Asp Glu Gln Glu Ser Ser Gly
        675                 680                 685

Ala Val Ser Tyr Thr Val Glu Leu Lys Arg Tyr Gly Gly Pro Leu Gly
    690                 695                 700

Ile Thr Ile Ser Gly Thr Glu Glu Pro Phe Asp Pro Ile Ile Ile Ser
705                 710                 715                 720

Gly Leu Thr Lys Arg Gly Leu Ala Glu Arg Thr Gly Ala Ser Met Leu
                725                 730                 735

Gly Thr Ala Tyr Trp Pro Ser Xaa Ser Val Ser Leu Lys Gly Arg Pro
            740                 745                 750

Leu Ser Glu Ala Ile His Leu Leu Gln Val Ala Gly Glu Thr Val Thr
        755                 760                 765

Leu Lys Ile Lys Lys Gln Leu Asp Arg Pro Leu Leu Pro Arg Gln Ser
    770                 775                 780

Gly Ser Leu Ser Glu Ala Ser Asp Val Asp Asp Pro Pro Glu Ala
785                 790                 795                 800

Leu Lys Gly Gly Leu Leu Thr Thr His Phe Ser Pro Ala Val Pro Ser
                805                 810                 815

Val Asp Ser Ala Val Glu Ser Trp Gly Ser Ser Ala Thr Glu Gly Gly
            820                 825                 830

Phe Gly Gly Ser Gly Ser Tyr Thr Pro Gln Val Ala Val Arg Ser Val
        835                 840                 845

Thr Pro Gln Glu Trp Arg Ser Ser Arg Leu Lys Ser Ser Pro Pro Pro
    850                 855                 860

Leu Glu Pro Arg Arg Thr Ser Tyr Thr Pro Gly Pro Thr Asp Glu Ser
865                 870                 875                 880

Phe Pro Glu Glu Glu Glu Gly Asp Trp Glu Pro Pro Met Ser Pro Ala
                885                 890                 895
```

```
Pro Gly Pro Ala Arg Glu Glu Gly Phe Trp Arg Val Leu Gly Glu Ala
            900                 905                 910
Leu Glu Asp Leu Glu Ser Cys Gly Gln Ser Glu Leu Leu Arg Glu Leu
            915                 920                 925
Glu Ala Ser Ile Met Thr Gly Thr Val Gln Ser Val Ala Val Asp Gly
            930                 935                 940
Arg Pro Gly Ser Arg Pro Trp Arg Arg Ser Arg Glu Val Gly Thr Ser
945                 950                 955                 960
Pro Glu Asp Leu Gln Glu Leu Leu Pro Thr Pro Leu Glu Met His
            965                 970                 975
Arg Val Thr Leu His Lys Asp Pro Val Arg Asn Asp Phe Gly Phe Ser
            980                 985                 990
Val Ser Asp Gly Leu Leu Glu Lys Gly Val Tyr Val His Thr Val Arg
            995                 1000                1005
Ile Asp Gly Pro Ala Gln His Gly Gly Leu Gln Pro Phe Asp Arg Leu
            1010                1015                1020
Leu Gln Val Asn His Val Arg Thr Arg Asp Phe Asp Cys Cys Leu Ala
1025                1030                1035                1040
Val Pro Leu Leu Ala Glu Leu Gly Xaa Pro
            1045                1050
```

(2) INFORMATION FOR SEQ ID NO:50:

(i) SEQUENCE CHARACTERISTICS:
       (A) LENGTH: 1050 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:50:

```
Cys Gly Arg Gln Arg Lys Xaa Ala Ser Ser Arg Leu Arg Gly Cys Gly
1                   5                   10                  15
Ala Ala Ala Gly Arg Leu Gln Gly Ser Gly Ser Gly Thr Cys Arg Arg
            20                  25                  30
Ala Lys Val Met Leu Ala Val Ser Leu Asn Trp Arg Leu Gly Val Val
            35                  40                  45
Pro Arg Arg Pro Lys Asn Asp Gly Pro Tyr Ser Lys Gly Gly Lys Asp
            50                  55                  60
Thr Ala Gly Thr Asp Gly Ala Leu Val Cys Arg Arg Gln Ser Ile Pro
65                  70                  75                  80
Glu Glu Phe Arg Gly Ile Thr Met Val Glu Leu Ile Lys Arg Glu Gly
            85                  90                  95
Ser Thr Leu Gly Leu Thr Ile Ser Gly Gly Thr Asp Lys Asp Gly Lys
            100                 105                 110
Pro Arg Val Ser Asn Leu Arg Pro Gly Gly Leu Ala Ala Arg Ser Asp
            115                 120                 125
Leu Leu Asn Val Gly Asp Tyr Ile Arg Ser Val Asn Gly Ile Arg Leu
            130                 135                 140
Thr Arg Leu Arg His Asp Glu Ile Ile Thr Leu Leu Lys Asn Val Gly
145                 150                 155                 160
Glu Arg Val Val Leu Glu Val Glu Tyr Glu Leu Pro Pro Ala Pro
            165                 170                 175
Glu Asn Asn Pro Arg Ile Ile Ser Lys Thr Val Asp Val Ser Leu Tyr
            180                 185                 190
```

-continued

```
Lys Glu Gly Asn Ser Phe Gly Phe Val Leu Arg Gly Ala His Glu
        195                 200                 205
Asp Leu His Lys Ser Arg Pro Leu Val Leu Thr Tyr Val Arg Pro Gly
        210                 215                 220
Gly Pro Ala Asn Arg Glu Gly Ser Leu Lys Val Gly Asp Arg Leu Leu
225                 230                 235                 240
Ser Ile Xaa Gly Ile Pro Leu His Gly Ala Ser His Ala Thr Ala Ile
                245                 250                 255
Ala Thr Leu Gln Gln Cys Ser His Glu Ala Leu Phe Gln Val Glu Tyr
            260                 265                 270
Asp Val Ala Thr Pro Asp Thr Val Ala Asn Ala Ser Gly Pro Leu Val
        275                 280                 285
Val Glu Ile Ala Lys Thr Pro Gly Ser Ala Leu Gly Ile Ser Leu Thr
    290                 295                 300
Thr Gly Ser His Arg Asn Lys Pro Ala Ile Thr Ile Asp Arg Ile Lys
305                 310                 315                 320
Pro Ala Ser Val Val Asp Lys Asn Gly Ala Leu His Ala Gly Glu His
                325                 330                 335
Ile Leu Ala Ile Asp Gly Thr Ser Thr Glu His Cys Ser Leu Val Glu
            340                 345                 350
Ala Thr Lys Leu Leu Ala Ser Val Thr Glu Lys Val Arg Leu Glu Ile
        355                 360                 365
Leu Pro Ala Pro Gln Ser Arg Arg Pro Leu Lys Pro Pro Glu Ala Val
    370                 375                 380
Arg Ile Gln Arg Ser Glu Gln Leu His His Trp Asp Pro Cys Val Pro
385                 390                 395                 400
Ser Cys His Ser Pro Arg Pro Ser His Cys Arg Ala Pro Thr Trp Ala
                405                 410                 415
Pro Gly Gly Gln Asp Gln Ser Arg Ser Val Ser Ser Thr Pro Phe Ser
            420                 425                 430
Ser Pro Thr Met Asn Pro Ala Phe Pro Cys Ala Asn Ala Ser Thr Leu
        435                 440                 445
Pro Arg Gly Pro Met Ser Pro Arg Thr Thr Ala Gly Arg Arg Arg Gln
    450                 455                 460
Arg Arg Lys Glu His Arg Ser Ser Leu Ser Leu Ala Ser Ser Thr Val
465                 470                 475                 480
Gly Pro Gly Gly Gln Ile Val His Thr Glu Thr Thr Glu Val Val Leu
                485                 490                 495
Cys Gly Asp Pro Leu Ser Gly Phe Gly Leu Gln Leu Gln Gly Gly Ile
            500                 505                 510
Phe Ala Thr Glu Thr Leu Ser Ser Pro Pro Leu Val Arg Phe Ile Glu
        515                 520                 525
Pro Asp Ser Pro Ala Glu Arg Cys Gly Leu Leu Gln Val Gly Asp Arg
    530                 535                 540
Val Leu Ala Ile Asn Gly Ile Ala Thr Glu Asp Gly Thr Met Glu Glu
545                 550                 555                 560
Ala Asn Gln Leu Leu Arg Asp Ala Ala Leu Ala Arg Lys Ile Val Leu
                565                 570                 575
Glu Ile Glu Phe Asp Val Ala Glu Ser Val Ile Pro Ser Ser Gly Thr
            580                 585                 590
Phe His Val Lys Leu Pro Lys Arg Arg Gly Val Glu Leu Gly Ile Thr
        595                 600                 605
Ile Ser Ser Ala Ser Arg Lys Arg Gly Glu Pro Leu Ile Ile Ser Asp
    610                 615                 620
```

```
Ile Lys Lys Gly Ser Val Ala His Arg Thr Gly Thr Leu Glu Pro Gly
625                 630                 635                 640

Asp Lys Leu Leu Ala Ile Asp Asn Ile Arg Leu Asp His Cys Pro Met
                645                 650                 655

Glu Tyr Ala Val Gln Ile Leu Pro Gln Cys Glu Asp Leu Val Lys Leu
                660                 665                 670

Lys Ile Arg Lys Asp Glu Asp Asn Ser Asp Glu Gln Glu Ser Ser Gly
                675                 680                 685

Ala Val Ser Tyr Thr Val Glu Leu Lys Arg Tyr Gly Pro Leu Gly
                690                 695                 700

Ile Thr Ile Ser Gly Thr Glu Glu Pro Phe Asp Pro Ile Ile Ile Ser
705                 710                 715                 720

Gly Leu Thr Lys Arg Gly Leu Ala Glu Arg Thr Gly Ala Ser Met Leu
                725                 730                 735

Gly Thr Ala Tyr Trp Pro Ser Xaa Ser Val Ser Leu Lys Gly Arg Pro
                740                 745                 750

Leu Ser Glu Ala Ile His Leu Leu Gln Val Ala Gly Glu Thr Val Thr
                755                 760                 765

Leu Lys Ile Lys Lys Gln Leu Asp Arg Pro Leu Leu Pro Arg Gln Ser
770                 775                 780

Gly Ser Leu Ser Glu Ala Ser Asp Val Asp Glu Asp Pro Pro Glu Ala
785                 790                 795                 800

Leu Lys Gly Gly Leu Leu Thr Thr His Phe Ser Pro Ala Val Pro Ser
                805                 810                 815

Val Asp Ser Ala Val Glu Ser Trp Gly Ser Ser Ala Thr Glu Gly Gly
                820                 825                 830

Phe Gly Gly Ser Gly Ser Tyr Thr Pro Gln Val Ala Val Arg Ser Val
                835                 840                 845

Thr Pro Gln Glu Trp Arg Ser Ser Arg Leu Lys Ser Ser Pro Pro Pro
850                 855                 860

Leu Glu Pro Arg Arg Thr Ser Tyr Thr Pro Gly Pro Thr Asp Glu Ser
865                 870                 875                 880

Phe Pro Glu Glu Glu Glu Gly Asp Trp Glu Pro Pro Met Ser Pro Ala
                885                 890                 895

Pro Gly Pro Ala Arg Glu Glu Gly Phe Trp Arg Val Leu Gly Glu Ala
                900                 905                 910

Leu Glu Asp Leu Glu Ser Cys Gly Gln Ser Glu Leu Leu Arg Glu Leu
                915                 920                 925

Glu Ala Ser Ile Met Thr Gly Thr Val Gln Ser Val Ala Val Asp Gly
930                 935                 940

Arg Pro Gly Ser Arg Pro Trp Arg Arg Ser Arg Glu Val Gly Thr Ser
945                 950                 955                 960

Pro Glu Asp Leu Gln Glu Leu Leu Pro Thr Pro Leu Glu Met His
                965                 970                 975

Arg Val Thr Leu His Lys Asp Pro Val Arg Asn Asp Phe Gly Phe Ser
                980                 985                 990

Val Ser Asp Gly Leu Leu Glu Lys Gly Val Tyr Val His Thr Val Arg
                995                 1000                1005

Ile Asp Gly Pro Ala Gln His Gly Leu Gln Pro Phe Asp Arg Leu
                1010                1015                1020

Leu Gln Val Asn His Val Arg Thr Arg Asp Phe Asp Cys Cys Leu Ala
1025                1030                1035                1040

Val Pro Leu Leu Ala Glu Leu Gly Xaa Pro
```

1045    1050

(2) INFORMATION FOR SEQ ID NO:51:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:51:

Asp Ile Gln Leu Glu Arg Gly Asn Ser Gly Leu Gly Phe Ser Ile Ala
1               5                   10                  15

Gly Gly Thr Asp Asn Pro His Ile Gly Thr Asp Thr Ser
            20                  25

(2) INFORMATION FOR SEQ ID NO:52:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:52:

Glu Ile Asp Leu Val Lys Gly Gly Lys Lys Leu Gly Phe Ser Ile Ala
1               5                   10                  15

Gly Gly Ile Gly Asn Gln His Ile Pro Gly Asp Asn Gly
            20                  25

(2) INFORMATION FOR SEQ ID NO:53:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:53:

Thr Ile Thr Ile Gln Lys Gly Pro Gln Gly Leu Gly Phe Asn Ile Val
1               5                   10                  15

Gly Gly Glu Asp Gly Gln Gly
            20

(2) INFORMATION FOR SEQ ID NO:54:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:54:

Glu Ile Thr Leu Glu Arg Gly Asn Ser Gly Leu Gly Phe Ser Ile Ala
1               5                   10                  15

Gly Gly Thr Asp Asn Pro His Ile Gly Asp Asp Pro Ser
            20                  25

(2) INFORMATION FOR SEQ ID NO:55:

(i) SEQUENCE CHARACTERISTICS:
    (A) LENGTH: 29 amino acids
    (B) TYPE: amino acid
    (C) STRANDEDNESS:
    (D) TOPOLOGY: linear (ii) MOLECULE TYPE: peptide (xi) SEQUENCE DESCRIPTION: SEQ ID NO:55:

Glu Ile Lys Leu Ile Lys Gly Pro Lys Gly Leu Gly Phe Ser Ile Ala
1               5                   10                  15

Gly Gly Val Gly Asn Gln His Ile Pro Gly Asp Asn Ser
            20                  25

(2) INFORMATION FOR SEQ ID NO:56:

(i) SEQUENCE CHARACTERISTICS:
        (A) LENGTH: 23 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:56:

Arg Ile Val Ile His Arg Gly Ser Thr Gly Leu Gly Phe Asn Ile Val
1               5                   10                  15

Gly Gly Glu Asp Gly Glu Gly
            20

(2) INFORMATION FOR SEQ ID NO:57:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:57:

Glu Ile Thr Leu Glu Arg Gly Asn Ser Gly Leu Gly Phe Ser Ile Ala
1               5                   10                  15

Gly Gly Thr Asp Asn Pro His Ile Gly Asp Asp Ser Ser
            20                  25

(2) INFORMATION FOR SEQ ID NO:58:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:58:

Glu Ile Lys Leu Ile Lys Gly Pro Lys Gly Leu Gly Phe Ser Ile Ala
1               5                   10                  15

Gly Gly Val Gly Asn Gln His Ile Pro Gly Asp Asn Ser
            20                  25

(2) INFORMATION FOR SEQ ID NO:59:

(i) SEQUENCE CHARACTERISTICS:
        (A) LENGTH: 23 amino acids
        (B) TYPE: amino acid (C) STRANDEDNESS:
           (D) TOPOLOGY: linear (ii) MOLECULE TYPE: peptide (xi) SEQUENCE DESCRIPTION: SEQ ID NO:59:

Lys Val Val Leu His Arg Gly Ser Thr Gly Leu Gly Phe Asn Ile Val
1               5                   10                  15

Gly Gly Glu Asp Asp Glu Gly
            20

(2) INFORMATION FOR SEQ ID NO:60:

(i) SEQUENCE CHARACTERISTICS:
           (A) LENGTH: 28 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:60:

Thr Val Val Glu Leu Met Lys Lys Glu Gly Thr Thr Leu Gly Leu Thr
1               5                   10                  15

Val Ser Gly Gly Ile Asp Lys Asp Gly Lys Pro Arg
            20                  25

(2) INFORMATION FOR SEQ ID NO:61:

(i) SEQUENCE CHARACTERISTICS:
           (A) LENGTH: 28 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:61:

Glu Val Thr Leu His Lys Glu Gly Asn Thr Phe Gly Phe Val Ile Arg
1               5                   10                  15

Gly Gly Ala His Asp Asp Arg Asn Lys Ser Arg Pro
            20                  25

(2) INFORMATION FOR SEQ ID NO:62:

(i) SEQUENCE CHARACTERISTICS:
           (A) LENGTH: 26 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:62:

Leu Val Glu Val Ala Lys Thr Pro Gly Ala Ser Leu Gly Val Ala Leu
1               5                   10                  15

Thr Thr Ser Val Cys Cys Asn Lys Gln Val
            20                  25

(2) INFORMATION FOR SEQ ID NO:63:

(i) SEQUENCE CHARACTERISTICS:
           (A) LENGTH: 30 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:63:

Glu Val Val Leu Thr Ala Asp Pro Val Thr Gly Phe Gly Ile Gln Leu
1               5                  10                  15

Gln Gly Ser Val Phe Ala Thr Glu Thr Leu Ser Ser Pro Pro
            20                  25                  30

(2) INFORMATION FOR SEQ ID NO:64:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:64:

His Val Lys Leu Pro Lys Lys His Ser Val Glu Leu Gly Ile Thr Ile
1               5                  10                  15

Ser Ser Pro Ser Ser Arg Lys Pro Gly Asp Pro
            20                  25

(2) INFORMATION FOR SEQ ID NO:65:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:65:

Thr Val Glu Leu Lys Arg Tyr Gly Gly Pro Leu Gly Ile Thr Ile Ser
1               5                  10                  15

Gly Thr Glu Glu Pro Phe Asp Pro
            20

(2) INFORMATION FOR SEQ ID NO:66:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:66:

Lys Val Thr Leu Tyr Lys Asp Ser Gly Met Glu Asp Phe Gly Phe Ser
1               5                  10                  15

Val Ala Asp Gly Leu Leu Glu Lys Gly Val Tyr Val Lys Asn
            20                  25                  30

(2) INFORMATION FOR SEQ ID NO:67:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:67:

Ile Tyr Ile Thr Lys Leu Ile Ser Gly Gly Ala Ala Ala Ala Asp Gly

```
                  1               5                  10                 15
Arg Leu Ser Ile Asn Asp Ile Ile Val Ser Val Asn Asp Val Ser
                20                  25                 30

(2) INFORMATION FOR SEQ ID NO:68:

(i) SEQUENCE CHARACTERISTICS:
        (A) LENGTH: 33 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:68:

Ile Tyr Val Thr Lys Leu Thr Asp Gly Gly Arg Ala Gln Val Asp Gly
 1               5                  10                  15

Arg Leu Ser Ile Gly Asp Lys Leu Ile Ala Val Arg Thr Asn Gly Ser
                20                  25                  30

Glu (2) INFORMATION FOR SEQ ID NO:69:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:69:

Ile Tyr Val Ser Phe Ile Leu Ala Gly Gly Pro Ala Asp Leu Gly Ser
 1               5                  10                  15

Glu Leu Lys Arg Gly Asp Gln Leu Leu Ser Val Asn Asn Val Asn
                20                  25                  30

(2) INFORMATION FOR SEQ ID NO:70:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:70:

Ile Phe Asp Thr Lys Ile Ile Pro Gly Gly Ala Ala Ala Gln Asp Gly
 1               5                  10                  15

Arg Leu Arg Val Asn Asp Ser Ile Leu Phe Val Asn Glu Val Asp
                20                  25                  30

(2) INFORMATION FOR SEQ ID NO:71:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:71:

Ile Tyr Val Thr Lys Ile Ile Glu Gly Gly Ala Ala His Lys Asp Gly
 1               5                  10                  15
```

Arg Leu Gln Ile Gly Asp Lys Ile Leu Ala Val Asn Ser Val Gly
            20                  25                  30

(2) INFORMATION FOR SEQ ID NO:72:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:72:

Ile Phe Ile Ser Phe Ile Leu Ala Gly Gly Pro Ala Asp Leu Ser Gly
1               5                   10                  15

Glu Leu Arg Lys Gly Asp Gln Ile Leu Ser Val Asn Gly Val Asp
            20                  25                  30

(2) INFORMATION FOR SEQ ID NO:73:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:73:

Ile Phe Ile Thr Lys Ile Ile Thr Gly Gly Ala Ala Ala Gln Asp Gly
1               5                   10                  15

Arg Leu Arg Val Asn Asp Cys Ile Leu Arg Val Asn Glu Ala Asp
            20                  25                  30

(2) INFORMATION FOR SEQ ID NO:74:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:74:

Ile Tyr Val Thr Lys Ile Ile Glu Gly Gly Ala Ala His Lys Asp Gly
1               5                   10                  15

Arg Leu Gln Ile Gly Asp Lys Leu Leu Ala Val Asn Ser Val Cys
            20                  25                  30

(2) INFORMATION FOR SEQ ID NO:75:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:75:

Ile Phe Ile Ser Phe Ile Leu Ala Gly Gly Pro Ala Asp Leu Ser Gly
1               5                   10                  15

Glu Leu Arg Lys Gly Asp Arg Ile Ile Ser Val Asn Ser Val Asp
            20                  25                  30

(2) INFORMATION FOR SEQ ID NO:76:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:76:

```
Val Ser Asn Leu Arg Gln Gly Gly Ile Ala Ala Arg Ser Asp Gln Leu
1               5                   10                  15

Asp Val Gly Asp Tyr Ile Lys Ala Val Asn Gly Ile Asn
            20                  25
```

(2) INFORMATION FOR SEQ ID NO:77:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:77:

```
Val Val Ile Thr Cys Val Arg Pro Gly Gly Pro Asp Asp Arg Glu Gly
1               5                   10                  15

Thr Ile Lys Pro Gly Asp Arg Leu Leu Ser Val Asp Gly Ile Arg
            20                  25                  30
```

(2) INFORMATION FOR SEQ ID NO:78:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:78:

```
Ile Val Ile Asp Lys Ile Lys Ser Ala Ser Ile Ala Asp Arg Cys Gly
1               5                   10                  15

Ala Leu His Val Gly Asp His Ile Leu Ser Ile Asp Gly Thr Ser
            20                  25                  30
```

(2) INFORMATION FOR SEQ ID NO:79:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:79:

```
Ile Ile Ser Tyr Ile Glu Ala Asp Ser Pro Ala Glu Arg Cys Gly Val
1               5                   10                  15

Leu Gln Ile Gly Asp Arg Val Met Ala Ile Asn Gly Ile Pro
            20                  25                  30
```

(2) INFORMATION FOR SEQ ID NO:80:

(i) SEQUENCE CHARACTERISTICS:
        (A) LENGTH: 31 amino acids (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:80:

Leu Val Ile Ser Asp Ile Lys Lys Gly Ser Val Ala His Arg Thr Gly
1               5                   10                  15

Thr Leu Glu Leu Gly Asp Lys Leu Leu Ala Ile Asp Asn Ile Arg
            20                  25                  30

(2) INFORMATION FOR SEQ ID NO:81:

(i) SEQUENCE CHARACTERISTICS:
            (A) LENGTH: 31 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:81:

Ile Ile Ile Ser Ser Ile Thr Lys Gly Gly Leu Ala Glu Arg Thr Gly
1               5                   10                  15

Ala Ile His Ile Gly Asp Arg Ile Leu Ala Ile Asn Ser Ser Ser
            20                  25                  30

(2) INFORMATION FOR SEQ ID NO:82:

(i) SEQUENCE CHARACTERISTICS:
            (A) LENGTH: 23 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:82:

Ile Arg Pro Ala Gly Pro Gly Asp Leu Gly Gly Leu Lys Pro Tyr Asp
1               5                   10                  15

Arg Leu Leu Gln Val Asn His
            20

(2) INFORMATION FOR SEQ ID NO:83:

(i) SEQUENCE CHARACTERISTICS:
            (A) LENGTH: 27 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:83:

Val Val Asp Val Pro His Ala Ser Ala Val Asp Ala Leu Lys Lys Ala
1               5                   10                  15

Gly Asn Val Val Lys Leu His Val Lys Arg Lys
            20                  25

(2) INFORMATION FOR SEQ ID NO:84:

(i) SEQUENCE CHARACTERISTICS:
            (A) LENGTH: 29 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:84:

Lys Asn Leu Glu Asn Val Thr His Glu Leu Ala Val Ala Thr Leu Lys
1               5                   10                  15

Ser Ile Thr Asp Lys Val Thr Leu Ile Ile Gly Lys Thr
            20                  25

(2) INFORMATION FOR SEQ ID NO:85:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:85:

Leu Thr His Ala Thr His Glu Glu Ala Ala Gln Ala Leu Lys Thr Ser
1               5                   10                  15

Gly Gly Val Val Thr Leu Leu Ala Gln Tyr Arg Pro
            20                  25

(2) INFORMATION FOR SEQ ID NO:86:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:86:

Val Arg Glu Val Thr His Ser Ala Ala Val Glu Ala Leu Lys Glu Ala
1               5                   10                  15

Gly Ser Ile Val Arg Leu Tyr Val Met Arg Arg
            20                  25

(2) INFORMATION FOR SEQ ID NO:87:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:87:

Leu Glu Asp Val Met His Glu Asp Ala Val Ala Ala Leu Lys Asn Thr
1               5                   10                  15

Tyr Asp Val Val Tyr Leu Lys Val Ala Lys Pro
            20                  25

(2) INFORMATION FOR SEQ ID NO:88:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:88:

```
Leu Arg Asn Ala Ser His Glu Gln Ala Ala Ile Ala Leu Lys Asn Ala
1               5                   10                  15

Gly Gln Thr Val Thr Ile Ile Ala Gln Tyr Lys
                20                  25
```

(2) INFORMATION FOR SEQ ID NO:89:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:89:

```
Val Arg Asp Val Thr His Ser Lys Ala Val Glu Ala Leu Lys Glu Ala
1               5                   10                  15

Gly Ser Ile Val Arg Leu Tyr Val Lys Arg Arg
                20                  25
```

(2) INFORMATION FOR SEQ ID NO:90:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:90:

```
Leu Glu Glu Val Thr His Glu Glu Ala Val Thr Ala Leu Lys Asn Thr
1               5                   10                  15

Ser Asp Phe Val Tyr Leu Lys Ala Ala Lys Pro
                20                  25
```

(2) INFORMATION FOR SEQ ID NO:91:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:91:

```
Leu Arg Ala Ala Ser His Glu Gln Ala Ala Ala Ala Leu Lys Asn Ala
1               5                   10                  15

Gly Gln Ala Val Thr Ile Val Ala Gln Tyr Arg
                20                  25
```

(2) INFORMATION FOR SEQ ID NO:92:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:92:

```
Leu Ala Lys Phe Arg His Asp Glu Ile Ile Ser Leu Leu Lys Asn Val
1               5                   10                  15

Gly Glu Arg Val Val Leu Glu Val Glu Tyr Glu
```

```
                20              25

(2) INFORMATION FOR SEQ ID NO:93:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:93:

Leu Leu Gly Thr Thr His Ala Glu Ala Met Ser Ile Leu Lys Gln Cys
1               5                  10                  15

Gly Asp Glu Ala Thr Leu Leu Ile Glu Tyr Asp
                20              25

(2) INFORMATION FOR SEQ ID NO:94:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:94:

Met Glu Tyr Cys Thr Leu Ala Glu Ala Thr Gln Phe Leu Gly Asn Thr
1               5                  10                  15

Thr Asp Gln Val Lys Leu Glu Ile Leu Pro His His Gln Thr Arg
                20              25                  30

(2) INFORMATION FOR SEQ ID NO:95:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:95:

Thr Glu Asp Ser Thr Phe Glu Glu Ala Asn Gln Leu Leu Arg Asp Ser
1               5                  10                  15

Ser Ile Thr Ser Lys Val Thr Leu Glu Ile Glu Phe
                20              25

(2) INFORMATION FOR SEQ ID NO:96:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:96:

Leu Asp Ser Cys Ser Met Glu Asp Ala Tyr Gln Ile Leu Gln Gln Cys
1               5                  10                  15

Glu Asp Leu Val Lys Leu Lys Ile Arg Lys Asp
                20              25

(2) INFORMATION FOR SEQ ID NO:97:
```

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:97:

Leu Lys Gly Lys Pro Leu Ser Glu Asp Ile His Leu Leu Gln Met Ala
1               5                   10                  15

Gly Glu Thr Val Thr Leu Lys Ile Lys Lys Gln
            20                  25

(2) INFORMATION FOR SEQ ID NO:98:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:98:

Val Arg Thr Arg Asp Phe Asp Cys Cys Leu Val Val Asp Leu Ile Ala
1               5                   10                  15

Glu Ser Gly Asn Lys Leu Asp Leu Val Ile Ser Arg Asn
            20                  25

(2) INFORMATION FOR SEQ ID NO:99:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:99:

Tyr Lys Glu Gly Tyr Asn Val Tyr Gly Ile Glu Ser Val Lys Ile
1               5                   10                  15

(2) INFORMATION FOR SEQ ID NO:100:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:100:

Tyr Lys Glu Gly Tyr Asn Val Tyr Gly Arg Glu Ser Val Lys Ile
1               5                   10                  15

(2) INFORMATION FOR SEQ ID NO:101:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:101:

```
Tyr Lys Glu Gly Tyr Asn Val Tyr Gly Ile Arg Ser Val Lys Ile
1               5                   10                  15
```

(2) INFORMATION FOR SEQ ID NO:102:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:102:

```
Tyr Lys Glu Gly Tyr Asn Val Tyr
1               5
```

(2) INFORMATION FOR SEQ ID NO:103:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:103:

```
Cys Met Ser His Ser Ser Gly Met Pro Leu Gly Ala Thr Gly Leu
1               5                   10                  15
```

(2) INFORMATION FOR SEQ ID NO:104:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:104:

```
Asn Arg Arg Val Tyr Lys Xaa Met Pro Ser Ile Glu Ser Asp Val
1               5                   10                  15
```

(2) INFORMATION FOR SEQ ID NO:105:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:105:

```
Asn Gly His Val Tyr Glu Lys Leu Ser Ser Ile Glu Ser Asp Val
1               5                   10                  15
```